(12) United States Patent
Jurcak et al.

(10) Patent No.: US 7,518,000 B2
(45) Date of Patent: Apr. 14, 2009

(54) THIENOPYRAZOLES

(75) Inventors: John Gerald Jurcak, Bethlehem, PA (US); Matthieu Barrague, Hoboken, NJ (US); Timothy Alan Gillespy, Hillsborough, NJ (US); Michael Louis Edwards, Morristown, NJ (US); Kwon Yon Musick, Raritan, NJ (US); Phillip Marvin Weintraub, Warren, NJ (US); Yan Du, Bridgewater, NJ (US); Ramalinga M. Dharanipragada, Belle Mead, NJ (US); Ashfaq Ahmed Parkar, Piscataway, NJ (US)

(73) Assignee: Aventis Pharmaceuticals, Inc., Bridgewater, NJ (US)

( * ) Notice: Subject to any disclaimer, the term of this patent is extended or adjusted under 35 U.S.C. 154(b) by 207 days.

(21) Appl. No.: 11/368,566

(22) Filed: Mar. 6, 2006

(65) Prior Publication Data

US 2007/0254937 A1    Nov. 1, 2007

Related U.S. Application Data

(63) Continuation of application No. PCT/US2004/023814, filed on Jul. 23, 2004.

(60) Provisional application No. 60/501,159, filed on Sep. 8, 2003.

(51) Int. Cl.
  *C07D 495/02*  (2006.01)
  *C07D 231/54*  (2006.01)
(52) U.S. Cl. ..................... 549/50; 548/360.5

(58) Field of Classification Search ............... 549/50; 548/360.5
See application file for complete search history.

(56) References Cited

U.S. PATENT DOCUMENTS

| 6,358,978 B1 | 3/2002 | Stilz et al. |
| 6,462,036 B1 | 10/2002 | Doyle et al. |
| 2002/0161022 A1 | 10/2002 | Reich et al. |
| 2003/0139463 A1 | 7/2003 | Reich et al. |

FOREIGN PATENT DOCUMENTS

WO   WO03/024969 A1   3/2003

OTHER PUBLICATIONS

U.S. Appl. No. 10/828,012, filed Apr. 20, 2004, Babin et al.

*Primary Examiner*—D. Margaret Seaman
*Assistant Examiner*—Nizal S Chandrakumar
(74) *Attorney, Agent, or Firm*—James W. Bolcsak

(57) ABSTRACT

Thienopyrazoles of formula I, their preparation, pharmaceutical compositions comprising these compounds, and their pharmaceutical uses in the treatment of disease states capable of being modulated by the inhibition of the protein kinases, in particular interleukin-2 inducible tyrosine kinase (ITK).

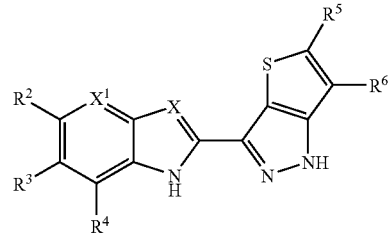

12 Claims, 1 Drawing Sheet

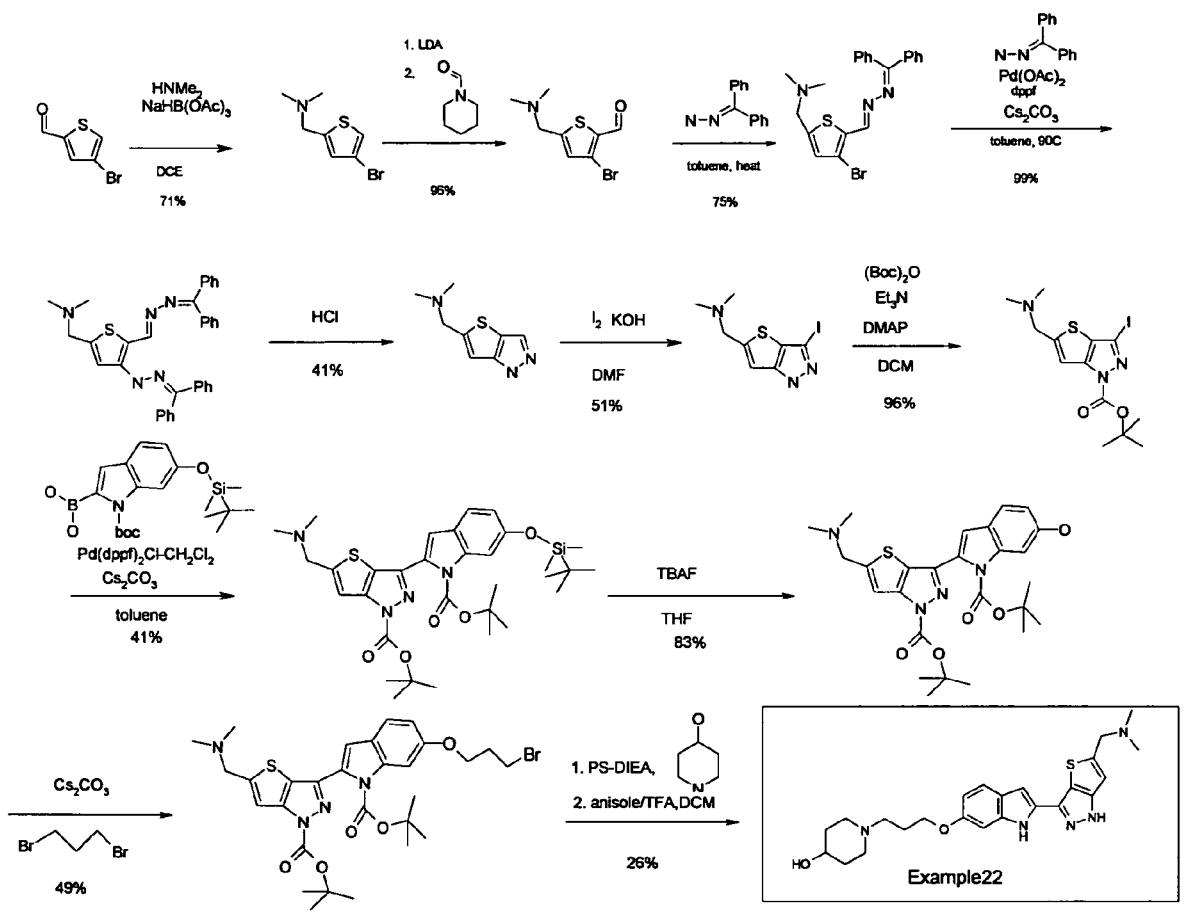

THIENOPYRAZOLES

This application is a continuation of International application No. PCT/US2004/023814, filed Jul. 23, 2004 which is incorporated herein by reference in its entirety; which claims the benefit of priority of U.S. Provisional Patent Application No. 60/501,159, filed Sep. 8, 2003, which is also incorporated herein by reference in its entirety.

FIELD OF THE INVENTION

This invention is directed to thienopyrazoles of Formula I, their preparation, pharmaceutical compositions comprising these compounds, and their pharmaceutical use in the treatment of disease states capable of being modulated by the inhibition of the protein kinases, in particular interleukin-2 inducible tyrosine kinase (ITK).

BACKGROUND OF THE INVENTION

Protein kinases are a family of enzymes that participate in the signalling events which control the activation, growth and differentiation of cells in response to extracellular mediators and to changes in the environment. In general, these kinases fall into several groups; those which preferentially catalyse the phosphorylation of hydroxy groups of serine and/or threonine residues and those which preferentially catalyse the phosphorylation of hydroxy groups of tyrosine residues [S. K. Hanks and T. Hunter, FASEB. J., 1995, 9, pages 576-596]. Such phosphorylations may greatly modify the function of the proteins; thus, protein kinases play an important role in regulating a wide variety of cell processes including, especially, metabolism, cell proliferation, cell differentiation or cell survival.

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or underproduction of cytokines or growth factors also participating in the transduction of signals upstream or downstream of the kinase. In all of these instances, selective inhibition of the action of the kinase might be expected to have a beneficial effect.

ITK, is a T cell specific tyrosine kinase of the Tec family that is required for normal Th2 function. Asthma is a disease characterised by increased Th2 cytokine production including IL-4. An inhibitor of ITK should therefore have an impact on disease progression in asthma through inhibition of Th2 cytokine production.

We have now found a novel group of thienopyrazoles, which have valuable pharmaceutical properties, in particular, the ability to inhibit protein kinases, more particularly, the ability to inhibit the protein kinase ITK.

SUMMARY OF THE INVENTION

Thus, in one aspect, the invention is directed to compounds of Formula I,

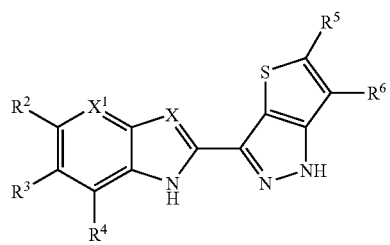

Formula I wherein:

X is N, or C—$R^7$;

$X^1$ is N, or C—$R^1$;

$R^1$, $R^2$, $R^3$, $R^4$, $R^5$ and $R^6$ are independently hydrogen, optionally substituted acyl, optionally substituted alkyl, optionally substituted alkoxy, optionally substituted acylamino, optionally substituted alkenyl, optionally substituted alkoxyalkyl, $(Y^1)(Y^2)NC(=O)$—, $(Y^1)(Y^2)N$—, optionally substituted alkoxycarbonyl, optionally substituted alkylsulfinyl, optionally substituted alkylsulfonyl, optionally substituted alkylsulfonylcarbamoyl, optionally substituted alkylthio, optionally substituted alkynyl, optionally substituted aroyl, optionally substituted aryl, optionally substituted aroylamino, optionally substituted arylalkyl, optionally substituted arylalkoxy, optionally substituted arylalkyloxyalkyl, optionally substituted arylalkyloxycarbonyl, optionally substituted aryloxyalkyl, optionally substituted arylalkylthio, optionally substituted aryloxy, optionally substituted aryloxycarbonyl, optionally substituted arylsulfinyl, optionally substituted arylsulfonyl, optionally substituted arylsulfonylcarbamoyl, optionally substituted arylthio, optionally substituted cycloalkenyl, optionally substituted cycloalkoxyalkyl, optionally substituted cycloalkyl, optionally substituted cycloalkylalkyl, optionally substituted cycloalkyloxy, optionally substituted heteroaroyl, optionally substituted heteroaroylamino, optionally substituted heteroarylalkyl, optionally substituted heteroarylalkoxy, optionally substituted heteroarylalkyloxyalkyl, optionally substituted heteroaryloxy, optionally substituted heteroaryloxyalkyl, optionally substituted heterocycloalkyl, optionally substituted heteroarylsulfonylcarbamoyl, optionally substituted heterocycloalkylalkyl, optionally substituted heterocycloalkyloxy, optionally substituted heterocycloalkyloxyalkyl, halo, hydroxy, trifluoromethyl, nitro, optionally substituted hydroxyalkyl, carboxy, or cyano;

$R^5$ and $R^6$, together with the two double-bonded carbons to which they are attached, may also form an optionally substituted benzene ring;

$R^7$ is hydrogen, halo or optionally substituted alkyl; and $Y^1$ and $Y^2$ are independently hydrogen, optionally substituted alkyl, optionally substituted aryl, optionally substituted heteroaryl, or $Y^1$ and $Y^2$, together with the nitrogen to which they are attached form an optionally substituted heteroaryl group, or an optionally substituted heterocycloalkyl group; or a prodrug, acid bioisostere, pharmaceutically acceptable salt or solvate of such compound; or a prodrug, or acid bioisostere of such salt or solvate.

Preferred compounds of the present invention are those of Formula I wherein X is N.

Further preferred compounds of the present invention are those of Formula I wherein X is C—R$^7$, particularly C—H or C-halo.

Compounds of Formula I wherein X$^1$ is N are also preferred.

Compounds of Formula I wherein X$^1$ is C—R$^1$, particularly C—H, are also preferred.

Compounds of Formula I wherein one of R$^2$ and R$^3$ is hydrogen, and the other is hydrogen, optionally substituted acyl, optionally substituted alkoxy, optionally substituted alkoxycarbonyl, optionally substituted alkyl, halo or (Y$^1$)(Y$^2$)NC(=O)— are also preferred.

Compounds of Formula I wherein R$^4$ is hydrogen are also preferred.

Compounds of Formula I wherein R$^5$ is hydrogen, optionally substituted alkoxycarbonyl, optionally substituted alkyl, optionally substituted aryl, carboxy, or (Y$^1$)(Y$^2$)NC(=O)— are also preferred.

Compounds of Formula I wherein R$^6$ is hydrogen are also preferred.

Compounds of Formula I wherein R$^5$ and R$^6$, together with the two double-bonded carbons to which they are attached, form an optionally substituted benzene ring, are also preferred.

It is to be understood that this invention covers all appropriate combinations of the particular and preferred groupings referred to herein.

A particular group of compounds of the invention are compounds of Formula (Ia)

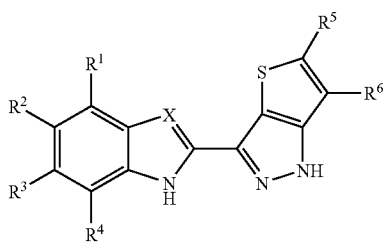

Formula (Ia)

wherein X, R$^1$, R$^2$, R$^3$, R$^4$, R$^5$ and R$^6$ are as hereinbefore defined, or a prodrug, acid bioisostere, pharmaceutically acceptable salt or solvate of such compound; or a prodrug, or acid bioisostere of such salt or solvate.

Compounds of Formula (Ia) in which X represents:
(i) N;
(ii) C—Br;
(iii) C—H;
are preferred.

Compounds of Formula I(a) wherein R$^1$ represents hydrogen are preferred.

Compounds of Formula I(a) wherein one of R$^2$ and R$^3$ represents H and the other represents:
(i) hydrogen
(ii) optionally substituted acyl [e.g.

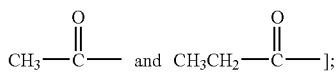];

(iii) optionally substituted alkoxy [e.g.

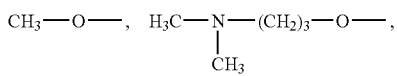
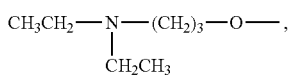
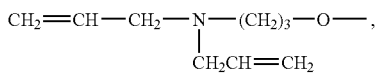
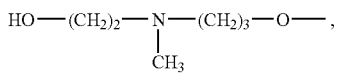
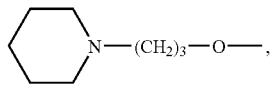
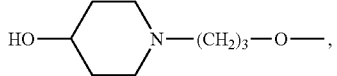
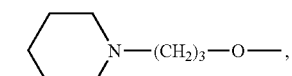
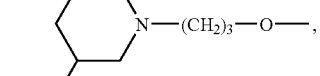
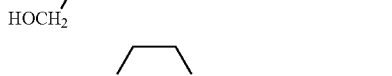
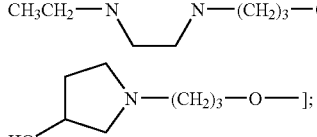];

(iv) optionally substituted alkoxycarbonyl [e.g.

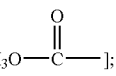];

or
(v) optionally substituted alkyl [e.g.

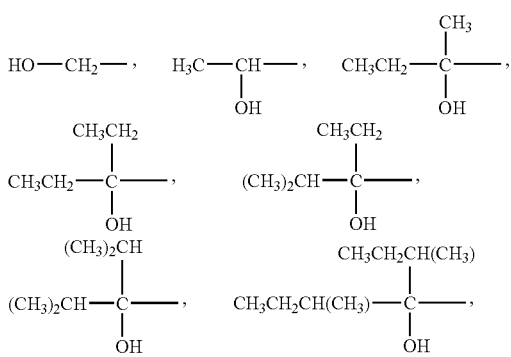

-continued
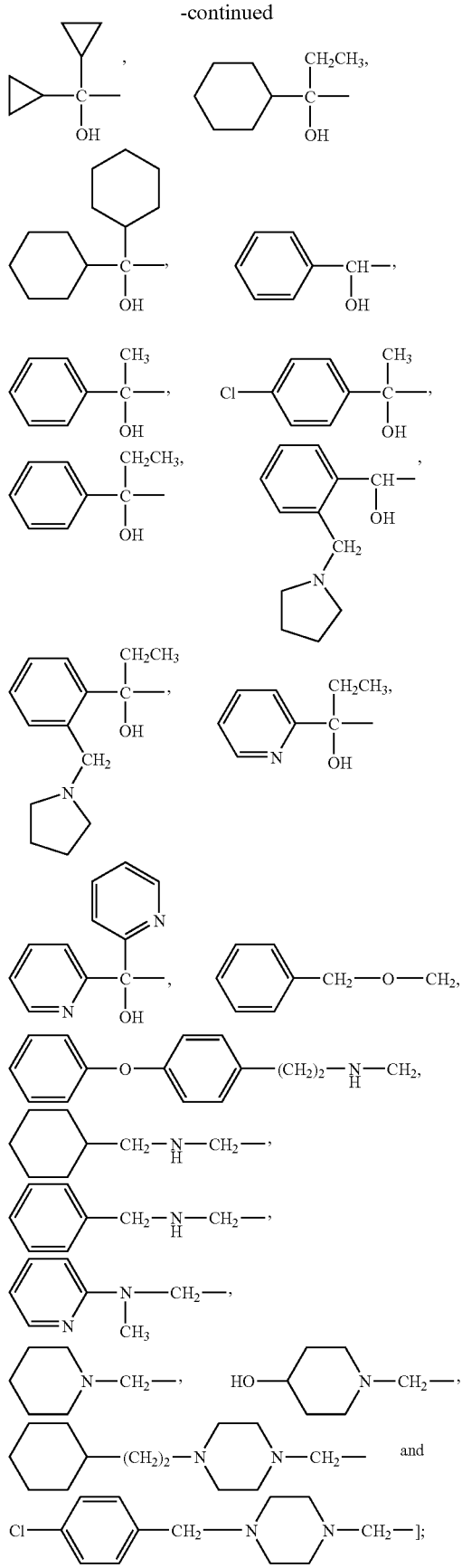
(vi) halo [e.g. bromo]; or
(vii) $(Y^1)(Y^2)NC(=O)—$ [e.g.
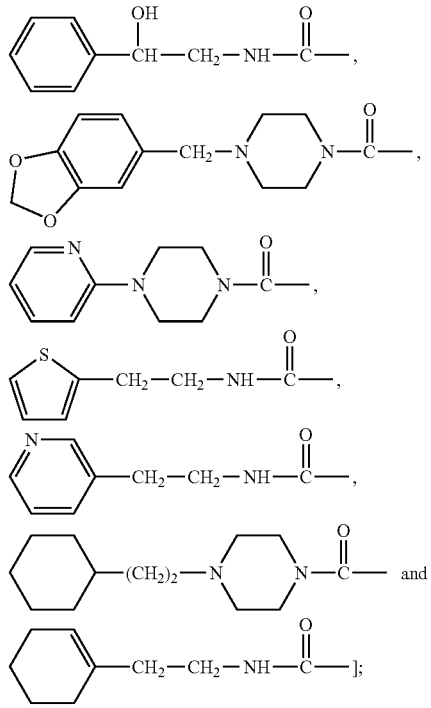
are preferred.
Compounds of Formula I(a) wherein $R^4$ is hydrogen are preferred.
Compounds of Formula I(a) wherein $R^5$ represents:
(i) hydrogen;
(ii) optionally substituted alkoxycarbonyl [e.g.
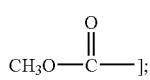
(ii) optionally substituted alkyl [e.g. $HO—CH_2—$,
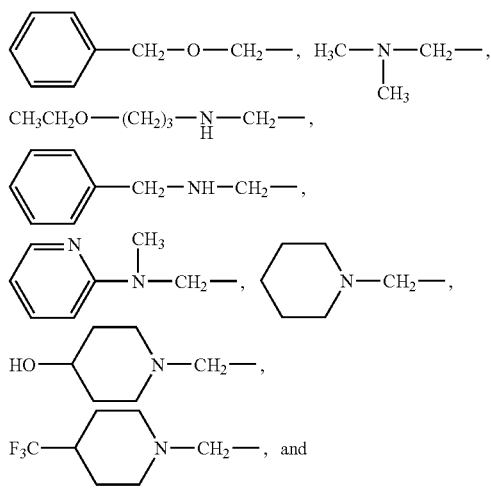

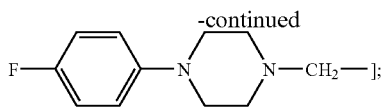

(iii) optionally substituted aryl [e.g.

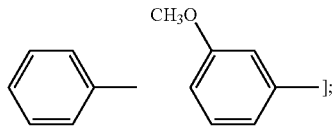

(iv) carboxy; or
(iv) (Y¹)(Y²)NC(=O)— [e.g.

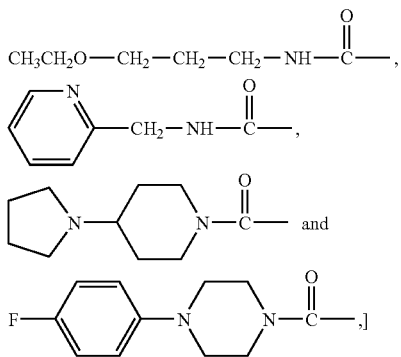

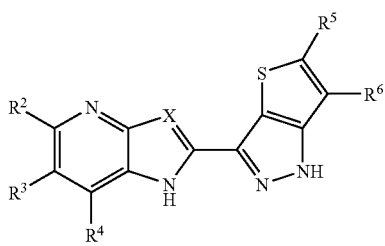

are preferred.

Compounds of Formula I(a) wherein $R^6$ is hydrogen are preferred.

Another particular group of compounds of the invention are compounds of formula (Ib)

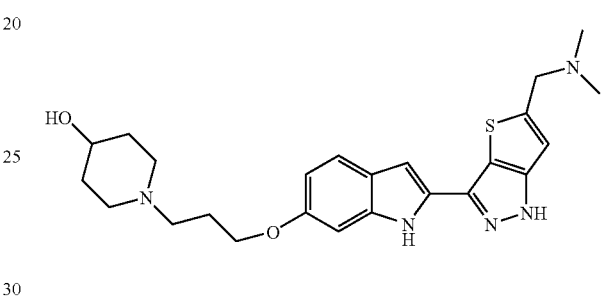

wherein $R^2$, $R^3$, $R^4$, $R^5$ and $R^6$ are as hereinbefore defined.

Nomenclature:

The compounds of Formula I and the intermediates and starting materials used in their preparation are named in accordance with IUPAC rules of nomenclature in which the characteristic groups have decreasing priority for citation as the principle group as follows: acids, esters, amides, etc. Alternatively, the compounds are named by AutoNom 4.0 (Beilstein Information Systems, Inc.). For example, a compound of Formula I in which $X^1$ is C—H, X is C—H, $R^2$ is hydrogen, $R^3$ is 3-(4-hydroxy-piperidin-1-yl)-propyloxy

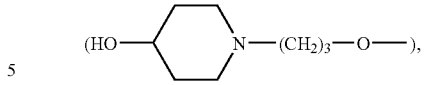

$R^4$ is hydrogen, $R^5$ is dimethylaminomethyl

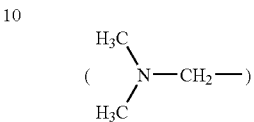

and $R^6$ is hydrogen; that is, a compound having the following structure:

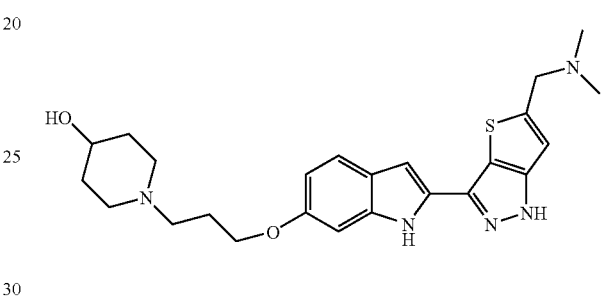

is named 1-{3-[2-(5-dimethylaminoethyl-1H-thieno[3,2-c] pyrazol-3-yl)-1h-indol-6-yloxy]-propyl}-piperidin-4-ol.

Particular embodiments of the present invention include the following compounds of Formula I:

2-(1H-thieno[3,2-c]pyrazol-3-yl)-1H-benzimidazole, Example 1;
6-methoxy-2-(1H-thieno[3,2-c]pyrazol-3-yl)-1H-benzimidazole, Example 2;
3-(6-methoxy-1H-benzimidazol-2-yl)-1H-benzo[4,5]thieno [3,2-c]pyrazole, Example 3;
6-(3-piperidin-1-ylpropoxy)-2-(1H-thieno[3,2-c]pyrazol-3-yl)-1H-benzimidazole, Example 4;
5-(3-piperidin-1-yl-propoxy)-2-(1H-thieno[3,2c]pyrazol-3-yl)-indole, Example 5;
1-{3-[2-(1H-thieno[3,2-c]pyrazol-3-yl)-1H-indol-6-yloxy]-propyl}-piperidin-4-ol, Example 6;
6-(3-piperidin-1-yl-propoxy)-2-(1H-thieno[3,2-c]pyrazol-3-yl)-1H-indole, Example 7;
1-{3-[2-(1H-thieno[3,2-c]pyrazol-3-yl)-1H-indol-6-yloxy]-propyl}-piperidin-3-ol, Example 8;
(1-{3-[2-(1H-thieno[3,2-c]pyrazol-3-yl)-1H-indol-6-yloxy]-propyl}-piperidin-3-yl)-methanol, Example 9;
6-[3-(4-ethyl-piperazin-1-yl)-propoxy]-2-(1H-thieno[3,2-c] pyrazol-3-yl)-1H-indole, Example 10;
dimethyl-{3-[2-(1H-thieno[3,2-c]pyrazol-3-yl)-1H-indol-6-yloxy]-propyl}-amine, Example 11;
diethyl-{3-[2-(1H-thieno[3,2-c]pyrazol-3-yl)-1H-indol-6-yloxy]-propyl}-amine, Example 12;
diallyl-{3-[2-(1H-thieno[3,2-c]pyrazol-3-yl)-1H-indol-6-yloxy]-propyl}-amine, Example 13;
1-{3-[2-(1H-thieno[3,2-c]pyrazol-3-yl)-1H-indol-6-yloxy]-propyl}-pyrrolidin-3-ol, Example 14;
2-(methyl-{3-[2-(1H-thieno[3,2-c]pyrazol-3-yl)-1H-indol-6-yloxy]-propyl}-amino)-ethanol, Example 15;
1-{3-[2-(1H-thieno[3,2-c]pyrazol-3-yl)-1H-indol-5-yloxy]-propyl}-piperidin-4-ol, Example 16;

1-{3-[2-(1H-thieno[3,2-c]pyrazol-3-yl)-1H-indol-5-yloxy]-propyl}-piperidin-3-ol, Example 17;

(1-{3-[2-(1H-thieno[3,2-c]pyrazol-3-yl)-1H-indol-5-yloxy]-propyl}-piperidin-3-yl)-methanol, Example 18;

1-{3-[2-(1H-thieno[3,2-c]pyrazol-3-yl)-1H-indol-5-yloxy]-propyl}-pyrrolidin-3-ol, Example 19;

3-(5-(3-piperidin-1-yl-propoxy)-1H-Benzoimidazol-2-yl)-1H-benzo[4,5]theino[3,2-c]pyrazole, Example 20;

2-{1H-thieno[3,2-c]pyrazol-3-yl)-1H-indol-5-carboxylic acid(2-thiophen-2-yl-ethyl)-amide, Example 21;

1-{3-[2-(5-dimethylaminoethyl-1H-thieno[3,2-c]pyrazol-3-yl)-1h-indol-6-yloxy]-propyl}-piperidin-4-ol, Example 22;

2-(1-tert-butoxycarbonyl-1H-thieno[3,2-c]pyrazol-3-yl)-5-(tert-butyl-dimethyl-silanyloxy)-indole-1-carboxylic acid tert-butyl ester;

2-(1-tert-butoxycarbonyl-1H-thieno[3,2-c]pyrazol-3-yl)-6-(tert-butyl-dimethyl-silanyloxy)-indole-1-carboxylic acid tert-butyl ester;

2-(1-tert-butoxycarbonyl-5-dimethylaminomethyl-1H-thieno[3,2-c]pyrazol-3-yl)-6-(tert-butyl-dimethyl-silanyloxy)-indole-1-carboxylic acid tert-butyl ester;

2-(1-tert-butoxycarbonyl-5-dimethylaminomethyl-1H-thieno[3,2-c]pyrazol-3-yl)-6-hydroxy-indole-1-carboxylic acid tert-butyl ester;

[2-(1H-thieno[3,2-c]pyrazol-3-yl)-1H-indol-5-yl]-methanol, Example 23;

phenyl-[2-(1H-thieno[3,2-c]pyrazol-3-yl)-1H-indol-5-yl]-methanol, Example 24;

phenyl-[2-(1H-thieno[3,2-c]pyrazol-3-yl)-1H-indol-5-yl]-methanone, Example 25;

1-phenyl-1-[2-(1H-thieno[3,2-c]pyrazol-3-yl)-1H-indol-5-yl]-ethanol, Example 26;

(S)-1-phenyl-1-[2-(1H-thieno[3,2-c]pyrazol-3-yl)-1H-indol-5-yl]-ethanol, Example 27;

1-[2-(1H-thieno[3,2-c]pyrazol-3-yl)-1H-indol-5-yl]-propan-1-one, Example 28;

1-cyclohexyl-1-[2-(1H-thieno[3,2-c]pyrazol-3-yl)-1H-indol-5-yl]-propan-1-ol, Example 29;

1-cyclohexyl-1-[2-(1H-thieno[3,2-c]pyrazol-3-yl)-1H-indol-5-yl]-propan-1-ol, enantiomer 1, Example 30;

1-pyridin-2-yl-1-[2-(1H-thieno[3,2-c]pyrazol-3-yl)-1H-indol-5-yl]-propan-1-ol, Example 31;

2-[2-(1H-thieno[3,2-c]pyrazol-3-yl)-1H-indol-5-yl]-butan-2-ol, Example 32;

(R)-2-[2-(1H-thieno[3,2-c]pyrazol-3-yl)-1H-indol-5-yl]-butan-2-ol, Example 33A;

(S)-2-[2-(1H-thieno[3,2-c]pyrazol-3-yl)-1H-indol-5-yl]-butan-2-ol, Example 33B 1-(2-pyrrolidin-1-ylmethyl-phenyl)-1-[2-(1H-thieno[3,2-c]pyrazol-3-yl)-1H-indol-5-yl]-propan-1-ol, Example 34;

3-(5-acetyl-1-tert-butoxycarbonyl-1H-indol-2-yl)-thieno[3,2-c]pyrazole-1,5-dicarboxylic acid 1-tert-butyl ester 5-methyl ester, Example 35;

3-(5-acetyl-1H-indol-2-yl)-1H-thieno[3,2-c]pyrazole-5-carboxylic acid methyl ester, Example 36;

3-(5-hydroxymethyl-1H-indol-2-yl)-1H-thieno[3,2-c]pyrazole-5-carboxylic acid, Example 37;

[4-(4-fluoro-phenyl)-piperazin-1-yl]-[3-(5-hydroxymethyl-1H-indol-2-yl)-1H-thieno[3,2-c]pyrazol-5-yl]-methanone, Example 38;

3-(5-hydroxymethyl-1H-indol-2-yl)-1H-thieno[3,2-c]pyrazole-5-carboxylic acid (3-ethoxy-propyl)-amide, Example 39;

3-(5-hydroxymethyl-1H-indol-2-yl)-1H-thieno[3,2-c]pyrazole-5-carboxylic acid methyl ester, Example 40;

3-(5-hydroxymethyl-1H-indol-2-yl)-1H-thieno[3,2-c]pyrazole-5-carboxylic acid (pyridin-2-ylmethyl)-amide, Example 41;

5-bromo-2-(1H-thieno[3,2-c]pyrazol-3-yl)-1H-indole, Example 42;

2-(1H-thieno[3,2-c]pyrazol-3-yl)-1H-indole-6-carboxylic acid methyl ester, Example 43;

dicyclopropyl-[2-(1H-thieno[3,2-c]pyrazol-3-yl)-1H-indol-6-yl]-methanol, Example 44;

(4-benzo[1,3]dioxol-5-ylmethyl-piperazin-1-yl)-[2-(1H-thieno[3,2-c]pyrazol-3-yl)-1H-indol-6-yl]-methanone, Example 45;

[4-(2-cyclohexyl-ethyl)-piperazin-1-yl]-[2-(1H-thieno[3,2-c]pyrazol-3-yl)-1H-indol-6-yl]-methanone, Example 46;

2-(1H-thieno[3,2-c]pyrazol-3-yl)-1H-indole-6-carboxylic acid (2-hydroxy-2-phenyl-ethyl)-amide, Example 47;

2-(1H-thieno[3,2-c]pyrazol-3-yl)-1H-indole-6-carboxylic acid (2-cyclohex-1-enyl-ethyl)-amide, Example 48;

2-(1H-thieno[3,2-c]pyrazol-3-yl)-1H-indole-6-carboxylic acid (2-thiophen-2-yl-ethyl)-amide, Example 49;

(4-pyridin-2-yl-piperazin-1-yl)-[2-(1H-thieno[3,2-c]pyrazol-3-yl)-1H-indol-6-yl]-methanone, Example 50;

2-(1H-thieno[3,2-c]pyrazol-3-yl)-1H-indole-6-carboxylic acid (2-pyridin-3-yl-ethyl)-amide, Example 51;

cyclohexylmethyl-[2-(1H-thieno[3,2-c]pyrazol-3-yl)-1H-indol-5-ylmethyl]-amine, Example 52;

5-[4-(4-Chloro-benzyl)-piperazin-1-ylmethyl]-2-(1H-thieno[3,2-c]pyrazol-3-yl)-1H-indole, Example 53;

[2-(4-phenoxy-phenyl)-ethyl]-[2-(1H-thieno[3,2-c]pyrazol-3-yl)-1H-indol-5-ylmethyl]-amine, Example 54;

3-[6-(3-piperidin-1-yl-propoxy)-1H-benzoimidazol-2-yl]-1H-benzo[4,5]thieno[3,2-c]pyrazole, Example 55;

1-{3-[2-(5-phenyl-1H-thieno[3,2-c]pyrazol-3-yl)-1H-indol-6-yloxy]-propyl}-piperidin-3-ol, Example 56;

1-{3-[2-(5-Phenyl-1H-thieno[3,2-c]pyrazol-3-yl)-1H-indol-6-yloxy]-propyl}-piperidin-4-ol, Example 57;

2-(5-phenyl-1H-thieno[3,2-c]pyrazol-3-yl)-6-(3-piperidin-1-yl-propoxy)-1H-indole, Example 58;

1-(3-{2-[5-(3-methoxy-phenyl)-1H-thieno[3,2-c]pyrazol-3-yl]-1H-indol-6-yloxy}-propyl)-piperidin-4-ol, Example 59;

5-methoxy-2-(1H-thieno[3,2-c]pyrazol-3-yl)-1H-pyrrolo[3,2-b]pyridine, Example 60;

3-bromo-6-(3-piperidin-1-yl-propoxy)-2-(1H-thieno[3,2-c]pyrazol-3-yl)-1H-indole, Example 61;

{3-[6-(3-piperidin-1-yl-propoxy)-1H-indol-2-yl]-1H-thieno[3,2-c]pyrazol-5-yl}-methanol, Example 62;

1-{3-[6-(3-piperidin-1-yl-propoxy)-1H-indol-2-yl]-1H-thieno[3,2-c]pyrazol-5-ylmethyl}-piperidin-4-ol, Example 63;

2-{5-[4-(4-fluoro-phenyl)-piperazin-1-ylmethyl]-1H-thieno[3,2-c]pyrazol-3-yl}-6-(3-piperidin-1-yl-propoxy)-1H-indole, Example 64;

methyl-{3-[6-(3-piperidin-1-yl-propoxy)-1H-indol-2-yl]-1H-thieno[3,2-c]pyrazol-5-ylmethyl}-pyridin-2-yl-amine, Example 65;

benzyl-{3-[6-(3-piperidin-1-yl-propoxy)-1H-indol-2-yl]-1H-thieno[3,2-c]pyrazol-5-ylmethyl}-amine, Example 66;

6-(3-piperidin-1-yl-propoxy)-2-[5-(4-trifluoromethyl-piperidin-1-ylmethyl)-1H-thieno[3,2-c]pyrazol-3-yl]-1H-indole, Example 67;

[2-(5-piperidin-1-ylmethyl-1H-thieno[3,2-c]pyrazol-3-yl)-1H-indol-5-yl]-methanol, Example 68;

1-{3-[2-(5-benzyloxymethyl-1H-thieno[3,2-c]pyrazol-3-yl)-1H-indol-6-yloxy]-propyl}-piperidin-4-ol, Example 69;

3-[2-(1H-thieno[3,2-c]pyrazol-3-yl)-1H-indol-6-yl]-pentan-3-ol, Example 70;
3-[2-(5-benzyloxymethyl-1H-thieno[3,2-c]pyrazol-3-yl)-1H-indol-6-yl]-pentan-3-ol, Example 71;
[2-(5-benzyloxymethyl-1H-thieno[3,2-c]pyrazol-3-yl)-1H-indol-6-yl]-di-pyridin-2-yl-methanol, Example 72;
1-{3-[6-(1-ethyl-1-hydroxy-propyl)-1H-indol-2-yl]-1H-thieno[3,2-c]pyrazol-5-ylmethyl}-piperidin-4-ol, Example 73;
3-[2-(5-dimethylaminomethyl-1H-thieno[3,2-c]pyrazol-3-yl)-1H-indol-6-yl]-pentan-3-ol, Example 74;
3-(2-{5-[4-(pyridin-4-yloxy)-piperidin-1-ylmethyl]-1H-thieno[3,2-c]pyrazol-3-yl}-1H-indol-6-yl)-pentan-3-ol, Example 75;
3-[2-(5-piperazin-1-ylmethyl-1H-thieno[3,2-c]pyrazol-3-yl)-1H-indol-6-yl]-pentan-3-ol, Example 76;
3-[2-(5-piperazin-1-yl-1H-thieno[3,2-c]pyrazol-3-yl)-1H-indol-6-yl]-pentan-3-ol, Example 77;
3-{2-[5-(3-cyclopropyl-[1,2,4]oxadiazol-5-yl)-1H-thieno[3,2-c]pyrazol-3-yl]-1H-indol-6-yl}-pentan-3-ol, Example 78;
3-[2-(5-pyridin-4-yl-1H-thieno[3,2-c]pyrazol-3-yl)-1H-indol-6-yl]-pentan-3-ol, Example 79;
bis-(1-methyl-piperidin-4-yl)-[2-(1H-thieno[3,2-c]pyrazol-3-yl)-1H-indol-6-yl]-methanol, Example 80;
3-[2-(5-difluoromethyl-1H-thieno[3,2-c]pyrazol-3-yl)-1H-indol-6-yl]-pentan-3-ol, Example 81;
4-[2-(1H-thieno[3,2-c]pyrazol-3-yl)-1H-indol-6-yl]-piperidin-4-ol, Example 82;
6-(4-fluoro-piperidin-4-yl)-2-(1H-thieno[3,2-c]pyrazol-3-yl)-1H-indole, Example 83;
2-[2-(1H-thieno[3,2-c]pyrazol-3-yl)-1H-indol-6-yl]-butan-2-ol, Example 84;
1-[2-(1H-thieno[3,2-c]pyrazol-3-yl)-1H-indol-6-yl]-ethanone, Example 85;
3-[3-piperidin-4-yl-2-(1H-thieno[3,2-c]pyrazol-3-yl)-1H-indol-6-yl]-pentan-3-ol, Example 86;
3-[3-pyridin-4-yl-2-(1H-thieno[3,2-c]pyrazol-3-yl)-1H-indol-6-yl]-pentan-3-ol, Example 87;
3-[3-(4-methyl-piperazin-1-yl)-2-(1H-thieno[3,2-c]pyrazol-3-yl)-1H-indol-6-yl]-pentan-3-ol, Example 88;
3-[3-morpholin-4-ylmethyl-2-(1H-thieno[3,2-c]pyrazol-3-yl)-1H-indol-6-yl]-pentan-3-ol, Example 89;
4-[2-(1H-thieno[3,2-c]pyrazol-3-yl)-1H-indol-6-yl]-tetrahydro-pyran-4-ol, Example 90;
3-{2-[5-(1-hydroxy-1-methyl-ethyl)-1H-thieno[3,2-c]pyrazol-3-yl]-1H-indol-6-yl}-pentan-3-ol, Example 91;
3-[2-(5-methoxymethyl-1H-thieno[3,2-c]pyrazol-3-yl)-3-pyridin-4-yl-1H-indol-6-yl]-pentan-3-ol, Example 92;
4-[2-(5-methoxymethyl-1H-thieno[3,2-c]pyrazol-3-yl)-1H-indol-6-yl]-tetrahydro-pyran-4-ol, Example 93;
3-[2-(5-methoxymethyl-1H-thieno[3,2-c]pyrazol-3-yl)-3-piperazin-1-yl-1H-indol-6-yl]-pentan-3-ol, Example 94;
3-[2-(5-methoxymethyl-1H-thieno[3,2-c]pyrazol-3-yl)-3-morpholin-4-ylmethyl-1H-indol-6-yl]-pentan-3-ol, Example 95;
2-{3-[6-(1-ethyl-1-hydroxy-propyl)-1H-indol-2-yl]-1H-thieno[3,2-c]pyrazol-5-yl}-tetrahydro-furan-3-carbonitrile, Example 96;
3-[2-(5-methoxymethyl-1H-thieno[3,2-c]pyrazol-3-yl)-3-methyl-1H-indol-6-yl]-pentan-3-ol, Example 97; and
3-[2-(5-methoxymethyl-1H-thieno[3,2-c]pyrazol-3-yl)-3-piperidin-4-yl-1H-indol-6-yl]-pentan-3-ol, Example 98;

and prodrugs, acid bioisosteres, pharmaceutically acceptable salts or solvates of such compounds or prodrugs, and acid bioisosteres of such salts or solvates. The properties of these particular compounds are summarized in Table 1 below.

BRIEF DESCRIPTION OF THE DRAWINGS

FIG. 1 is chemical synthetic scheme depicting the process of making a compound of the present invention.

DETAILED DESCRIPTION OF THE PREFERRED EMBODIMENTS

In the present specification, the term "compounds of the invention", and equivalent expressions, are meant to embrace compounds of Formulas I as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Pharmaceutically effective amount" is meant to describe an amount of compound, composition, medicament or other active ingredient effective in producing the desired therapeutic effect.

"Acid bioisostere" means a group which has chemical and physical similarities producing broadly similar biological properties to a carboxy group (see Lipinski, Annual Reports in Medicinal Chemistry, 1986, 21, page 283 "Bioisosterism In Drug Design"; Yun, Hwahak Sekye, 1993, 33, pages 576-579 "Application Of Bioisosterism To New Drug Design"; Zhao, Huaxue Tongbao, 1995, pages 34-38 "Bioisosteric Replacement And Development Of Lead Compounds In Drug Design"; Graham, Theochem, 1995, 343, pages 105-109 "Theoretical Studies Applied To Drug Design:ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH—CN, sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acyl" means an H—CO— or alkyl-CO— group in which the alkyl group is as described herein. Exemplary acyl groups include

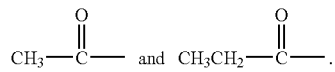

"Optionally substituted acyl" means an acyl group which may be substituted on the alkyl portion by one or more alkyl group substituents. Exemplary substituted acyl groups include

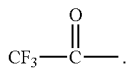

"Acylamino" is an acyl-NH— group wherein acyl is as defined herein. "Optionally substituted acylamino" means an acylamino group which may be substituted on the alkyl portion by one or more alkyl group substituents.

"Alkenyl" means an aliphatic hydrocarbon group containing one or more carbon-carbon double bonds and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl. "Optionally substituted alkenyl" means an alkenyl group which may be substituted by one or more alkyl group substituents.

"Alkoxy" means an alkyl-O— group in which the alkyl group is as described herein. Exemplary alkoxy groups include methoxy, ethoxy, n-propoxy, i-propoxy, n-butoxy and heptoxy. "Optionally substituted alkoxy" means an alkoxy group which may be substituted on the alkyl portion by one or more alkyl group substituents. Exemplary substituted alkoxy groups include

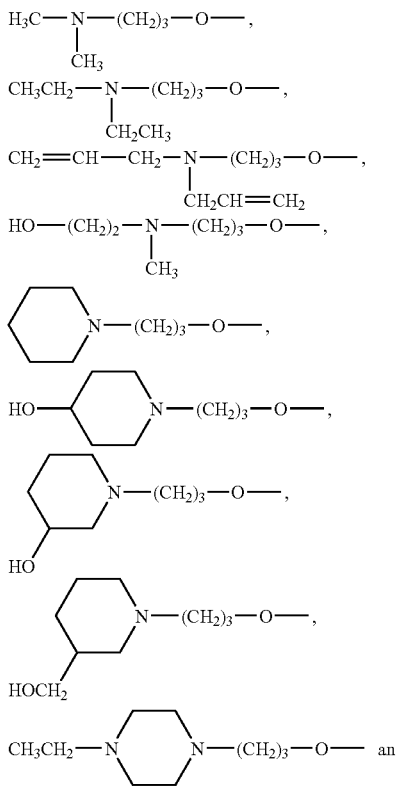

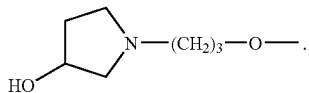

"Alkoxyalkyl" means an alkyl-O-alkyl- group in which the alkyl group is as described herein. Exemplary alkoxymethyl groups include methoxymethyl and ethoxymethyl. "Optionally substituted alkoxyalkyl" means an alkoxyalkyl which may be substituted on the alkyl portions by one or more alkyl group substituents.

"Alkoxycarbonyl" means an alkyl-O—CO— group in which the alkyl group is as described herein. Exemplary alkoxycarbonyl groups include methoxy- and ethoxycarbonyl. "Optionally substituted alkoxycarbonyl" means an alkoxycarbonyl which may be substituted on the alkyl portions by one or more alkyl group substituents.

"Alkyl" means, unless otherwise specified, an aliphatic hydrocarbon group which may be straight or branched having about 1 to about 15 carbon atoms in the chain. Particular alkyl groups have from 1 to about 6 carbon atoms. Exemplary alkyl groups include $C_{1-6}$alkyl groups such as methyl, ethyl, n-propyl, isopropyl, n-butyl, sec-butyl, isobutyl and t-butyl. "Optionally substituted alkyl" means an alkyl group which may be substituted by one or more alkyl group substituents, where "alkyl group substituent" includes, for example, acyl, acylamino, alkoxy, alkoxycarbonyl, alkylenedioxy, alkylsulfinyl, alkylsulfonyl, alkylthio, optionally substituted aroyl, optionally substituted aroylamino, optionally substituted aryl, optionally substituted arylalkyl, optionally substituted arylalkyloxy, optionally substituted arylalkyloxycarbonyl, optionally substituted arylalkylthio, optionally substituted aryloxy, optionally substituted aryloxycarbonyl, optionally substituted arylsulfinyl, optionally substituted arylsulfonyl, optionally substituted arylthio, carboxy, cyano, cycloalkenyl, halo, optionally substituted heteroaroyl, optionally substituted heteroaryl, optionally substituted heteroarylalkyl, optionally substituted heteroarylalkyloxy, optionally substituted heteroaroylamino, optionally substituted heteroaryloxy, optionally substituted heterocycloalkyl, hydroxy, nitro, oxo, trifluoromethyl, $Y^7Y^8N$—, $Y^7Y^8NCO$—, $Y^7Y^8NSO_2$—, where $Y^7$ and $Y^8$ are independently hydrogen, alkyl, aryl, arylalkyl, heteroaryl or heteroarylalkyl. Exemplary substituted alkyl groups include

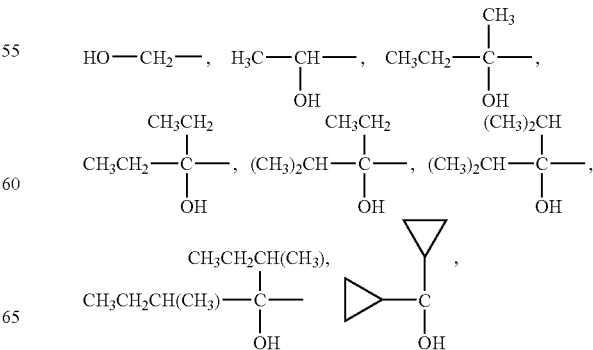

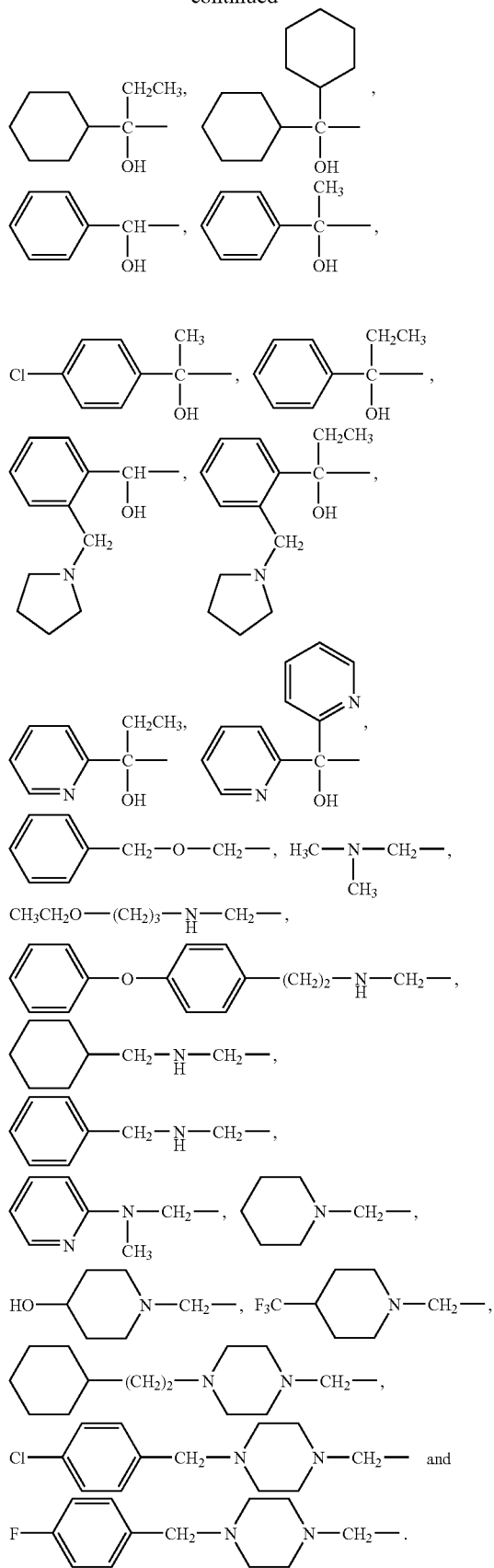

"Alkylene" means a straight or branched bivalent hydrocarbon chain having from 1 to about 15 carbon atoms. Particular alkylene groups are the lower alkylene groups having from 1 to about 6 carbon atoms. Exemplary groups include methylene and ethylene.

"Alkylsulfinyl" means an alkyl-SO— group in which the alkyl group is as previously described. Preferred groups are those in which the alkyl group is $C_{1-6}$alkyl. "Optionally substituted alkylsulfinyl" means an alkylsulfinyl which may be substituted on the alkyl portion with one or more alkyl group substituents.

"Alkylsulfonyl" means an alkyl-SO$_2$— group in which the alkyl group is as previously described. Preferred groups are those in which the alkyl group is $C_{1-6}$alkyl. "Optionally substituted alkylsulfonyl" means an alkylsulfonyl which may be substituted on the alkyl portion with one or more alkyl group substituents.

"Alkylsulfonylcarbamoyl" means an alkyl-SO$_2$—NH—C(=O)— group in which the alkyl group is as previously described. Preferred alkylsulfonylcarbamoyl groups are those in which the alkyl group is $C_{1-6}$alkyl. "Optionally substituted alkylsulfonylcarbamoyl" means an alkylsulfonylcarbamoyl group which may be substituted on the alkyl portion with one or more alkyl group substituents.

"Alkylthio" means an alkyl-S— group in which the alkyl group is as previously described. Exemplary alkylthio groups include methylthio, ethylthio, isopropylthio and heptylthio. "Optionally substituted alkylthio" means an alkylthio group which may be substituted on the alkyl portion by one or more alkyl group substituents.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 6 carbon atoms in the chain. Exemplary alkynyl groups include ethynyl, propynyl, n-butynyl, i-butynyl, 3-methylbut-2-ynyl, and n-pentynyl. "Optionally substituted alkynyl" means an alkynyl group which may be substituted with one or more alkyl group substituents.

"Aroyl" means an aryl-CO— group in which the aryl group is as described herein. Exemplary groups include benzoyl and 1- and 2-naphthoyl. "Optionally substituted aroyl" means an aroyl group, the aryl portion of which may be substituted by one or more aryl group substituents as defined herein.

"Aroylamino" is an aroyl-NH— group wherein aroyl is as previously defined. "Optionally substituted aroylamino" means an aroylamino group which may be substituted on the aryl portion by one or more aryl group substituents.

"Aryl" as a group or part of a group denotes: (i) a monocyclic or multicyclic aromatic carbocyclic moiety of about 6 to about 14 carbon atoms, such as phenyl or naphthyl; or (ii) partially saturated multicyclic aromatic carbocyclic moiety in which an aryl and a cycloalkyl or cycloalkenyl group are fused together to form a cyclic structure, such as a tetrahydronaphthyl, indenyl or indanyl ring. "Optionally substituted aryl" groups may be substituted with one or more aryl group substituents which may be the same or different, where "aryl group substituent" includes, for example, acyl, acylamino, alkoxy, alkoxycarbonyl, alkyl, alkylenedioxy, alkylsulfinyl, alkylsulfonyl, alkylthio, aroyl, aroylamino, aryl, arylalkyl, arylalkyloxy, arylalkyloxycarbonyl, arylalkylthio, aryloxy, aryloxycarbonyl, arylsulfinyl, arylsulfonyl, arylthio, carboxy, cyano, halo, heteroaroyl, heteroaryl, heteroarylalkyl, heteroarylalkyloxy, heteroaroylamino, heteroaryloxy, heterocycloalkylalkyl, hydroxy, nitro, trifluoromethyl, $Y^5Y^6N$—, $Y^5Y^6NCO$—, $Y^5Y^6NSO_2$—, where $Y^5$ and $Y^6$ are independently hydrogen, alkyl, aryl, arylalkyl, heteroaryl and heteroarylalkyl, or $Y^5$ and $Y^6$, together with the nitrogen atom to which they are attached, form a nitrogen-containing saturated alicyclic ring containing from 3 to 7 members.

"Optionally substituted benzene ring" means a benzene ring which may be substituted by one or more aryl group substituents.

"Arylalkyl" means an aryl-alkyl-group in which the aryl and alkyl moieties are as previously described. Preferred arylalkyl groups contain a $C_{1-6}$alkyl moiety. Exemplary arylalkyl groups include benzyl, 2-phenethyl and naphthlenemethyl. "Optionally substituted arylalkyl" means an arylalkyl group which may be substituted on the aryl portion by one or more aryl group substituents, and which may be substituted on the alkyl portion by one or more alkyl group substituents. Exemplary substituted arylalkyl groups include

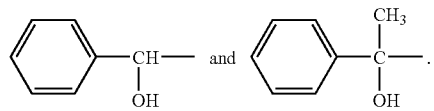

"Arylalkyloxy" means an arylalkyl-O— group in which the arylalkyl group is as previously described. Exemplary arylalkyloxy groups include benzyloxy and 1- or 2-naphthalenemethoxy. "Optionally substituted arylalkyloxy" means an arylalkyloxy group which may be substituted on the aryl portion by one or more aryl group substituents, and on the alkyl portion by one or more alkyl group substituents.

"Arylalkyloxyalkyl" means an arylalkyl-O-alkyl- group in which the arylalkyl and alkyl groups are as previously described. Exemplary arylalkyloxyalkyl groups include benzyloxymethyl and 1- or 2-naphthalenemethoxymethyl. "Optionally substituted arylalkyloxyalkyl" means an arylalkyloxyalkyl group which may be substituted on the aryl portion by one or more aryl group substituents, and on the alkyl portions by one or more alkyl group substituents.

"Arylalkyloxycarbonyl" means an arylalkyl-O—CO— group in which the arylalkyl group is as previously described. An exemplary arylalkyloxycarbonyl group is benzyloxycarbonyl. "Optionally substituted arylalkyloxycarbonyl" means an arylalkyloxycarbonyl group which may be substituted on the aryl portion by one or more aryl group substituents, and on the alkyl portion by one or more alkyl group substituents.

"Aryloxyalkyl" means an aryl-O-alkyl group. An exemplary aryloxyalkyl group is phenoxymethyl. "Optionally substituted aryloxyalkyl" is an aryloxyalkyl group which may be substituted on the aryl portion by one or more aryl group substituents, and on the alkyl portion by one or more alkyl group substituents.

"Arylalkylthio" means an arylalkyl-S— group in which the arylalkyl group is as previously described. An exemplary arylalkylthio group is benzylthio. "Optionally substituted arylalkylthio" is an arylalkylthio group which may be substituted on the aryl portion by one or more aryl group substituents, and on the alkyl portion by one or more alkyl group substituents.

"Aryloxy" means an aryl-O— group in which the aryl group is as previously described. Exemplary aryloxy groups include optionally substituted phenoxy and naphthoxy. "Optionally substituted aryloxy" means an aryloxy group which may be substituted on the aryl portion by one or more aryl group substituents.

"Aryloxycarbonyl" means an aryl-O—CO— group in which the aryl group is as previously described. Exemplary aryloxycarbonyl groups include phenoxycarbonyl and naphthoxycarbonyl. "Optionally substituted aryloxycarbonyl" means an aryloxycarbonyl group which may be substituted on the aryl portion by one or more aryl group substituents.

"Arylsulfinyl" means an aryl-SO— group in which the aryl group is as previously described. "Optionally substituted arylsulfinyl" means an arylsulfinyl group which may be substituted on the aryl portion by one or more aryl group substituents.

"Arylsulfonyl" means an aryl-$SO_2$— group in which the aryl group is as previously described. "Optionally substituted arylsulfonyl" means an arylsulfinyl group which may be substituted on the aryl portion by one or more aryl group substituents.

"Arylsulfonylcarbamoyl" means an aryl-$SO_2$—NH—C(=O)— group in which the aryl group is as previously described. "Optionally substituted arylsulfonylcarbamoyl" means an arylsulfonylcarbamoyl group which may be substituted on the aryl portion by one or more aryl group substituents.

"Arylthio" means an aryl-S— group in which the aryl group is as previously described. Exemplary arylthio groups include phenylthio and naphthylthio. "Optionally substituted arylthio" means an arylthio group which may be substituted on the aryl portion by one or more aryl group substituents.

"Cycloalkenyl" means a non-aromatic monocyclic or multicyclic ring system containing at least one carbon-carbon double bond and having about 5 to about 10 carbon atoms. Exemplary monocyclic cycloalkenyl rings include cyclopentenyl, cyclohexenyl and cycloheptenyl. Exemplary multicyclic cycloalkenyl ring include norbornenyl. "Optionally substituted cycloalkenyl" means a cycloalkenyl group which may be substituted by one or more alkyl group substituents.

"Cycloalkoxyalkyl" means a cycloalkyl-O-alkyl-group in which the cycloalkyl group is as described hereinafter. Exemplary cycloalkoxyalkyl groups include cyclopropyloxymethyl and cyclopentyloxymethyl. "Optionally substituted cycloalkoxyalkyl" means a cycloalkoxyalkyl group which may be substituted by one or more alkyl group substituents.

"Cycloalkyl" means a non-aromatic monocyclic or multicyclic ring system of about 3 to about 10 carbon atoms. Exemplary monocyclic cycloalkyl rings include cyclopropyl, cyclopentyl, cyclohexyl and cycloheptyl. Exemplary multicyclic cycloalkyl rings include perhydronaphthyl, adamant-(1- or 2-)yl and norbornyl and spirocyclic groups e.g. spiro[4,4]non-2yl. "Optionally substituted cycloalkyl" means a cycloalkyl group which may be substituted by alkyl or one or more alkyl group substituents.

"Cycloalkylalkyl" means a cycloalkyl-alkyl-group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl. "Optionally substituted cycloalkylalkyl" means a cycloalkylalkyl group which may be substituted by alkyl or one or more alkyl group substituents.

"Cycloalkyloxy" means a cycloalkyl-O— group in which the cycloalkyl group is as described herein. Exemplary cycloalkyloxy groups include cyclopropyloxy, cyclopentyloxy, cyclohexyloxy and cycloheptyloxy. "Optionally substituted cycloalkyloxy" means a cycloalkyloxy group which may be substituted on the alkyl portion by one or more alkyl group substituents.

"Halo" or "halogen" means fluoro, chloro, bromo, or iodo.

"Heteroaroyl" means a heteroaryl-CO— group in which the heteroaryl group is as described herein. Exemplary groups include pyridylcarbonyl. "Optionally substituted heteroaroyl" means a heteroaroyl group which may be substituted with one or more aryl group substituents.

"Heteroaroylamino" means a heteroaroyl-NH— group in which the heteroaroyl moiety is as previously described. "Optionally substituted heteroaroylamino" means a heteroaroylamino group which may be substituted with one or more aryl group substituents.

"Heteroaryl" as a group or part of a group denotes an aromatic monocyclic or multicyclic organic moiety of about 5 to about 14 ring members in which one or more of the ring members is/are element(s) other than carbon, for example nitrogen, oxygen or sulfur. Examples of suitable heteroaryl groups include benzimidazolyl, furyl, imidazolyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups. "Optionally substituted heteroaryl" means a heteroaryl group which may be substituted by one or more aryl group substituents.

"Heteroarylalkyl" means a heteroaryl-alkyl-group in which the heteroaryl and alkyl moieties are as previously described. Preferred heteroarylalkyl groups contain a $C_{1-4}$alkyl moiety. Exemplary heteroarylalkyl groups include pyridylmethyl. "Optionally substituted heteroarylalkyl" means a heteroarylalkyl group which may be substituted on the heteroaryl portion by one or more aryl group substituents, and which may be substituted on the alkyl portion by one or more alkyl group substituents.

"Heteroarylalkoxy" means an heteroarylalkyl-O— group in which the heteroarylalkyl group is as previously described. Exemplary heteroaryloxy groups include pyridylmethoxy. "Optionally substituted heteroarylalkoxy" means a heteroarylalkoxy group which may be substituted on the heteroaryl portion by one or more aryl group substituents, and which may be substituted on the alkyl portion by one or more alkyl group substituents.

"Heteroarylalkyloxyalkyl" means a heteroarylalkyl-O-alkyl- group in which the heteroarylalkyl and alkyl groups are as previously described. Exemplary heteroarylalkyloxyalkyl groups include 4-pyridylmethoxymethyl and 3- or 4-quinolinemethoxymethyl. "Optionally substituted heteroarylalkyloxyalkyl" means a heteroarylalkyloxyalkyl group which may be substituted on the heteroaryl portion by one or more aryl group substituents, and on the alkyl portions by one or more alkyl group substituents.

"Heteroaryloxy" means an heteroaryl-O— group in which the heteroaryl group is as previously described. Exemplary heteroaryloxy groups include pyridyloxy. "Optionally substituted heteroaryloxy" means a heteroaryloxy group which may be substituted on the heteroaryl portion by one or more aryl group substituents.

"Heteroaryloxyalkyl" means a heteroaryl-O-alkyl group in which heteroaryl and alkyl are as described herein. "Optionally substituted heteroaryloxyalkyl" means a heteroaryloxyalkyl group which may be substituted on the heteroaryl portion by one or more aryl group substituents, and on the alkyl portion by one ore more alkyl group substituents.

"Heteroarylsulfonylcarbamoyl" means a heteroaryl-SO$_2$—NH—C(=O)— group in which the heteroaryl group is as previously described. "Optionally substituted heteroarylsulfonylcarbamoyl" means a heteroarylsulfonylcarbamoyl group which may be substituted with one or more aryl group substituents.

"Heterocycloalkyl" means a non-aromatic or partially aromatic monocyclic or multicyclic organic moiety of about 5 to about 14 ring members which contains one or more heteroatoms selected from O, S or NY$^9$, where Y$^9$ is hydrogen, optionally substituted alkyl, optionally substituted aryl, optionally substituted arylalkyl, cycloalkylalkyl, optionally substituted heteroaryl or optionally substituted heteroarylalkyl. Exemplary heterocycloalkyl groups include morpholine, piperidine, piperazine, pyrrolidine, tetrahydrofuran and perhydropyran. "Optionally substituted heterocycloalkyl" means a heterocycloalkyl group which may be substituted by alkyl or by one or more alkyl group substituents.

"Heterocycloalkylalkyl" means a heterocycloalkyl-alkyl-group in which the heterocycloalkyl and alkyl moieties are as previously described. "Optionally substituted heterocycloalkylalkyl" means a heterocycloalkylalkyl group which may be substituted by alkyl or one or more alkyl group substituents.

"Heterocycloalkyloxy" means a heterocycloalkyl-O— group in which heterocycloalkyl is as previously defined. "Optionally substituted heterocycloalkyloxy" means a heterocycloalkyloxy group which may be substituted on the heterocycloalkyloxy portion by alkyl or by one or more alkyl group substituents.

"Heterocycloalkyloxyalkyl" means a heterocycloalkyl-O-alkyl group in which heterocycloalkyl is as previously defined. "Optionally substituted heterocycloalkyloxyalkyl" means a heterocycloalkyloxyalkyl group which may be substituted on the heterocycloalkyloxy portion or the alkyl portion by one or more alkyl group substituents.

"Hydroxyalkyl" means a HO-alkyl- group in which alkyl is as previously defined. Preferred hydroxyalkyl groups contain $C_{1-4}$alkyl. Exemplary hydroxyalkyl groups include hydroxymethyl and 2-hydroxyethyl. "Optionally substituted hydroxyalkyl" means a hydroxyalkyl group which may be substituted on the alkyl portion by one or more alkyl group substituents.

"$Y^7Y^8N$—" means a substituted or unsubstituted amino group, wherein $Y^7$ and $Y^8$ are as previously described. Exemplary groups include amino ($H_2N$—), methylamino, ethylmethylamino, dimethylamino and diethylamino.

"$Y^7Y^8NCO$—" means a substituted or unsubstituted carbamoyl group, wherein $Y^7$ and $Y^8$ are as previously described. Exemplary groups are carbamoyl ($H_2NCO$—) and dimethylcarbamoyl ($Me_2NCO$—).

"$Y^7Y^8NSO_2$—" means a substituted or unsubstituted sulfamoyl group, wherein $Y^7$ and $Y^8$ are as previously described. Exemplary groups are sulfamoyl ($H_2NSO_2$—) and dimethylsulfamoyl ($Me_2NSO_2$—).

"Prodrug" means a compound which is convertible in vivo by metabolic means (e.g. by hydrolysis) to a compound of Formula I, including N-oxides thereof. For example an ester of a compound of Formula I containing a hydroxy group may be convertible by hydrolysis in vivo to the parent molecule. Alternatively an ester of a compound of Formula I containing a carboxy group may be convertible by hydrolysis in vivo to the parent molecule.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates, methanolates, and the like.

Suitable esters of compounds of Formula I containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and quinates.

Suitable esters of compounds of Formula I containing a carboxy group, are for example those described by F. J. Leinweber, Drug Metab. Res., 1987, 18, page 379.

An especially useful class of esters of compounds of Formula I containing a hydroxy group, may be formed from acid moieties selected from those described by Bundgaard et. al., J. Med. Chem., 1989, 32, page 2503-2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulfonates, ethanesulfonates, benzenesulfonates, p-toluenesulfonates, cyclohexylsulfamates and quinates.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

The compounds of the invention are ITK inhibitors and therefore have useful pharmacological activity. Accordingly, they are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention are inhibitors of ITK, according to tests described in the literature, and tests described hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of ITK. For example, compounds of the present invention are useful in the treatment of asthma.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

It will be appreciated that compounds of the present invention may contain asymmetric centers. These asymmetric centers may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of Formula I hereinabove. Such isomers can be separated from their mixtures, by the application or adaptation of known methods, for example chromatographic techniques and recrystallisation techniques, or they are separately prepared from the appropriate isomers of their intermediates. Additionally, in situations where tautomers of the compounds of Formula I are possible, the present invention is intended to include all tautomeric forms of the compounds.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or an aqueous alcohol solution or other suitable solvents containing the appropriate acid and isolating the salt by evaporating the solution, or by reacting the free base and acid in an organic solvent, such as tetrahydrofuran, in which case the salt separates directly or can be obtained by concentration of the solution.

Compounds of this invention can be regenerated from their acid addition salts by the application or adaptation of known methods. For example, parent compounds of the invention can be regenerated from their acid addition salts by treatment with an alkali, e.g. aqueous sodium bicarbonate solution or aqueous ammonia solution.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from water.

The starting materials and intermediates which are not commercially available may be prepared by the application or adaptation of known methods, for example methods as described in the Examples or their obvious chemical equivalents.

The present invention is further exemplified but not limited by the following illustrative Examples.

The 2-(1H-thieno[3,2-c]pyrazol-3-yl 1H-benzimidazoles of the present invention are generally prepared as shown in Scheme I.
Scheme I
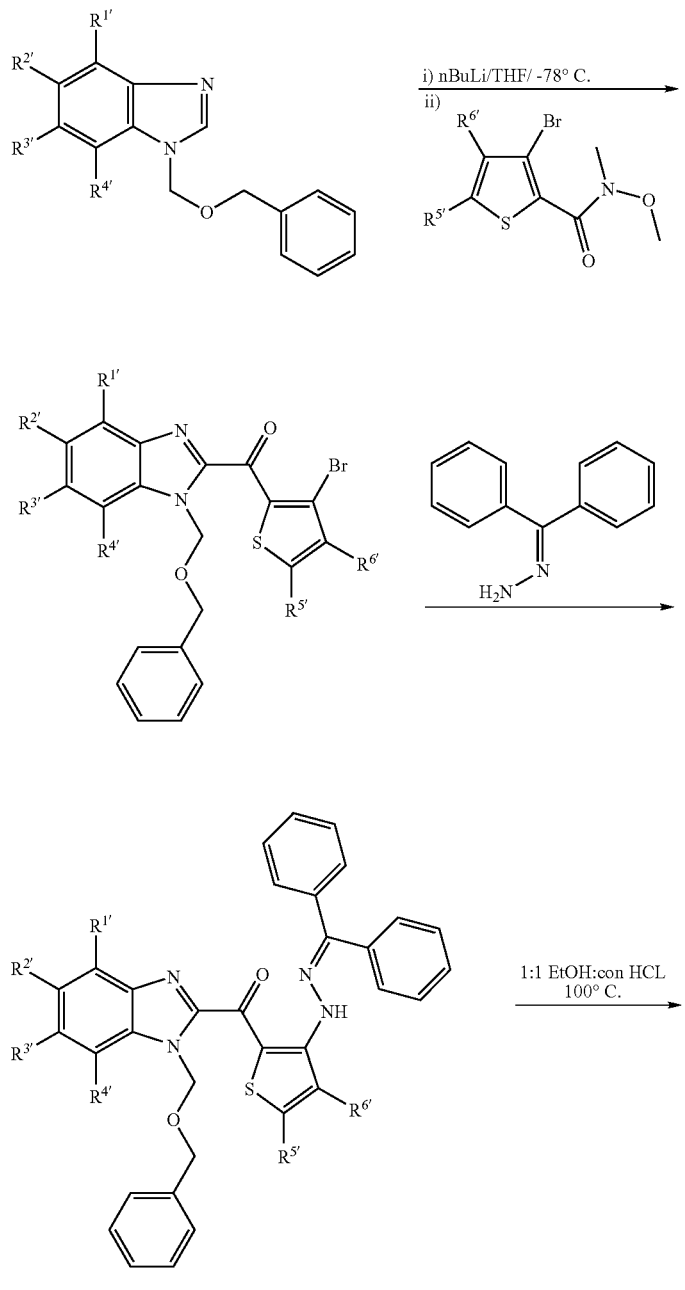
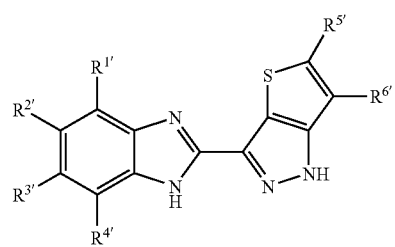

The 3-(1H-benzimidazol-2-yl) 1H-[benzo[4,5]thieno[3,2-c]pyrazoles of the present invention are generally prepared as shown in Scheme II.
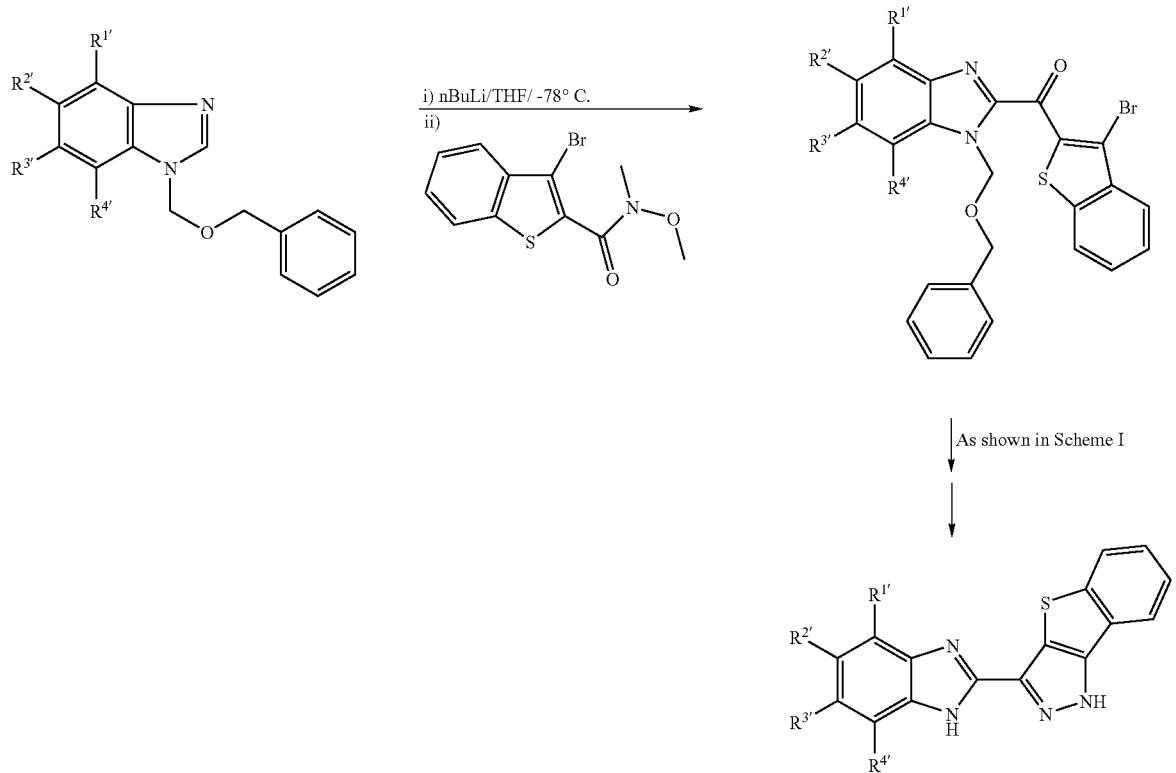
The 2-(1H-thieno[3,2-c]pyrazol-3-yl)-1H-indoles of the present invention are generally prepared as shown in Scheme III.
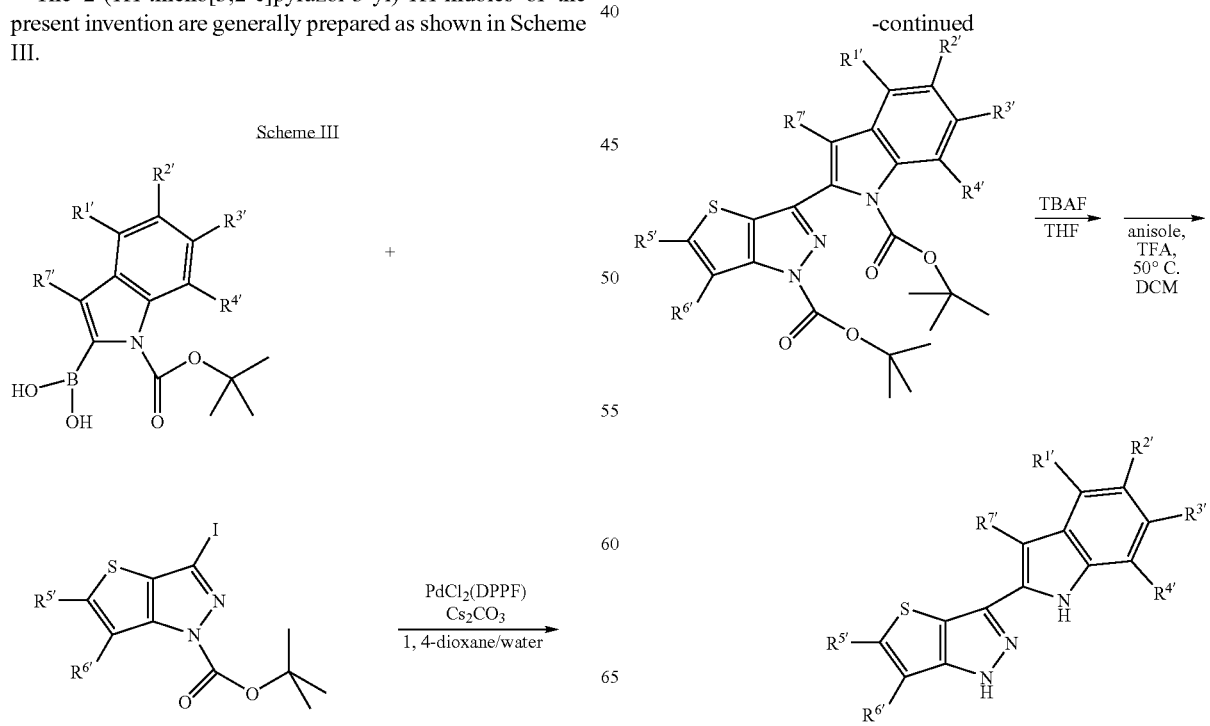

In Schemes I, II, III, V, VI, VII and VIII $R^{1'}$, $R^{2'}$, $R^{3'}$, $R^{4'}$, $R^{5'}$, $R^{6'}$ and $R^{7'}$ are $R^1$, $R^2$, $R^3$, $R^4$, $R^5$, $R^6$ and $R^7$, respectively, as defined herein, or are protected forms thereof, or intermediate groups thereto.

In particular, the aminoalkoxy-2-(1H-thieno[3,2-c]pyrazol-3-yl)-1H-indoles of the present invention are prepared as shown in Scheme IV.

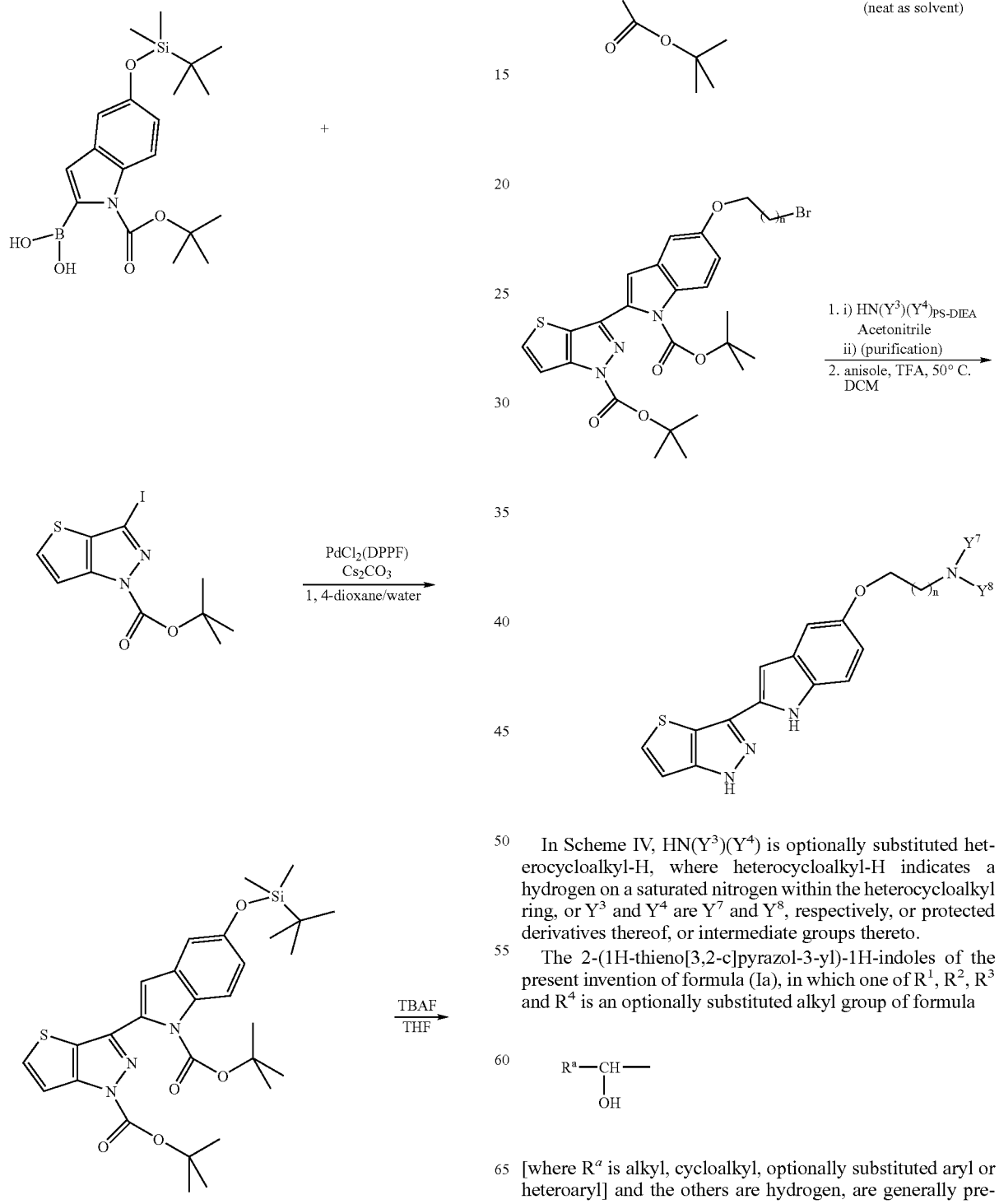

In Scheme IV, HN(Y³)(Y⁴) is optionally substituted heterocycloalkyl-H, where heterocycloalkyl-H indicates a hydrogen on a saturated nitrogen within the heterocycloalkyl ring, or $Y^3$ and $Y^4$ are $Y^7$ and $Y^8$, respectively, or protected derivatives thereof, or intermediate groups thereto.

The 2-(1H-thieno[3,2-c]pyrazol-3-yl)-1H-indoles of the present invention of formula (Ia), in which one of $R^1$, $R^2$, $R^3$ and $R^4$ is an optionally substituted alkyl group of formula

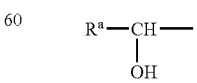

[where $R^a$ is alkyl, cycloalkyl, optionally substituted aryl or heteroaryl] and the others are hydrogen, are generally prepared as shown in Scheme V.

Scheme V
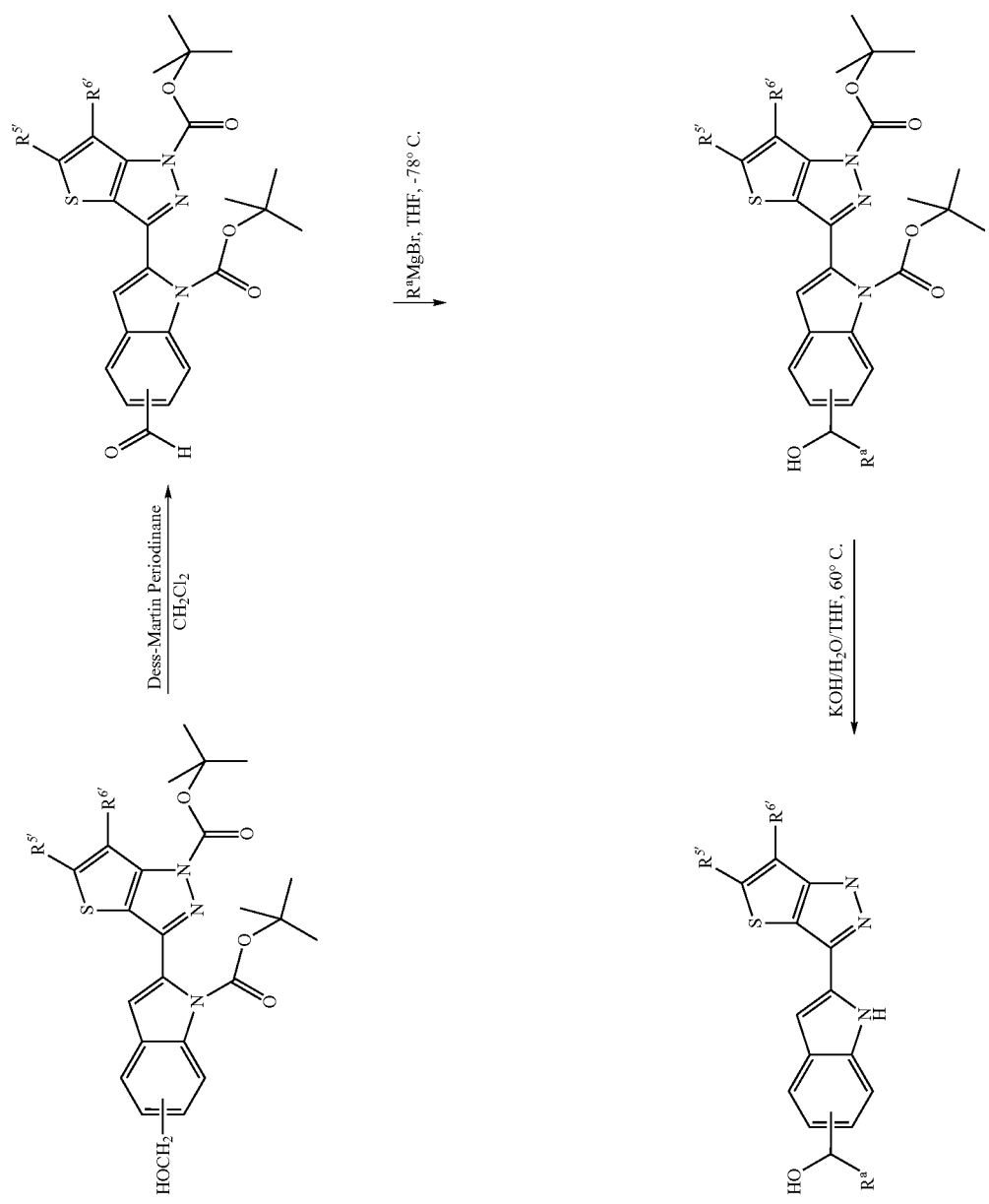

Examples of

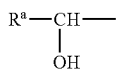

include

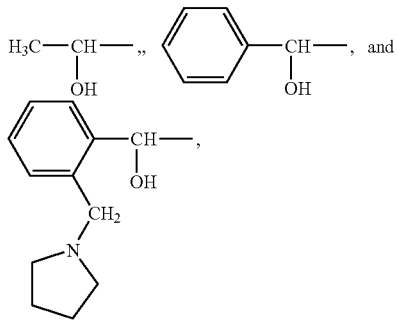

The 2-(1H-thieno[3,2-c]pyrazol-3-yl)-1H-indoles of the present invention of formula (Ia), in which one of $R^1$, $R^2$, $R^3$ and $R^4$ is an optionally substituted alkyl group of formula

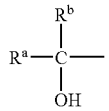

[where $R^a$ and $R^b$ are optionally substituted alkyl, optionally substituted cycloalkyl, optionally substituted aryl or optionally substituted heteroaryl] and the others are hydrogen, are generally prepared as shown in Scheme VI.

Scheme VI

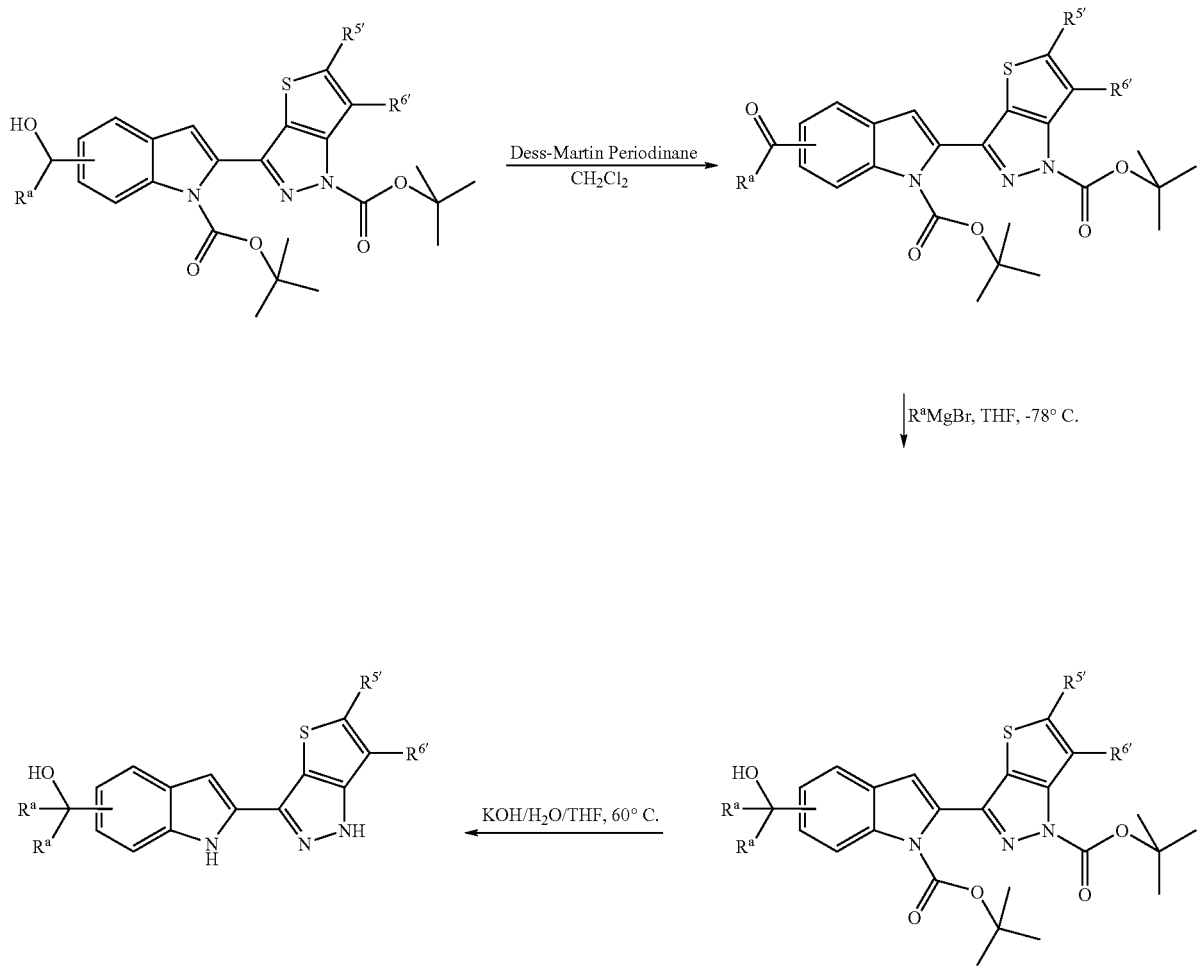

Examples of

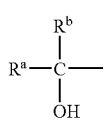

include

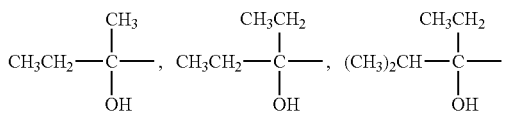

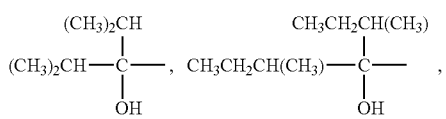

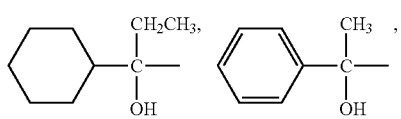

The 2-(1H-thieno[3,2-c]pyrazol-3-yl)-1H-indoles of the present invention of formula (Ia), in which one of $R^1$, $R^2$, $R^3$ and $R^4$ is an optionally substituted alkyl group of formula

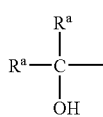

[where $R^a$ is optionally substituted alkyl, optionally substituted cycloalkyl, optionally substituted aryl or optionally substituted heteroaryl] and the others are hydrogen, are also generally prepared as shown in Scheme VII Scheme VII

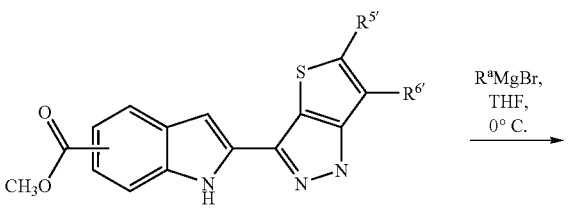

Examples of $R^a\!-\!\overset{R^a}{\underset{OH}{C}}\!-$ in scheme VII include

The 2-(1H-thieno[3,2-c]pyrazol-3-yl)-1H-indoles of the present invention of formula (Ia) in which one of $R^1$, $R^2$, $R^3$ and $R^4$ is hydrogen and the other is optionally substituted acyl, optionally substituted aroyl or optionally substituted heteroaroyl and the others are hydrogen, are generally prepared as shown in Scheme VIII.

Scheme VIII
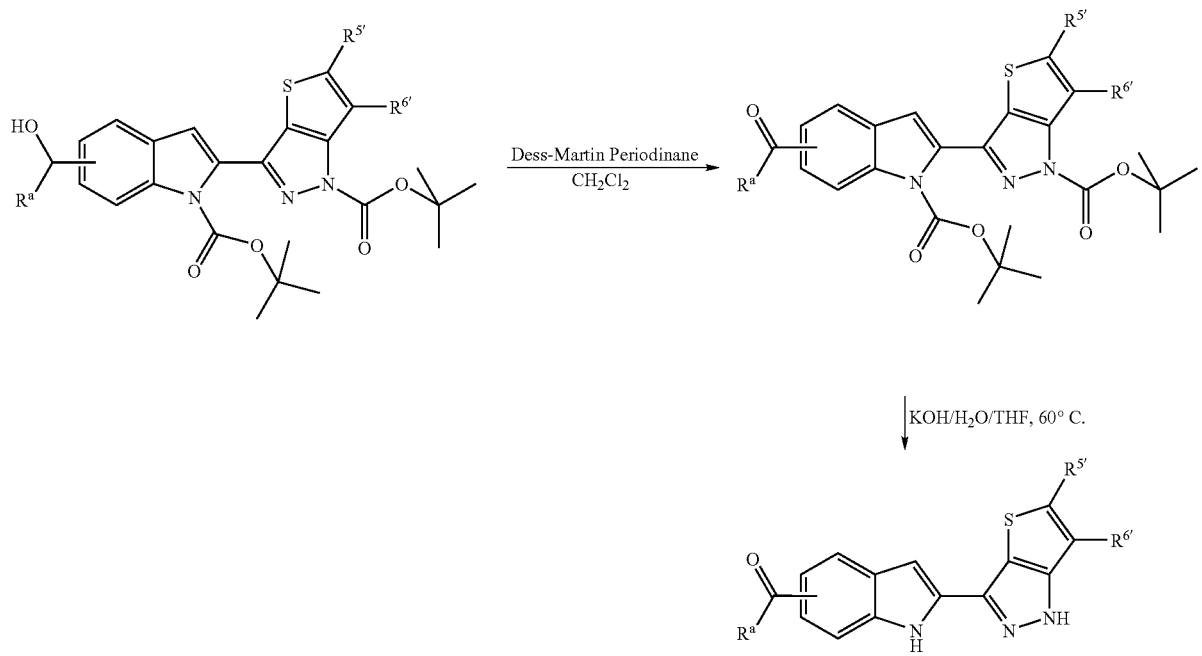
The 2-(1H-thieno[3,2-c]pyrazol-3-yl)-1H-indoles of the present invention of formula (Ia), in which one of $R^1$, $R^2$, $R^3$ and $R^4$ is $(Y^1)(Y^2)NC(=O)-$ and the others are hydrogen, are generally prepared as shown in Scheme IX.
Scheme IX
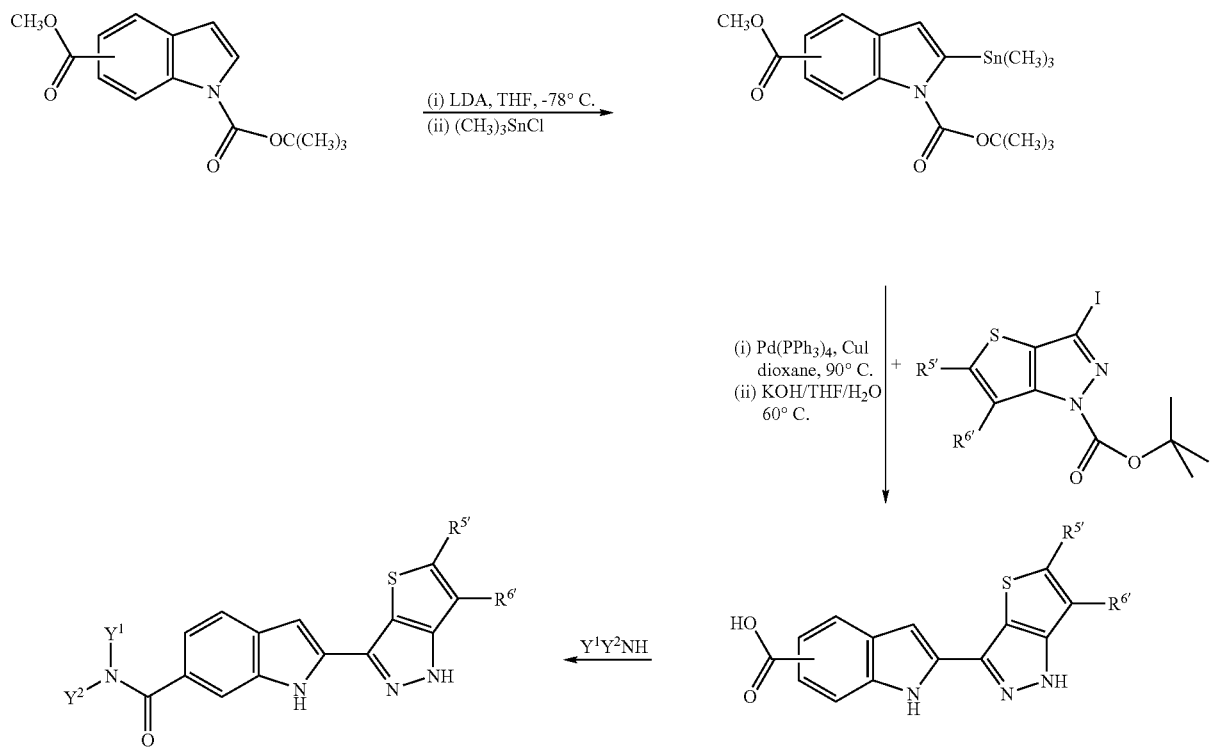

Examples of $(Y^1)(Y^2)NC(=O)—$ in scheme IX include

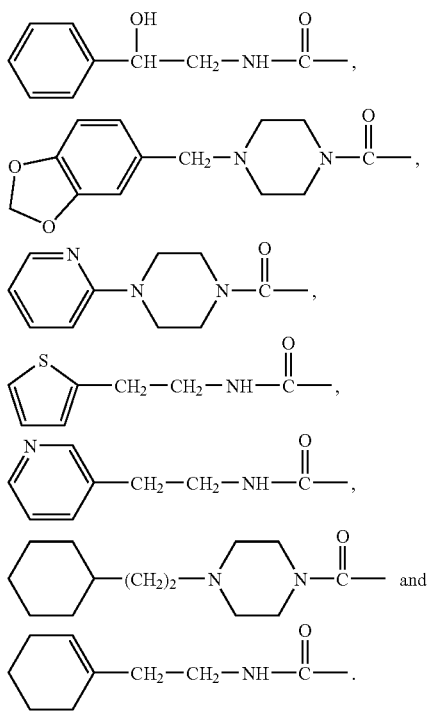

The 2-(1H-thieno[3,2-c]pyrazol-3-yl)-1H-indoles of the present invention of formula (Ia), in which one of $R^1$, $R^2$, $R^3$ and $R^4$ is methyl substituted by $Y^7Y^8N—$ (where $Y^7$ and $Y^8$ are independently hydrogen, alkyl, aryl, arylalkyl, heteroaryl or heteroarylalkyl) and the others are hydrogen, are generally prepared as shown in Scheme X.

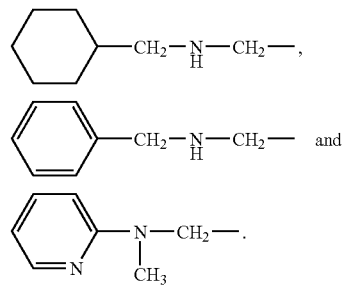

Compounds of the invention may also be prepared by interconversion of other compounds of the invention.

Thus, for example, compounds of formula (I) containing a carboxy group may be prepared by hydrolysis of the corresponding esters. The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I) containing a carboxy group may be prepared by acid catalysed removal of the tert-butyl group of the corresponding tert-butyl esters Scheme X

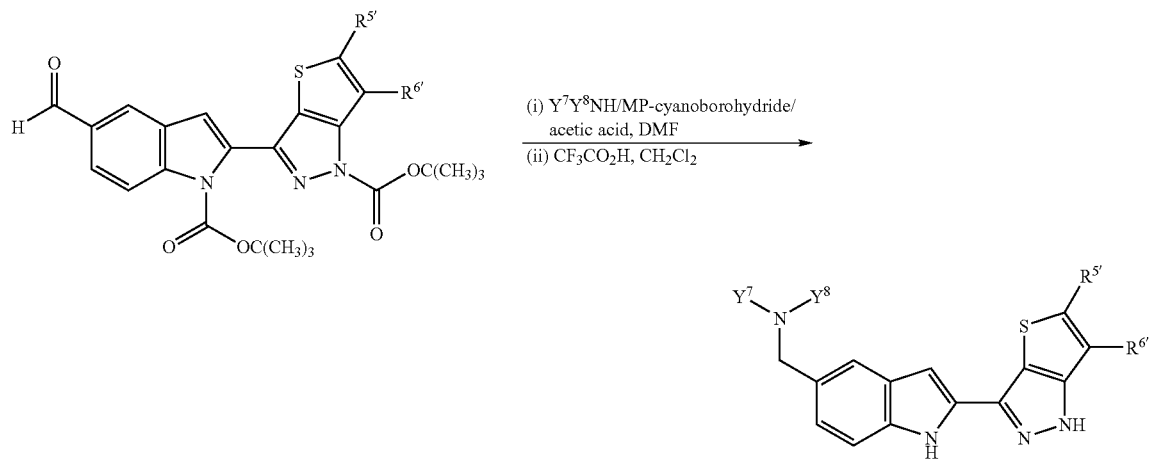

Examples of methyl substituted by $Y^7Y^8N—$ in scheme X include using standard reaction conditions, for example reaction with trifluoroacetic acid at a temperature at about room temperature.

As another example compounds of formula (I) containing a carboxy group may be prepared by hydrogenation of the corresponding benzyl esters. The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol.

As another example of the interconversion process, compounds of formula (I) containing a $Y^1Y^2N$—C(=O)— group may be prepared by coupling compounds of formula (I) containing a carboxy group, with an amine of formula $Y^1Y^2NH$, to give an amide bond using standard peptide coupling procedures. Examples include (i) coupling in the presence of O-(7-azabenzotriazol-1-yl)-1,1,3,3-tetramethyluronium hexafluorophosphate and triethylamine (or diisopropylethylamine) in tetrahydrofuran (or dimethylformamide) at room temperature, (ii) coupling in the presence of a carbodiimide, for example dicyclohexylcarbodiimide in the presence of triethylamine, (iii) treatment with 1-hydroxybenzotriazole and a carbodiimide, such as 1-(3-dimethylaminopropyl)-3-ethylcarbodiimide, in an inert solvent such as dimethylformamide and at a temperature at about room temperature. Thus, for example, 3-(5-hydroxymethyl-1H-indol-2-yl)-1H-thieno[3,2-c]pyrazole-5-carboxylic acid (Example 37) may be reacted with 1-(4-fluorophenyl)piperazine in the presence of 1-ethyl-3-(3-dimethylaminopropyl)carbodiimide and 1-hydroxybenzotriazole to produce[4-(4-fluoro-phenyl)-piperazin-1-yl]-[3-(5-hydroxymethyl-1H-indol-2-yl)-1H-thieno[3,2-c]pyrazol-5-yl]-methanone (Example 38).

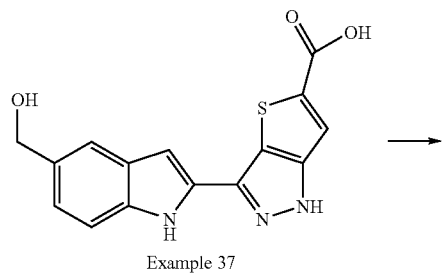

Example 37

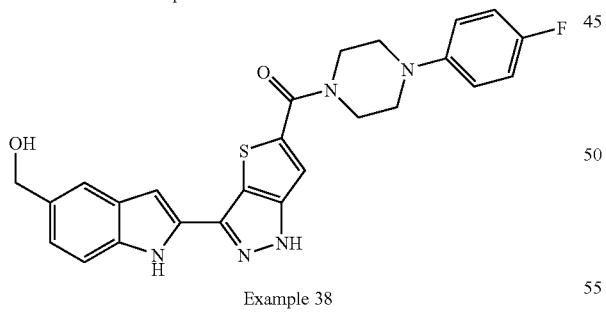

Example 38

Unless otherwise indicated, the following conditions apply to the procedures used in the Examples provided herein.

Chiral separations are performed using a ChiralPak AD 20 μM column (250×20 mmID) using isocratic elution conditions with 80:20:0.1 mixture of heptane/ethanol/diethylamine, total run time 30 minutes with a flow rate of 1.0 mL/minute and detection at 254 nM.

Chiral resolution and fraction analyses are performed using a ChiralPak AD 10 μM column (250×4.6 mmID) using isocratic elution conditions with 70:30:0.2 mixture of heptane/ethanol/diethylamine, total run time 30 minutes with a flow rate of 1.0 mL/minute and detection at 254 nM.

LC/MS analyses are performed using the following method: Agilent 1100 Series HPLC with a YMC CombiScreen Pro C18 5.5 μm 4.6 mm by 33 mm reverse phase column using gradient elution with a mixture of (A) acetonitrile/0.1% trifluoroacetic acid and (B) water/0.1% trifluoroacetic acid (5% A:95% B to 95% A:5% B over 5.1 minutes) with a 1.2 mL/minute flow rate; Agilent 1100 Series wellplate autosampler with 2 μL injection; Agilent 1100 Series diode array detector with 215, 254 and 320 nM wavelength detection; Hewlett Packard 1100 Series mass spectrometer with electrospray and positive ionisation.

$^1H$ nuclear magnetic resonance spectra (NMR) are recorded on a 300 MHz Varian Mercury spectrometer. In the nuclear magnetic resonance spectra (NMR) the chemical shifts (δ) are expressed in ppm relative to tetramethylsilane. Abbreviations have the following significances: s=singlet; d=doublet; t=triplet; m=multiplet; q=quartet; dd=doublet of doublets; ddd=doublet of double doublets.

Melting point determinations are performed on a Büchi 535 melting point apparatus and reported in degree Celsius.

$R_f$ determinations are performed utilizing pre-coated thin layer chromatography plates with silica gel 60 $F_{254}$.

EXAMPLE 1

2-(1H-Thieno[3,2-c]pyrazol-3-yl)-1H-benzimidazole

EXAMPLE 1A

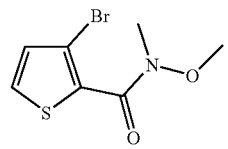

Oxalyl chloride (0.601 mL, 6.99 mmol, 1.2 eq) is added to a mixture of 3-bromothiophene-2-carboxylic acid (1.20 g, 5.80 mmol), N,N-dimethylformamide (several drops, catalytic amount), and anhydrous dichloromethane (25 mL) at ambient temperature under nitrogen over 20 minutes. The reaction is stirred for 17 hours, purged with nitrogen, and concentrated under reduced pressure to afford a tan solid. The crude 3-bromothiophene-2-carbonyl chloride is dissolved in dichloromethane (25 mL) and added dropwise, over 10 minutes, to a 0° C. solution of N,O-dimethylhydroxylamine hydrochloride (843 mg, 8.64 mmol), diisopropylethylamine (2.50 mL, 14.3 mmol), and dichloromethane (25 mL). The reaction is allowed to gradually warm to ambient temperature overnight. The reaction is washed with water, dried over magnesium sulfate, and concentrated under reduced pressure. The crude product is purified by chromatography on silica, eluting with 1:1 ethyl acetate/heptane, to give 3-bromothiophene-2-carboxylic acid methoxy-methyl-amide, as a white solid: TLC $R_f$ 0.33 (silica, 1:1 ethyl acetate/heptane);

LC/MS: (M+H 249.94, $R_T$=2.18 minutes); $^1$H NMR [(CD$_3$)$_2$SO), 300 MHz]: δ 7.85 (d, 1H, J=5.3 Hz), 7.17 (d, 1H, 5.3 Hz), 3.62 (s, 3H), 3.24 (s, 3H).

EXAMPLE 1B

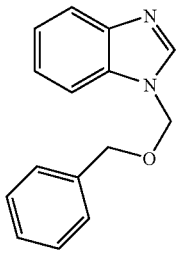

A mixture of benzimidazole (10.0 g, 84.6 mmol), benzyl chloromethylether (5.9 mL, 42 mmol), and acetonitrile is heated at reflux for 6 hours. The solvent is removed under reduced pressure, the resulting slurry taken up in dichloromethane, and washed with water. The organic layer is dried over magnesium sulfate and concentrated under reduced pressure. The crude material is chromatographed on silica, eluting with 9:1 ethyl acetate/dichloromethane, to give an orange solid. The product is chromatographed a second time on silica, eluting with 8:2 ethyl acetate/dichloromethane, to give an orange solid. Trituration of the solid with ether gives 1-benzyloxymethyl-1H-benzimidazole as a beige solid.

EXAMPLE 1C

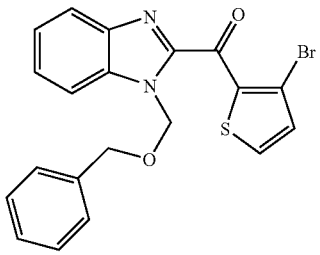

To a stirred solution of 1-benzyloxymethyl-1H-benzimidazole (648 mg, 2.72 mmol, Example 1B) in tetrahydrofuran (15 mL) at −78° C. under nitrogen is added n-butyllithium (1.30 mL of a 2.5 M solution in hexanes, 3.25 mmol) over 5 minutes and the resulting yellow solution is stirred at −78° C. After 25 minutes, a solution of 3-bromo-thiophene-2-carboxylic acid methoxy-methyl-amide (680 mg, 2.72 mmol, Example 1A) in tetrahydrofuran (10 mL) is added over 15 minutes and the reaction stirred at −78° C. After 1 hour the reaction is warmed to ambient temperature and stirred for an additional 2 hours. The reaction is quenched with saturated ammonium chloride and the mixture extracted with ethyl acetate. The organic layer is washed with water and brine successively, dried over magnesium sulfate, and concentrated under reduced pressure to a yellow oil. The crude material is chromatographed on silica, eluting with 40% ethyl acetate/heptane, to give the product. Trituration with ether/heptane affords (1-benzyloxymethyl-1H-benzimidazol-2-yl)-(3-bromothiophen-2-yl)methanone as an off-white powder; TLC $R_f$ 0.52 (silica, 1:1 ethyl acetate/heptane); LC/MS: (M+H 427.0, $R_T$=3.84 minutes); $^1$H NMR[(CD$_3$)$_2$SO), 300 MHz]: δ 8.18 (d, 1H, 5.2 Hz), 7.90-7.82 (m, 2H), 7.55-7.50 (m, 1H), 7.45-7.38 (m, 2H), 7.25-7.17 (m, 5H), 6.13 (s, 2H), 4.58 (s, 2H).

EXAMPLE 1D

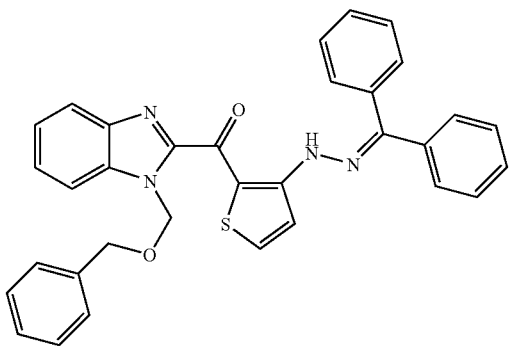

A mixture of (1-benzyloxymethyl-1H-benzimidazol-2-yl)-(3-bromothiophen-2-yl)methanone (500 mg, 1.06 mmol, Example 1C), benzophenone hydrazone (276 mg, 1.41 mmol), palladium(II) acetate (13.4 mg, 0.06 mmol), 1,1'-Bis(diphenylphosphino)-ferrocene (57.5 mg, 0.104 mmol), cesium carbonate (570 mg, 1.75 mmol), and toluene (10 mL) under nitrogen is stirred at 90° C. for 15 hours. The dark reaction is cooled to ambient temperature, diluted with ethyl acetate, filtered, and the insolubles washed with ethyl acetate. The combined filtrate and washings were washed with water and brine successively, dried over magnesium sulfate, and then concentrated under reduced pressure to afford a yellow oil. The crude material is chromatographed on silica, eluting with 80% dichloromethane/heptane, to give [3-(N'-benzhydrylidene-hydrazino)-thiophen-2-yl]-(1-benzyloxymethyl-1H-benzoimidazol-2-yl)-methanone as a yellow-orange powder: TLC $R_f$ 0.30 (silica, 80% dichloromethane/heptane); LC/MS: (M+H 543.1, $R_T$=4.68 minutes); $^1$H NMR [(CD$_3$)$_2$SO), 300 MHz]: δ 11.64 (s, 1H), 8.08 (d, 1H, 5.5 Hz), 7.84-7.13 (m, 20 H), 6.00 (s, 2H), 4.46 (s, 2H).

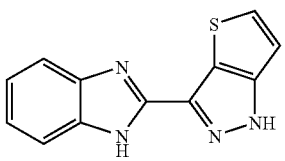

A mixture of [3-(N'-benzhydrylidene-hydrazino)-thiophen-2-yl]-(1-benzyloxymethyl-1H-benzoimidazol-2-yl)-methanone (300 mg, 0.553 mmol, Example 1D), concentrated hydrochloric acid (4 mL), and ethanol (12 mL) is heated at 75° C. for 260 minutes. The reaction is allowed to cool to ambient temperature, diluted with water (40 mL), and basified with 5% aqueous potassium carbonate. The mixture is extracted with ethyl acetate and the combined extracts washed with water and brine successively. The organic layer is dried over potassium carbonate and concentrated under reduced pressure to give a brown solid. The solid is chromatographed on silica. Step gradient elution with 70% ethyl acetate/heptane, 80% ethyl acetate/heptane, and 90% ethyl acetate/heptane provided an orange solid. Trituration with ethyl acetate/heptane gave 2-(1H-thieno[3,2-c]pyrazol-3-yl)-1H-benzoimidazole as a beige powder: TLC R$_f$0.28 (silica, 75% ethyl acetate/heptane); LC/MS: (M+H 241.0, R$_T$=2.15 minutes); $^1$H NMR [(CD$_3$)$_2$SO), 300 MHz]: δ 13.56 (s, 1H), 12.94 (2, 1h), 7.78 (d, 1H, 5.3 Hz), 7.69 (d, 1H, 7.3 Hz), 7.48 (d, 1H, 7.0 Hz), 7.22-7.15 (m, 3H).

EXAMPLE 2

6-Methoxy-2-(1H-thieno[3,2-c]pyrazol-3-yl)-1H-benzoimidazole

EXAMPLE 2A

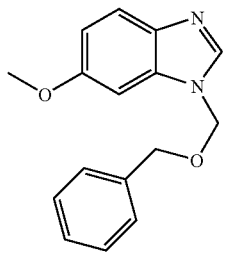

To an ambient solution of 5-methoxybenzoimidazole (6.18 g, 41.7 mmol) in dimethylformamide (60 mL) under nitrogen is added sodium hydride (1.84 g of 60% oil dispersion, 46.0 mmol) in two portions and the reaction stirred at ambient temperature. After 0.5 hour, a solution of benzyl chloromethylether (7.83 g, 50 mmol) in dimethylformamide (40 mL) is added dropwise over 15 minutes and the reaction stirred at ambient temperature overnight. The reaction mixture is poured into water (500 ml) and extracted three times with ethyl acetate (150 mL). The combined extracts are washed with water and brine successively, dried over magnesium sulfate, and concentrated under reduced pressure to give a yellow oil. The oil is chromatographed on silica. Step gradient elution with ethyl acetate, 5% methanol/ethyl acetate, and 10% methanol/ethyl acetate provided 3.02 g (27%) of 1-benzyloxymethyl-6-methoxy-1H-benzoimidazole as a waxy solid: TLC R$_f$0.23 major (silica, ethyl acetate); LC/MS: (M+H 269.1, R$_T$=2.49 minutes) and 3.83 g (34%) of 1-benzyloxymethyl-5-methoxy-1H-benzoimidazole as an oil: TLC R$_f$0.15 major (silica, ethyl acetate); LC/MS: (M+H 269.1 R$_T$=2.34 minutes).

EXAMPLE 2B

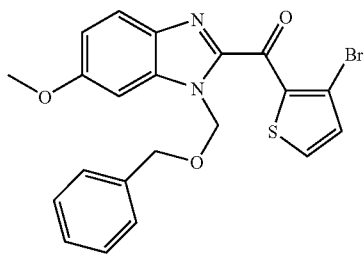

To a stirred solution of 1-benzyloxymethyl-6-methoxy-1H-benzoimidazole (1.00 g, 3.72 mmol, Example 2A) in anhydrous tetrahydrofuran (15 mL) at −78° C. under nitrogen is added n-butyllithium (1.80 mL of a 2.5 M solution in hexanes, 4.5 mmol) over 8 minutes and the resulting yellow solution is stirred a −78° C. After 25 minutes, a solution of 3-bromo-thiophene-2-carboxylic acid methoxy-methyl-amide (1.03 g, 4.12 mmol) in tetrahydrofuran (10 mL) is added over 20 minutes, to the reaction at −78° C. The reaction is allowed to gradually warm to ambient temperature overnight. The reaction is poured into 10% aqueous ammonium chloride (75 mL) and the mixture extracted twice with ethyl acetate (50 mL). The organic layer is washed with water and brine successively, dried over magnesium sulfate, and concentrated under reduced pressure to a yellow oil. The crude material is chromatographed on silica, eluting with 30% ethyl acetate/heptane followed by 40% ethyl acetate/heptane, to give a waxy solid. Trituration with 25% ethyl acetate/heptane afforded 546 mg (32%) of (1-benzyloxmethyl-6-methoxy-1H-benzoimidazol-2-yl)-(3-bromo-thiophen-2-yl)-methanone, as a powder: TLC R$_f$0.43 (silica, 40% ethyl acetate/heptane); LC/MS: (M+H 457, R$_T$=3.85 minutes); $^1$H NMR [(CD$_3$)$_2$SO), 300 MHz]: δ 8.14 (d, 5.2 Hz, 1H), 7.76 (d, 9.0 Hz, 1H), 7.36 (d, 5.0 Hz, 1H), 7.29-7.20 (m, 6H), 7.04 (dd, 2.5, 9.0 Hz, 1H), 6.13 (s, 2H), 4.59 (s, 2H), 3.87 (s, 3H).

EXAMPLE 2C

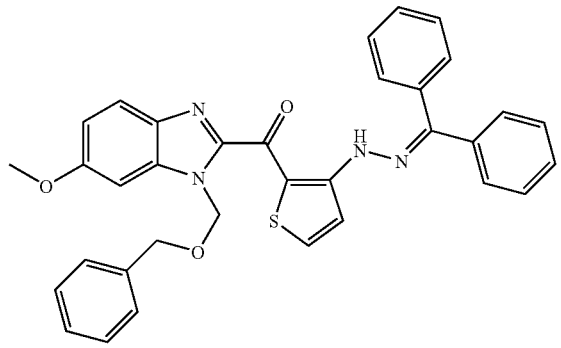

A mixture of 1-Benzyloxymethyl-6-methoxy-1H-benzoimidazol-2-yl)-(3-bromo-thiophen-2-yl)-methanone (680 mg, 1.49 mmol, Example 2B), benzophenone hydrazone (408 mg, 2.08 mmol), palladium(II) acetate (17.0 mg, 0.05 mmol), 1,1'-bis(diphenylphosphino)-ferrocene (82.0 mg, 0.148 mmol), cesium carbonate (775 mg, 2.38 mmol), and toluene (15 mL) under nitrogen is stirred at 90° C. for 20 hours. The dark reaction is cooled to ambient temperature, diluted with ethyl acetate (25 mL), filtered, and the insolubles washed with ethyl acetate (25 mL). The filtrate is washed with water and brine successively, dried over magnesium sulfate, and concentrated under reduced pressure, to afford a black viscous material. The crude material is chromatographed on silica, eluting with dichloromethane, to give 605 mg (70%) of [3-(N'-benzhydrylidene-hydrazino)-thiophen-2-yl]-(1-benzyloxymethyl-6-methoxy-1H-benzoimidazol-2-yl)-methanone as a brittle red foam: TLC R$_f$0.27 (silica, dichloromethane); LC/MS: M+H 573.2, R$_T$=4.62 minutes.

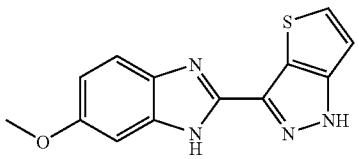

A mixture of [3-(N'-benzhydrylidene-hydrazino)-thiophen-2-yl]-(1-benzyloxymethyl-6-methoxy-1H-benzoimidazol-2-yl)-methanone (300 mg, 0.553 mmol, Example 2C), concentrated hydrochloric acid (4 mL), and ethanol (12 mL) is heated at 75° C. with stirring for 260 minutes. The reaction is allowed to cool to ambient temperature, diluted with water (40 mL), and basified with 5% aqueous potassium carbonate. The mixture is extracted with ethyl acetate and the combined extracts washed with water and brine successively. The organic layer is dried over potassium carbonate and concentrated under reduced pressure to give a brown solid. The solid is chromatographed on silica. Step gradient elution with 70% ethyl acetate/heptane, 80% ethyl acetate/heptane, and 90% ethyl acetate/heptane provided an orange solid. Trituration with ethyl acetate/heptane gave 6-methoxy-2-(1H-thieno[3,2-c]pyrazol-3-yl)-1H-benzoimidazole as a beige powder: TLC $R_f$ 0.28 (silica, 75% ethyl acetate/heptane); LC/MS: M+H 241.0, $R_T$=2.15 minutes; $^1$H NMR [(CD$_3$)$_2$SO), 300 MHz]: two species observed (ca. 60:40), presumed to be slowly exchanging imidazole tautomers, with chemical shifts of resolved resonances reported as major (minor); δ 13.48 (13.51) brs (1H; NH of benzimidazole), 12.79 brs (1H; NH of pyrazole), 7.77 d (1H, J=5 Hz; H-α of thiophene), 7.57 (7.35) d (1H, J=8.5 Hz; H-7 of benzimidazole), 7.20 d (1H, J=5 Hz; H-β of thiophene), 6.96 (7.25) d (1H, J=2 Hz; H-4 of benzimidazole), 6.82 m (1H; H-6 of benzimidazole), 3.80 (3.32) s (3H; methoxy). Chemical shifts are referenced to internal dimethyl sulfoxide-D$_5$ (δ 2.50).

EXAMPLE 3

3-(6-Methoxy-1H-benzimidazol-2-yl)-1H-benzo[4,5]thieno[3,2-c]pyrazole

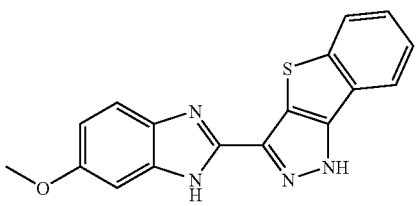

This compound (LC/MS: M+H 321.07, $R_T$=2.47 minutes)) is prepared using procedures similar to those of Example 2, substituting 3-bromo-benzothiophene-2-carboxylic acid methoxy-methyl-amide

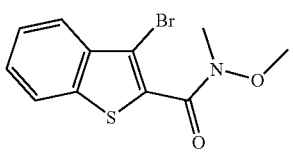

for 3-bromo-thiophene-2-carboxylic acid methoxy-methyl-amide in the coupling step of Example 2B.

EXAMPLE 4

6-(3-Piperidin-1-ylpropoxy)-2-(1H-thieno[3,2-c]pyrazol-3-yl)-1H-benzimidazole

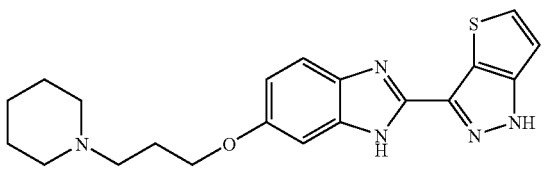

This compound (LC/MS: M+H 382.1, $R_T$=2.02 minutes)) is prepared using procedures similar to those of Example 2, substituting 6-(3-piperidin-1-ylpropoxy)-1H-benzimidazole

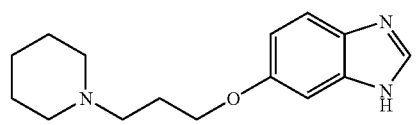

for 5-methoxybenzimidazole in Example 2A.

EXAMPLE 5

5-(3-Piperidin-1-yl-propoxy)-2-(1H-thieno[3,2-c]pyrazol-3-yl)-indole

Step 1.

EXAMPLE 5A

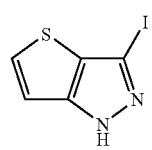

To a solution of 1H-thieno[3,2-c]pyrazole (160 mg, 1.29 mmol) and iodine (490 mg, 1.94 mmol) in dimethyl formamide (5 mL) is added potassium hydroxide (220 mg, 3.87 mmol). The mixture is stirred at room temperature for 30 minutes. A solution of sodium bisulfite (200 mg) in water (2 mL) is then added. It is extracted twice with diethyl ether. The combined organic layers are dried over magnesium sulfate and concentrated. The residue is chromatographed (n-heptane-ethyl acetate, 90:100) to afford 195 mg (60%) of 3-iodo- 1H-thieno[3,2-c]pyrazole as a beige powder. LC/MS: $R_T$=2.50 minutes, 250.90 m/e (M+1).

Step 2.

EXAMPLE 5B

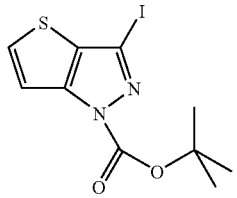

To a suspension of 3-iodo-1H-thieno[3,2-c]pyrazole (195 mg, 0.78 mmol, Example 5A) in dichloromethane (5 mL) is added triethylamine (110 mL, 0.86 mmol) followed by di-tert-butyl-dicarbonate (205 mg, 0.94 mmol) and 4-dimethylaminopyridine (20 mg, 0.16 mmol). The resulting solution is stirred at room temperature for 30 minutes. It is then diluted with dichloromethane and washed with water then brine. The organic layer is dried over magnesium sulfate and concentrated. The residue is chromatographed through silica gel (n-heptane-ethyl acetate, 90:10 as eluant) to produce 220 mg (81%) of 3-iodo-thieno[3,2-c]pyrazole-1-carboxylic acid tert-butyl ester as a yellow powder. LC/MS: $R_T$=3.45 minutes, 372.94 m/e (M+Na).

Step 3.

EXAMPLE 5C

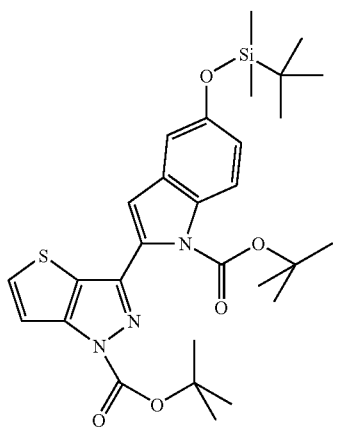

To a solution of 3-iodo-thieno[3,2-c]pyrazole-1-carboxylic acid tert-butyl ester (200 mg, 0.57 mmol, Example 5B) and bis-(diphenylphosphinoferrocene)-dichloro palladium (complex with dichloromethane 1:1, 21 mg, 0.03 mmol) in 1,4-dioxane (5 mL) is added 5-(tert-butyl-dimethyl-silanoxy)-1-(tert-butoxycarbonyl)-1H-indole-2-boronic acid (335 mg, 0.86 mmol, prepared as described in Example 4-6 of International Patent Application Publication No. WO 02/32861) followed by a solution of cesium carbonate (741 mg, 2.28 mmol) in water (2 mL). The mixture is stirred at reflux for 15 minutes. Then it is diluted with ethyl acetate and washed with water and brine. The organic layer is dried over magnesium sulfate and concentrated. The residue is chromatographed through silica gel (n-heptane-ethyl acetate, 95:05 as eluant) to afford 200 mg (61%) of 2-(1-tert-butoxycarbonyl-1H-thieno [3,2-c]pyrazol-3-yl)-5-(tert-butyl-dimethyl-silanoxy)-indole-1-carboxylic acid tert-butyl ester as a white foam. LC/MS: $R_T$=4.29 minutes, 570.1 m/e.

Step 4.

EXAMPLE 5D

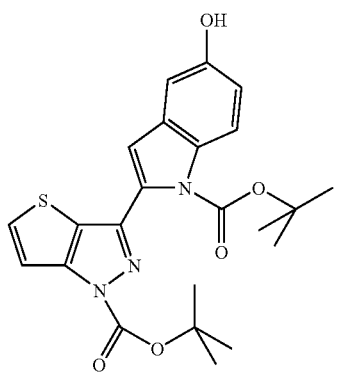

To a solution of 2-(1-tert-butoxycarbonyl-1H-thieno[3,2-c]pyrazol-3-yl)-5-(tert-butyl-dimethyl-silanoxy)-indole-1-carboxylic acid tert-butyl ester (320 mg, 0.56 mmol, Example 5C) in tetrahydrofuran (5 mL) at 0° C. is added TBAF (1.0 M in tetrahydrofuran, 0.67 mL, 0.67 mmol). The solution is stirred at 0° C. for 30 minutes. The solvent is then removed and the residue is chromatographed through silica gel (dichloromethane-ethyl acetate, 95:05 to 90:10 as eluant) to produce 205 mg (80%) 2-(1-tert-butoxycarbonyl-1H-thieno[3,2-c]pyrazol-3-yl)-5-hydroxy-indole-1-carboxylic acid tert-butyl ester as an orange foam. LC/MS: $R_T$=3.74 minutes, 456.0 m/e.

Step 5.

EXAMPLE 5E

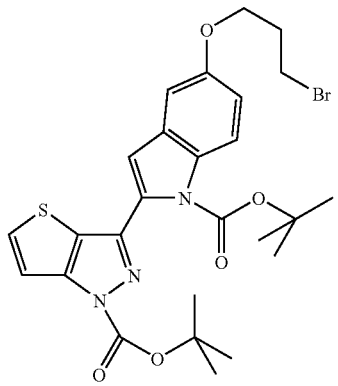

To a solution of 2-(1-tert-butoxycarbonyl-1H-thieno[3,2-c]pyrazol-3-yl)-5-hydroxy-indole-1-carboxylic acid tert-butyl ester (195 mg, 0.43 mmol, Example 5D) in 1,3-dibromopropane (2 mL) is added cesium carbonate (350 mg, 1.08 mmol). The resulting suspension is heated at 100° C. for 30 minutes. It is then filtered and concentrated. The residue is chromatographed through silica gel (ethyl acetate-n-heptane, 05:95 to 20:80 as eluant) to provide 103 mg (42%) of 5-(3-bromo-propoxy)-2-(1-tert-butoxycarbonyl-1H-thieno[3,2-c]pyrazol-3-yl)-indole-1-carboxylic acid tert-butyl ester as a yellow glass. LC/MS: $R_T$=4.38 minutes, 576.11 m/e.

Step 6.

5-(3-Piperidin-1-yl-propoxy)-2-(1H-thieno[3,2-c]pyrazol-3-yl)-indole

To a solution of 5-(3-Bromo-propoxy)-2-(1-tert-butoxycarbonyl-1H-thieno[3,2-c]pyrazol-3-yl)-indole-1-carboxylic acid tert-butyl ester (100 mg, 0.17 mmol, Example 5E) in acetonitrile (4 mL) is added piperidine (33 µL, 0.34 mmol) and PS-DIEA (polymer supported DIEA, 3.86 mmol/g, 45 mg, 0.34 mmol). The mixture is heated at 70° C. for 2 hours. The PS-DIEA is filtered and the solvent is removed under reduced pressure. The residue is dissolved in dichloromethane (DCM) (1 mL). Anisole (0.4 mL) is added followed by trifluoroacetic acid (TFA) (0.5 mL). The bright orange solution is stirred at 50° C. for 1 h and is then loaded directly onto an ion exchange cartridge (VARIAN, mega bond elut SCX, 5 g) washed with methanol and eluted with 1.0M ammonia in methanol. The appropriate fractions are collected and concentrated. The residue is chromatographed (n-heptane-ethyl acetate, 95:05 to 90:10 as eluant) to produce 44 mg of impure product. The beige powder is triturated in dichloromethane to provide 5-(3-piperidin-1-yl-propoxy)-2-(1H-thieno[3,2-c]pyrazol-3-yl)-indole [12 mg, 18%, Example 5] as a white powder. LC/MS: $R_T$=2.20 minutes, 381.18 m/e. $^1$H NMR [(CD$_3$)$_2$SO), 300 MHz]: δ 13.25 (brs, 1H) and 11.39 (brs, 1H) [indole and pyrazole NH protons], 7.74 (d, J=5 Hz, 1H) and 7.19 (d, J=5 Hz, 1H) [thiophene protons], 7.29 (brd, J=8.5 Hz, 1H) [H-7 of indole], 7.07 (d, J=2 Hz, 1H) [H-4 of indole], 6.74 (dd, J=8.5, 2 Hz, 1H) [H-6 of indole], 6.56 (brd, J=1.5 Hz, 1H) [H-3 of indole], 3.96 (t, J=6 Hz, 2H) [—OCH2-], 2.50 (m, 6H), 1.91 (m, 2H), 1.53 (m, 4H), 1.40 (m, 3H).

The following Examples 6 to 22 are prepared by procedures similar to those of the previous examples.

EXAMPLE 6

1-{3-[2-(1H-Thieno[3,2-c]pyrazol-3-yl)-1H-indol-6-yloxy]-propyl}-piperidin-4-ol

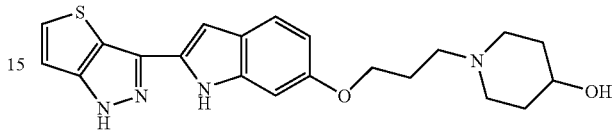

LC/MS: $R_T$=2.17 minutes, observed M+H=397.18

EXAMPLE 7

6-(3-Piperidin-1-yl-propoxy)-2-(1H-thieno[3,2-c]pyrazol-3-yl)-1H-indole

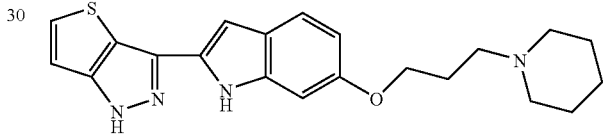

LC/MS: $R_T$=2.35 minutes, observed M+H=381.18

EXAMPLE 8

1-{3-[2-(1H-Thieno[3,2-c]pyrazol-3-yl)-1H-indol-6-yloxy]-propyl}-piperidin-3-ol

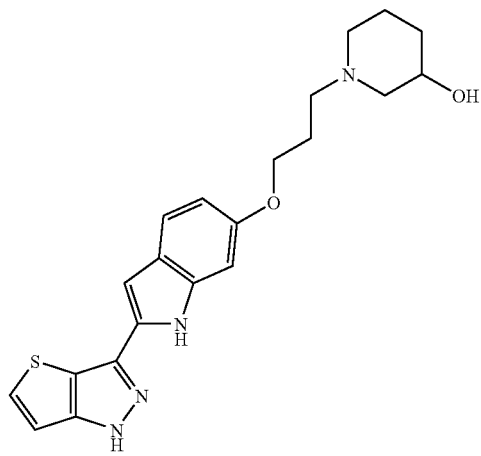

LC/MS: $R_T$=2.45 minutes, observed M+H=397.4

EXAMPLE 9

(1-{3-[2-(1H-Thieno[3,2-c]pyrazol-3-yl)-1H-indol-6-yloxy]-propyl}-piperidin-3-yl)-methanol

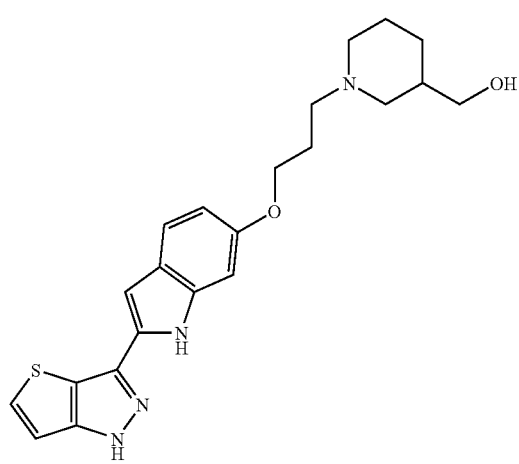

LC/MS: $R_T$=2.49 minutes, observed M+H=411.2

EXAMPLE 10

6-[3-(4-Ethyl-piperazin-1-yl)-propoxy]-2-(1H-thieno[3,2-c]pyrazol-3-yl)-1H-indole

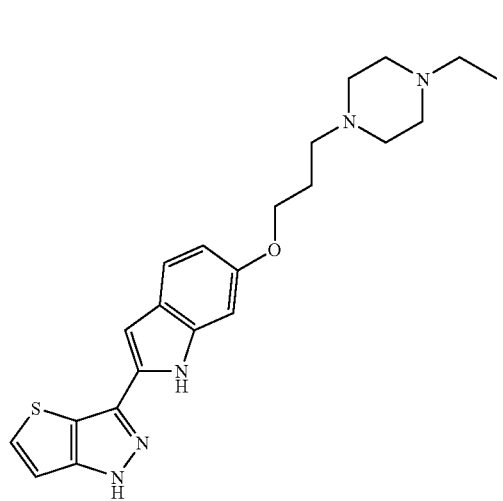

LC/MS: $R_T$=2.27 minutes, observed M+H=410.4

EXAMPLE 11

Dimethyl-{3-[2-(1H-thieno[3,2-c]pyrazol-3-yl)-1H-indol-6-yloxy]-propyl}-amine

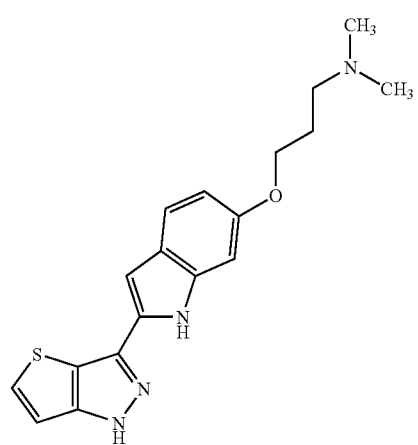

LC/MS: $R_T$=2.23 minutes, observed M+H=341.16

EXAMPLE 12

Diethyl-{3-[2-(1H-thieno[3,2-c]pyrazol-3-yl)-1H-indol-6-yloxy]-propyl}-amine

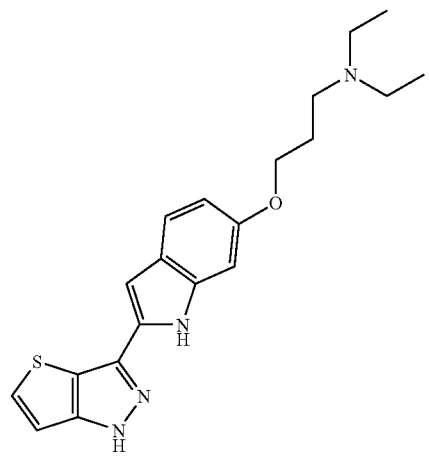

LC/MS: $R_T$=2.35 minutes, observed M+H=369.19

EXAMPLE 13

Diallyl-{3-[2-(1H-thieno[3,2-c]pyrazol-3-yl)-1H-indol-6-yloxy]-propyl}-amine

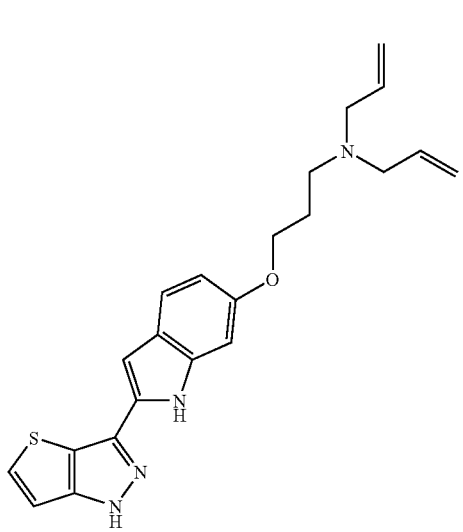

LC/MS: $R_T$=2.48 minutes, observed M+H=393.14

EXAMPLE 14

1-{3-[2-(1H-Thieno[3,2-c]pyrazol-3-yl)-1H-indol-6-yloxy]-propyl}-pyrrolidin-3-ol

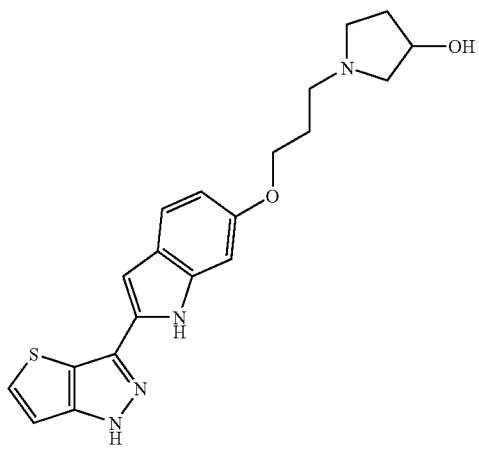

LC/MS: $R_T$=2.2 minutes, observed M+H=383.17

EXAMPLE 15

2-(Methyl-{3-[2-(1H-thieno[3,2-c]pyrazol-3-yl)-1H-indol-6-yloxy]-propyl}-amino)-ethanol

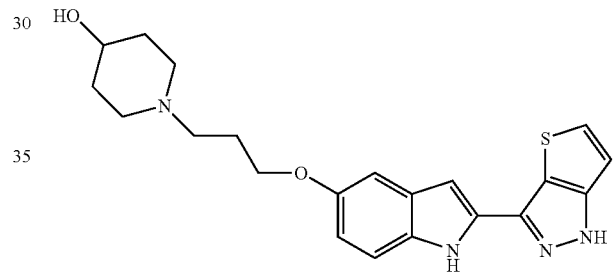

LC/MS: $R_T$=2.13 minutes, observed M+H=371.25

EXAMPLE 16

1-{3-[2-(1H-Thieno[3,2-c]pyrazol-3-yl)-1H-indol-5-yloxy]-propyl}-piperidin-4-ol

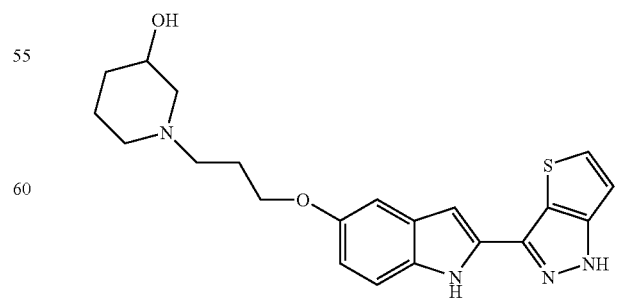

LC/MS: $R_T$=2.03 minutes, observed M+H=397.17

EXAMPLE 17

1-{3-[2-(1H-Thieno[3,2-c]pyrazol-3-yl)-1H-indol-5-yloxy]-propyl}-piperidin-3-ol

LC/MS: $R_T$=1.87 minutes, observed M+H=397.2

EXAMPLE 18

(1-{3-[2-(1H-Thieno[3,2-c]pyrazol-3-yl)-1H-indol-5-yloxy]-propyl}-piperidin-3-yl)-methanol

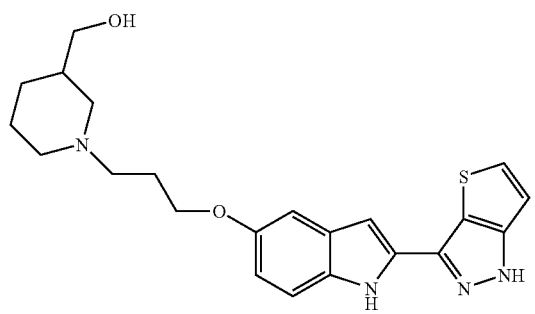

LC/MS: R$_T$=2.07 minutes, observed M+H=411.18

EXAMPLE 19

1-{3-[2-(1H-Thieno[3,2-c]pyrazol-3-yl)-1H-indol-5-yloxy]-propyl}-pyrrolidin-3-ol

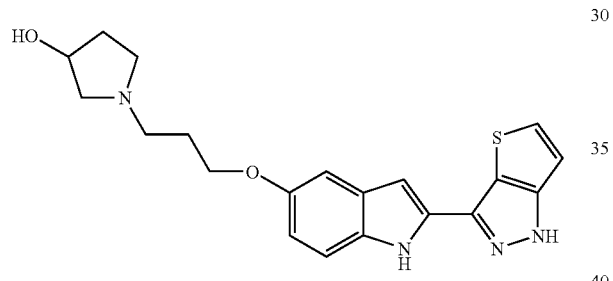

LC/MS: R$_T$=2.48 minutes, observed M+H=383.2

EXAMPLE 20

3-(5-(3-Piperidin-1-yl-propoxy)-1H-Benzoimidazol-2-yl)-1H-benzo[4,5]theino[3,2-c]pyrazole hydrochloride

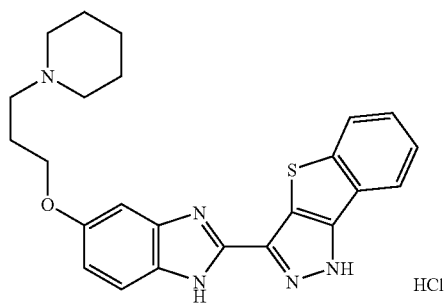

LC/MS: R$_T$=2.49 minutes, observed M+H=432.18

EXAMPLE 21

2-{1H-Thieno[3,2-c]pyrazol-3-yl)-1H-indol-5-carboxylic acid(2-thiophen-2-yl-ethyl)-amide

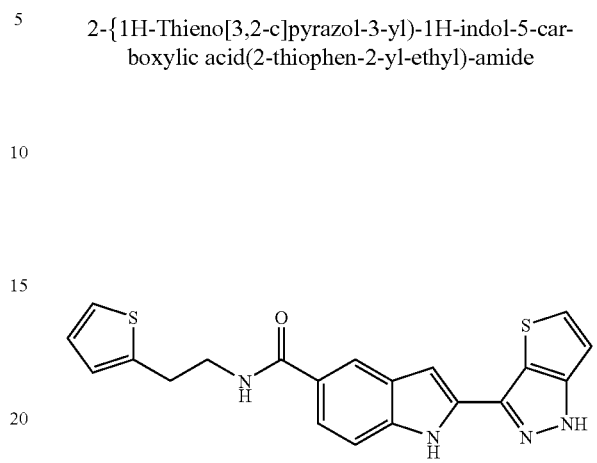

LC/MS: R$_T$=3.22 minutes, observed M+H=393.2

EXAMPLE 22

1-{3-[2-(5-Dimethylaminoethyl-1H-thieno[3,2-c]pyrazol-3-yl)-1h-indol-6-yloxy]-propyl}-piperidin-4-ol

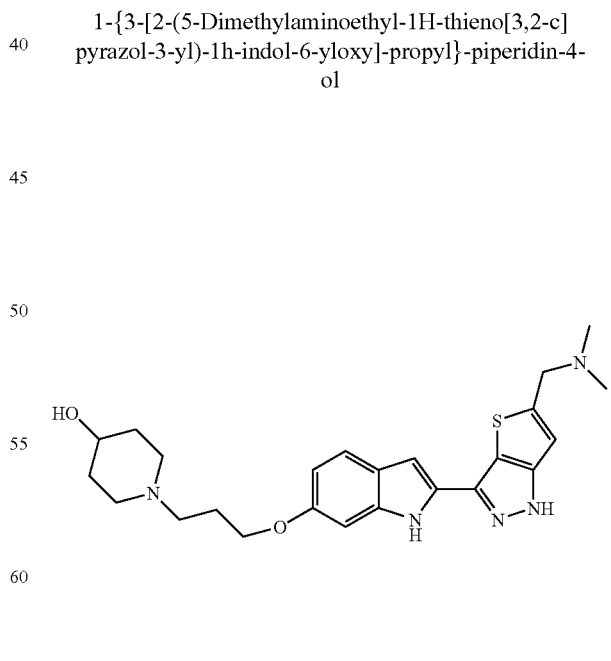

LC/MS: R$_T$=1.87 minutes, observed M+H=454

EXAMPLE 23

[2-(1H-Thieno[3,2-c]pyrazol-3-yl)-1H-indol-5-yl]-methanol

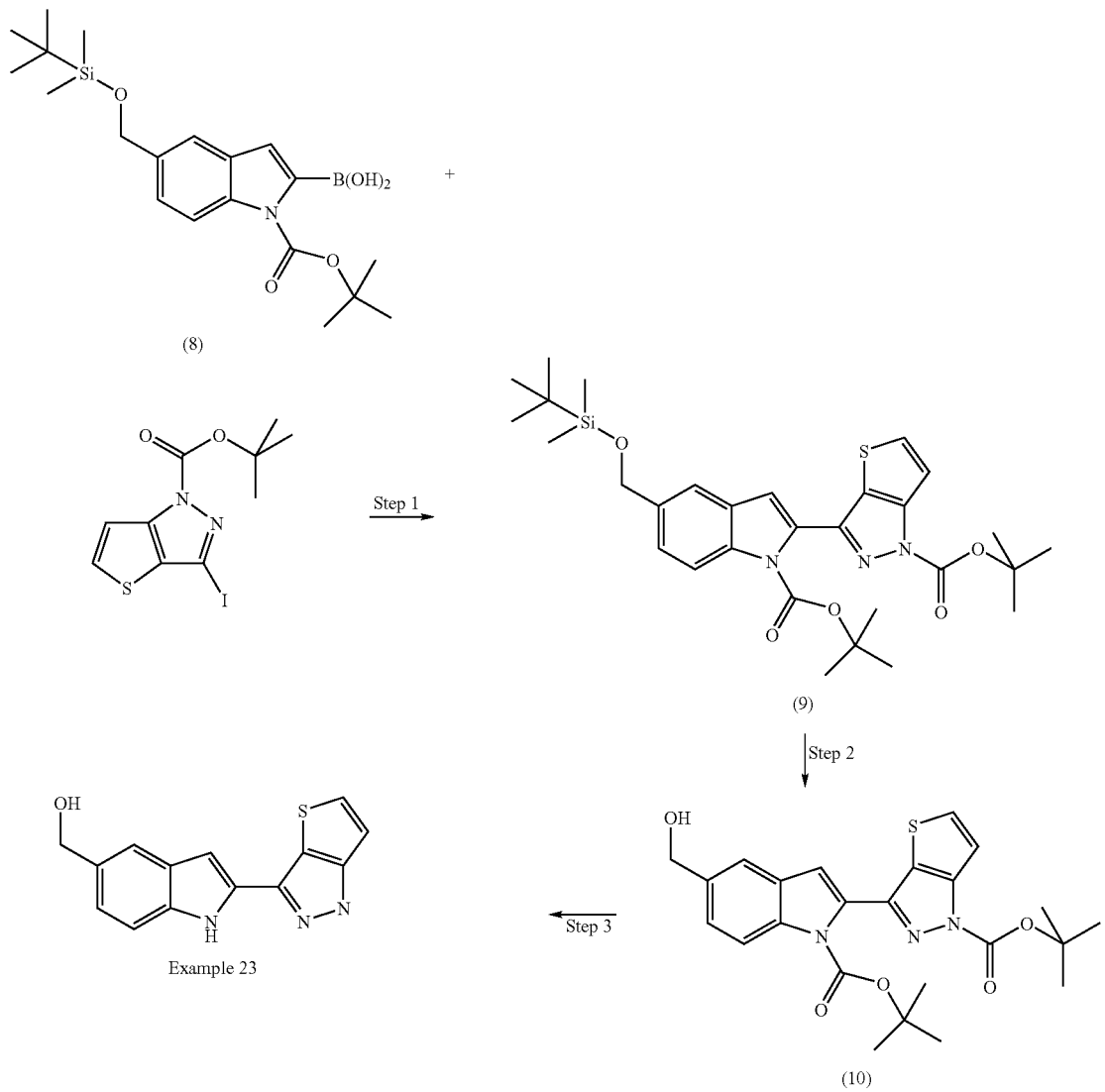

Step 1. A mixture of 5-(tert-butyl-dimethyl-silanyloxymethyl)-1H-indole-2-boronic acid 1-carboxylic acid tert-butyl ester [3.82 g, 9.42 mmol, Intermediate (8), prepared as described in Example 1-4 of International Patent Application Publication No. WO 02/32861], 3-iodo-thieno[3,2-c]pyrazole-1-carboxylic acid tert-butyl ester [4.0 g, 11.42 mmol, Example 5B above], tetrakis(triphenylphosphine)palladium (0) (544 mg, 0.470 mmol), potassium carbonate (2M aqueous, 12 mL) in tetrahydrofuran (60 mL) is purged with $N_2$ for 10 minutes then heated to 55-60° C. for 7.5 hours. The reaction is diluted with ethyl acetate (50 mL) and washed with water (20 mL). Water layer is back extracted with ethyl acetate (50 mL). The combined ethyl acetate phases are dried over sodium sulfate. The residue is chromatographed on 35 g silica gel cartridge (5-30% ethyl acetate gradient in heptane) to give 2-(1-tert-butoxycarbonyl-1H-thieno[3,2-c]pyrazol-3-yl)-5-(tert-butyl-dimethyl-silanyloxymethyl)-indole-1-carboxylic acid tert-butyl ester [3.8 g, 69%, Intermediate (9)]; $^1$H NMR [$(CD_3)_2SO$)]: δ 8.08 (2H, m), 7.64 (1H, s), 7.38 (2H, m), 7.14 (1H, s), 4.81 (2H, s, —OC$\underline{H}_2$), 1.65 (9H, s), 1.32 (9H, s) 0.92 (9H, s, Si(C$\underline{H}_3$)$_3$), 0.10 (6H, s, Si(C$\underline{H}_2$)); LC/MS: 584 (M+H).

Step 2. A solution of 2-(1-tert-butoxycarbonyl-1H-thieno[3,2-c]pyrazol-3-yl)-5-(tert-butyl-dimethyl-silanyloxymethyl)-indole-1-carboxylic acid tert-butyl ester [3.8 g, 6.51 mmol, Intermediate (9)]) in anhydrous tetrahydrofuran (40 mL) is cooled to 0° C. To it is added tetrabutylammonium fluoride (1M in tetrahydrofuran, 10 mL) drop wise. Stirred at 0° C. for 20 minutes then at room temperature for 20 minutes. Water (20 mL) is added and extracted three times with ethyl acetate (30 mL). The combined ethyl acetate phases are washed with brine and dried over sodium sulfate. The residue is chromatographed on 35 g silica gel (10-50% ethyl acetate in heptane) to give 2-(1-tert-butoxycarbonyl-1H-thieno[3,2-c]pyrazol-3-yl)-5-hydroxymethyl-indole-1-carboxylic acid tert-butyl ester [2.63 g, 85%, Intermediate (10)] as white solid; $^1$H NMR [(CD$_3$)$_2$SO)]: δ 8.05 (2H, m), 7.62 (1H, s), 7.38 (2H, m), 7.02 (1H, s), 5.21 (1H, t), 4.6 (2H, d), 1.64 (9H, s), 1.25 (9H, s); LC/MS: 470 (M+H).

Step 3. To a solution of 2-(1-tert-butoxycarbonyl-1H-thieno[3,2-c]pyrazol-3-yl)-5-hydroxymethyl-indole-1-carboxylic acid tert-butyl ester [200 mg, 0.426 mmol, Intermediate (10)] in tetrahydrofuran (5 mL) is added KOH (1M aqueous, 2.5 mL) and heated to 60° C. for 20 hours. The solvent is removed and dissolved crude in water. The water layer is neutralized with 3N hydrochloric acid then extracted twice with ethyl acetate (20 mL). The combined ethyl acetate phases are washed with brine and dried over sodium sulfate. Purification by chromatography using 10 g silica gel cartridge (50% ethyl acetate in heptane then ethyl acetate) afforded [2-(1H-thieno[3,2-c]pyrazol-3-yl)-1H-indol-5-yl]-methanol (84 mg, 74%, Example 23) as a light yellow solid; $^1$H NMR [(CD$_3$)$_2$SO)]: δ 13.22 (1H, s), 11.43 (1H, s), 7.77 (1H), 7.56 (1H), 7.38 (1H), 7.20 (1H), 7.04 (1H), 6.61 (1H), 5.02 (1H, OH), 4.57 (2H, —CH$_2$OH); LC/MS: 270 (M+H).

EXAMPLE 24

Phenyl-[2-(1H-thieno[3,2-c]pyrazol-3-yl)-1H-indol-5-yl]-methanol

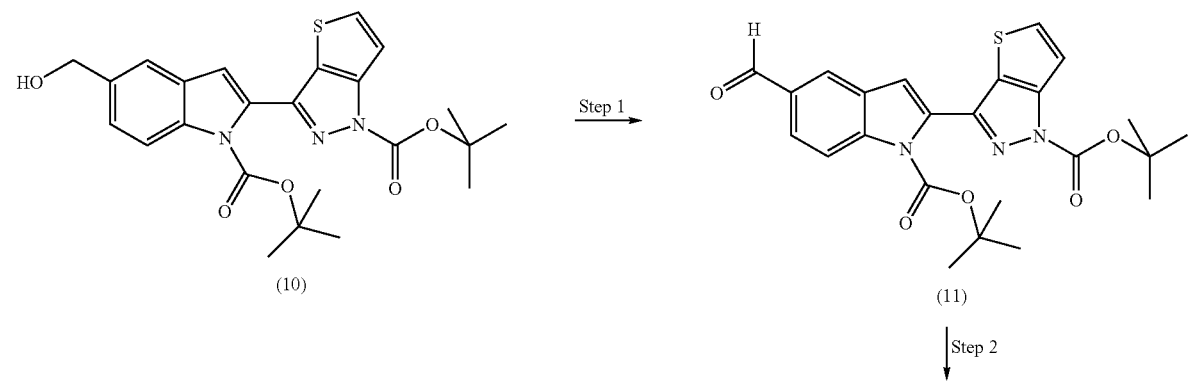

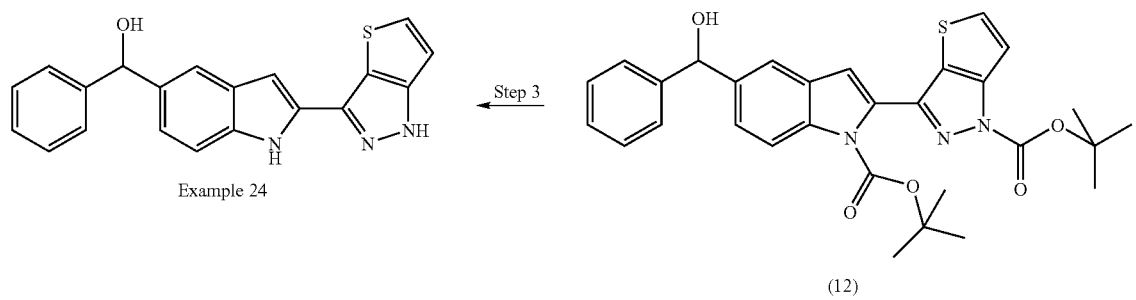

Step 1. To a solution of 2-(1-tert-butoxycarbonyl-1H-thieno[3,2-c]pyrazol-3-yl)-5-hydroxymethyl-indole-1-carboxylic acid tert-butyl ester [373 mg, 0.794 mmol Intermediate (10)] in Dichloromethane (20 mL) is added Dess-Martin Periodinane (407 mg, 0.959 mmol). Stirred at room temperature for 30 minutes. Water (10 mL) is added and stirred for 30 minutes at room temperature. The reaction mixture is dissolved with ethyl acetate (30 mL) and washed twice with a mixture of 10% $Na_2S_2O_3$/saturated $NaHCO_3$ (4 ML) solution. The ethyl acetate phase is washed with water, $NaHCO_3$, brine and dried over sodium sulfate. The residue is chromatographed on 10 g silica gel cartridge eluting with 30 to 40% ethyl acetate gradient in heptane to afford 2-(1-tert-butoxycarbonyl-1H-thieno[3,2-c]pyrazol-3-yl)-5-formyl-indole-1-carboxylic acid tert-butyl ester [300 mg, 81%, Intermediate (11)] as a white solid; $^1$H NMR [$(CD_3)_2SO$)]: δ 10.079 (1H, s, CHO), 8.323 (1H, s), 8.318 (1H, d), 8.017 (1H, s), 7.978 (1H, d), 7.391 (1H, d), 7.345 (1H, s), 1.660 (9H, s), 1.341 (9H, s); TLC data $R_f$=0.37 (30% ethyl acetate in heptane).

Step 2. To a solution of 2-(1-tert-butoxycarbonyl-1H-thieno[3,2-c]pyrazol-3-yl)-5-formyl-indole-1-carboxylic acid tert-butyl ester [100 mg, 0.214 mmol, Intermediate (11)] in anhydrous tetrahydrofuran (5 mL) is added phenylmagnesium bromide (1M in tetrahydrofuran, 1 mL) at −78° C. The resulting reaction mixture is stirred at the same temperature for 1 h then quenched it by the addition of water at 0° C. (4 mL). The reaction mixture is extracted three times with ethyl acetate (30 mL). Combined ethyl acetate phases are washed with brine, dried over sodium sulfate and filtered. Evaporation of the solvent in vacuo yielded 2-(1-tert-butoxycarbonyl-1H-thieno[3,2-c]pyrazol-3-yl)-5-(hydroxy-phenyl-methyl)-indole-1-carboxylic acid tert-butyl ester [99 mg, 85%, Intermediate (12)] as a white foam; LC/MS: (M+H, 546).

Step 3. The mixture of 2-(1-tert-butoxycarbonyl-1H-thieno[3,2-c]pyrazol-3-yl)-5-(hydroxy-phenyl-methyl)-indole-1-carboxylic acid tert-butyl ester [99 mg, 0.181 mmol, Intermediate (12)] in tetrahydrofuran (2 mL) and KOH (1M aqueous, 1 mL) is stirred at 60° C. under nitrogen for 22 hours. The solvent is removed in vacuo. To this slurry mixture is added water (2 mL) and brought pH to 6 by addition of 2N hydrochloric acid. The product is extracted three times with dichloromethane (20 mL) and the combined extracts are washed with brine then dried over sodium sulfate. The residue is chromatographed on 10 g silica gel cartridge, eluting with 50 to 100% ethyl acetate gradient in heptane to afford phenyl-[2-(1H-thieno[3,2-c]pyrazol-3-yl)-1H-indol-5-yl]-methanol [56 mg, 89%, Example 24] as a off-white solid; LC/MS: 346 (M+H), 328 [(M−18)+H]; TLC data: $R_f$=0.14 (50% ethyl acetate in heptane).

EXAMPLE 25

Phenyl-[2-(1H-thieno[3,2-c]pyrazol-3-yl)-1H-indol-5-yl]-methanone

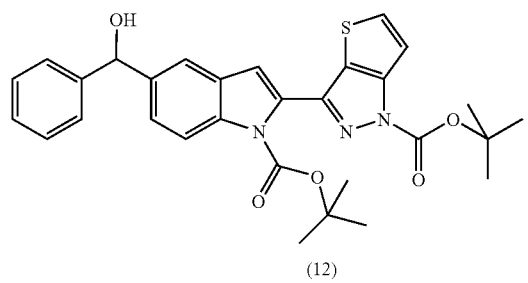

(12)

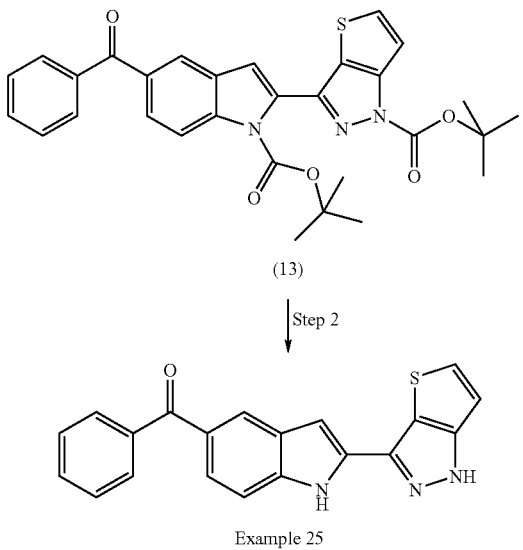

(13)

Example 25

Step 1. To a solution of 2-(1-tert-butoxycarbonyl-1H-thieno[3,2-c]pyrazol-3-yl)-5-(hydroxy-phenyl-methyl)-indole-1-carboxylic acid tert-butyl ester [640 mg, 1.17 mmol, Intermediate (12)] in Dichloromethane (25 mL) is added Dess-Martin Periodinane (677 mg, 1.69 mmol) and stirred at room temperature. After 30 minutes water (5 mL) is added and stirred for 10 minutes. The reaction mixture is diluted with dichloromethane (50 mL) and washed twice with a mixture of 10% $Na_2S_2O_3$/saturated $NaHCO_3$ (5 mL), $NaHCO_3$ (10 mL), water (10 mL), brine and dried over sodium sulfate. The residue is chromatographed on 35 g silica gel cartridge, eluting with 30% ethyl acetate/Heptane to afford 5-benzoyl-2-(1-tert-butoxycarbonyl-1H-thieno[3,2-c]pyrazol-3-yl)-indole-1-carboxylic acid tert-butyl ester [440 mg, 69%, Intermediate (13)] as a white solid; LC/MS: 544 (M+H).

Step 2. A mixture of 5-benzoyl-2-(1-tert-butoxycarbonyl-1H-thieno[3,2-c]pyrazol-3-yl)-indole-1-carboxylic acid tert-butyl ester [122 mg, 0.224 mmol, Intermediate (13)] in tetrahydrofuran (9 mL) and 1M KOH(aqueous, 2 mL) is heated at 60° C. oil bath overnight. The solvent is removed and added water (5 mL). The water layer is neutralized with 3N hydrochloric acid and extracted three times with ethyl acetate (20 mL). The combined ethyl acetate phases are washed with brine and dried over sodium sulfate. The residue is chromatographed on 10 g silica gel cartridge, eluting with 50 to 100% ethyl acetate gradient in heptane to afford phenyl-[2-(1H-thieno[3,2-c]pyrazol-3-yl)-1H-indol-5-yl]-methanone (58 mg, 75%, Example 25) as a pale yellow solid; $^1$H NMR [(CD$_3$)$_2$SO)]: δ 13.38 (1H, s), 12.09 (1H, s), 8.05 (1H), 7.78 (8H, m), 7.23 (1H, d, J=5.2 Hz), 6.87 (1H); LC/MS: 344 (M+H).

EXAMPLE 26

1-Phenyl-1-[2-(1H-thieno[3,2-c]pyrazol-3-yl)-1H-indol-5-yl]-ethanol

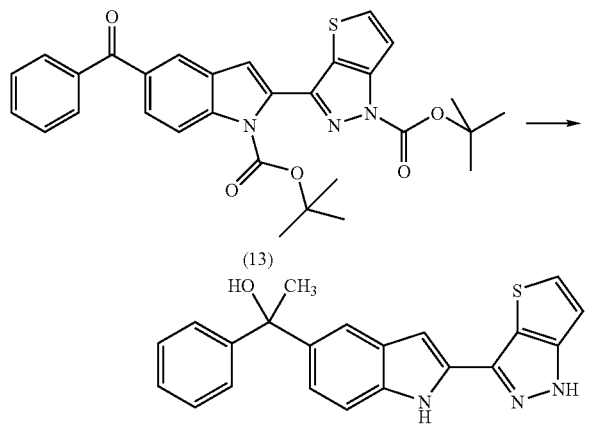

To a solution of 5-benzoyl-2-(1-tert-butoxycarbonyl-1H-thieno[3,2-c]pyrazol-3-yl)-indole-1-carboxylic acid tert-butyl ester [Intermediate (13)] in anhydrous tetrahydrofuran (5 mL) is added methylmagnesium bromide (1M in tetrahydrofuran, 0.8 mL) at −78° C. Stirred under nitrogen for 30 minutes. Added another 0.88 mL of methylmagnesium bromide and let the reaction warm to room temperature slowly. After overnight water/saturated ammonium chloride (2 mL) is added at 0° C. and extracted twice with ethyl acetate (25 mL). The combined ethyl acetate phases are washed with brine and dried over sodium sulfate. The residue is chromatographed on 10 g silica gel, eluting with 30 to 50% ethyl acetate gradient in heptane to afford 1-phenyl-1-[2-(1H-thieno[3,2-c]pyrazol-3-yl)-1H-indol-5-yl]-ethanol (56 mg, 71%, Example 26) as a beige solid; LC/MS: 360 (M+H); $^1$H NMR [(CD$_3$)$_2$SO)]: δ 13.20 (1H, s), 11.45 (1H, s), 7.73 (1H, d), 7.62 (1H, s), 7.43 (2H, m), 7.25 (6H, m), 6.59 (1H, s), 5.53 (1H, s), 1.86 (3H, s).

EXAMPLE 27

(S)-1-Phenyl-1-[2-(1H-thieno[3,2-c]pyrazol-3-yl)-1H-indol-5-yl]-ethanol

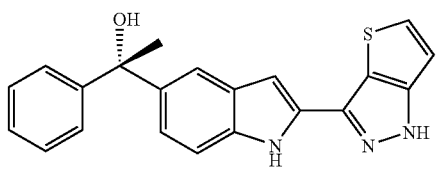

The racemic 1-phenyl-1-[2-(1H-thieno[3,2-c]pyrazol-3-yl)-1H-indol-5-yl]-ethanol (45 mg, Example 26) is purified by chiral HPLC (Column: chiralcel OD, 4.6 mmlID×250 mm, 10 micron. Mobile phase: 55% ethanol with 1 mmol ammonium trifluoroacetate and 45% heptane with 1 mmol ammonium trifluoroacetate) and the desired eluent fractions are concentrated and lyophilized to afford one of the enantiomers of 1-Phenyl-1-[2-(1H-thieno[3,2-c]pyrazol-3-yl)-1H-indol-5-yl]-ethanol (11 mg) as a white solid; chiral HPLC retention time 10.96 minutes at 215 nm.

EXAMPLE 28

1-[2-(1H-thieno[3,2-c]pyrazol-3-yl)-1H-indol-5-yl]-propan-1-one

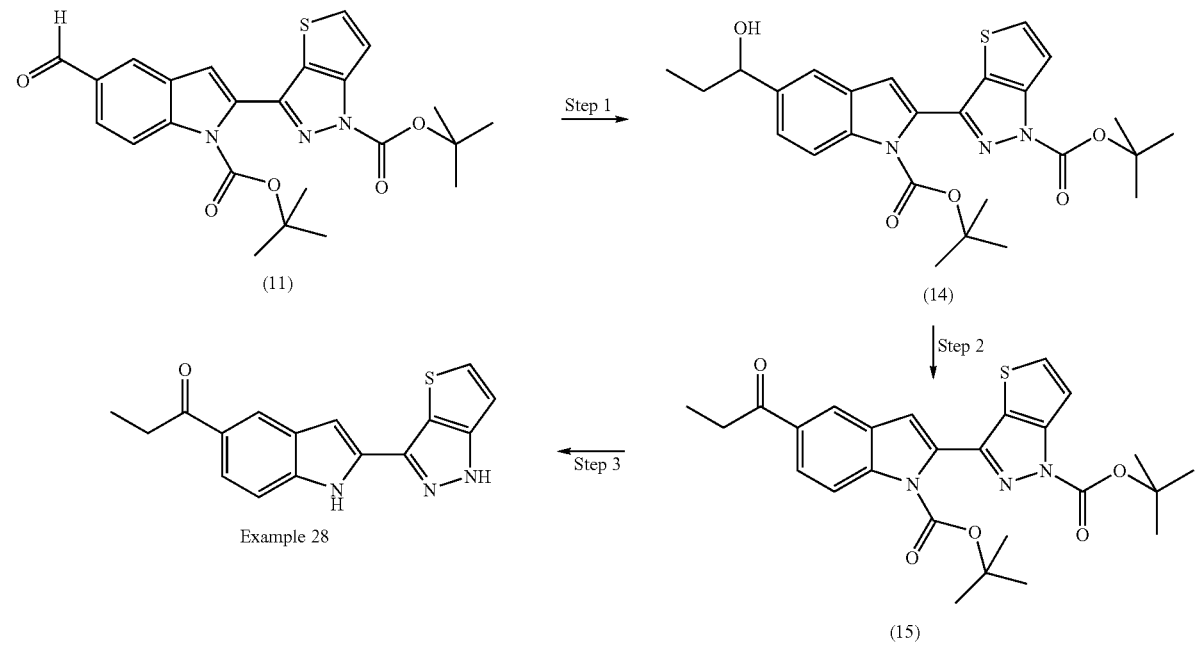

Step 1. By proceeding in a manner similar to that described in Step 2 of Example 24 but substituting ethyl magnesium bromide for phenylmagnesium bromide there is prepared 2-(1-tert-butoxycarbonyl-1H-thieno[3,2-c]pyrazol-3-yl)-5-(1-hydroxy-propyl)-indole-1-carboxylic acid tert-butyl ester [73%, Intermediate (14)] as a white solid.

Step 2. By proceeding in a manner similar to that described in Step 1 of Example 25 but substituting 2-(1-tert-butoxycarbonyl-1H-thieno[3,2-c]pyrazol-3-yl)-5-(1-hydroxy-propyl)-indole-1-carboxylic acid tert-butyl ester [Intermediate (14)] for 2-(1-tert-butoxycarbonyl-1H-thieno[3,2-c]pyrazol-3-yl)-5-(hydroxy-phenyl-methyl)-indole-1-carboxylic acid tert-butyl ester [Intermediate (12)] there is prepared 2-(1-tert-butoxycarbonyl-1H-thieno[3,2-c]pyrazol-3-yl)-5-propionyl-indole-1-carboxylic acid tert-butyl ester [73%, Intermediate (15)] as a white solid.

Step 3. By proceeding in a manner similar to that described in Step 2 of Example 25 but substituting 2-(1-tert-butoxycarbonyl-1H-thieno[3,2-c]pyrazol-3-yl)-5-propionyl-indole-1-carboxylic acid tert-butyl ester [Intermediate (15)] for 5-benzoyl-2-(1-tert-butoxycarbonyl-1H-thieno[3,2-c]pyrazol-3-yl)-indole-1-carboxylic acid tert-butyl ester [Intermediate (13)] there is prepared 1-[2-(1H-thieno[3,2-c]pyrazol-3-yl)-1H-indol-5-yl]-propan-1-one [94%, Example 28] is isolated as white solid; $^1$H NMR [(CD$_3$)$_2$SO)]: δ 13.34 (1H, s), 11.98 (1H, s), 8.31 (1H, s), 7.77 (2H, m), 7.47 (1H, d, J=8.5 Hz), 7.21 (1H, d, J=5.2 Hz), 6.79 (1H, s), 3.07 (2H, q, —C$\underline{H}_2$CH$_3$), 1.13 (3H, t, —C$\underline{H}_3$); LC/MS: 296 (M+H).

EXAMPLE 29

1-Cyclohexyl-1-[2-(1H-thieno[3,2-c]pyrazol-3-yl)-1H-indol-5-yl]-propan-1-ol

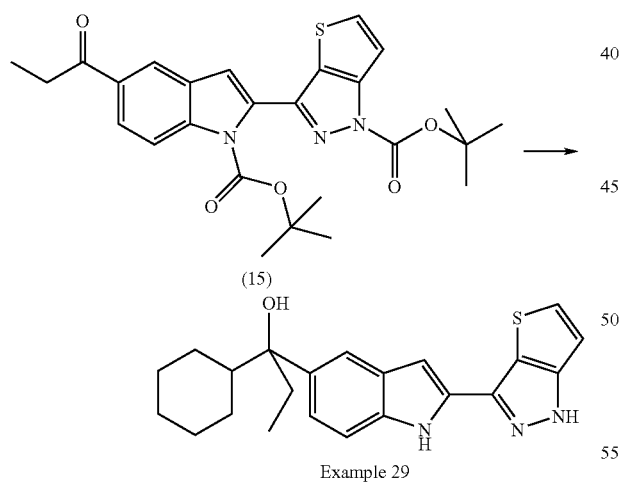

Example 29

A solution of 2-(1-tert-butoxycarbonyl-1H-thieno[3,2-c]pyrazol-3-yl)-5-propionyl-indole-1-carboxylic acid tert-butyl ester [400 mg, 0.807 mmol, Intermediate (15)] in anhydrous tetrahydrofuran (20 mL) is cooled to −78° C. under nitrogen. To it is added cyclohexyl magnesium bromide (2M in tetrahydrofuran, 1 mL). After stirring for 20 minutes, the cooling bath is removed and the reaction temperature is brought to room temperature over 20 minutes. The reaction mixture is cooled to 0° C. and quenched with the addition of saturated ammonium chloride (6 mL) followed by water (20 mL). The aqueous layer is extracted three times with ethyl acetate (40 mL). The combined extracts are washed with brine and dried over sodium sulfate and filtered over 5 g silica gel cartridge and washed the cartridge with ethyl acetate (20 mL). The filtrate is removed in vacuo to afford alcohol (520 mg) as an orange foam.

The orange foam (520 mg, 0.862 mmol) is dissolved in tetrahydrofuran (15 mL) and treated with 1M KOH (aqueous, 15 mL) and heated at 70° C. oil bath overnight. The solvent is removed, water added and neutralized with 3N hydrochloric acid. The product is extracted three times with ethyl acetate (20 mL). The combined ethyl acetate phases are washed with brine and dried over sodium sulfate. Purification by chromatography (10 g silica gel cartridge, 50% ethyl acetate/heptane) gave 1-cyclohexyl-1-[2-(1H-thieno[3,2-c]pyrazol-3-yl)-1H-indol-5-yl]-propan-1-ol (150 mg, 46%, Example 29) as a cream solid; $^1$H NMR [(CD$_3$)$_2$SO)]: δ 13.21 (1H, s), 11.41 (1H, s), 7.75 (1H, d), 7.53 (1H), 7.29 (1H), 7.20 (1H), 7.11 (1H), 6.59 (1H), 4.21 (1H, OH), 1.91 (3H, br m), 1.78 (1H, br d), 1.68 (3H, br t), 1.39 (1H, br d), 1.25-0.87 (5H, m), 0.63 (3H, t); LC/MS: 380 (M+H).

EXAMPLE 30

1-Cyclohexyl-1-[2-(1H-thieno[3,2-c]pyrazol-3-yl)-1H-indol-5-yl]-propan-1-ol, enantiomer 1

The racemic mixture 1-cyclohexyl-1-[2-(1H-thieno[3,2-c]pyrazol-3-yl)-1H-indol-5-yl]-propan-1-ol (145 mg, Example 29) is purified by chiral HPLC (Column: chiralcel OJ. Mobile phase: 40% heptane/60% ethanol/0.05% DEA) and the desired eluent fractions are concentrated and lyophilized to afford chiral alcohol 1-cyclohexyl-1-[2-(1H-thieno[3,2-c]pyrazol-3-yl)-1H-indol-5-yl]-propan-1-ol, enantiomer 1 [51 mg, Example 30] as a white solid; chiral HPLC retention time 12.57 minutes at 215 nm; $^1$H NMR [(CD$_3$)$_2$SO)]: δ 13.22 (1H, s), 11.39 (1H, s), 7.75 (1H, d, J=5 Hz), 7.53 (1H, s), 7.32 (1H, J=8.7 Hz), 7.20 (1H, d, J=5.2 Hz), 7.11 (1H, dd), 6.60 (1H, s), 4.21 (1H, s, OH), 1.87 (3H, br m), 1.71 (1H, br d), 1.59 (3H, br t), 1.18 (1H, br d), 1.18-0.87 (5H, m), 0.63 (3H, t); LC/MS: 380 (M+H).

EXAMPLE 31

1-Pyridin-2-yl-1-[2-(1H-thieno[3,2-c]pyrazol-3-yl)-1H-indol-5-yl]-propan-1-ol

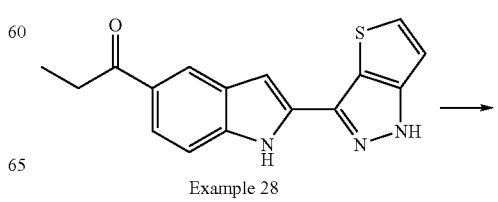

Example 28

-continued

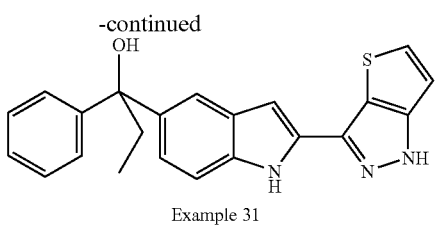

Example 31

To a solution of 2-bromopyridine (224 mg, 1.42 mmol) in anhydrous tetrahydrofuran (2 mL) is added n-BuLi (1.6 M in hexane, 0.95 mL, 1.52 mmol) at −78° C. under nitrogen. After stirring for 20 minutes, to it is added a solution of 1-[2-(1H-thieno[3,2-c]pyrazol-3-yl)-1H-indol-5-yl)-propan-1-one (140 mg, 0.473 mmol, Example 28) in anhydrous tetrahydrofuran (4 mL) drop wise. After 30 minutes, the cooling bath is removed and continued stirring at ambient temp for 30 minutes. The reaction is quenched by the addition of saturated ammonium chloride (4 mL) followed by water (4 mL). The reaction mixture is extracted with ethyl acetate (120 mL). Ethyl acetate phase is washed with water, brine and dried over sodium sulfate. Purification by chromatography (10 g silica gel cartridge, 30-60% ethyl acetate gradient in heptane) afforded product. It is then dissolved with minimum amount of methanol and triturated with water to give 1-pyridin-2-yl-1-[2-(1H-thieno[3,2-c]pyrazol-3-yl)-1H-indol-5-yl]-propan-1-ol (171 mg, 31%, Example 31) as a beige solid; $^1$H NMR [(CD$_3$)$_2$SO)]: δ 13.195 (1H, s), 11.417 (1H, s), 8.472 (1H, d), 7.742-7.661 (4H, m) 7.259-7.166 (4H, m), 6.59 (1H, s), 5.697 (1H, s, OH), 2.361 (2H, m), 0.785 (3H, t); LC/MS: 375 (M+H).

EXAMPLE 32

2-[2-(1H-Thieno[3,2-c]pyrazol-3-yl)-1H-indol-5-yl]-butan-2-ol

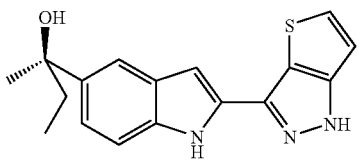

(15)

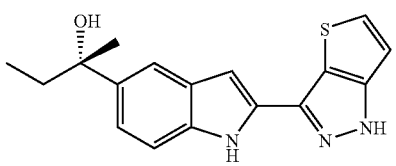

Example 32

A solution of 2-(1-tert-butoxycarbonyl-1H-thieno[3,2-c]pyrazol-3-yl)-5-propionyl-indole-1-carboxylic acid tert-butyl ester [450 mg, 0.908 mmol, Intermediate (15)] in anhydrous tetrahydrofuran (25 mL) that is cooled to −78° C. is added methylmagnesium bromide (1M in tetrahydrofuran, 3 mL) via syringe under nitrogen. After stirring for 30 minutes cooling bath is removed and brought the reaction to room temperature. The reaction is cooled to −78° C. then additional 5 mL of methyl magnesium bromide is added. After 30 minutes, the cooling bath is removed and reaction temperature is brought to room temperature. After 4 hours, it is quenched by the addition of saturated ammonium chloride (6 mL). After stirring for 10 minutes, water (20 mL) is added and extracted three times with ethyl acetate (40 mL). The combined ethyl acetate phases are washed with brine and dried over sodium sulfate. Purification by chromatography (35 g silica gel cartridge, 1:1 ethyl acetate /heptane) afforded 2-[2-(1H-thieno[3,2-c]pyrazol-3-yl)-1H-indol-5-yl]-butan-2-ol [148 mg, 52%, Example 32] as a white solid; $^1$H NMR [(CD$_3$)$_2$SO)]: δ 13.204 (1H, s), 11.402 (1H, s), 7.743 (1H, d), 7.595 (1H, s), 7.333-7.192 (3H, m), 6.598 (1H, s), 4.658 (1H, s, OH), 1.728 (2H, q), 1.461 (3H, s), 0.702 (3H, t); LC/MS: 312 (M+H).

EXAMPLE 33A & EXAMPLE 33B (R)-2-[2-(1H-Thieno[3,2-c]pyrazol-3-yl)-1H-indol-5-yl]-butan-2-ol and (S)-2-[2-(1H-Thieno[3,2-c]pyrazol-3-yl)-1H-indol-5-yl]-butan-2-ol

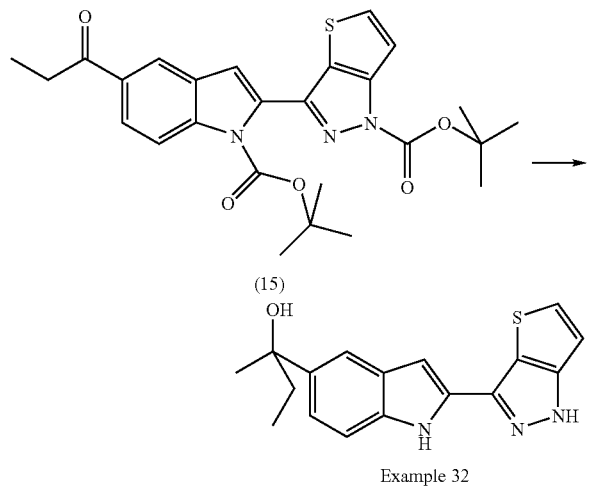

Example 33A and

Example 33B

The racemic mixture 2-[2-(1H-thieno[3,2-c]pyrazol-3-yl)-1H-indol-5-yl]-butan-2-ol [Example 32] is purified by chiral HPLC (Column: chiralcel OJ. Mobile phase: 40% heptane/60% ethanol/0.05% DEA) and the desired eluent fractions are concentrated and lyophilized to afford (R)-2-[2-(1H-thieno[3,2-c]pyrazol-3-yl)-1H-indol-5-yl]-butan-2-ol and (S)-2-[2-(1H-thieno[3,2-c]pyrazol-3-yl)-1H-indol-5-yl]-butan-2-ol isomers. One isomer has chiral HPLC retention time 11.52 minutes at 254 nm; $^1$H NMR [(CD$_3$)$_2$SO)]: δ 13.21 (1H, s), 11.40 (1H, s), 7.73 (1H, d, J=5.2 Hz), 7.58 (1H, s), 7.32 (1H, d, J=8.5 Hz), 7.18 (2H, m), 6.59 (1H, s), 4.65 (1H, s), 1.73 (2H, q), 1.44 (3H, s), 0.70 (3H, t); LC/MS 312 (M+H)] and the other isomer has chiral HPLC retention time 14.35 min at 254 nm; $^1$H NMR [(CD$_3$)$_2$SO)]: δ 13.23 (1H, s), 11.41 (1H, s), 7.75 (1H, d, J=5.2 Hz), 7.60 (1H, s), 7.34 (1H, d, J=8.5 Hz), 7.20 (2H, m), 6.61 (1H, s), 4.67 (1H, s), 1.77 (2H, q), 1.46 (3H, s), 0.72 (3H, t); LC/MS 312 (M+H)].

EXAMPLE 34

1-(2-Pyrrolidin-1-ylmethyl-phenyl)-1-[2-(1H-thieno[3,2-c]pyrazol-3-yl)-1H-indol-5-yl]-propan-1-ol

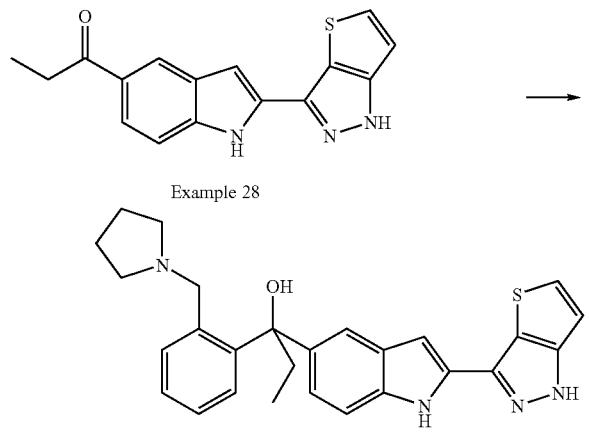

To cooled (−40° C.) solution of 1-[2-(1H-thieno[3,2-c]pyrazol-3-yl)-1H-indol-5-yl]-propan-1-one (110 mg, 0.372 mmol, Example 28) in anhydrous tetrahydrofuran (2 mL) is added (2-(1-pyrrolidinylmethyl)phenyl)magnesium bromide (0.25 M in tetrahydrofuran) under nitrogen. After 1 h, the cooling bath is removed and the reaction temperature brought to room temperature. After overnight it is quenched by the addition of saturated ammonium chloride (2 mL). The resulting precipitate is dissolved with water and extracted three times with ethyl acetate (2 mL). The combined extracts are washed with brine and dried over sodium sulfate. Purification by chromatography (10 silica gel cartridge, 1:1 ethyl acetate/heptane) afforded 1-(2-pyrrolidin-1-ylmethyl-phenyl)-1-[2-(1H-thieno[3,2-c]pyrazol-3-yl)-1H-indol-5-yl]-propan-1-ol (50 mg, Example 34) as white powder; $^1$H NMR [(CD$_3$)$_2$SO)]: δ 13.22 (1H, s), 11.48 (1H, s), 8.73 (1H, s), 7.74 (2H, m), 7.45 (1H, s), 7.41 (1H, t), 7.39-7.25 (4H, m), 6.93 (1H, d), 6.59 (1H, s), 2.68 (1H, d), 2.45 (2H), 2.25 (4H), 2.08 (1H), 1.74 (4H, m), 0.75 (3H, t); LC/MS: 457 (M+H).

EXAMPLE 35

3-(5-Acetyl-1-tert-butoxycarbonyl-1H-indol-2-yl)-thieno[3,2-c]pyrazole-1,5-dicarboxylic acid 1-tert-butyl ester 5-methyl ester

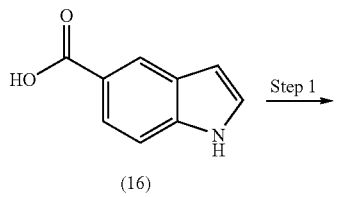

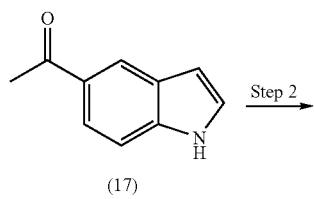

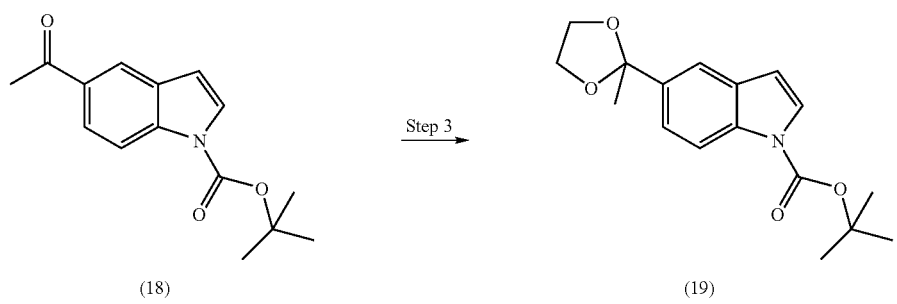

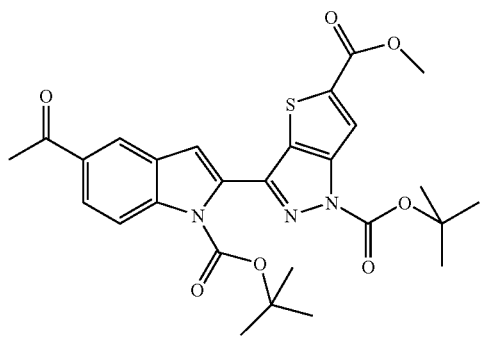

Example 35

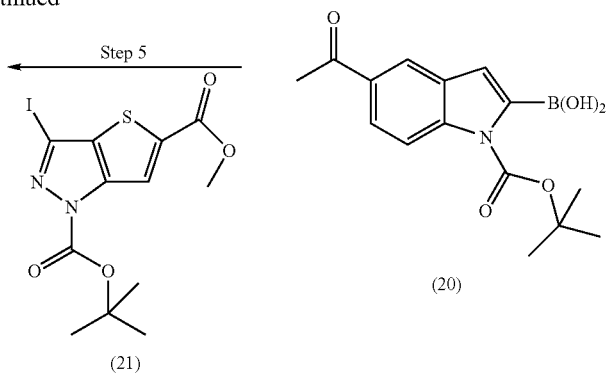

(20)

(21)

Step 1. To a solution of indole-5-carboxylic acid [10 g, 62.05 mmol, Intermediate (16)] in anhydrous tetrahydrofuran (1000 mL) is added methyl lithium (1.6M in diethyl ether, 150 mL) drop wise over 60 minutes periods. The resulting precipitate is stirred at ambient temp for 40 hours.

The reaction is cooled to 0° C. and quenched by the cautious addition of water (5 mL) until boiling stopped. The solvent is removed in vacuo and the slurry mixture is partitioned between dichloromethane (500 mL) and water (100 mL). Dichloromethane layer is washed with 1N hydrochloric acid (20 mL), saturated $NaHCO_3$ (20 mL), brine and dried over sodium sulfate. The residue is chromatographed on 110 g silica gel cartridge (30 to 50% ethyl acetate gradient in heptane) to afford 1-(1H-indol-5-yl)-ethanone [5.0 g, 50.6%, Intermediate (17)] as colorless oil. Oil solidified on standing; $^1$H NMR ($CDCl_3$): δ 8.846 (1H, br s), 8.356 (1H, s), 7.917 (1H, d), 7.449-7.297 (2H, m), 6.690 (1H), 2.713 (3H, s); LC/MS: 160 (M+H).

Step 2. To a solution of 1-(1H-indol-5-yl)-ethanone [5 g, 31.41 mmol, Intermediate (17)] and 4-(dimethylamino)pyridine (39.4 mg) in tetrahydrofuran (60 mL) is added di-tert-butyl-dicarbonate (1M in tetrahydrofuran, 32 mL) drop wise at 0° C. over 55 minutes. Stirred 10 minutes then water (30 mL) is added and the product extracted three times with ethyl acetate (50 mL). The combined ethyl acetate layers are washed with brine and dried over sodium sulfate. The residue is chromatographed on 110 g silica gel cartridge (15-20% ethyl acetate gradient in heptane) afforded 5-acetyl-indole-1-carboxylic acid tert-butyl ester [1.28 g, 81%, Intermediate (18)] as colorless oil. Oil solidified on standing; $^1$H NMR ($CDCl_3$): δ 8.201 (2H), 7.966 (1H), 7.657 (1H), 6.661 (1H), 2.672 (3H), 1.701 (9H); LC/MS: 260 (M+H).

Step 3. A mixture of 5-acetyl-indole-1-carboxylic acid tert-butyl ester [4.85 g, 18.70 mmol, Intermediate (18)], ethylene glycol (5.0 g), pyridinium ρ-toluenesulfonate (100 mg) in benzene (35 mL) is refluxed under $N_2$ with a Dean-Stark trap for 24 hours. To this resulting dark reaction mixture is added solid $NaHCO_3$ (2.5 g). After stirring for 15 minutes, it is filtered under suction and washed three times with ethyl acetate (30 mL). The filtrate is washed twice with water (10 mL) and dried over sodium sulfate. The crude is chromatographed on 10 g silica gel cartridge (heptane then 10% ethyl acetate in heptane) afforded 5-(2-methyl-[1,3]dioxolan-2-yl)-indole-1-carboxylic acid tert-butyl ester [Intermediate (19)] as colorless oil; $^1$H NMR ($CDCl_3$): δ 8.128 (1H, d), 7.706 (1H, s), 7.625 (1H), 7.475 (1H, dd), 6.591 (1H, d), 4.106 (2H, m), 3.843 (2H, m), 1.742 (3H, s), 1.703 (9H, s); LC/MS: 304 (M+H).

Step 4. To a solution of 5-(2-methyl-[1,3]dioxolan-2-yl)-indole-1-carboxylic acid tert-butyl ester [4.96 g, 16.35 mmol, Intermediate (19)] in anhydrous tetrahydrofuran (20 mL) is added triisopropyl borate (4.61 g, 24.51 mmol) and cooled to 0° C. under $N_2$. To it is added LDA (1.8 M in heptane/tetrahydrofuran/ethylbenzene, 14 mL) drop wise at 0° C. over 40 minutes periods. After another 35 minutes, the reaction is quenched by the addition of aqueous 2N hydrochloric acid at 0° C. The white solid precipitated is slowly acidified with 3N hydrochloric acid till pH=3. The mixture became solution which is extracted twice with ethyl acetate (100 mL). The combined ethyl acetate phases are dried over sodium sulfate and filtered. The solid crude is triturated with acetonitrile and water to obtain 5-acetyl-2-methyl-indole-1-carboxylic acid tert-butyl ester (4.76 g, 96%, Intermediate (20)] as light yellow solid; $^1$H NMR ($CDCl_3$): δ 8.30 (2.67, 3H), 8.18 (1H, d), 7.90 (1H, d), 6.78 (1H, s), 2.61 (3H, s), 1.62 (9H, s); LC/MS: $ESI^+$ 304 (M+H)

Alternatively, the crude can be purified by chromatography on silica gel by elution with ethyl acetate in heptane.

Step 5. In a Smith process vial (10-20 mL capacity) is placed 5-acetyl-2-methyl-indole-1-carboxylic acid tert-butyl ester (436 mg, 1.44 mmol, Intermediate (20)], 3-iodo-thieno[3,2-c]pyrazole-1,5-dicarboxylic acid 1-tert-butyl ester 5-methyl ester [392 mg, 0.960 mmol, Intermediate (21)], [1,1'-bis(diphenylphosphino)-ferrocene]dichloropalladium with dichloromethane adduct (78 mg, 0.0955 mmol), cesium carbonate (938 mg, 2.88 mmol) and a mixture of 1,4-dioxane/water (10:2 mL). The reaction tube is filled with $N_2$ and sealed using capping device. The reaction mixture is heated at 90° C. via microwave (Personal chemistry optimizer) for 10 minutes. Water is pipetted out and added solid sodium sulfate. The organic phase is directly loaded onto 10 g silica gel cartridge and chromatographed on 35 g silica gel cartridge (20-30% ethyl acetate gradient in heptane) to afford 3-(5-acetyl-1-tert-butoxycarbonyl-1H-indol-2-yl)-thieno[3,2-c]pyrazole-1,5-dicarboxylic acid 1-tert-butyl ester 5-methyl ester (230 mg, Example 35) as white solid; $^1$H NMR [$(CD_3)_2$ SO)]: δ 8.388 (1H, s), 8.199 (1H), 8.055 (1H), 7.901 (1H, s), 7.339 (1H, s), 3.914 (3H, s), 2.662 (3H, s) 1.671 (9H, s), 1.365 (9H, s); LC/MS: 540 (M+H).

Intermediate (21)

3-iodo-thieno[3,2-c]pyrazole-1,5-dicarboxylic acid 1-tert-butyl ester 5-methyl ester used in Step 5 of Example 35 was prepared as follows:

continued overnight. The cooled mixture is diluted with ethyl acetate (100 mL), filtered and the filtrate is concentrated to a black solid which is purified by chromatography, eluting with heptane-25% ethyl acetate, heptane-35% ethyl acetate, heptane-40% ethyl acetate, heptane-50% ethyl acetate, heptane-60% ethyl acetate. Fractions containing pure product are combined and concentrated to afford 1-acetyl-1 H-thieno[3,2-c]pyrazole-5-carboxylic acid methyl ester [9.74 g, 49.3%, Intermediate (25)].

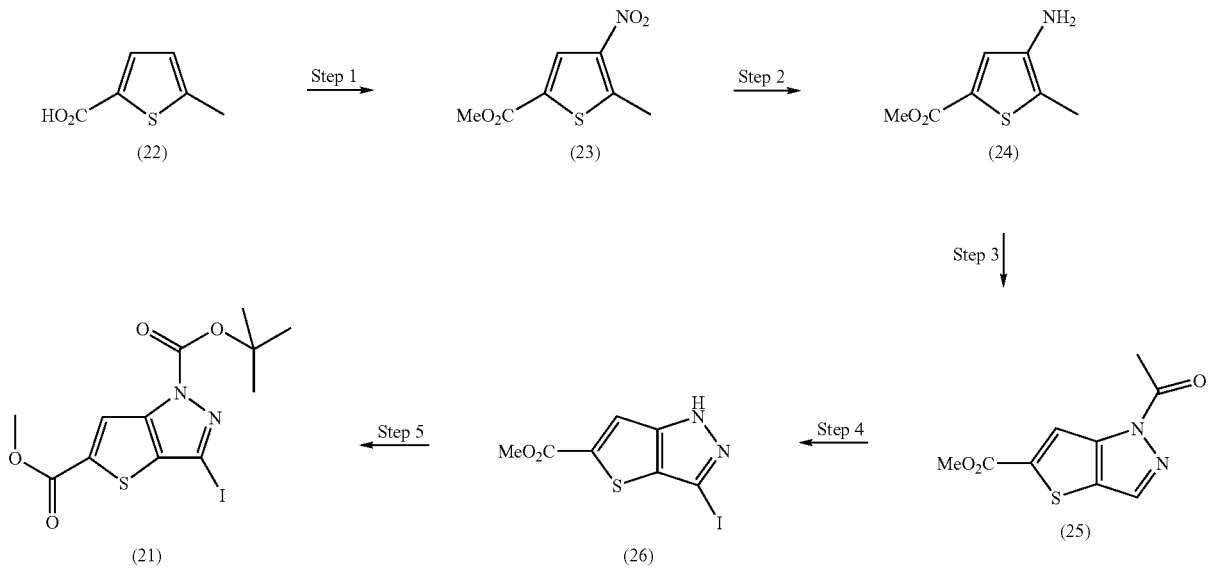

Step 1. 5-Methyl-4-nitro-thiophene-2-carboxylic acid is prepared according to Snider et al. (H. R. Snider and L. A. Carpino, J. F. Zack, Jr., J. F. Mills, *J. Am. Chem. Soc.*, 1951, 79, 2556-2559) from commercially available 5-methylthiophene-2-carboxylic acid and is esterified according to known processes (P. Cogolli, F. Maiolo, L. Testaferri, M. Tiecco, M. Tingoli, *J. Chem. Soc., Perkin I*, 1980, 1331-1335; V. M. Colburn, B. Iddon, H. Shuschitzky, *J. Chem. Soc., Perkin I*, 1977, 2436-2441) to obtain 5-methyl-4-nitro-thiophene-2-carboxylic acid methyl ester [Intermediate (23)].

Step 2. 5-Methyl-4-nitro-thiophene-2-carboxylic acid methyl ester [15.09 g., 75.0 mM, Intermediate (23)] is dissolved in ethyl acetate (200 mL) to which 10% palladium on charcoal (1.03 g) is added and the mixture is shaken under 50 psi of hydrogen. The catalyst is removed by filtration and the solvent is removed leaving 4-amino-5-methyl-thiophene-2-carboxylic acid methyl ester [12.82 g., 99.8%, Intermediate (24)] as a yellow solid; MS 171.9 (100%, M+1).

Step 3. A magnetically stirred mixture of potassium acetate (4.52 g, 46.1 mM) in toluene (100 mL) containing 4-amino-5-methyl-thiophene-2-carboxylic acid methyl ester [12.8 g, 74.7 mM, Intermediate (24)] is warmed to dissolve the amine. Acetic anhydride (13.8 mL, 124.9 mM) is added to this mixture and it is heated in an oil bath. Isoamyl nitrite (9.73 mL, 72.4 mM) is added over 30 minutes. Heating at 93° C. is Step 4. To a suspension of 1-acetyl-1H-thieno[3,2-c]pyrazole-5-carboxylic acid methyl ester [1.3 g, 5.79 mmol, Intermediate (25)] in methanol (30 mL) is added sodium methoxide (25 wt % in methanol). The resulting solution mixture is stirred at 60° C. oil bath for 20 minutes. The oil bath is removed and stirred for 5 minutes. To this is added a solution of iodine (1.76 g, 6.93 mmol) in dimethyl formamide (2 mL). The reaction mixture then heated to 60° C. for 1 hour. The solvent is removed in vacuo. The crude is partitioned between ethyl acetate (100 mL) and water (100 mL) and aqueous layer is further extracted with twice ethyl acetate (25 mL). The combined ethyl acetate phases are washed with brine, dried over sodium sulfate and filtered. The solvent is removed in vacuo to give 3-iodo-1H-thieno[3,2-c]pyrazole-5-carboxylic acid methyl ester [1.58 g, 89%, Intermediate (26)] as light yellow solid; $^1$H NMR [(CD$_3$)$_2$SO)]: δ 13.80 (1H, brs, NH), 7.947 (1H, s), 3.870 (3H, s).

Step 5. To a mixture of 3-iodo-1H-thieno[3,2-c]pyrazole-5-carboxylic acid methyl ester [1.5 g, 4.87 mmol, Intermediate (26)] in tetrahydrofuran (120 mL) is added 4(dimethylamino)pyridine (8 mg) and di-tert-butyl-dicarbonate (1M in tetrahydrofuran, 5.3 mL) dropwise at room temperature. After stirring for 30 minutes, the solvent is removed in vacuo. The solid is suspended in a mixture of ethyl acetate, heptane and methanol and stirred for a while. The solid is filtered and vacuum dried to give 3-iodo-thieno[3,2-c]pyrazole-1,5-dicarboxylic acid 1-tert-butyl ester 5-methyl ester [1.72 g, 87%, Intermediate (21)] as off-white solid; ¹H NMR [(CD₃)₂SO)]: δ 6.880 (1H, s), 3.900 (3H, s), 1.633 (9H, s); LC/MS: 409 (M+H).

EXAMPLE 36

3-(5-Acetyl-1H-indol-2-yl)-1H-thieno[3,2-c]pyrazole-5-carboxylic acid methyl ester

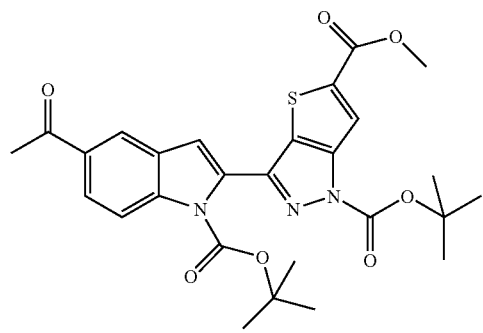

Example 35

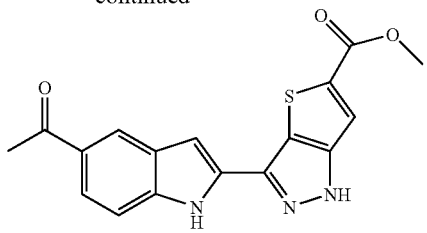

Example 36

A solution of 3-(5-acetyl-1-tert-butoxycarbonyl-1H-indol-2-yl)-thieno[3,2-c]pyrazole-1,5-dicarboxylic acid 1-tert-butyl ester 5-methyl ester (115 mg, 0.213 mmol, Example 35) in tetrahydrofuran (5 mL) is treated with 2N hydrochloric acid (aqueous, 3 mL) and heated at 70° C. for 17 hours. The reaction is cooled to room temperature and neutralized with Na₂CO₃ (aqueous). The aqueous phase is extracted three times with ether (10 mL). Combined ether phases are washed with brine and dried over sodium sulfate. Purification by chromatography on 10 g silica gel cartridge (50-70% ethyl acetate gradient in heptane) afforded 3-(5-acetyl-1H-indol-2-yl)-1H-thieno[3,2-c]pyrazole-5-carboxylic acid methyl ester (15 mg, Example 36) as white solid; ¹H NMR [(CD₃)₂SO)]: δ 13.82 (1H, s), 12.13 (1H, s), 8.34 (1H, s), 7.97 (1H, s), 7.78 (1H, d), 7.50 (1H, d), 6.90 (1H, s), 3.91 (3H, s), 2.61 (3H, s); LC/MS: 340 (M+H).

EXAMPLE 37

3-(5-Hydroxymethyl-1H-indol-2-yl)-1H-thieno[3,2-c]pyrazole-5-carboxylic acid

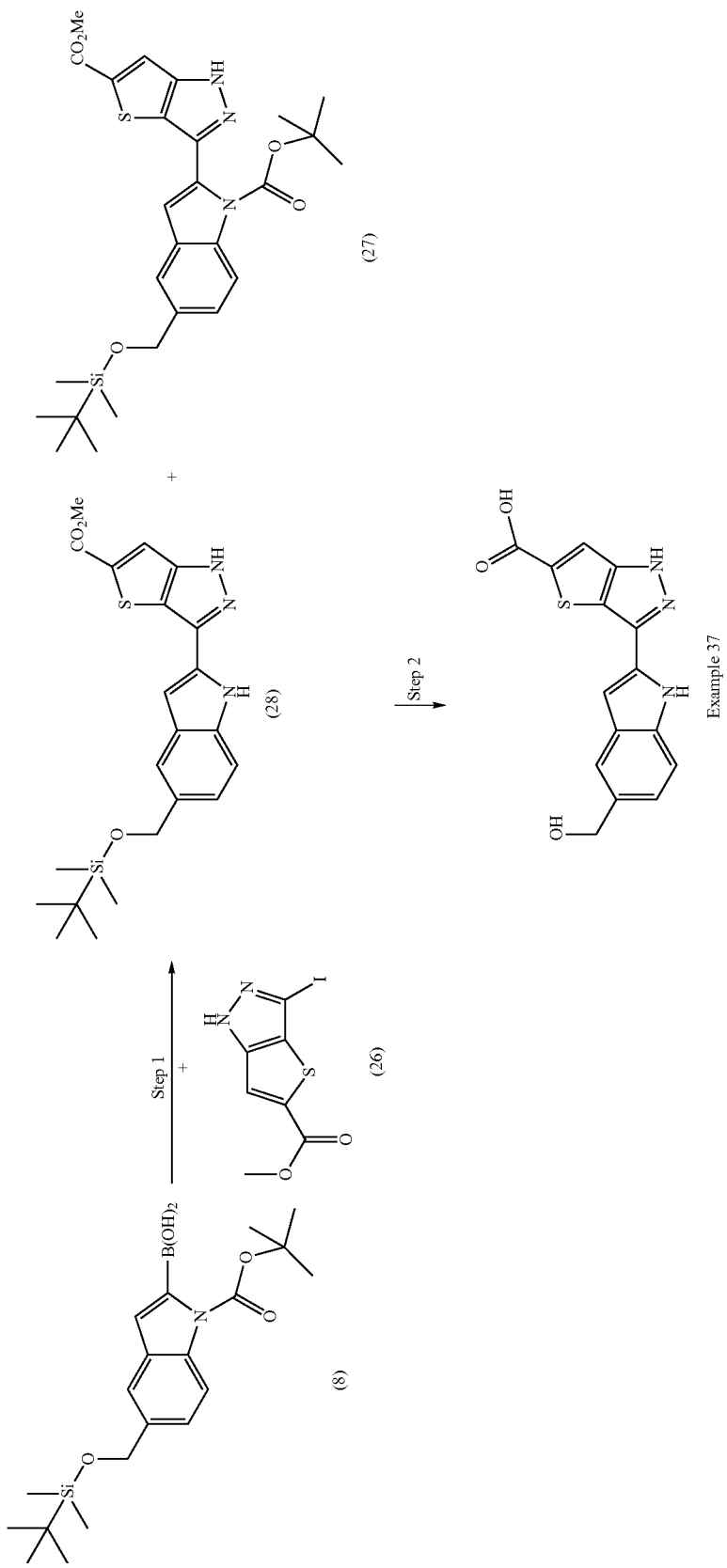

Step 1. In two separate Smith process vials (10-20 mL capacity) are added 3-iodo-1H-thieno[3,2-c]pyrazole-5-carboxylic acid methyl ester [420 mg, 1.36 mmol, Intermediate (26)], 5-(tert-butyl-dimethyl-silanyloxymethyl)-1H-indole-2-boronic acid 1-carboxylic acid tert-butyl ester [912 mg, 2.25 mmol, Intermediate (8), prepared as described in Example 1-4 of International Patent Application Publication No. WO 02/32861], potassium carbonate (2M, aqueous, 2.25 mL) tetrakis(triphenylphosphine)palladium(0) (87 mg, 0.0752 mmol), and a mixture of toluene/ethanol (9:3 mL). The reaction tube is filled with N₂ and sealed using capping device. The reaction mixture is heated to 120° C. using microwave (Personal chemistry optimizer) for 900 seconds. After reactions are over combined them into a flask, diluted with ethyl acetate (50 mL) and washed twice with water (10 mL), brine and dried over sodium sulfate. Purification by chromatography on 35 g silica gel cartridge (30-50% ethyl acetate gradient in heptane) gave two major fractions. The higher rising $R_f$ fractions are combined and evaporated solvent in vacuo to give 5-(tert-butyl-dimethyl-silanyloxymethyl)-2-(5-methoxycarbonyl-1H-thieno[3,2-c]pyrazol-3-yl)-indole-1-carboxylic acid tert-butyl ester [653 mg, Intermediate (27)] as light yellow solid. LC/MS: 542 (M+H). The lower rising $R_f$ fractions are combined and evaporated in vacuo to give product 3-[5-(tert-butyl-dimethyl-silanyloxymethyl)-1H-indol-2-yl]-1H-thieno[3,2-c]pyrazole-5-carboxylic acid methyl ester [253 mg, Intermediate (28)] as light yellow solid; LC/MS: 442 (M+H).

Step 2. To a solution of 3-[5-(tert-butyl-dimethyl-silanyloxymethyl)-1H-indol-2-yl]-1H-thieno[3,2-c]pyrazole-5-carboxylic acid methyl ester (1.0 g, 2.26 mmol, intermediate 28) in tetrahydrofuran (20 mL) is added sodium hydroxide (500 mg) and water (7 mL) and heated at 60° C. oil bath for 16 hours. To it is added water and adjusted pH to 4 with 2N hydrochloric acid. The product is extracted with three times ethyl acetate (50 mL). The combined ethyl acetate phases are washed with brine and dried over sodium sulfate. Purification by chromatography using silica gel (ethyl acetate then 10% methanol in ethyl acetate) afforded oil. The oil is dissolved in methanol and triturated with water to give 3-(5-hydroxymethyl-1H-indol-2-yl)-1H-thieno[3,2-c]pyrazole-5-carboxylic acid (286 mg, 91%, Example 37) as beige solid; ¹H NMR [(CD₃)₂SO)]: δ 13.572 (2H, br s), 11.570 (1H, s), 7.817 (1H), 7.509 (1H, s), 7.381 (1H, d), 7.104 (1H, d), 6.677 (1H, s), 5.004 (1H, OH), 4.550 (2H, CH₂OH); LC/MS: 313 (M+H).

EXAMPLE 38

[4-(4-Fluoro-phenyl)-piperazin-1-yl]-[3-(5-hydroxymethyl-1H-indol-2-yl)-1H-thieno[3,2-c]pyrazol-5-yl]-methanone

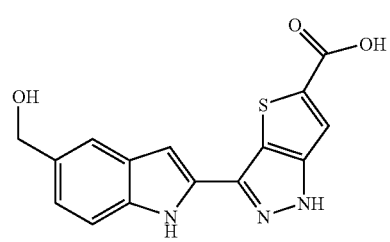

Example 37

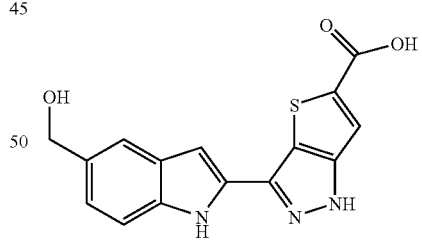

Example 38

To a solution of 3-(5-hydroxymethyl-1H-indol-2-yl)-1H-thieno[3,2-c]pyrazole-5-carboxylic acid [124 mg, 0.396 mmol, Example (37)] in dimethyl formamide (5 mL) is added 1-ethyl-3-(3-dimethylaminopropyl)carbodiimide (91 mg, 0.474 mmol) and 1-hydroxybenzotriazole (54 mg, 0.399 mmol). After stirring for 10 minutes, to it is added diisopropylethylamine (0.138 mL) and 1-(4-fluorophenyl)piperazine (79 mg, 0.438 mmol). The resulting yellow solution mixture is stirred at room temperature overnight. The reaction mixture is diluted in ethyl acetate (60 mL) and washed with water (3×10 mL), brine and dried over sodium sulfate. Purification by chromatography on silica gel (50% ethyl acetate/heptane then ethyl acetate) gave solid. The solid is redissolved in methanol and triturated with water to give [4-(4-fluoro-phenyl)-piperazin-1-yl]-[3-(5-hydroxymethyl-1H-indol-2-yl)-1H-thieno[3,2-c]pyrazol-5-yl]-methanone [110 mg, 56%, Example (38)] as cream solid, mp=156-158° C.; ¹H NMR [(CD₃)₂SO)]: δ 13.490 (1H, s), 11.59 (1H, s), 7.563 (2H), 7.356 (1H), 7.109-6.985 (5H, m), 6.648 (1H), 5.004 (1H, t, OH), 4.553 (2H, d, OCH₂), 3.856 (4H, br s), 3.208 (4H, br peak); LC/MS: 476 (M+H).

EXAMPLE 39

3-(5-Hydroxymethyl-1H-indol-2-yl)-1H-thieno[3,2-c]pyrazole-5-carboxylic acid (3-ethoxy-propyl)-amide

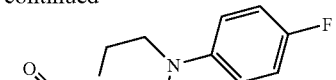

Example 37

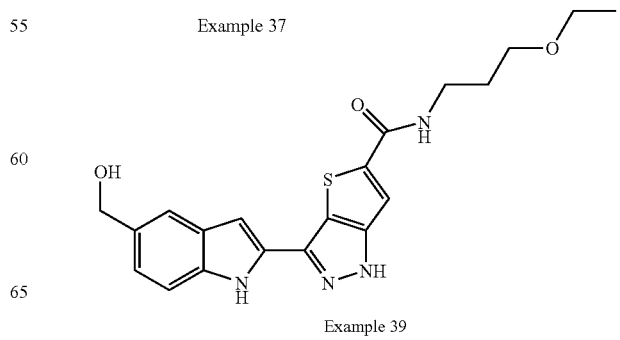

Example 39

To a mixture of 3-(5-hydroxymethyl-1H-indol-2-yl)-1H-thieno[3,2-c]pyrazole-5-carboxylic acid [159 mg, 0.507 mmol, Example 37], 1-hydroxybenzotriazole (116 mg, 0.858 mmol), PS-carbodiimide (1.2 mmol/g, 845 mg) in Dichloromethane (8 mL) and dimethyl formamide (2 mL) is stirred at room temperature for 25 minutes before addition of 3-ethoxypropylamine (45 mg, 0.436 mmol). After 4 h, PS-trisamine (4.03 mmol/g, 500 mg) is added and stirred for 6 hours. The reaction mixture is filtered and the resin washed under suction with Dichloromethane (3×15 mL). The filtrate is evaporated in vacuo. The crude is purified by chromatography on 10 g silica gel cartridge (ethyl acetate then 1% methanol in ethyl acetate) to give thick semi solid. It is redissolved in methanol and triturated with water to give 3-(5-hydroxymethyl-1H-indol-2-yl)-1H-thieno[3,2-c]pyrazole-5-carboxylic acid (3-ethoxy-propyl)-amide [30 mg, Example 39] as pale yellow solid; $^1$H NMR [(CD$_3$)$_2$SO)]: δ 13.490 (1H, s, NH), 11.56 (1H, NH, s), 8.70 (1H, t), 7.88 (1H, s), 7.51 (1H, s), 7.38 (1H, d), 7.10 (1H, s), 6.66 (1H, s), 5.01 (1H, t, OH), 4.55 (2H, HOCH$_2$—), 3.44 (6H, m), 1.80 (2H), 1.12 (3H, t); LC/MS: 399 (M+H).

EXAMPLE 40

3-(5-Hydroxymethyl-1H-indol-2-yl)-1H-thieno[3,2-c]pyrazole-5-carboxylic acid methyl ester

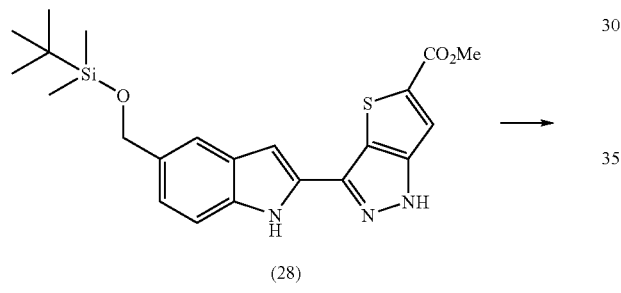

(28)

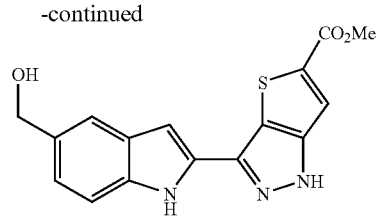

Example 40

A solution of 3-[5-(tert-butyl-dimethyl-silanyloxymethyl)-1H-indol-2-yl]-1H-thieno[3,2-c]pyrazole-5-carboxylic acid methyl ester [192 mg, 0.435 mmol, Intermediate (28)] is dissolved in tetrahydrofuran (10 mL) and treated with tetrabutylammonium fluoride (1.0 M in tetrahydrofuran, 0.52 mL) and stirred overnight. The reaction mixture is diluted in ethyl acetate and washed with water, brine and dried over sodium sulfate. The residue is chromatographed on 10 g silica gel cartridge (50% ethyl acetate in heptane then ethyl acetate) to obtain solid. Recrystallization from ethyl acetate and heptane afforded 3-(5-hydroxymethyl-1H-indol-2-yl)-1H-thieno[3,2-c]pyrazole-5-carboxylic acid methyl ester [90 mg, 73%, Example 40] as beige solid; $^1$H NMR [(CD$_3$)$_2$SO)]: δ 13.66 (1H, s), 11.60 (1H, s), 7.92 (1H, s), 7.51 (1H, s), 7.38 (1H, d, J=8.2 Hz), 7.10 (1H, d, J=8.2 Hz), 6.68 (1H, s), 5.75 (1H, br s, OH), 4.54 (2H, s, —CH$_2$OH), 3.90 (3H, s, —CO$_2$CH$_3$); LC/MS 328 (M++H).

EXAMPLE 41

3-(5-Hydroxymethyl-1H-indol-2-yl)-1H-thieno[3,2-c]pyrazole-5-carboxylic acid (pyridin-2-ylmethyl)-amide

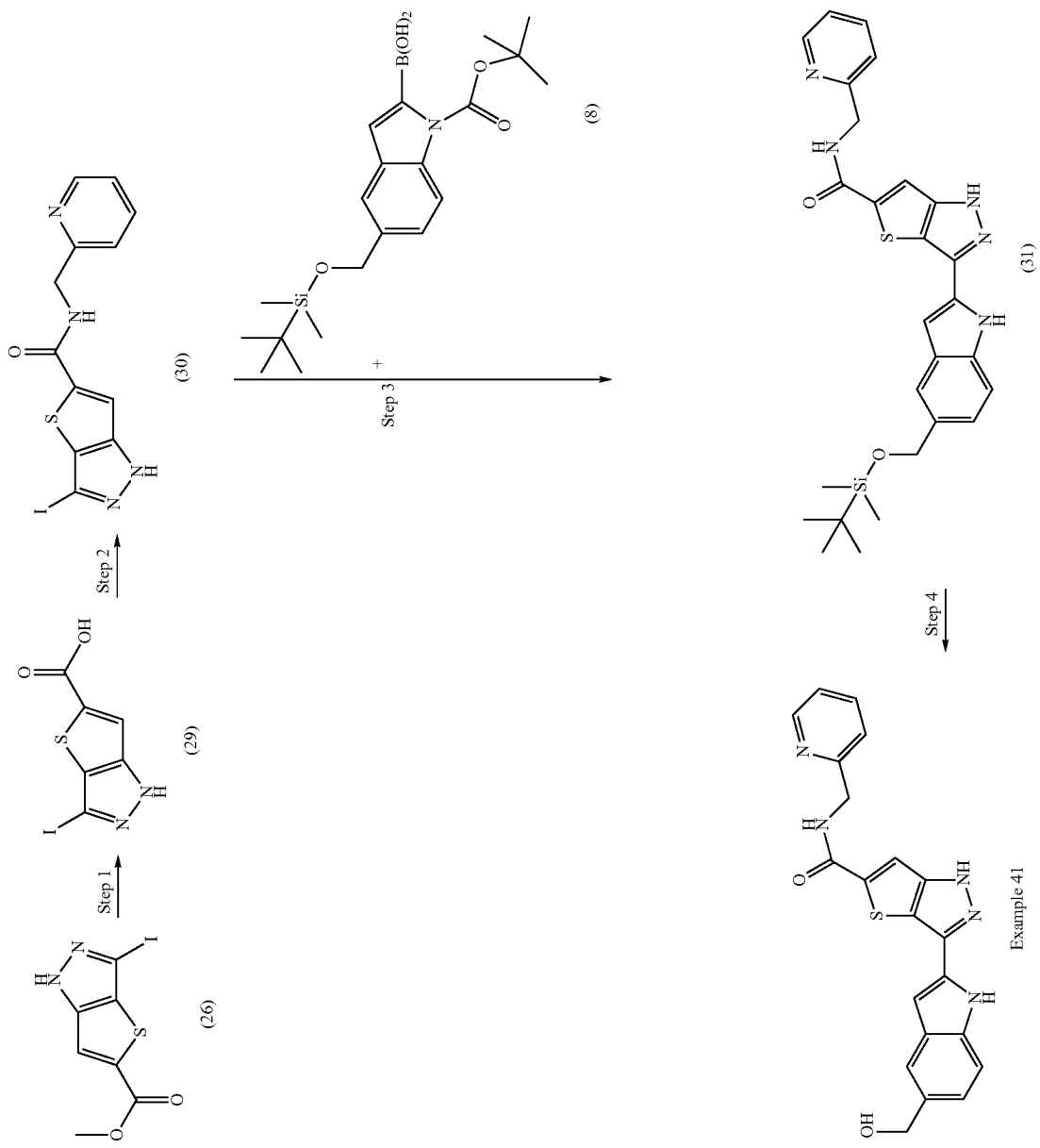

Step 1. To a solution of 3-iodo-1H-thieno[3,2-c]pyrazole-5-carboxylic acid methyl ester [4.5 g, 14.60 mmol, Intermediate (26)] in tetrahydrofuran (90 mL) is added potassium hydroxide (2.83 g, 50.44 mmol) and water (20 mL). The resulting reaction mixture is heated at 60° C. oil bath under for 2 hours. The solvent is removed in vacuo and dissolved crude in water (20 mL). The water layer is acidified using 2N hydrochloric acid till pH is 5. White solid precipitated are collected and rinsed with water. The filtrate is extracted three times with ethyl acetate (50 mL). The combined ethyl acetate phases are washed with brine and dried over magnesium sulfate and filtered. Combined solids and stirred in heptane and filtered to obtain 3-iodo-1H-thieno[3,2-c]pyrazole-5-carboxylic acid [2.15 g, 50%, Intermediate (29)] as white solid; $^1$H NMR [(CD$_3$)$_2$SO)]: δ 13.711 (1H, s), 7.832 (1H, s); LC/MS: 294 (M+H).

Step 2. A mixture of 3-iodo-1H-thieno[3,2-c]pyrazole-5-carboxylic acid [1.05 g, 3.57 mmol, Intermediate (29)], 1-ethyl-3-(3-dimethylaminopropyl)carbodiimide (821 mg, 4.28 mmol), 1-hydroxybenzotriazole (482 mg, 3.57 mmol) in dimethyl formamide (45 mL) is stirred at room temperature for 10 minutes. To it is added diisopropylethylamine (1.3 mL, 7.46 mmol) followed by a solution of 2-(aminomethyl)pyridine (425 mg, 3.93 mmol) in dimethyl formamide (2 mL). After stirring overnight, the reaction mixture is diluted with ethyl acetate (200 mL) and washed water, brine and dried over sodium sulfate. The residue is chromatographed on 35 g silica gel cartridge (ethyl acetate and 10% methanol in ethyl acetate) to give 3-iodo-1H-thieno[3,2-c]pyrazole-5-carboxylic acid (pyridin-2-ylmethyl)-amide [1.08 g, 79%, Intermediate (30)] as a light yellow solid; LC/MS: 385 (M+H); $^1$H NMR [(CD$_3$)$_2$SO)]: δ 13.67 (1H, s), 9.35 (1H, t), 8.53 (1H), 8.01 (1H), 7.80 (1H), 7.36 (1H, d), 7.28 (1H), 4.58 (2H, d).

Step 3. In a Smith process vial (10-20 mL capacity) is added 3-iodo-1H-thieno[3,2-c]pyrazole-5-carboxylic acid (pyridin-2-ylmethyl)-amide [255 mg, 0.664 mmol, Intermediate (30)], 5-(tert-butyl-dimethyl-silanyloxymethyl)-1H-indole-2-boronic acid 1-carboxylic acid tert-butyl ester [404 mg, 0.997 mmol, Intermediate (8), prepared as described in Example 1-4 of International Patent Application Publication No. WO 02/32861], tetrakis(triphenylphosphine)palladium (0) (77 mg, 0.0666 mmol), potassium carbonate (2M aqueous, 1 mL) and toluene/ethanol (6:3 mL). The reaction tube is filled with N$_2$ and sealed using capping device. The resulting reaction mixture is heated to 120° C. using a microwave (Personal chemistry optimizer) for 1020 s. The reaction mixture is diluted with ethyl acetate (50 mL), washed twice with water (10 mL), brine and dried over sodium sulfate. Purification by chromatography using 10 silica gel cartridge (50 ethyl acetate in heptane, ethyl acetate then 10% methanol in ethyl acetate) afforded 3-[5-(tert-butyl-dimethyl-silanyloxymethyl)-1H-indol-2-yl]-1 H-thieno[3,2-c]pyrazole-5-carboxylic acid (pyridin-2-ylmethyl)-amide [397 mg, Intermediate (31)] as yellow oil.

Step 4. To a solution of 3-[5-(tert-butyl-dimethyl-silanyloxymethyl)-1H-indol-2-yl]-1H-thieno[3,2-c]pyrazole-5-carboxylic acid (pyridin-2-ylmethyl)-amide [258 mg, 0.498 mmol, Intermediate (31)] in tetrahydrofuran (10 mL) is added tetrabutylammonium fluoride (1.0 M in tetrahydrofuran, 0.6 mL) and stirred at room temperature for 16 hours. Water is added and extracted three times with ethyl acetate (30 mL). The combined ethyl acetate phases are washed with brine and dried over sodium sulfate. Purification by chromatography on 10 g silica gel cartridge (9:1 ethyl acetate in methylene chloride then 8:1:1 ethyl acetate/methylene chloride/methanol) afforded 3-(5-hydroxymethyl-1H-indol-2-yl)-1H-thieno[3,2-c]pyrazole-5-carboxylic acid (pyridin-2-ylmethyl)-amide [85 mg, 43%, Example 41] as a white solid; $^1$H NMR [(CD$_3$)$_2$SO)]: δ 13.51 (1H, s, NH), 11.545 (1H, s, NH), 9.358 (1H, C(O)NH, t, J=5.7 Hz), 8.533 (1H, d, J=4.5 Hz), 7.990 (1H, s), 7.808 (1H, m), 7.503 (1H, s), 7.387-7.266 (3H, m), 7.097 (1H, d, J=8.1 Hz), 6.663 (1H, s), 5.021 (1H, OH, t, J=5.7 Hz), 4.612 (2H, d, J=6 Hz), 4.551 (2H, d, J=5.7 Hz); LC/MS: 404 (M+H).

EXAMPLE 42

5-Bromo-2-(1H-thieno[3,2-c]pyrazol-3-yl)-1H-indole

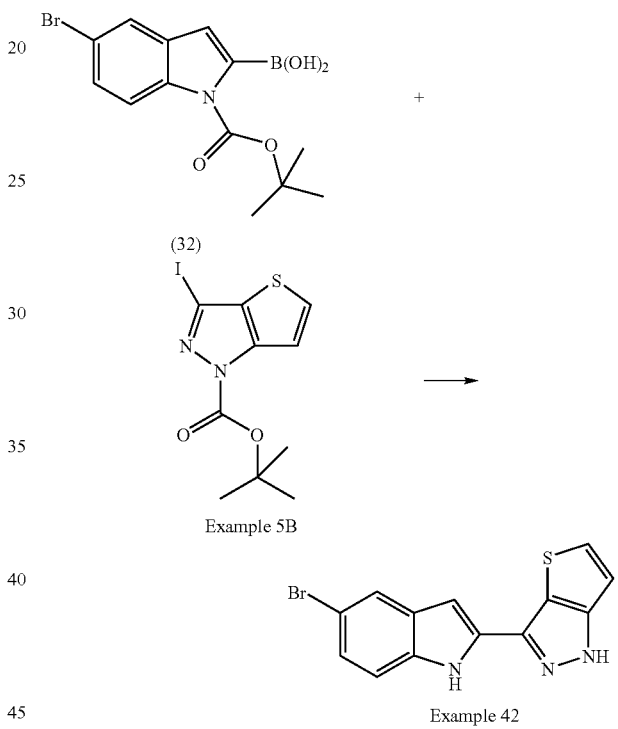

Example 5B

Example 42

In a Smith process vial (10-20 mL capacity) is placed 5-bromo-2-methyl-indole-1-carboxylic acid tert-butyl ester [290 mg, 1.11 mmol, Intermediate (32) prepared as described in J. Org. Chem 2002, 67, 7551], 3-iodo-thieno[3,2-c]pyrazole-1-carboxylic acid tert-butyl ester [250 mg, 0.714 mmol, Example 5B above], [1,1'-bis(diphenylphosphino)-ferrocene]dichloropalladium with dichloromethane adduct (58 mg, 0.0710 mmol), cesium carbonate (698 mg, 2.14 mmol) and a mixture of 1,4-dioxane/water (13:2 mL). The reaction tube is filled with nitrogen and sealed using capping device. The reaction mixture is heated at 90° C. via microwave (Personal chemistry optirnizer) for 20 minutes at high absorption. The content is transferred to separate funnel using ethyl acetate (60 mL). The ethyl acetate layer is washed with water (20 mL), brine and then dried over sodium sulfate. The crude is purified using 35 g silica gel cartridge (5 to 15% ethyl acetate gradient in heptane) to afford product (280 mg, 49%) as beige solid. The solid (90 mg, 0.174 mmol) is placed in a Smith vial (10-20 mL capacity). To it is added potassium carbonate (90 mg) and tetrahydrofuran/methanol/H₂O (10:5:3 mL). The reaction tube is sealed using capping device and heated at 70° C. for 10 minutes at normal absorption. The reaction mixture is diluted with ethyl acetate and washed with water, brine and dried over sodium sulfate. The crude is purified using 10 g silica gel cartridge (50% ethyl acetate in heptane) to give 5-bromo-2-(1H-thieno[3,2-c]pyrazol-3-yl)-1H-indole [44 mg, 80%, Example 42] as light yellow solid;

$^1$H NMR [(CD$_3$)$_2$SO)]: δ 13.33 (1H, s), 11.80 (1H, s), 7.76 (2H), 7.38 (1H), 7.21 (2H), 6.64 (1H, s); LC/MS: 317 (M+H).

EXAMPLE 43

2-(1H-Thieno[3,2-c]pyrazol-3-yl)-1H-indole-6-carboxylic acid methyl ester

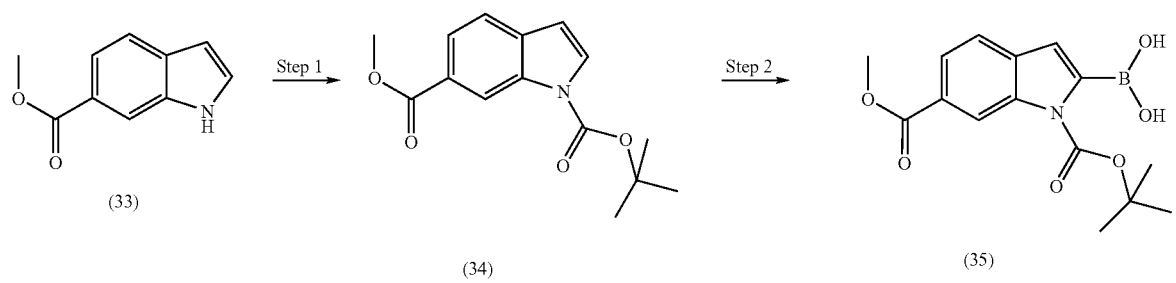

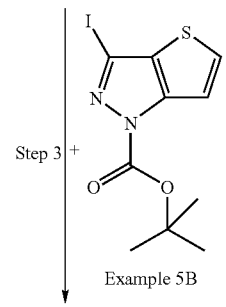

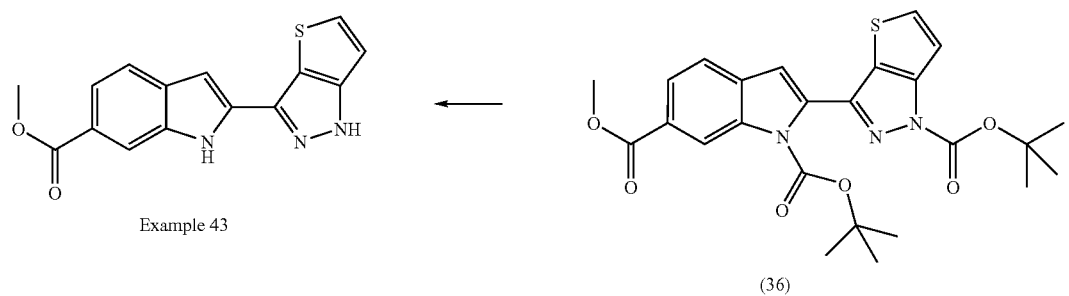

Step 1. To a solution of 1H-Indole-6-carboxylic acid methyl ester [26.65 g, 146 mmol, Intermediate (33)] and 4-(dimethylamino)pyridine (230 mg) in anhydrous tetrahydrofuran (490 mL) is added di-tert-butyl-dicarbonate (1M in tetrahydrofuran, 150 mL) drop wise over 40 minute periods. Stirred at room temperature for 100 minutes. The solvent is removed in vacuo and the mixture is redissolved in ethyl acetate (400 mL). The ethyl acetate layer is washed with water (20 mL), 0.5 N hydrochloric acid (20 mL), 10% $NaHCO_3$ (20 mL), water (20 mL), brine and dried over sodium sulfate then filtered over 5 g silica gel cartridge. The filtrate is reduced in vacuo to solid. The solid is recrystallized from a mixture of ethyl acetate and heptane to give indole-1,6-dicarboxylic acid 1-tert-butyl ester 6-methyl ester as a white solid (18.53 g). The recrystallisation step is repeated to give a second crop of indole-1,6-dicarboxylic acid 1-tert-butyl ester 6-methyl ester as a white solid (16.3 g). A third crop (5.17 g) of indole-1,6-dicarboxylic acid 1-tert-butyl ester 6-methyl ester is obtained from the mother liquor by silica gel chromatography; total yield of indole-1,6-dicarboxylic acid 1-tert-butyl ester 6-methyl ester [40 g, 100%, Intermediate (34)]; $^1H$ NMR (cdcl$_3$) δ 8.886 (1H, s), 7.937 (1H, d), 7.764 (1H), 7.621 (1H, d), 6.636 (1H), 3.972 (3H, s), 1.734 (9H, s); LC/MS: 276 (M+H).

Step 2. A solution of indole-1,6-dicarboxylic acid l-tert-butyl ester 6-methyl ester [13.32 g, 48.38 mmol, Intermediate (34)] and triisopropyl borate (13.65 g, 72.58 mmol) in anhydrous tetrahydrofuran (200 mL) is cooled to 0° C. under nitrogen. To it is added LDA (1.8 M in heptane/tetrahydrofuran/ethylbenzene, 35 mL) drop wise over 40 minute periods. Stirred at 0° C. for 1.5 hours. The reaction is quenched by the addition of 3N hydrochloric acid until pH~4 on pH paper. After stirring at 0° C. for 5 minutes, the mixture is partitioned between ethyl acetate (200 mL) and water (50 mL). The ethyl acetate layer is washed with brine and dried over sodium sulfate. The residue is purified on 300 g silica gel cartridge (30 to 50% ethyl acetate gradient in heptane then 100% ethyl acetate). The fractions containing higher $R_f$ spot are combined and removed solvent in vacuo to give off-white solid (2.32 g). $^1$HNMR and M/S confirmed it as recovered starting material, indole-1,6-dicarboxylic acid 1-tert-butyl ester 6-methyl ester. The fractions containing lower $R_f$ spot are combined and removed solvent in vacuo. The residual solid (14.2 g) is triturated with acetonitrile and water to give 6-methoxycarbonyl-1-tert-butoxycarbonyl-indole-2-boronic acid [11.8 g, 76.5%, Intermediate (35)] as a beige solid; $^1H$ NMR [(CD$_3$)$_2$SO)]: δ 8.764 (1H, s), 8.311 (2H, s, B(OH)$_2$), 7.795 (1H, d), 7.675 (1H, d), 6.713 (1H, s), 3.876 (3H, s), 1.621 (9H, s).

Step 3. A mixture of 6-methoxycarbonyl-1-tert-butoxycarbonyl-indole-2-boronic acid (3.24 g, 10.15 mmol Intermediate (35)], 3-iodo-thieno[3,2-c]pyrazole-1-carboxylic acid tert-butyl ester [2.37 g, 6.77 mmol, Example 5B above], [1,1'-bis (diphenylphosphino)-ferrocene]dichloropalladium with dichloromethane adduct (552 mg, 0.676 mmol), cesium carbonate (6.61 g, 20.29 mmol) and a mixture of 1,4-dioxane/water (40:10 mL). The resulting mixture is heated at 82° C. oil bath for 3 hours under nitrogen. The reaction mixture is poured into ethyl acetate (300 mL). The ethyl acetate layer is washed twice with water (20 mL), brine and dried over sodium sulfate. The crude reaction product is purified on 110 g silica gel cartridge (3% of a mixture of ethyl acetate in methylene chloride and 97% heptane) to afford 2-(1-tert-butoxycarbonyl-1H-thieno[3,2-c]pyrazol-3-yl)-indole-1,6-dicarboxylic acid 1-tert-butyl ester 6-methyl ester [1.68 g, 50%, Intermediate (36)] as white foam; $^1H$ NMR [(CD$_3$)$_2$SO)]: δ 8.975 (1H, s), 8.017 (1H), 7.669 (1H), 7.583 (1H), 7.379 (1H), 7.048 (1H, s), 3.986 (3H, s), 1.736 (9H, s), 1.440 (9H, s); LC/MS: 498 (M+H). A mixture of 1H-thieno[3,2-c]pyrazol-3-yl)-indole-1,6-dicarboxylic acid 1-tert-butyl ester 6-methyl ester or 2-(1-tert-butoxycarbonyl-1H-thieno[3,2-c]pyrazol-3-yl)-indole-1,6-dicarboxylic acid 6-methyl ester, and 2-(1-tert-butoxycarbonyl-1H-thieno[3,2-c]pyrazol-3-yl)-indole-1,6-dicarboxylic acid 1-tert-butyl ester 6-methyl ester material is also isolated (340 mg). 2-(1-Tert-butoxycarbonyl-1H-thieno[3,2-c]pyrazol-3-yl)-indole-1,6-dicarboxylic acid 1-tert-butyl ester 6-methyl ester [Intermediate (36)] is dissolved in methanol/tetrahydrofuran/water (20 mL, 10:5:3) and treated with potassium carbonate (300 mg). The resulting mixture is stirred at room temperature overnight. The reaction mixture is diluted with ethyl acetate (200 mL) and washed with water, brine and dried over sodium sulfate. The crude is purified on 35 g silica gel cartridge (50% ethyl acetate in heptane then ethyl acetate) to afford 2-(1H-thieno[3,2-c]pyrazol-3-yl)-1H-indole-6-carboxylic acid methyl ester [136 mg, Example 43] as a white powder; $^1H$ NMR [(CD$_3$)$_2$SO)]: δ 13.434 (1H, s), 12.044 (1H, s), 8.093 (1H, s), 7.789-7.631 (3H, m), 7.231 (1H, d, J=5.4 Hz), 6.752 (1H, s), 3.855 (3H, s); LC/MS: 298 (M+H).

EXAMPLE 44

Dicyclopropyl-[2-(1H-thieno[3,2-c]pyrazol-3-yl)-1H-indol-6-yl]-methanol

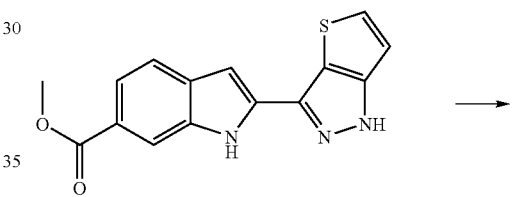

Example 43

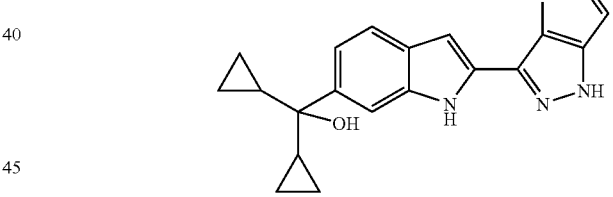

Example 44

To a mixture of 2-(1H-Thieno[3,2-c]pyrazol-3-yl)-1H-indole-6-carboxylic acid methyl ester (180 mg, 0.605 mmol, Example 43) in anhydrous tetrahydrofuran (8 mL) is added cyclopropylmagnesium bromide (6.0 mL, 0.5 M in tetrahydrofuran) at 0° C. The ice bath is removed and the reaction mixture stirred at room temperature for 4 hours. To it is added an additional cyclopropylmagnesium bromide (6 mL, 0.5 M in tetrahydrofuran) and stirred at room temperature overnight. The reaction is not completed (TLC) and added cyclopropylmagnesium bromide (6.0 mL). The solublized reaction mixture is then stirred overnight. The reaction is quenched at 0° C. by the addition of saturated ammonium chloride. The reaction mixture is partitioned between diethyl ether and water. The diethyl ether layer is washed with brined and dried over magnesium sulfate. The crude is chromatographed on 10 g silica gel cartridge (30-50% ethyl acetate gradient in heptane) to afford product (120 mg). The product is recrystallized as follows: In a Smith vial, a mixture of solid (120 mg) and ethyl acetate (2 mL) is heated at 70° C. using microwave (Personal chemistry optimizer) for 240 seconds at normal absorption. Upon cooling dicyclopropyl-[2-(1H-thieno[3,2-c]pyrazol-3-yl)-1H-indol-6-yl]-methanol crystallized as a white solid. mp 110-112° C.; $^1$H NMR [(CD$_3$)$_2$SO)]: δ 13.189 (1H, s), 11.440 (1H, s), 7.747 (1H, d, J=5.1 Hz), 7.631 (1H, s), 7.467 (1H, d, J=8.4 Hz), 7.249 (2H, m), 6.579 (1H, s), 4.304 (1H, s), 1.225 (2H), 0.581 (2H, m), 0.387 (4H, m), 0.195 (2H, m); LC/MS: 350 (M+H).

EXAMPLE 45

(4-Benzo[1,3]dioxol-5-ylmethyl-piperazin-1-yl)-[2-(1H-thieno[3,2-c]pyrazol-3-yl)-1H-indol-6-yl]-methanone

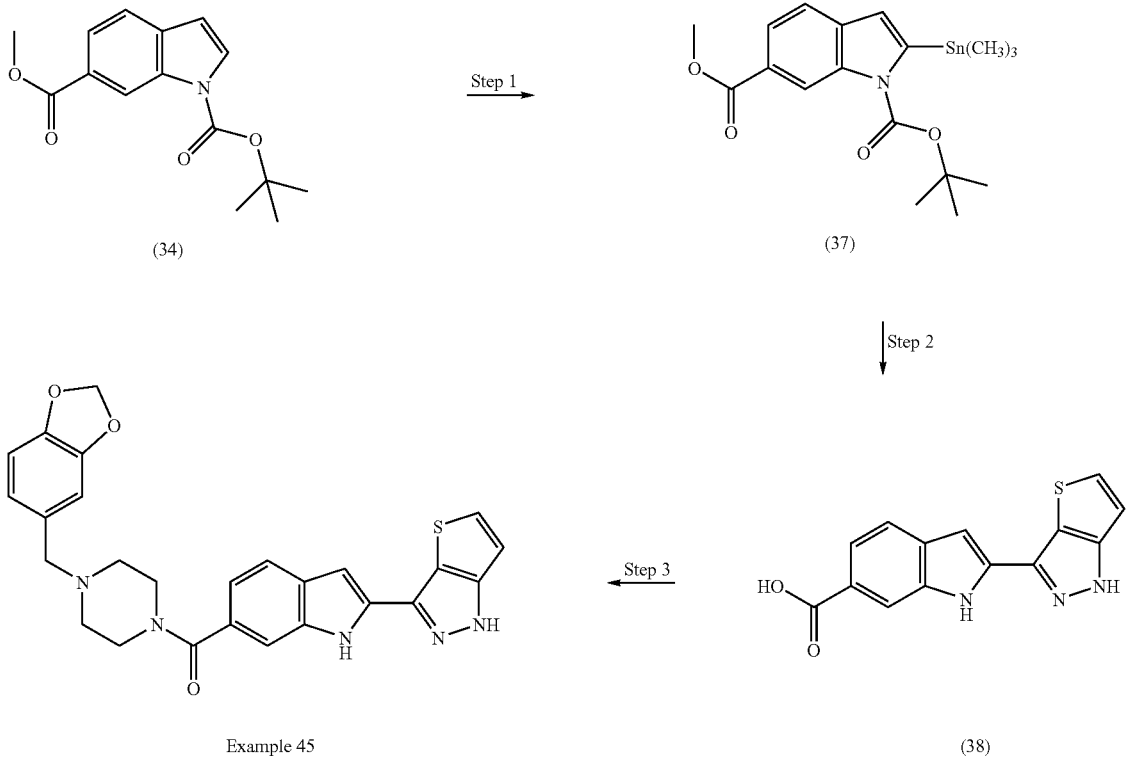

Step 1. A solution of lithium diisopropylamide (1.8M, 50.5 ml, 90.9 mmol, 2.5 eq) was added to a solution of indole-1,6-dicarboxylic acid, 1-tert-butyl ester-6-methyl ester [10 g, 38.4 mmol, Intermediate (34)] in tetrahydrofuran (160 ml) at −78° C. The resulting mixture was stirred for 2 hours at −78° C. before a solution of trimethyltin chloride in tetrahydrofuran (1M, 145.5 ml, 4 eq) was added. The resulting solution was warmed to 0° C. for 15 minutes and partitioned twice between ethyl acetate (150 ml) and aqueous half-saturated ammonium chloride solution (200 ml). The organic layers were combined and dried over magnesium sulfate and concentrated. The residue was purified by flash column chromatography (10% ethyl acetate in heptane) to give trimethyl (indole-1,6-dicarboxylic acid, 1-tert-butyl ester-6-methyl ester)tin [8.7 g, Intermediate (37)] LC/MS: 440 (M+H); R$_T$=2.5 minutes; $^1$H NMR [(CD$_3$)$_2$SO)]: δ 8.8 (1H, t), 7.8 (1H, d), 6.8 (1H, t), 3.9 (3H, s), 1.7 (9H, s).

Step 2. A solution of trimethyl(indole-1,6-dicarboxylic acid, 1-tert-butyl ester-6-methyl ester)tin [7.5 g, 17.1 mmol, 2 eq, Intermediate (37)] in dioxane (30 ml) was added in two equal portions over 2 hours to a solution of 3-iodo-thieno[3,2-c]pyrazole-1-carboxylic acid tert-butyl ester [3 g, 8.6 mmol 1 eq, Example 5B above], copper iodide (171 mg, 0.43 mmol, 0.1 eq) and tetrakis(triphenyl-phosphine) palladium (497 mg, 0.43 mmol, 0.05 eq) in dioxane. The mixture was heated to 90° C. and stirred for 24 hours. Then the solution was cooled to room temperature and partitioned three times between ethyl acetate (150 ml) and a 3:1 mixture of aqueous saturated NaHCO$_3$ solution and brine (300 ml). The combined organic layers were washed with brine (250 ml), dried over magnesium sulfate and concentrated. The residue was subjected to flash column chromatography (20% ethyl acetate in heptane) and a solution of the crude product (5.45 g, a mixture of 2-(1H-thieno[3,2-c]pyrazol-3-yl)-1H-indole-6-carboxylic acid methyl ester, 1H-thieno[3,2-c]pyrazol-3-yl)-indole-1,6-dicarboxylic acid 1-tert-butyl ester 6-methyl ester, 2-(1-tert-butoxycarbonyl-1H-thieno[3,2-c]pyrazol-3-yl)-indole-1,6-dicarboxylic acid 6-methyl ester, and 2-(1-tert-butoxycarbonyl-1H-thieno[3,2-c]pyrazol-3-yl)-indole-1,6-dicarboxylic acid 1-tert-butyl ester 6-methyl ester) in a mixture of tetrahydrofuran and water (50 ml, 1:1) was treated with potassium hydroxide (1.1 g, 19 mmol, 2 eq) at 60° C. The reaction mixture was stirred overnight and then cooled to room temperature. To the solution 1N hydrochloric acid was added to make pH around 6. The solid was filtered, washed with water, heptane and dried to afford 2-(1H-thieno[3,2-c]pyrazol-3-yl)-1H-indole-6-carboxylic acid [3.18 g, Intermediate (38)] which was used without further purification. LC/MS: 282 (M−H, negative mode).

Step 3. The mixture of 2-(1H-thieno[3,2-c]pyrazol-3-yl)-1H-indole-6-carboxylic acid [100 mg, 1.5 eq, Intermediate (38)], PS-DCC (2 eq) and HOBT (1.7 eq) in DCM (5 ml) was shaken for 15 minutes. Then 1-benzo[1,3]dioxol-5-ylmethyl-piperazine was added and the reaction mixture was shaken at room temperature overnight. PS-trisamine (4 eq) was added and the mixture was shaken at room temperature overnight. The resin was filtered, washed with DCM and the filtrate was concentrated. The residue was purified by column chromatography (20% ethyl acetate in heptane) affording (4-benzo[1,3]dioxol-5-ylmethyl-piperazin-1-yl)-[2-(1H-thieno[3,2-c]pyrazol-3-yl)-1H-indol-6-yl]-methanone [Example 45]. LC/MS: 486 (M+H), $R_T$=2.35minutes; $^1$H NMR [(CD$_3$)$_2$SO)]: δ 11.8 (1H, s), 8.0 (1H, s), 7.8 (1H, d), 7.6 (d, 1H), 7.4 (1H, s), 7.2 (1H, d), 7.0 (d, 1H), 6.8 (2H, m), 6.6 (2H,m).

The following Examples 46 to 51 are prepared by procedures similar to those of the previous example.

EXAMPLE 46

[4-(2-Cyclohexyl-ethyl)-piperazin-1-yl]-[2-(1H-thieno[3,2-c]pyrazol-3-yl)-1H-indol-6-yl]-methanone

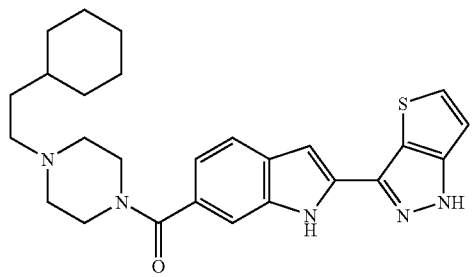

This compound [LC/MS: 462 (M+H), $R_T$=8.7 minutes; $^1$H NMR [(CD$_3$)$_2$SO)]: δ13.4 (1H, S), 11.8 (1H, S), 7.8 (1H, d), 7.6 (1H, d), 7.4 (1H, s), 7.2 (1H, d),7.0 (1H,d), 6.7 (1H, d), 2.8 (6H,m), 1.6 (4H, m), 0.9-1.3 (13H,m)] is prepared using procedures similar to those of Example 45, substituting 1-(2-cyclohexyl-ethyl)-piperazine for 1-benzo[1,3]dioxol-5-ylmethyl-piperazine in step 3.

EXAMPLE 47

2-(1H-Thieno[3,2-c]pyrazol-3-yl)-1H-indole-6-carboxylic acid (2-hydroxy-2-phenyl-ethyl)-amide

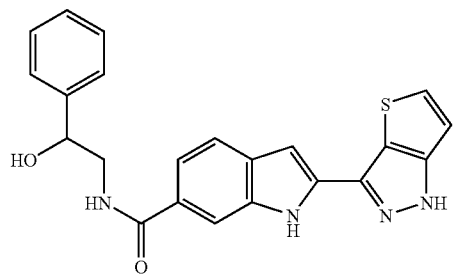

This compound [LC/MS: 403 (M+H), $R_T$=2.72 minutes; $^1$H NMR [(CD$_3$)$_2$SO)]: δ 13.4 (1H,s), 11.8 (1H,s), 8.4 (1H,t), 7.96 (1H,m), 7.89 (1H,m), 7.78 (1H, m), 7.2-7.6 (11H, m), 6.8 (1H,s), 5.6 (1H,d), 4.8 (1h, d), 3.6 (2H, m)] is prepared using procedures similar to those of Example 45, substituting 2-amino-1-phenyl-ethanol for 1-benzo[1,3]dioxol-5-ylmethyl-piperazine in step 3.

EXAMPLE 48

2-(1H-Thieno[3,2-c]pyrazol-3-yl)-1H-indole-6-carboxylic acid (2-cyclohex-1-enyl-ethyl)-amide

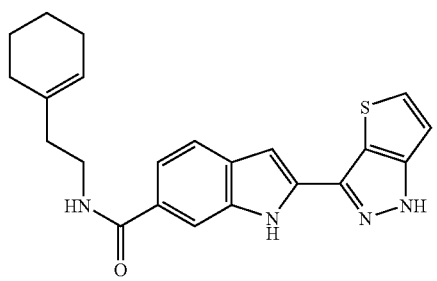

This compound [LC/MS: 391 (M+H); $R_T$=3.3 minutes; $^1$H NMR [(CD$_3$)$_2$SO)]: δ13.4 (1H,s), 11.8 (1H,s), 8.2 (1H, t), 7.9(1H, s), 7.7 (1H, d), 7.6 (1H,m), 7.4 (1H, m), 7.2 (1H, d), 6.6 (1H, d), 5.4 (1H, d), 2.2 (1H, m), 2.0(4H,m), 1.2-1.4(1H, m)] is prepared using procedure similar to those of Example 45, substituting 2-cyclohex-1-enyl-ethylamine for 1-benzo[1,3]dioxol-5-ylmethyl-piperazine in step 3.

EXAMPLE 49

2-(1H-Thieno[3,2-c]pyrazol-3-yl)-1H-indole-6-carboxylic acid (2-thiophen-2-yl-ethyl)-amide

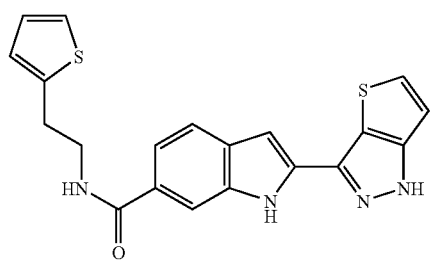

This compound [LC/MS: 393 (M+H), $R_T$=2.98 minutes; $^1$H NMR [(CD$_3$)$_2$SO)]: δ 13.4 (1H, d), 11.8 (1H, d), 8.6 (1H, t), 8.0 (1H, s), 7.8 (1H, d), 7.5 (1H, d), 7.4 (1H, m), 7.3 (1H, d) 7.2 (1H, m), 7.0 (1H, m), 6.8 (1H, s), 3.6 (2H, m), 3.0 (2H, m)] is prepared using procedures similar to those of Example 45, substituting 2-thiophen-2-yl-ethylamine for 1-benzo[1,3]dioxol-5-ylmethyl-piperazine in step 3.

EXAMPLE 50

(4-Pyridin-2-yl-piperazin-1-yl)-[2-(1H-thieno[3,2-c]pyrazol-3-yl)-1H-indol-6-yl]-methanone

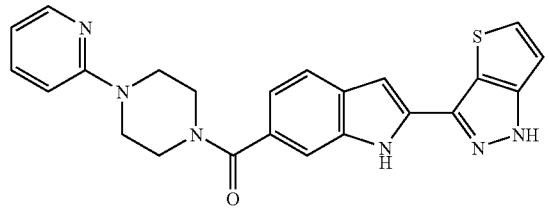

This compound [LC/MS: 428 (M+H), $R_T$=1.99 minutes] is prepared using procedures similar to those of Example 45, substituting 1-pyridin-2-yl-piperazine for 1-benzo[1,3]dioxol-5-ylmethyl-piperazine in step 3.

EXAMPLE 51

2-(1H-Thieno[3,2-c]pyrazol-3-yl)-1H-indole-6-carboxylic acid (2-pyridin-3-yl-ethyl)-amide

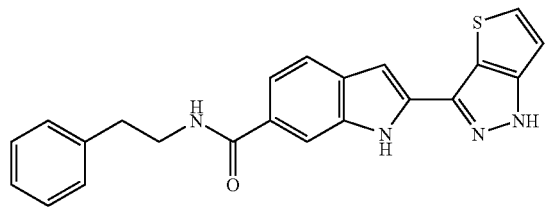

This compound [LC/MS: 387 (M+H), $R_T$=1.89 minutes] is prepared using procedures similar to those of Example 45, substituting 2-pyridin-3-yl-ethylamine for 1-benzo[1,3]dioxol-5-ylmethyl-piperazine in step 3.

EXAMPLE 52

Cyclohexylmethyl-[2-(1H-thieno[3,2-c]pyrazol-3-yl)-1H-indol-5-ylmethyl]-amine

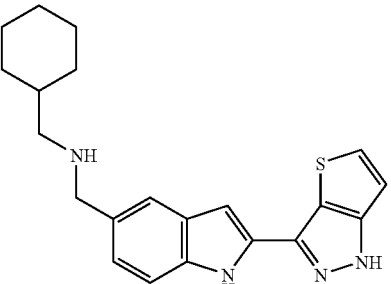

(11)

Example 52

A mixture of 2-(1-tert-butoxycarbonyl-1H-thieno[3,2-c]pyrazol-3-yl)-5-formyl-indole-1-carboxylic acid tert-butyl ester [200 mg, 1 eq, Intermediate (11) prepared as described in Step 1 of Example 24], aminomethylcyclohexane (1.1 eq), MP-cyanoborohydride (macroporous triethylammonium methylpolystyrene cyanoborohydride, 1.5 eq), and acetic acid (0.5 ml) in dimethyl formamide (10 ml) at room temperature was shaken overnight. The resin was filtered and the filtrate was poured into water. The mixture was extracted twice with ethyl acetate; the extract was dried over magnesium sulfate and concentrated. The residue was purified by silica gel column (eluted by 20% methanol in ethyl acetate) to yield a mixture of 2-(1-tert-butoxycarbonyl-1H-thieno[3,2-c]pyrazol-3-yl)-5-[(cyclohexylmethyl-amino)-methyl]-indole-1-carboxylic acid tert-butyl ester [major product, LC/MS: 565 (M+H), $R_T$=3.5 minutes], 5-[(cyclohexylmethyl-amino)-methyl]-2-(1H-thieno[3,2-c]pyrazol-3-yl)-indole-1-carboxylic acid tert-butyl ester and 3-{5-[(cyclohexylmethyl-amino)-methyl]-1H-indol-2-yl}-thieno[3,2-c]pyrazole-1-carboxylic acid tert-butyl ester. This mixture was treated with trifluoroacetic acid in dichloromethane (10 ml, 1:1) at room temperature for 2 hours and the reaction mixture was passed through SCX column eluting with 7N ammonia in methanol affording cyclohexylmethyl-[2-(1H-thieno[3,2-c]pyrazol-3-yl)-1H-indol-5-ylmethyl]-amine [Example 52]. LC/MS: 365 (M+H), $R_T$=2.5 minutes; $^1$H NMR [(CD$_3$)$_2$SO)]: δ 11.4 (1H, s), 7.8 (d, 2H), 7.5 (1H, s), 7.4 (1H, d), 7.2 (1H, d), 7.0 (1H, d), 6.6 (1H, s), 3.8 (2H, s) 2.2 (2H, d), 1.8-2.0 (4H, m), 1.0-1.2 (4H, m), 0.8-1.0 (3H, m).

EXAMPLE 53

5-[4-(4-Chloro-benzyl)-piperazin-1-ylmethyl]-2-(1H-thieno[3,2-c]pyrazol-3-yl)-1H-indole

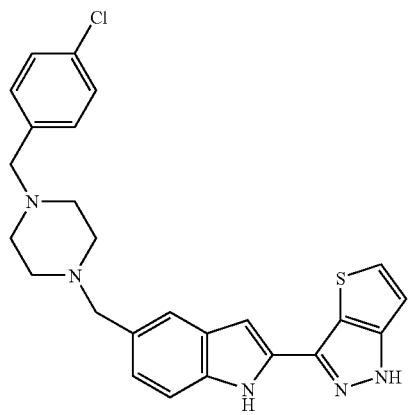

Example 53

This compound [LC/MS: 462 (M+H); $^1$H NMR [(CD$_3$)$_2$SO)]: δ 13.2 (1H, s), 11.6 (1H, s), 7.8 (d, 1H), 7.45 (1H), 7.3-7.4 (6H, m), 7.2 (1H,m), 6.6 (1H, s), 3.5 (4H, m), 3.3-3.4 (6H,m), 3.3 (1H,m), 2.9(1H, m)] is prepared using procedures similar to those of Example 52, substituting 1-(4-chloro-benzyl)-piperazine for C-cyclohexyl-methylamine in step 1.

EXAMPLE 54

[2-(4-Phenoxy-phenyl)-ethyl]-[2-(1H-thieno[3,2-c]pyrazol-3-yl)-1H-indol-5-ylmethyl]-amine

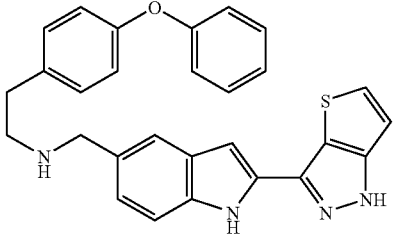

Example 54

This compound [LC/MS: 465 (M+H); δ13.2 (1H, S), 11.4 (1H, S), 7.8 (1H, d), 7.5(1H, s), 7.4 (3H, m), 7.3 (3H, m), 7.2 (2H, m), 6.8 (4H, m), 6.6 (1H, d), 3.8 (2H, s), 2.6-2.8 (4H, m] is prepared using procedures similar to those of Example 52, substituting 2-(4-phenoxy-phenyl)-ethylamine for aminomethylcyclohexane in step 1.

EXAMPLE 55

3-[6-(3-Piperidin-1-yl-propoxy)-1H-benzoimidazol-2-yl]-1H-benzo[4,5]thieno[3,2-c]pyrazole hydrochloride

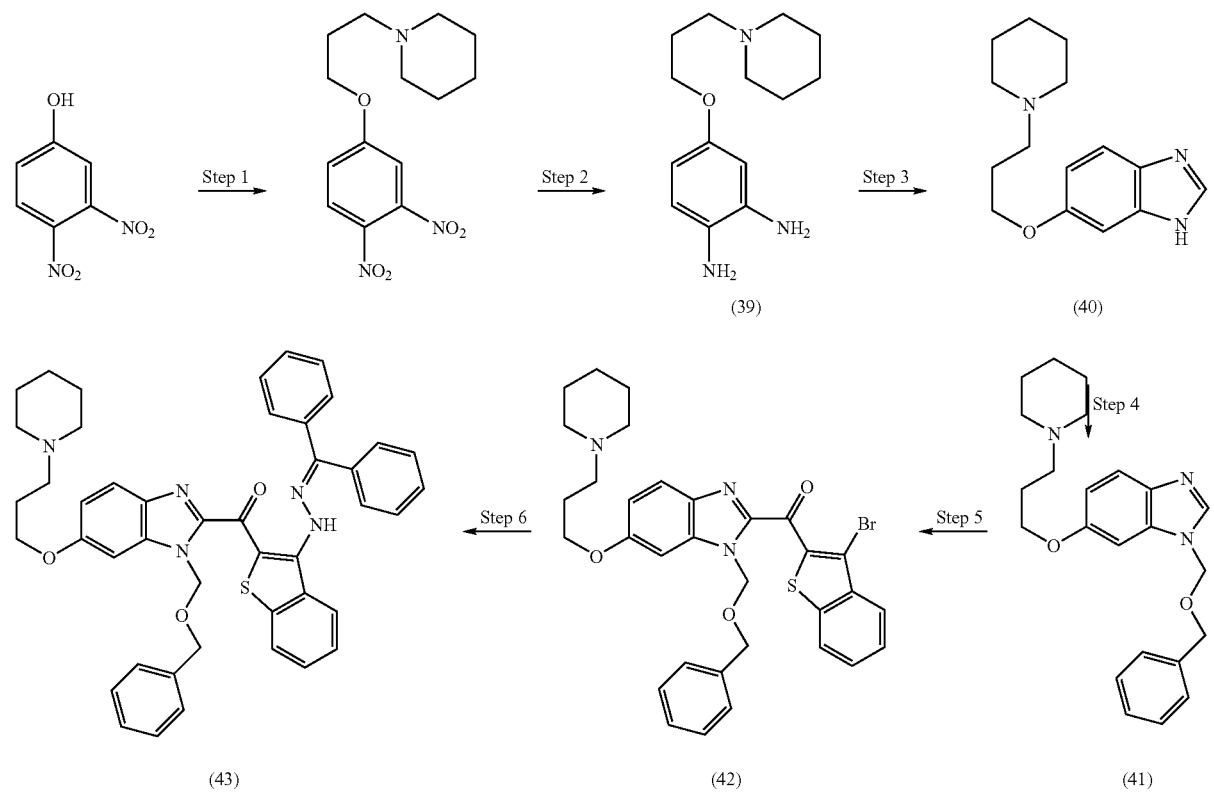

Step 7

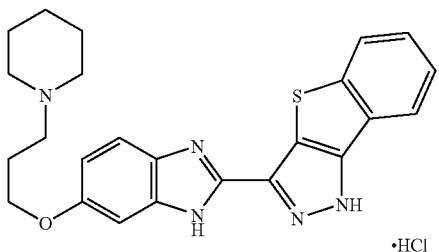

Example 55

·HCl

Step 1. To a stirred solution of 3,4-dinitrophenol (2 g, 10.9 mmol, 1 eq) in dimethyl formamide (40 ml), chloropropyl piperidine hydrochloride (2.8 g, 14.2 mmol, 1.3 eq) and potassium carbonate (3.2 g, 22.9 mmol, 2.1 eq) were added. The mixture was heated to 100° C. for 4 hours and the reaction was cooled to room temperature. The mixture was passed through a SCX column and eluted with 7N ammonia in methanol, the eluent was concentrated and the residue was subjected to chromatography on silica gel (100 g) to yield 1-[3-(3,4-dinitro-phenoxy)-propyl]-piperidine [3.45 g] as a yellow oil.

Step 2. 1-[3-(3,4-Dinitro-phenoxy)-propyl]-piperidine [3.2 g] was dissolved in methanol (20 ml) and palladium on carbon (1.12 g, 10%) and formic acid (2 ml) was added. The mixture was hydrogenated at 50 psi for 3 hours and the mixture was filtered through celite. The filtrate was concentrated to afford 4-(3-piperidin-1-yl-propoxy)-benzene-1,2-diamine [2.45 g, Intermediate (39)] product as a dark oil. LC/MS: 250 (M+H).

Step 3. A mixture of 4-(3-piperidin-1-yl-propoxy)-benzene-1,2-diamine [2.2 g, Intermediate (39)] and formic acid (20 ml) at 100° C. was stirred for 3 hours and then cooled to room temperature and passed through a SCX column. The column was eluted with 7N ammonia in methanol to yield 6-(3-piperidin-1-yl-propoxy)-1H-benzoimidazole [3.45 g, Intermediate (40)] as a dark oil.; LC/MS: 260 (M+H).

Step 4. To a stirred solution of 6-(3-piperidin-1-yl-propoxy)-1H-benzoimidazole [2.6 g, Intermediate (40)] in dimethyl formamide (20 ml), sodium hydride (0.44 g, 60% dispersion in oil) in two portions was added under nitrogen followed by benzyl-chloromethyl ether (1.89 g) in dimethyl formamide (5 ml) in a dropwise manner. The reaction mixture was stirred at room temperature overnight, then poured into water (150 ml) and then extracted three times with ethyl acetate (50 ml). The combined extracts were washed with water and brine, dried over magnesium sulfate, filtered and concentrated. Chromatography on silica gel yields 1-benzyloxymethyl-6-(3-piperidin-1-yl-propoxy)-1H-benzoimidazole [5.7 g, Intermediate (41)]. LC/MS: 380 (M+H).

Step 5. 1-benzyloxymethyl-6-(3-piperidin-1-yl-propoxy)-1H-benzoimidazole [460 mg, Intermediate (41)] was dissolved in tetrahydrofuran (15 ml, dry) under nitrogen and thesolution was cooled to 0° C. n-Butyllithium (2 ml, 1.3 mmol, 2.4 eq) was added and the solution was stirred for 0.5 hour.

Then, the mixture was warmed to room temperature, and a second portion of n-butyllithium (1 ml, 1.2 eq) was added and stirring was continued for 0.5 hour. Then 3-bromo-benzo[b]thiophene-2-carboxylic acid methoxy-methyl-amide (401 mg, 1.1 eq) was added and the new solution was stirred at room temperature overnight. The solution was passed through a SCX column and the residue was subjected to chromatography to yield [1-benzyloxymethyl-6-(3-piperidin-1-yl-propoxy)-1H-benzoimidazol-2-yl]-(3-bromo-benzo[b]thiophen-2-yl)-methanone [40 mg, Intermediate (42)].

Step 6. A mixture of [1-benzyloxymethyl-6-(3-piperidin-1-yl-propoxy)-1H-benzoimidazol-2-yl]-(3-bromo-benzo[b]thiophen-2-yl)-methanone [40 mg, Intermediate (42)], benzophenone hydrazone (18 mg, 1.4 eq), Pd(OAc) (0.9 mg, 0.05 eq)), DPPF(3.8 mg, 0.1 eq) and cesium carbonate (33.7 mg, 1.6 eq) in 5 ml toluene under nitrogen was heated at 90° C. overnight. The reaction was cooled to room temperature and the mixture was passed through a SCX column and eluted with 7N ammonia in methanol to yield [3-(N'-benzhydrylidene-hydrazino)-benzo[b]thiophen-2-yl]-[1-benzyloxymethyl-6-(3-piperidin-1-yl-propoxy)-1H-benzoimidazol-2-yl]-methanone [200 mg, Intermediate (43)].

Step 7. A mixture of [3-(N'-benzhydrylidene-hydrazino)-benzo[b]thiophen-2-yl]-[1-benzyloxymethyl-6-(3-piperidin-1-yl-propoxy)-1H-benzoimidazol-2-yl]-methanone [200 mg, Intermediate (43)] and concentrated HBr (2 ml) in ethanol (4 ml) was heated at 90° C. overnight. The solution cooled to room temperature and the mixture was passed through a SCX column. Eluting with 7N ammonia in methanol yields 3-[6-(3-piperidin-1-yl-propoxy)-1H-benzoimidazol-2-yl]-1H-benzo[4,5]thieno[3,2-c]pyrazole (72.1 mg). This material was dissolved in HCl/1,4-dioxane (2 ml, 4M) and methanol (0.05 ml) and the mixture was concentrated and dried to afford 3-[6-(3-piperidin-1-yl-propoxy)-1H-benzoimidazol-2-yl]-1H-benzoimidazol-2-yl]-1H-benzo[4,5]thieno[3,2-c]pyrazole hydrochloride [85.1 mg, Example 55]. LC/MS: 432 (M+H), $R_T$=2.49 minutes; $^1$H NMR [$(CD_3)_2SO$]: δ 9.6 (1H, s), 8.0 (1H, t), 7.4 (2H, m), 7.3 (1H, s), 7.2 (1H, m), 6.9 (1H, m), 6.8 (1H, m), 4.2 (2H, t), 3.6-3.7 (4H, m), 3.5-3.6 (2H, m), 3.4 (1H, m), 3.2 (1H, m), 2.8 (2H, m), 2.2 (2H, m), 1.8 (1H, m), 1.4(1H, m).

EXAMPLE 56
1-{3-[2-(5-Phenyl-1H-thieno[3,2-c]pyrazol-3-yl)-1H-indol-6-yloxy]-propyl}-piperidin-3-ol
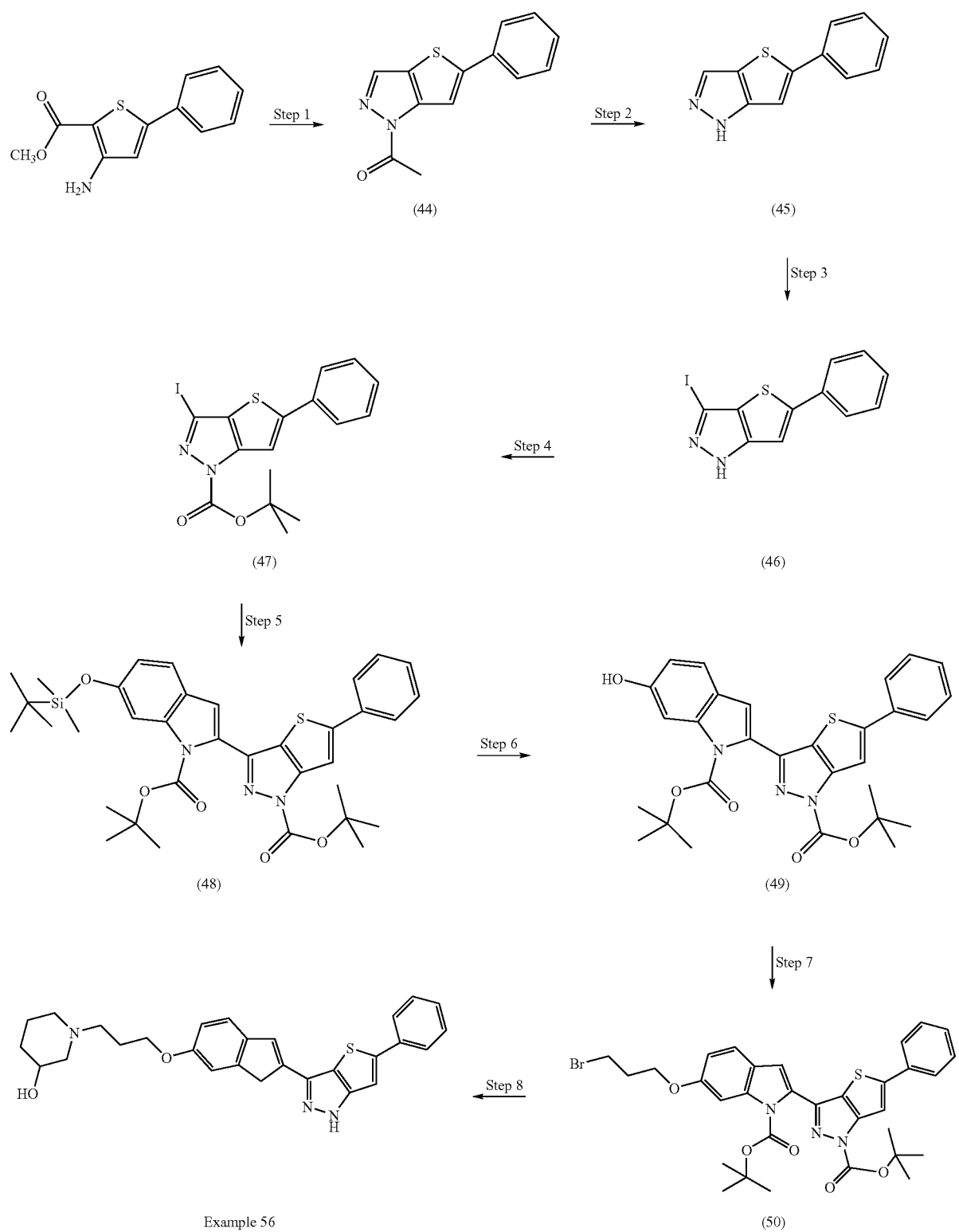

Step 1. 1-(5-phenyl-thieno[3,2-c]pyrazol-1-yl)-ethanone [Intermediate (44), LC/MS: 243.1(M+H), R$_T$=3.45 minutes; $^1$H NMR (300 Mhz, CDCl$_3$): δ 7.84 (s,1H), 7.78 (s, 1H), 7.64 (m, 2H), 7.43-7.31 (m, 3H), 2.75 (s, 3H)] is prepared using procedures similar to those described hereinabove for Intermediate (25) substituting 2-phenyl-5-methyl-thiophene for 5-methylthiophene-2-carboxylic acid in step 1.

Step 2. To a mixture of 1-(5-phenyl-thieno[3,2-c]pyrazol-1-yl)-ethanone [3.82 g, 15.8 mmol, Intermediate (44)] and ethanol (50 mL) was added 6 N hydrochloric acid (50.0 mL, 300 mmol) in one portion and the resulting mixture heated at 70° C. After 18 hours, the reaction was cooled to ambient temperature and neutralized with 25% aqueous potassium carbonate. The mixture was diluted with water (200 mL) and aged at 0° C. for 1 hour. The resulting solid was collected, washed three times with water (50 mL), and then dried under vacuum to give 5-phenyl-1H-thieno[3,2-c]pyrazole [2.93 g, 92%, Intermediate (45)] as a beige powder. LC/MS: 201.0 (M+H), R$_T$=3.15 minutes).

Step 3. Crushed KOH (1.09 g, 6.49 mmol) was added in one portion to a stirred mixture of 5-phenyl-1H-thieno[3,2-c]pyrazole [1.30 g, 6.49 mmol, Intermediate (45)], iodine (2.47 g, 9.73 mmol), and dimethylformamide (15 mL) under nitrogen at room temperature and the dark reaction was stirred at room temperature. After 3 hours, 10% aqueous NaHSO$_3$ (40 mL) was added with stirring. The resulting slurry was diluted with water (40 mL) and the mixture stirred at room temperature for 5 minutes. The solid was colleted by filtration, washed three times with water (20 mL) and then dried under high vacuum at 40° C. to give 3-iodo-5-phenyl-1H-thieno[3,2-c]pyrazole [1.94 g 91%, Intermediate (46)] as a tan powder. TLC R$_f$ 0.52 (silica, 70% ethyl acetate/heptane); LC/MS: 326.94 (M+H), R$_T$=3.38 minutes; $^1$H NMR [600 Mhz, (CD$_3$)$_2$SO]: δ 13.51 (br s 1H), 7.73 (m, 2H), 7.69 (br s, 1H), 7.46 (m, 2H), 7.38 (m, 1 Hz).

Step 4. 4-Dimethylaminopyridine (195 mg, 1.60 mmol) was added to a mixture of 3-iodo-5-phenyl-1H-thieno[3,2-c]pyrazole [2.60 g, 7.97 mmol, Intermediate (46)], di-tert-butyl dicarbonate (2.78 g, 12.7 mmol), and anhydrous dichloromethane (30 mL) at room temperature with stirring. The resulting solution was stirred at room temperature. After 16 hours, the reaction was diluted with dichloromethane (20 mL), washed with water (50 mL) and brine (40 mL) successively, dried over magnesium sulfate, and concentrated under reduced pressure to an amber oil. The crude product was chromatographed on silica, eluting with dichloromethane to give 3-iodo-5-phenyl-thieno[3,2-c]pyrazole-1-carboxylic acid tert-butyl ester [2.56 g, 75%, Intermediate (47)] as an off-white solid. TLC R$_f$ 0.41 (silica, dichloromethane); LC/MS: 449.0 (M+Na), R$_T$=4.23 minutes).

Step 5. A mixture of 5-(tert-butyl-dimethyl-silanyloxymethyl)-1H-indole-2-boronic acid 1-carboxylic acid tert-butyl ester [2.39 g, 6.11 mmol, Intermediate (8), prepared as described in Example 1-4 of International Patent Application Publication No. WO 02/32861], 3-iodo-5-phenyl-thieno[3,2-c]pyrazole-1-carboxylic acid tert-butyl ester [2.00 g, 4.69 mmol, Intermediate (47)], cesium carbonate (6.11 g, 17.0 mmol), [1,1'-bis(diphenylphosphino)ferrocene]dichloropalladium(II) complex with dichloromethane (1:1) (230 mg, 0.282 mmol), 1,4-dioxane (40 mL), and water (10 mL) was purged with nitrogen and then heated at 90° C. with stirring under nitrogen. After 1.5 hours, the reaction was cooled to room temperature, diluted with ethyl acetate (125 mL), and washed twice with water (50 mL) and brine (50 mL) successively. The organic layer was dried over magnesium sulfate and the solvent was removed under reduced pressure to give a dark residue. The residue was chromatographed on silica, eluting with dichloromethane to give 2-(1-tert-butoxycarbonyl-5-phenyl-1H-thieno[3,2-c]pyrazol-3-yl)-6-(tert-butyl-dimethyl-silanyloxy)-indole-1-carboxylic acid tert-butyl ester [2.55 g, 84%, Intermediate (48)] as a tan foam. TLC R$_f$ 0.31 (silica, dichloromethane); LC/MS: 646.2 (M+H), R$_T$=3.05 minutes).

Step 6. To a solution of 2-(1-tert-butoxycarbonyl-5-phenyl-1H-thieno[3,2-c]pyrazol-3-yl)-6-(tert-butyl-dimethyl-silanyloxy)-indole-1-carboxylic acid tert-butyl ester [2.44 g, 3.78 mmol, Intermediate (48)] in tetrahydrofuran (25 mL) at 0° C. was added tetrabutylammonium fluoride (4.20 mL of a 1M THF solution, 4.20 mmol) in one portion with stirring. After 40 minutes, the reaction was partitioned between ethyl acetate (75 mL) and 10% aqueous ammonium chloride (50 mL) and the layers separated. The organics were washed with water (50 mL) and brine (50 mL) successively, dried over magnesium sulfate, and the solvent removed under reduced pressure to give an amber foam. The crude product was chromatographed on silica, eluting with 10% ethyl acetate/dichloromethane, to yield 2-(1-tert-butoxycarbonyl-5-phenyl-1H-thieno[3,2-c]pyrazol-3-yl)-6-hydroxy-indole-1-carboxylic acid tert-butyl ester [1.99 g, 99%, Intermediate (49)] as a tan foam. TLC R$_f$ 0.31 (silica, 10% ethyl acetate/dichloromethane); LC/MS: 532.2 (M+H), R$_T$=4.31 minutes; $^1$H NMR [300 Mhz, (CD$_3$)$_2$SO]: δ 9.73 (s, 1H) 7.84-7.81 (m, 2H), 7.76 (s, 1H), 7.61 (d, J=2 Hz, 1H), 7.56-7.44 (m, 4H), 7.07 (s, 1H), 6.84 (dd, J=2, 8 Hz, 1H), 1.71 (s, 9H), 1.40 (s, 9H).

Step 7. A mixture of 2-(1-tert-butoxycarbonyl-5-phenyl-1H-thieno[3,2-c]pyrazol-3-yl)-6-hydroxy-indole-1-carboxylic acid tert-butyl ester [950 mg, 1.79 mmol, Intermediate (49)], cesium carbonate (1.75 g, 5.37 mmol), and 1,3-dibromopropane (6.0 mL) was heated at 90° C. under nitrogen. After 1.5 hours, the mixture was cooled to ambient temperature, filtered, and the insolubles washed twice with dichloromethane (10 mL). The filtrate was concentrated in vacuo to yield a cloudy oil. The crude product was chromatographed on silica, eluting first with 80% dichloromethane/heptane and then 100% dichloromethane to give 6-(3-bromo-propoxy)-2-(1-tert-butoxycarbonyl-5-phenyl-1H-thieno[3,2-c]pyrazol-3-yl)-indole-1-carboxylic acid tert-butyl ester [760 mg, 65%, intermediate 50] as a white foam. TLC R$_f$ 0.37 (silica, dichloromethane); LC/MS: 674 (M+Na), R$_T$=2.60 minutes.

Step 8. A mixture of 6-(3-bromo-propoxy)-2-(1-tert-butoxycarbonyl-5-phenyl-1H-thieno[3,2-c]pyrazol-3-yl)-indole-1-carboxylic acid tert-butyl ester [300 mg, 0.460 mmol, Intermediate (50)], 3-hydroxypiperidine (73.0 mg, 0.722 mmol), potassium carbonate (191 mg, 1.38 mmol), potassium iodide (39.0 mg, 0.235 mmol), and anhydrous acetonitrile (5 mL) was heated at 70° C. with shaking at 200 rpm. After 20 hours, the reaction was cooled to ambient temperature, filtered, the insolubles washed with dichloromethane/methanol (5:1), and the filtrate concentrated under reduced pressure to give a dark residue. The residue was chromatographed on silica, eluting with 20% methanol/dichloromethane (20 mL) followed by 1 M ammonia in methanol/dichloromethane 1:9 (30 mL), to give 2-(1-tert-butoxycarbonyl-5-phenyl-1H-thieno [3,2-c] pyrazol-3-yl)-6-[3-(3-hydroxy-piperidin-1-yl)-propoxy]-indole-1-carboxylic acid tert-butyl ester (329 mg) as a brittle green foam. LC/MS: 673.3 (M+H), 74% UV purity). To a solution of 2-(1-tert-butoxycarbonyl-5-phenyl-1H-thieno[3, 2-c]pyrazol-3-yl)-6-[3-(3-hydroxy-piperidin-1-yl)-propoxy]-indole-1-carboxylic acid tert-butyl ester (326 mg), anisole (1.0 mL), and dichloromethane (1.0 mL) at ambient temperature was added trifluoroacetic acid (1.0 mL) and the resulting amber solution heated at 45° C. After 2 hours, the reaction was cooled to ambient temperature and added to a Varian Mega Bond Elut SCX column (5 g) that was conditioned with methanol. The product was washed with methanol (30 mL) and eluted with a 1 M ammonia in methanol solution. Fractions with product were combined and concentrated under reduced pressure to give a white solid. Trituration of the solid with methanol/ether (1:4) provided 1-{3-[2-(5-phenyl-1H-thieno[3,2-c]pyrazol-3-yl)-1H-indol-6-yloxy]-propyl}-piperidin-3-ol [163 mg, 75%, Example 56] as an off-white powder. TLC $R_f$ 0.55 (silica, 20% 1 M $NH_3$ in methanol/80% dichloromethane); mp: 213-216° C.; LC/MS: 473.2 (M+H), $R_T$=2.67 minutes; $^1$H NMR [300 Mhz, $(CD_3)_2$SO]: δ 13.31 (br s 1H), 11.39 (br s, 1H), 7.79 (m, 2H), 7.66 (s, 1H), 7.51-7.36 (m, 4H), 6.93 (d, J=2 Hz, 1H), 6.67 (dd, J=2, 8.5 Hz, 1H), 6.60 (d, J=1.5 Hz, 1H), 4.58 (d, J=5 Hz, 1H), 3.99 (t, J=6.5 Hz, 2H), 3.47 (m, 1H), 2.85 (dm, J=11 Hz, 1H), 2.68 (dm, J=11 Hz, 1H), 2.45 (m, 2H), 1.95-1.67 (m, 5H), 1.62 (dm, J=13.5 Hz, 1H), 1.40 (m, 1H), 1.07 (m, 1H).

EXAMPLE 57

1-{3-[2-(5-Phenyl-1H-thieno[3,2-c]pyrazol-3-yl)-1H-indol-6-yloxy]-propyl}-piperidin-4-ol

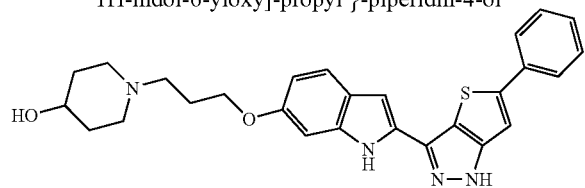

This compound [TLC $R_f$ 0.44 (silica, 20% 1 M ammonia in methanol/80% dichloromethane); mp: 239-242° C.; LC/MS: 473.2 (M+H), $R_T$=2.94 minutes; $^1$H NMR [600 Mhz, $(CD_3)_2$SO]: δ 13.30 (br s 1H), 11.37 (br s, 1H), 7.80 (d, J=7.7 Hz, 2H), 7.65 (s, 1H), 7.50-7.44 (m, 3H), 7.39 (m, 1H), 6.94 (d, J=1.3 Hz, 1H), 6.67 (dd, J=2, 8.6 Hz, 1H), 6.61 (s, 1H), 4.52 (d, J=4.2 Hz, 1H), 3.99 (t, J=6.4 Hz, 2H), 3.44 (m, 1H), 2.72 (m, 2H), 2.42 (m, 2H), 2.01 (m, 2H), 1.88 (m, 2H), 1.71 (m, 2H), 1.42-1.36 (m, 2H)] is prepared using procedures similar to those of Example 56, substituting 4-hydroxypiperidine for 3-hydroxypiperidine in step 8.

EXAMPLE 58

2-(5-Phenyl-1H-thieno[3,2-c]pyrazol-3-yl)-6-(3-piperidin-1-yl-propoxy)-1H-indole

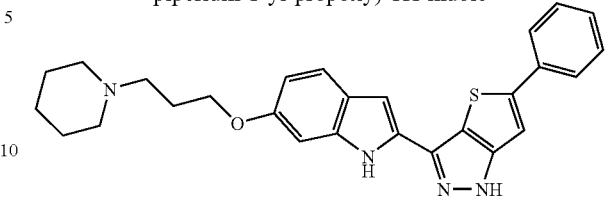

A mixture of 6-(3-bromo-propoxy)-2-(1-tert-butoxycarbonyl-5-phenyl-1H-thieno[3,2-c]pyrazol-3-yl)-indole-1-carboxylic acid tert-butyl ester [300 mg, 0.460 mmol, Intermediate 50)], piperidine (60.2 mg, 0.707 mmol), potassium carbonate (191 mg, 1.38 mmol), potassium iodide (40.0 mg, 0.241 mmol), and anhydrous acetonitrile (5.0 mL) was heated at 70° C. with shaking at 200 rpm. After 20 hours, the reaction was cooled to ambient temperature, filtered, the insolubles washed three times with dichloromethane (5 mL), and the filtrate concentrated under reduced pressure to give a dark residue. The residue was chromatographed on silica, eluting with 10%—1 M ammonia in methanol/90% dichloromethane, to give 2-(1-tert-butoxycarbonyl-5-phenyl-1H-thieno[3,2-c]pyrazol-3-yl)-6-[3-(piperidin-1-yl)-propoxy]-indole-1-carboxylic acid tert-butyl ester (310 mg) as a brittle green foam: LC/MS: 657.3, (M+H), $R_T$=3.92 minutes, 50% UV purity). A mixture of this material (300 mg), 4 M aqueous potassium carbonate (5.0 mL), tetrahydrofuran (5.0 mL) and methanol (5.0 mL) was heated at 60° C. for 2 hours. After cooling to room temperature, the solvent was removed in vacuo to give a solid. The crude solid was suspended in water (25 ml) and the mixture stirred at room temperature for 0.5 hours. The solid was collected by filtration and dried to give a grey solid. Trituration of the solid with 20% methanol/ether provided 2-(5-phenvyl-1H-thieno[3,2-c]pyrazol-3-yl)-6-(3-piperidin-1-yl-propoxy)-1H-indole [90.0 mg, 43%, Example 58] as a grey solid. TLC $R_f$ 0.37 (silica, 14% 1 M ammonia in methanol/86% dichloromethane); LC/MS: 457.3 (M+H), $R_T$=2.93 minutes; $^1$H NMR [300 Mhz, $(CD_3)_2$SO]: δ 13.30 (br s 1H), 11.39 (br s, 1H), 7.78 (D, J=7 Hz, 2H), 7.64 (s, 1H), 7.49-7.35 (m, 4H), 6.92 (s, 1H), 6.65 (d, J=8.5 Hz, 1H), 6.59 (s, 1H), 3.98 (t, J=6 Hz, 2H), 2.43-2.33 (m, 6H), 1.88 (m, 2H), 1.50-1.39 (m, 6H).

EXAMPLE 59

1-(3-{2-[5-(3-Methoxy-phenyl)-1H-thieno[3,2-c]pyrazol-3-yl]-1H-indol-6-yloxy}-propyl)-piperidin-4-ol

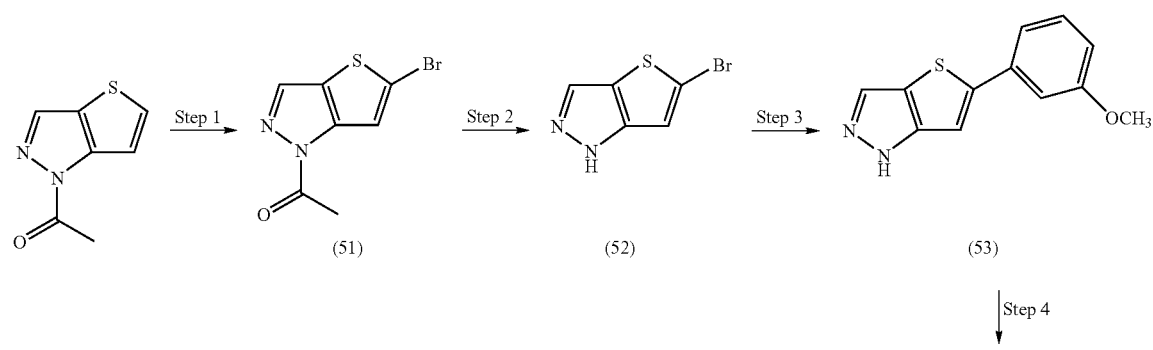

Step 4

-continued

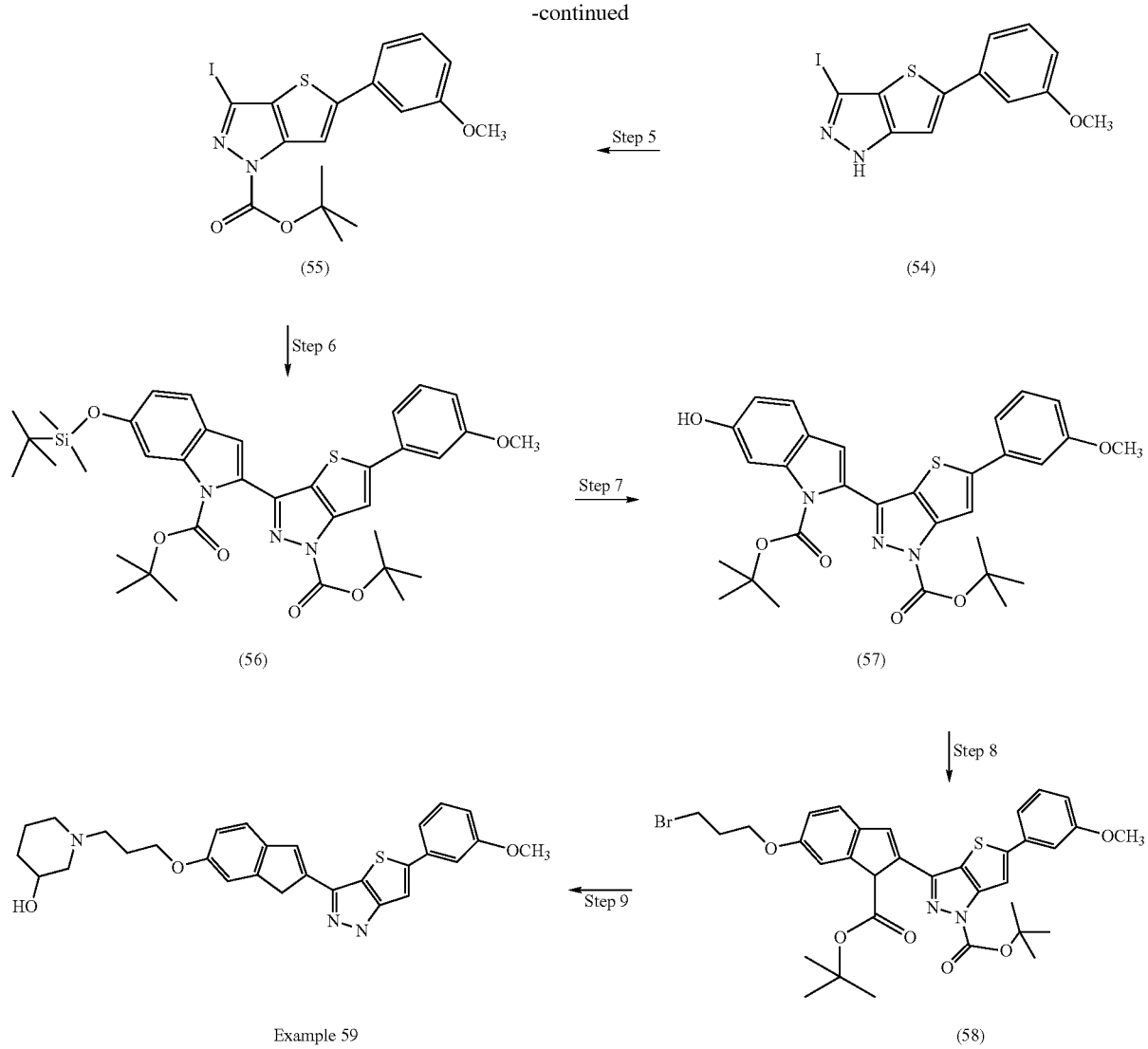

Example 59

Step 1. A mixture of 1-(thieno[3,2-c]pyrazol-1-yl)-ethanone (5.00 g, 30.1 mmol), N-bromosuccinimide (16.1 g, 90.4 mmol), and chloroform (100 mL) was heated at 50° C. under nitrogen for 5 hours. The orange mixture was stirred at room temperature for an additional 17 hours. The red-orange mixture was filtered, the insolubles washed twice with dichloromethane (60 mL). The filtrate was washed with 10% aqueous NaHSO$_3$ (60 mL) and then twice with water (60 mL), then dried over magnesium sulfate, and concentrated under reduced pressure. The residue was purified by silica gel column chromatography, eluting with 30% ethyl acetate/heptane to 50% ethyl acetate/heptane to give 1-(5-bromo-thieno[3,2-c]pyrazol-1-yl)-ethanone [6.21 g, 84%, Intermediate (51)] as an off-white solid. TLC R$_f$ 0.50 (silica, 40% ethyl acetate/heptane). LC/MS: 244.93 (M+H), R$_T$=3.10 minutes; $^1$H NMR [300 Mhz, (CD$_3$)$_2$SO]: δ 8.12 (s, 1H), 7.67 (s, 1H), 2.67 (s, 3H).

Step 2. A mixture of 1-(5-bromo-thieno[3,2-c]pyrazol-1-yl)-ethanone [12.0 g, 49.0 mmol Intermediate (51)], 1,4-dioxane (120 mL), and 2 M aqueous potassium carbonate (80.0 mL) was stirred at 95° C. under nitrogen. After 20 hours, the reaction mixture was cooled to room temperature and then diluted with ethyl acetate (200 mL). The mixture was washed twice with water (100 mL) and brine (100 mL) successively, dried over magnesium sulfate, and concentrated in vacuo. The product was dried under vacuum to give 5-bromo-1H-thieno[3,2-c]pyrazole [9.48 g, 95%, Intermediate (52)] as an off-white solid. TLC R$_f$ 0.26 (silica, 1:1 ethyl acetate/heptane); LC/MS: 202.93 (M+H), R$_T$=2.79 minutes; $^1$H NMR (300 Mhz, CDCl$_3$) δ 10.8 (br s, 1H), 7.70 (s, 1 H), 7.12 (s, 1H).

Step 3. A solution of 5-bromo-1H-thieno[3,2-c]pyrazole [8.00 g, 39.4 mmol Intermediate (52)] in dimethylformamide (50 mL) was added dropwise to a room temperature mixture of sodium hydride (1.74 g, 60% oil dispersion, 43.5 mmol) and dimethylformamide (10 mL) over 5 minutes and the resulting mixture stirred at room temperature for 30 minutes. 2-(Trimethylsilyl)ethoxymethyl chloride (9.85 g, 5.91 mmol) was added dropwise and the resulting white slurry was stirred at room temperature for 21 hours. The reaction mixture was diluted with water (300 mL) and extracted twice with ethyl acetate (125 mL). The combined extracts were washed with water (100 mL) and brine (100 mL) successively, dried over magnesium sulfate, and concentrated. The crude product was chromatographed on silica, eluting first with 30% ethyl acetate/heptane and then 40% ethyl acetate/heptane to afford a mixture of 5-bromo-1-(2-trimethylsilanyl-ethoxymethyl)-1H-thieno[3,2-c]pyrazole and 5-bromo-2-(2-trimethylsilanyl-ethoxymethyl)-2H-thieno[3,2-c]pyrazole [12.1 g, (92%)]. LC/MS: 333.0 (M+H), $R_T$=3.97 minutes and 333.0 (M+H), $R_T$=3.87 minutes.

A portion of this mixture of 5-bromo-1-(2-trimethylsilanyl-ethoxymethyl)-1H-thieno[3,2-c]pyrazole and 5-bromo-2-(2-trimethylsilanyl-ethoxymethyl)-2H-thieno[3,2-c]pyrazole (5.51 g, 16.5 mmol), 3-methoxyphenylboronic acid (3.77 g, 24.8 mmol), [1,1'-bis(diphenylphosphino)ferrocene]dichloropalladium(II), complex with dichloromethane (1.35 g, 1.65 mmol), 4 M aqueous potassium carbonate (16.5 mL, 66.0 mmol), and 1,4-dioxane (66.0 mL) was purged with nitrogen for 5 minutes then heated at 75° C. for 2.5 hours. The dark mixture was cooled to room temperature, diluted with ethyl acetate (250 mL), and washed twice with water (100 mL) and brine (100 mL) successively. The organics were dried over magnesium sulfate and concentrated to give an amber oil. The oil was chromatographed on silica, eluting first with 5% ethyl acetate/dichloromethane and then 10% ethyl acetate/dichloromethane to afford a mixture of 5-(3-methoxy-phenyl)-1-(2-trimethylsilanyl-ethoxymethyl)-1H-thieno[3,2-c]pyrazole and 5-(3-methoxy-phenyl)-2-(2-trimethylsilanyl-ethoxymethyl)-2H-thieno[3,2-c]pyrazole [4.58 g, 77%] as a cloudy amber oil. TLC $R_f$ 0.41 major and 0.35 minor (silica, 5% ethyl acetate/dichloromethane); LC/MS: 361.2 (M+H), $R_T$=4.14 minutes and 361.2 M+H), $R_T$=4.05 minutes.

A portion of this mixture of 5-(3-methoxy-phenyl)-1-(2-trimethylsilanyl-ethoxymethyl)-1H-thieno[3,2-c]pyrazole and 5-(3-methoxy-phenyl)-2-(2-trimethylsilanyl-ethoxymethyl)-2H-thieno[3,2-c]pyrazole (4.41 g, 12.2 mmol) and ethylenediamine (2.50 mL, 37.0 mmol) at room temperature under nitrogen was added tetrabutylammonium fluoride (61.0 mL of a 1 M tetrahydrofuran solution, 61.0 mmol) and the resulting solution heated at 70° C. After 21.5 hours, the reaction was cooled to room temperature and the solvent removed in vacuo. Water (150 mL) was added to the residue and the aqueous mixture extracted twice with ethyl acetate (100 mL). The combined extracts were washed with water (75 mL) and brine (75 mL) successively, dried over magnesium sulfate, and concentrated to give 5-(3-methoxy-phenyl)-1H-thieno[3,2-c]pyrazole [2.47 g, 87%, Intermediate (53)] as an off-white solid: TLC $R_f$ 0.45 (silica, ethyl acetate); LC/MS: 231.0 (M+H), $R_T$=3.20 minutes; $^1$H NMR (300 Mhz, CDCl$_3$) δ 10.65 (br s, 1H), 7.78 (s, 1H), 7.32 (m, 1H), 7.25-7.21 (m, 2H), 7.16 (m, 1H), 6.89 (m, 1H), 3.86 (s, 3H).

Step 4. Crushed potassium hydroxide (1.35 g, 24.1 mmol) was added in one portion to a solution of 5-(3-methoxyphenyl)-1H-thieno[3,2-c]pyrazole [1.85 g, 8.03 mmol, Intermediate (53)] and dimethylformamide at 0° C. with stirring. After 10 minutes, iodine (3.05 g, 12.0 mmol) was added in one portion and the dark reaction was stirred at 0° C. for 30 minutes and then at room temperature for 5 hours. The reaction was quenched with 10% aqueous NaHSO$_3$ (100 mL), the resulting white mixture diluted with water (100 ml) and the mixture aged at 5° C. overnight. The solid was colleted by filtration, washed with water (3×30 mL) and dried under vacuum at 40° C. to give 3-iodo-5-(3-methoxyphenyl)-1H-thieno[3,2-c]pyrazole [2.61 g, 91%, Intermediate (54)] as a tan powder.mp 159-163° C.; TLC $R_f$ 0.54 (silica, 80% ethyl acetate/heptane); LC/MS: 357.0 (M+H), $R_T$=3.60 minutes; $^1$H NMR (300 Mhz, CDCl$_3$) δ 11.3 (br s, 1H), 7.33 (m, 1H), 7.28-7.20 (m, 2H), 7.14 (m, 1H), 6.91 (m, 1H), 3.87 (s, 3H).

Step 5. Added 4-dimethylaminopyridine (102 mg, 0.835 mmol) to a room temperature mixture of 3-iodo-5-(3-methoxyphenyl)-1H-thieno[3,2-c]pyrazole [1.50 g, 4.21 mmol, Intermediate (54)], di-tert-butyl dicarbonate (1.38 g, 6.32 mmol), and anhydrous dichloromethane (40 mL) with stirring. The resulting solution was stirred at room temperature. After 20 h, the reaction was washed with water (2×30 mL), dried over magnesium sulfate, and concentrated under reduced pressure to a tan solid. The crude product was chromatographed on silica, eluting with dichloromethane to give 3-iodo-5-(3-methoxyphenyl)-thieno[3,2-c]pyrazole-1-carboxylic acid tert-butyl ester [1.68 g, 87%, Intermediate (55)] as an off-white solid: TLC $R_f$ 0.27 (silica, dichloromethane); LC/MS (M+H 457.0, RT 4.08 min); 1H NMR (300 Mhz, DMSO-d6) δ 7.75 (s, 1H), 7.40 (dd, J=7.5, 8.5 Hz, 1H), 7.32 (ddd, J=1, 1.5, 7.5 Hz, 1H), 7.28 (dd, J=1.5, 2.5 Hz, 1H), 7.01 (ddd, J=1, 2.5, 8.5 Hz), 3.84 (s, 3H), 1.65 (s, 9H).

Step 6. A mixture of 5-(tert-butyl-dimethyl-silanyloxymethyl)-1H-indole-2-boronic acid 1-carboxylic acid tert-butyl ester [1.67 g, 4.27 mmol, Intermediate (8), prepared as described in Example 1-4 of International Patent Application Publication No. WO 02/32861], 3-iodo-5-(3-methoxy-phenyl)-thieno[3,2-c]pyrazole-1-carboxylic acid tert-butyl ester (1.50 g, 3.29 mmol, Intermediate (55)], cesium carbonate (4.29 g, 13.2 mmol), [1,1'-bis(diphenylphosphino)ferrocene] dichloropalladium(II) complex with dichloromethane (1:1) (268 mg, 0.328 mmol), 1,4-dioxane (35 mL), and water (7.0 mL) was purged with nitrogen and then heated at 75° C. with stirring under nitrogen. After 70 minutes, the reaction was cooled to room temperature, diluted with ethyl acetate (100 mL), and washed twice with water (50 mL) and brine (50 mL) successively. The organic layer was dried over magnesium sulfate and the solvent was removed under reduced pressure to give a black oil. The oil was chromatographed on silica, eluting with dichloromethane to give 2-[1-tert-butoxycarbonyl-5-(3-methoxy-phenyl)-1H-thieno[3,2-c]pyrazol-3-yl]-6-(tert-butyl-dimethyl-silanyloxy)-indole-1-carboxylic acid tert-butyl ester [1.80 g, 81%, Intermediate (56)] as a beige foam. TLC $R_f$ 0.25 (silica, dichloromethane); LC/MS: 676.3 (M+H), $R_T$=3.82 minutes.

Step 7. To a solution of 2-[1-tert-butoxycarbonyl-5-(3-methoxy-phenyl)-1H-thieno[3,2-c]pyrazol-3-yl]-6-(tert-butyl-dimethyl-silanyloxy)-indole-1-carboxylic acid tert-butyl ester [1.70 g, 2.52 mmol, Intermediate (56)] in tetrahydrofuran (20 mL) at 0° C. was added tetrabutylammonium fluoride (2.80 mL of a 1M tetrahydrofuran solution, 2.80 mmol) in one portion with stirring. After 40 minutes, the orange reaction was partitioned between ethyl acetate (80 mL) and 10% aqueous ammonium chloride (40 mL) and the layers separated. The organics were washed with water (40 mL) and brine (40 mL) successively, dried over magnesium sulfate, and the solvent removed under reduced pressure. The crude product was chromatographed on silica, eluting with first 10% ethyl acetate/dichloromethane and then 20% ethyl acetate/dichloromethane, to give 1.54 g of a tan foam. Trituration with ether/heptane gave 2-[1-tert-butoxycarbonyl-5-(3-methoxyphenyl)-1H-thieno[3,2-c]pyrazol-3-yl]-6-hydroxy-indole-1-carboxylic acid tert-butyl ester [1.25 g, 88%, Intermediate (57)] as a white powder; TLC $R_f$ 0.23 (silica, 10% ethyl acetate/dichloromethane); LC/MS: 562.2 (M+H ), $R_T$=2.80 minutes.

Step 8. A mixture of 2-[1-tert-butoxycarbonyl-5-(3-methoxyphenyl)-1H-thieno[3,2-c]pyrazol-3-yl]-6-hydroxy-indole-1-carboxylic acid tert-butyl ester [1.19 g, 2.12 mmol, Intermediate (57)], cesium carbonate (2.07 g, 6.35 mmol), and 1,3- dibromopropane (8.0 mL) was heated at 75° C. under nitrogen. After 6 hours, the mixture was cooled to ambient temperature and let stand overnight. The mixture was filtered, and the insolubles washed twice with dichloromethane (10 mL). The filtrate was concentrated in vacuo to yield a golden oil. The crude product was chromatographed on silica, eluting with a gradient of 30% ethyl acetate/heptane to 50% ethyl acetate/heptane to give 6-(3-bromo-propoxy)-2-[1-tert-butoxycarbonyl-5-(3-methoxy-phenyl)-1H-thieno[3,2-c]pyrazol-3-yl]-indole-1-carboxylic acid tert-butyl ester [1.11 g, 76%, Intermediate (58)] as a white foam. TLC $R_f$ 0.46 (silica, 40% ethyl acetate/heptane); LC/MS: 682.2 (M+H), $R_T$=3.23 minutes.

Step 9. A mixture of 6-(3-bromo-propoxy)-2-[1-tert-butoxycarbonyl-5-(3-methoxy-phenyl)-1H-thieno[3,2-c]pyrazol-3-yl]-indole-1-carboxylic acid tert-butyl ester [250 mg, 0.366 mmol, Intermediate (58)], 4-hydroxypiperidine (90.0 mg, 0.889 mmol), potassium carbonate (245 mg, 1.77 mmol), potassium iodide (45.0 mg, 0.271 mmol), and anhydrous acetonitrile (4 mL) was heated at 70° C. with shaking at 200 rpm. After 18 hours, the reaction was cooled to ambient temperature for 30 minutes. To the reaction was added 4 M aqueous potassium carbonate (4.0 mL) and the mixture heated at 70° C. with shaking at 200 rpm for 30 minutes. After cooling to room temperature, the solvent was removed in vacuo and the mixture was diluted with ethyl acetate (40 mL). The organics were washed with water (20 mL) and brine (20 ml) successively, dried over Magnesium sulfate, and concentrated to a dark residue. The residue was chromatographed on silica, eluting first with 10%—1 M ammonia in methanol/90% dichloromethane then with 20%—1 M ammonia in methanol/80% dichloromethane to give 125 mg of a purple solid. Trituration of the solid with 20% methanol/ether provided of 1-(3-{2-[5-(3-methoxy-phenyl)-1H-thieno[3,2-c]pyaazol-3-yl]-1H-indol-6-yloxy}-propyl)-piperidin-4-ol [94.1 mg, 51%, Example 59] as a pale purple powder. TLC $R_f$ 0.40 (silica, 20% 1 M ammonia in methanol/80% dichloromethane); mp: 205-207° C.; LC/MS: 503.3 (M+H), $R_T$=2.22 minutes; $^1$H NMR [300 Mhz, (CD$_3$)$_2$SO]: δ 13.30 (br s 1H), 11.37(br s, 1H), 7.67 (2, 1H), 7.43 (d, J=8.5 Hz, 1H), 7.38-7.32 (m, 3H), 6.97-6.91 (m, 2H), 6.65 (dd, J=2, 8.5 Hz, 1H), 6.59 (s, 1H), 4.51 (d, 4 Hz, 1H), 3.98 (t, J=6 Hz, 2H), 3.85 (s, 3H), 3.41 (m, 1H), 2.72 (m, 2H), 2.42 (m, 2H), 2.01 (m, 2H) 1.92-1.83 (m, 2H), 1.71 (m, 2H), 1.44-1.32 (m, 2H).

EXAMPLE 60

5-Methoxy-2-(1H-thieno[3,2-c]pyrazol-3-yl)-1H-pyrrolo[3,2-b]pyridine

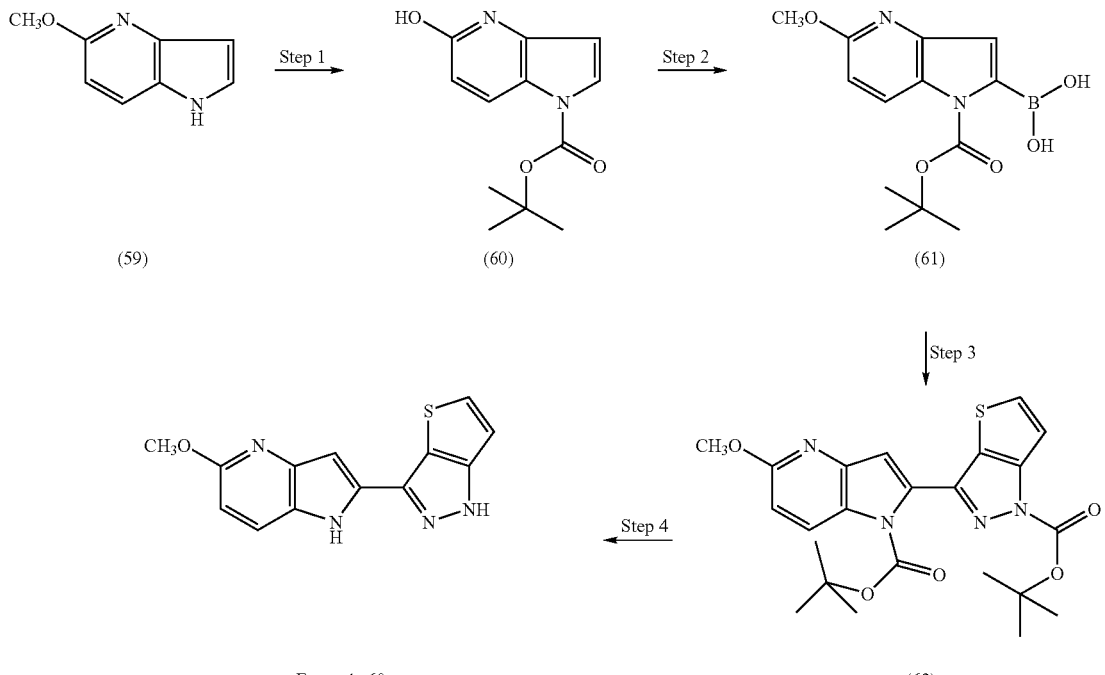

Example 60

Step 1. 4-Dimethylaminopyridine (102 mg, 0.835 mmol) was added to a mixture of 5-methoxy-pyrrolo[3,2-b]pyridine (4.50 g, 30.4 mmol, prepared according to procedures described in Liebigs Ann. Chem. 1988, 203-208), di-tert-butyl dicarbonate (10.7 g, 49.0 mmol), and anhydrous dichloromethane (100 mL) at room temperature with stirring. The resulting solution was stirred at room temperature overnight. The reaction was washed with water (75 mL) and brine (75 mL) successively, dried over magnesium sulfate, and concentrated under reduced pressure to an amber oil. The crude product was chromatographed on silica, eluting first with dichloromethane and then 10% ethyl acetate/dichloromethane to give 5-methoxy-pyrrolo[3,2-b]pyridine-1-carboxylic acid tert-butyl ester [7.06 g, 94%, Intermediate (60)] as a viscous amber oil. TLC $R_f$ 0.27 (silica, dichloromethane); LC/MS: 249.1 (M+H), $R_T$=3.60 minutes); $^1$H NMR [300 Mhz, (CD$_3$)$_2$SO]: δ 8.21 (d, J=9 Hz, 1H), 7.85 (d, J=4Hz, 1H), 6.76 (d, J=9 Hz, 1H), 6.70 (d, J=4 Hz, 1 H), 3.89 (s, 3H), 1.63 (s, 9H).

Step 2. A solution of tert-butyllithium (15.0 mL, of a 1.5 M solution in pentane, 22.5 mmol) was added in portions to a solution of 5-methoxy-pyrrolo[3,2-b]pyridine-1-carboxylic acid tert-butyl ester [4.66 g, 18.8 mmol, Intermediate (60)] in anhydrous tetrahydrofuran (85 mL) under nitrogen at −78° C. over 4 minutes. The resulting red reaction was stirred at −78° C. for 41 minutes. Triisopropyl borate (8.70 mL, 37.7 mmol) was added over 2 minutes and the red-brown reaction stirred at −78° C. for 20 minutes. The reaction was warmed to 0° C., stirred for 2.5 hours, and then water (50 mL) was added. After stirring at room temperature for 1 hour, the solvent was removed under reduced pressure. The aqueous mixture was basified with 5 N aqueous sodium hydroxide to pH 14. The mixture was extracted twice with ethyl acetate (30 mL). The aqueous layer was cooled to 0° C., acidified with 10% aqueous $KHSO_4$ to pH 4, and the resulting slurry aged at 0° C. for 15 minutes. The solid was collected, washed with water, and dried to yield 5-methoxy-1H-indole-2-boronic acid 1-carboxylic acid tert-butyl ester [2.48 g, 45%, Intermediate (61)] as a white powder. LC/MS: 293.16 (M+H), $R_T$=2.43 minutes; $^1$H NMR [300 Mhz, $(CD_3)_2SO$]: δ 8.28 (s, 2H), 8.23 (d, J=9 Hz, 1H), 6.70 (d, J=9 Hz, 1H), 6.58 (s, 1 H), 3.87 (s, 3H), 1.60 (s, 9H).

Step 3. A mixture of 5-methoxy-1H-indole-2-boronic acid 1-carboxylic acid tert-butyl ester [600 mg, 2.05 mmol, Intermediate (61)], 3-iodo-thieno[3,2-c]pyrazole-1-carboxylic acid tert-butyl ester [600 g, 1.71 mmol, Example 5B], cesium carbonate (2.23 g, 6.84 mmol), [1,1'-bis(diphenylphosphino)ferrocene]dichloropalladium(II) complex with dichloromethane (1:1) (93 mg, 0.114 mmol), 1,4-dioxane (12 mL), and water (3.0 mL) was purged with nitrogen and then heated at 90° C. with stirring under nitrogen. After 105 minutes, the reaction was cooled to room temperature, diluted with ethyl acetate (50 mL), and washed twice with water (25 mL) and brine (25 mL) successively. The organic layer was dried over magnesium sulfate and the solvent was removed under reduced pressure to give a brown foam The crude product was chromatographed on silica, eluting first with 5% ethyl acetate/dichloromethane and then 10% ethyl acetate/dichloromethane to give 2-(1-tert-butoxycarbonyl-1H-thieno[3,2-c]pyrazol-3-yl)-5-methoxy-pyrrolo[3,2-b]pyridine-1-carboxylic acid tert-butyl ester [470 mg (58%, Intermediate (62)] as a tan foam. TLC $R_f$0.46 (silica, 10% ethyl acetate/dichloromethane); LC/MS: 471.19 (M+H), $R_T$=4.02 minutes; $^1$H NMR [300 Mhz, $(CD_3)_2SO$]: δ 8.32 (d, J=9 Hz, 1H), 8.00 (d, J=5 Hz, 1H), 7.36 (d, J=5 Hz, 1H), 7.07 (s, 1 H), 6.88 (d, J=9 Hz, 1H), 3.92 (s, 3H), 1.65 (s, 9H), 1.33 (s, 9H).

Step 4. To a solution of 2-(1-tert-butoxycarbonyl-1H-thieno[3,2-c]pyrazol-3-yl)-5-methoxy-pyrrolo[3,2-b]pyridine-1-carboxylic acid tert-butyl ester [250 mg, 0.531 mmol, Intermediate (62)], anisole (1.0 mL), and dichloromethane (1.0 mL) at ambient temperature was added trifluoroacetic acid (1.0 mL) and the resulting solution heated at 45° C. After 1 hour, the green reaction solution was cooled to ambient temperature, basified with 5% aqueous potassium carbonate (30 mL), and the resulting mixture extracted twice with ethyl acetate (20 mL). The combined extracts were washed with water (20 mL) and brine (20 mL) successively, dried over magnesium sulfate, and concentrated in vacuo to an oily mixture. Trituration with ether/heptane (1:1) provided 5-methoxy-2-(1H-thieno[3,2-c]pyrazol-3-yl)-1H-pyrrolo[3,2-b]pyridine [107 mg, 74%, Example 60] as a tan powder. TLC $R_f$0.52 (silica, ethyl acetate); mp: 234-236° C.; LC/MS: 271.02 (M+H), $R_T$=2.03 minutes; $^1$H NMR [300 Mhz, $(CD_3)_2$ SO]: δ 13.32 (br s 1H), 11.67 (br s, 1H), 7.74 (d, J=5 Hz, 1H), 7.66 (d, J=9 Hz, 1H), 7.18 (d, J=5 Hz, 1H), 6.58-6.53 (m, 2H), 3.85 (s, 3H).

EXAMPLE 61

3-Bromo-6-(3-piperidin-1-yl-propoxy)-2-(1 H-thieno[3,2-c]pyrazol-3-yl)-1H-indole

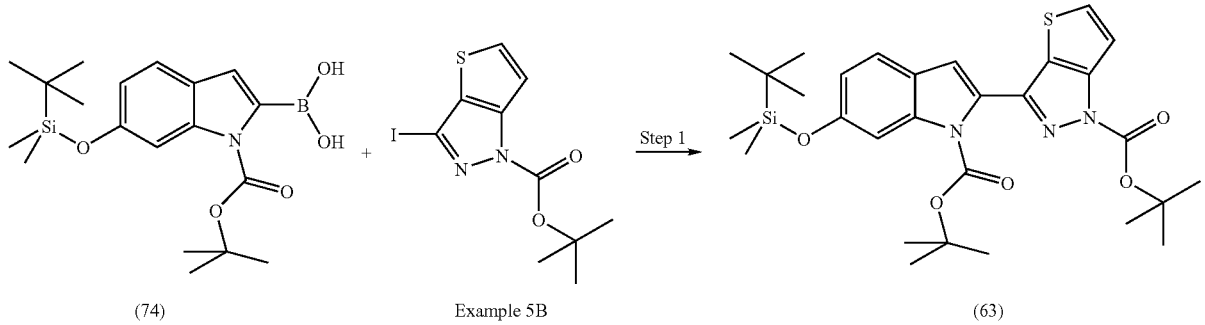

(74)   Example 5B   (63)

Step 2

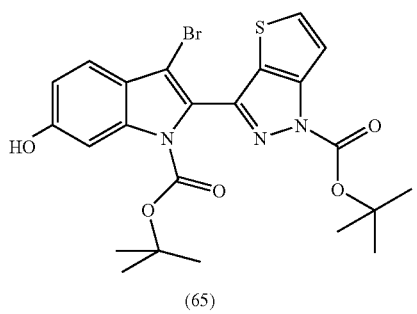 (65)

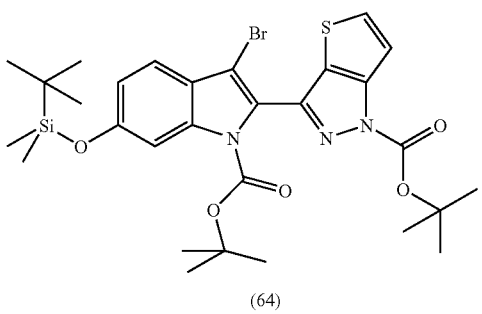 (64)

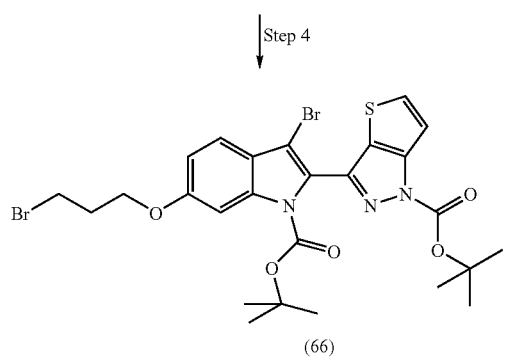 (66)

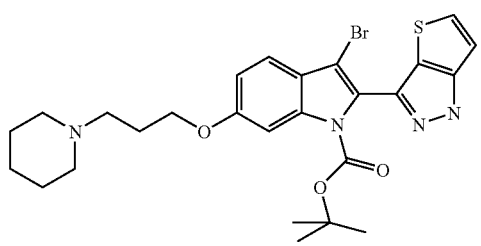

Example 61

Step 1. 2-(1-tert-butoxycarbonyl-1H-thieno[3,2-c]pyrazol-3-yl)-6-(tert-butyl-dimethyl-silanyloxy)-indole-1-carboxylic acid tert-butyl ester [Intermediate (63), LC-MS: 570 (M+H), $R_T$=4.2 minutes; $^1$H NMR [(CD$_3$)$_2$SO]: δ 7.98 (1H,d), 7.56 (2H,dd), 7.35(1H, d), 7.06 (1H, s), 6.86 (1H, dd), 1.65 (s, 9H), 1.33 (s, 3H), 0.99 (s, 9H), 0.23 (s, 6H)] was prepared in 46% yield using procedures similar to those of Example 5C, substituting 6-(tert-butyl-dimethylsilyloxy)-1H-indole-2-boronic acid [Intermediate (74), prepared by the application of method described in Example 4-6 of International Patent Application Publication No. WO 02/32861] for 5-(tert-butyl-dimethylsilanoxy)-1H-indole-2-boronic acid.

Step 2. To a solution of 2-(1-tert-butoxycarbonyl-1H-thieno[3,2-c]pyrazol-3-yl)-6-(tert-butyl-dimethyl-silanyloxy)-indole-1-carboxylic acid tert-butyl ester [0.87 g, 1.51 mmol, Intermediate (63)] in chloroform (15 mL) was added bromine (95 μL, 1.81 mmol). The reaction was stirred at room temperature overnight. A sodium bisulfite solution was added until the orange mixture turned to pale yellow. The mixture was extracted with diethyl ether. The organic layer was dried over magnesium sulfate and concentrated. The residue was chromatographed through silica gel (n-heptane/ethyl acetate, 95/5 then 80/20 as eluant) to provide 0.49 g of a monodeprotected product, 3-[3-bromo-6-(tert-butyl-dimethyl-silanyloxy)-1H-indol-2-yl]-thieno[3,2-c]pyrazole-1-carboxylic acid tert-butyl ester or 3-bromo-6-(tert-butyl-dimethyl-silanyloxy)-2-(1H-thieno[3,2-c]pyrazol-3-yl)-indole-1-carboxylic acid tert-butyl ester as a powder. This material was dissolved in dichloromethane (5 mL). Then di-tertbutyl dicarbonate (0.28 g, 1.10 mmol), triethylamine (0.15 mL, 0.98 mmol) and DMAP (0.03 g, 0.18 mmol) were added. The mixture was stirred at room temperature for 30 minutes. The solvent was removed. The residue was chromatographed through silica gel (n-heptane-ethyl acetate, 96:4 as eluant) to produce 3-bromo-2-(1-tert-butoxycarbonyl-1H-thieno[3,2-c]pyrazol-3-yl)-6-(tert-butyl-dimethyl-silanyloxy)-indole-1-carboxylic acid tert-butyl ester [0.33 g, 33%, Intermediate (64)] as a white powder. LC/MS: 648.1 (M+H), $R_T$=3.82 minutes.

Step 3. To a solution of 3-bromo-2-(1-tert-butoxycarbonyl-1H-thieno[3,2-c]pyrazol-3-yl)-6-(tert-butyl-dimethyl-silanyloxy)-indole-1-carboxylic acid tert-butyl ester [0.32 g, 49 mmol, Intermediate (64)] in tetrahydrofuran at 0° C. was added a 1.0 M TBAF solution in tetrahydrofuran (0.51 mL, 0.51 mmol). The resulting solution was stirred at 0° C. for 30 minutes. The solvent was removed. The residue was chromatographed through silica gel (dichloromethane/ethyl acetate, 95/05 as eluant) to produce 3-bromo-2-(1-tert-butoxycarbonyl-1H-thieno[3,2-c]pyrazol-3-yl)-6-hydroxy-indole-1-carboxylic acid tert-butyl ester [0.22g, 83%, Intermediate (65)] as an orange foam.

Step 4. To 3-bromo-2-(1-tert-butoxycarbonyl-1H-thieno[3,2-c]pyrazol-3-yl)-6-hydroxy-indole-1-carboxylic acid tert-butyl ester [0.22 g, 0.40 mmol, Intermediate (65)] in 1,3 dibromopropane (4 mL) was added cesium carbonate (0.33 g, 1.0 mmol). The resulting suspension was stirred at 75° C. for 1 hour then filtered. The insoluble was filtered off. The filtrate was concentrated. The residue was chromatographed through silica gel (n-heptane/ethyl acetate, 100/0 then 90/10) to provide 3-bromo-6-(3-bromo-propoxy)-2-(1-tert-butoxycarbonyl-1H-thieno[3,2-c]pyrazol-3-yl)-indole-1-carboxylic acid tert-butyl ester [0.19 g, 72%, Intermediate (66)] as a white foam. LC/MS: 654.0 (M+H), $R_T$=4.71 minutes.

Step 5. To 3-bromo-6-(3-bromo-propoxy)-2-(1-tert-butoxycarbonyl-1H-thieno[3,2-c]pyrazol-3-yl)-indole-1-carboxylic acid tert-butyl ester [0.17 g, 0.26 mmol, Intermediate (66)] in acetonitrile (4 mL) were added polymer supported DIEA (0.14 mg, 0.52 mmol) and 4-hydroxypiperidine (53 mg, 0.52 mmol). The mixture was gently stirred at 70° C. for 4 hours.

It was then filtered and concentrated. The residue was dissolved in dichloromethane (2 mL) and anisole (0.5 mL). Trifluoroacetic acid (0.5 mL) was added. The resulting bright yellow solution was stirred at 40° C. overnight as it turned to a greenish solution. It was directly loaded onto a cationic ion exchange column (SCX mega bond elut from VARIAN, 5 g), washed with methanol and eluted with 1.0 M ammonia in methanol. The appropriate fractions were combined and concentrated. The residue was chromatographed twice through silica gel (dichloromethane/1.0M ammonia in methanol, 85/15 as eluant) to provide 3-bromo-6-(3-piperidin-1-yl-propoxy)-2-(1H-thieno[3,2-c]pyrazol-3-yl)-1H-indole [29 mg, 23%, Example 61] as a purple powder. LC/MS: 475.08 (M+H), $R_T$=2.55 minutes; $^1$H NMR [300 Mhz, $(CD_3)_2SO$]: δ 13.45 (s, 1H), 11.59 (s, 1H), 7.69 (d, J=5.2 Hz, 1H), 7.27 (d, J=8.3 Hz, 1H), 7.15 (d, J=5.2 Hz, 1H), 6.91 (s, 1H), 6.75 (d, J=8.0 Hz, 1H), 4.60 (brs, 1H), 3.99 (m, 2 H), 3.47 (m, 1H), 2.80 (m, 2H), 2.11 (m, 2H), 1.92 (m, 2H), 1.73 (m, 2H), 1.42 (m, 2H), 1.13 (m, 2H).

EXAMPLE 62

{3-[6-(3-Piperidin-1-yl-propoxy)-1H-indol-2-yl]-1H-thieno[3,2-c]pyrazol-5-yl}-methanol

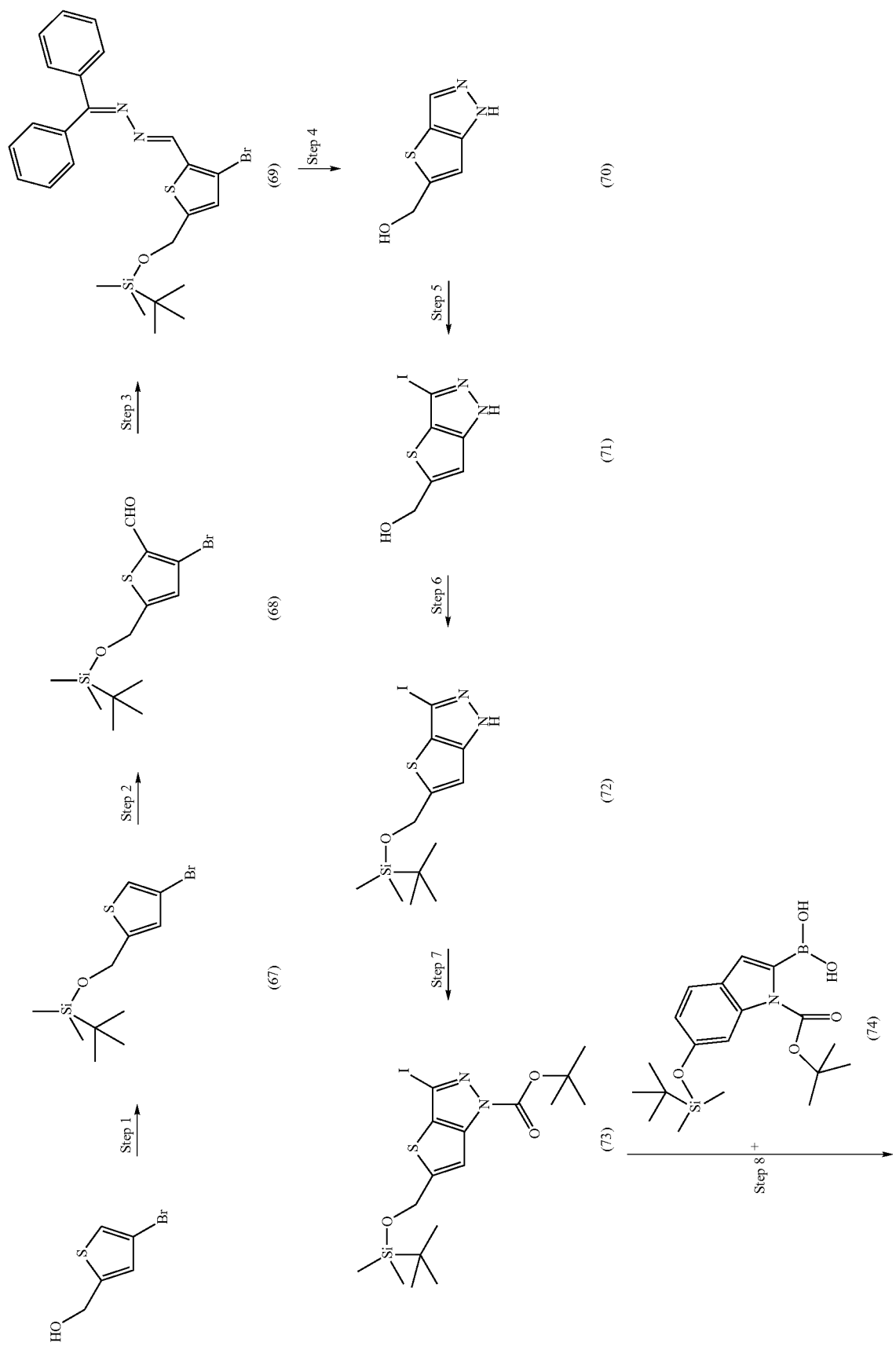

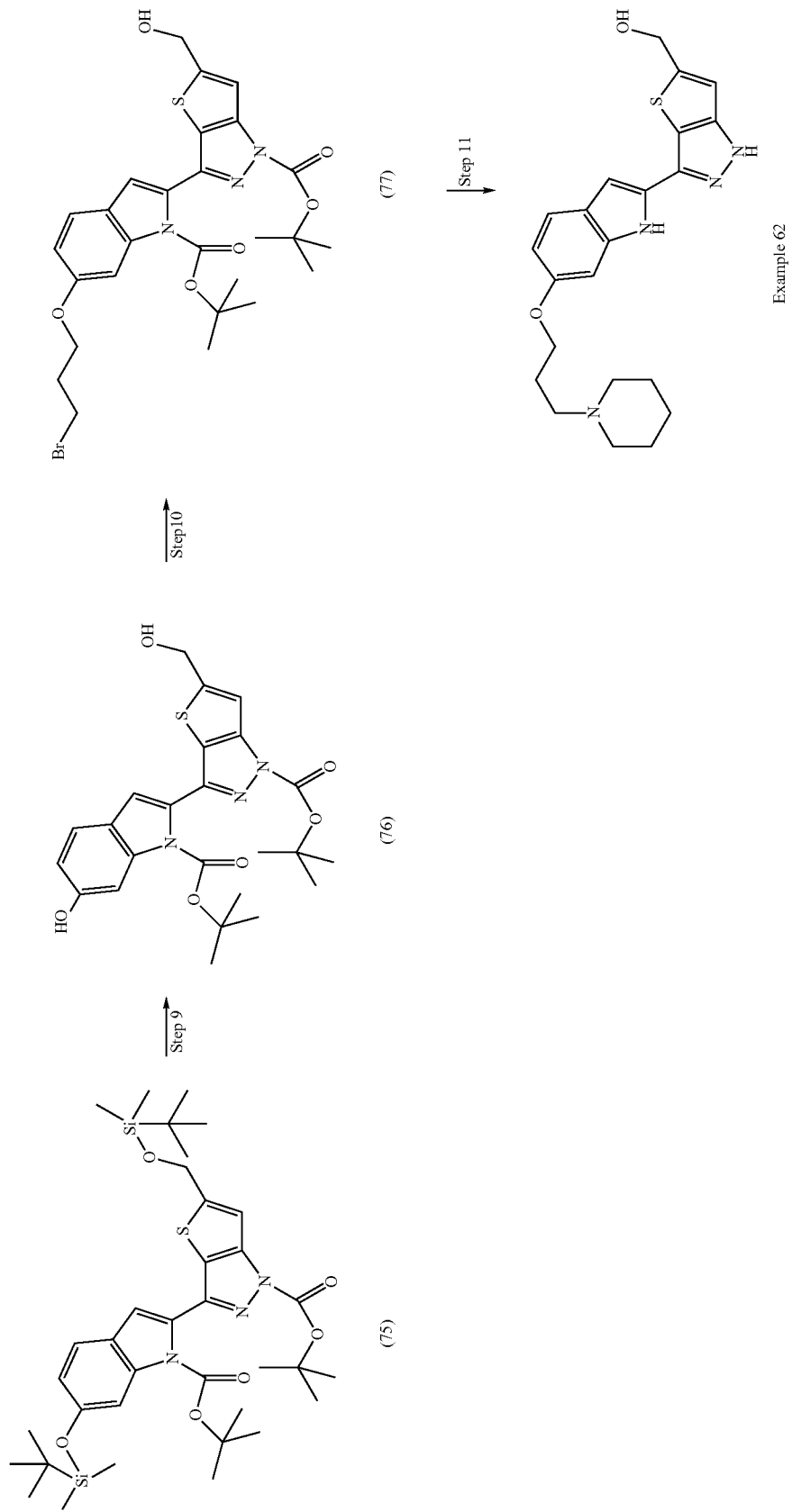

Step 1. To a solution of (4-bromo-thiophen-2-yl)-methanol (25 g, 130 mmol) in dichloromethane was added imidazole (9.7 g, 142 mmol) followed by tert-butyldimethylsilyl chloride (23.4 g, 156 mmol). The white suspension was stirred at room temperature for 30 minutes. The insoluble was filtered off. The filtrate was concentrated. The residual oil was chromatographed through silica gel (n-heptane/dichloromethane, 90/10 as eluant) to produce (4-bromo-thiophen-2-yl-methoxy)-tert-butyl-dimethyl-silane [34.6 g, Intermediate (67)] as a yellowish oil. LC/MS: 307.0 (M+H), $R_T$=4.38 minutes.

Step 2. To a solution of (4-bromo-thiophen-2-ylmethoxy)-tert-butyl-dimethyl-silane [34.6 g, 112.6 mmol, Intermediate (67)] in tetrahydrofuran (100 mL) at 0° C. under nitrogen atmosphere was added a 1.8 M LDA solution in tetrahydrofuran/heptane/ethylbenzene (68.8 mL, 123.9 mmol). Then N-formyl piperidine (15 mL, 135.1 mmol) was added. The dark green mixture was stirred at room temperature overnight and quenched with saturated aqueous ammonium chloride. It was extracted twice with ethyl acetate. The organic layer was dried over magnesium sulfate and concentrated. The residue was chromatographed through silica gel (n-heptane/ethyl acetate, 90/10 as eluant) to afford 3-bromo-5-(tert-butyl-dimethyl-silanyloxymethyl)-thiophene-2-carbaldehyde [30.1 g, 80%, Intermediate (68)].

Step 3. To a solution of 3-bromo-5-(tert-butyl-dimethyl-silanyloxymethyl)-thiophene-2-carbaldehyde [30.1 g, 89.7 mmol, Intermediate (68)] in ethanol (350 mL) was added benzophenone hydrazone (20 g, 104.7 mmol). The resulting yellow solution was stirred at reflux for 6 hours. The solvent was then removed and the residue was chromatographed through silica gel (n-heptane/dichloromethane, 20/80 as eluant) to produce N-benzhydrylidene-N'-[1-[3-bromo-5-(tert-butyl-dimethyl-silanyloxymethyl)-thiophen-2-yl]-methylidene]-hydrazine [41.3 g, Intermediate (69)]. LC/MS: 515.1 (M+H), (2 isomers detected) $R_T$=4.17 minutes and 4.34 minutes.

Step 4. To a solution of N-benzhydrylidene-N'-[1-[3-bromo-5-(tert-butyl-dimethyl-silanyloxymethyl)-thiophen-2-yl]-methylidene]-hydrazine [41.2 g, 80.2 mmol, Intermediate (69)] in toluene (500 mL) were added benzophenone hydrazone (18.9 g, 96.2 mmol), cesium carbonate (44.3 g, 136.3 mmol) then 1,1'-diphenylphosphinoferrocene (6.66 g, 12 mmol), and palladium acetate (1.35 g, 6 mmol). The orange mixture was stirred at 90° C. for 20 hours. The insoluble was filtered off and the filtrate was concentrated. The residue was chromatographed (n-heptane/ethyl acetate, 90/10). The resulting dark orange oil (45.7 g) was dissolved in ethanol (400 mL), then concentrated hydrochloric acid (150 mL) was added. The dark red mixture was stirred at 75° C. overnight. A 2.5 N solution of sodium hydroxide in water was added until pH is neutral. The mixture was then extracted twice with ethyl acetate. The organic layer was dried over magnesium sulfate and concentrated. The residue was chromatographed through silica gel (n-heptane/ethyl acetate, 50/50 then 20/80 as eluant) to afford (1H-thieno[3,2-c]pyrazol-5-yl)-methanol [3.3 g, 27%, Intermediate (70)] as an orange powder.

Step 5. To a solution of (1H-thieno[3,2-c]pyrazol-5-yl)-methanol [3.2 g, 20.8 mmol, Intermediate (70)] in solution in dimethyl formamide (40 mL) were added potassium hydroxide (3.5 g, 62.3 mmol) and iodine (7.9 g, 31.1 mmol). The mixture was stirred at room temperature for 5 hours. A concentrated solution of sodium bisulfite in water was added until the orange color disappeared. The resulting mixture was extracted several times with ethyl acetate. The combined organic layers were dried over magnesium sulfate and concentrated. The residue was triturated in dichloromethane to produce (3-iodo-1H-thieno[3,2-c]pyrazol-5-yl)-methanol [5.3 g, 91%, Intermediate (71)]. LC/MS: 280.91 (M+H), $R_T$=1.93 minutes; $^1$H NMR [300 Mhz, $(CD_3)_2SO$]: δ13.23 (s, 1H), 7.12 (s, 1H), 5.64 (t, J=6.6 Hz, 1H), 4.63 (d, J=6.5 Hz, 1H).

Step 6. To (3-iodo-1H-thieno[3,2-c]pyrazol-5-yl)-methanol [2.89 g, 10.3 mmol, Intermediate (71)] in dimethyl formamide (20 mL) was added imidazole (1.4 g, 20.6 mmol) and tert-butyldimethylsilyl chloride (2.63 g, 17.5 mmol). The resulting solution was stirred at room temperature for 5 minutes. It was then diluted with water and was extracted twice with ethyl acetate. The organic layer was washed with water, dried over magnesium sulfate and concentrated. The residue was chromatographed through silica gel (n-heptane/ethyl acetate, 100/0 then 90/10 then 70/30 as eluant) to produce 5-(tert-butyl-dimethyl-silanyloxymethyl)-3-iodo-1H-thieno [3,2-c]pyrazole [3.5g, 85%, Intermediate (72)] as a white powder. LC/MS: 395.0 (M+H), $R_T$=3.95 minutes.

Step 7. To 5-(tert-butyl-dimethyl-silanyloxymethyl)-3-iodo-1H-thieno[3,2-c]pyrazole [3.40 g, 8.62 mmol, Intermediate (72)] in dichloromethane (80 mL) were added DMAP (0.22 g, 1.72 mmol) and ditertbutyl dicarbonate (2.26 g, 10.34 mmol). The mixture was stirred at room temperature for 30 min. The solvent was then removed. The residue was chromatographed through silica gel (dichloromethane as eluant) to produce 5-(tert-butyl-dimethyl-silanyloxymethyl)-3-iodo-thieno[3,2-c]pyrazole-1-carboxylic acid tert-butyl ester [3.57 g, 84%, Intermediate (73)]. LC/MS: 495.07 (M+H), $R_T$=4.37 minutes. ps Step 8. To a solution of 6-(tert-butyl-dimethyl-silanoxy)-1H-indole-2-boronic acid [3.57 g, 9.13 mmol, Intermediate (74), prepared by the application of method described in Example 4-6 of International Patent Application Publication No. WO 02/32861] and 5-(tert-butyl-dimethyl-silanyloxymethyl)-3-iodo-thieno[3,2-c]pyrazole-1-carboxylic acid tert-butyl ester [3.47 g, 7.02 mmol, Intermediate (73)] in solution in 1,4-dioxane (60 mL) was added [1,1'-bis(diphenylphosphino)-ferrocene]dichloropalladium(II) (complex with dichloromethane (1:1)) (385 mg, 0.53 mmol). An aqueous solution (25 mL) of cesium carbonate (9.14 g, 28.08 mmol) was added. The mixture was stirred at 80° C. for 1 hour. It was allowed to cool down to room temperature, and was extracted three times with ethyl acetate. The organic layer was dried over magnesium sulfate and concentrated. The residue was chromatographed through silica gel (n-heptane/ethyl acetate, 95/05 then 90/10) to produce 2-[1-tert-butoxycarbonyl-5-(tert-butyl-dimethyl-silanyloxymethyl)-1H-thieno[3,2-c] pyrazol-3-yl]-6-(tert-butyl-dimethyl-silanyloxy)-indole-1-carboxylic acid tert-butyl ester [3.8 g, 76%, Intermediate (75)]. LC/MS: 714.38 (M+H), $R_T$=3.27 minutes.

Step 9. To a solution of 2-[1-tert-butoxycarbonyl-5-(tert-butyl-dimethyl-silanyloxymethyl)-1H-thieno[3,2-c]pyrazol-3-yl]-6-(tert-butyl-dimethyl-silanyloxy)-indole-1-carboxylic acid tert-butyl ester [3.2 g, 4.5 mmol, Intermediate (75)] in tetrahydrofuran (30 mL) at 0° C. was added a 1.0 M TBAF solution in tetrahydrofuran. The green solution was stirred at 0° C. until the reaction is complete and was then diluted with water. The resulting mixture was extracted with ethyl acetate. The organic layer was dried over magnesium sulfate and concentrated. The residue was chromatographed through silica gel (dichloromethane/ethyl acetate, 90/10 as eluant) to produce 2-(1-tert-butoxycarbonyl-5-hydroxymethyl-1H-thieno[3,2-c]pyrazol-3-yl)-6-hydroxy-indole-1-carboxylic acid tert-butyl ester [1.5 g (66%, Intermediate (76)]. LC/MS: 486.2 (M+H), R$_T$=3.30 minutes.

Step 10. To a suspension of 2-(1-tert-butoxycarbonyl-5-hydroxymethyl-1H-thieno[3,2-c]pyrazol-3-yl)-6-hydroxy-indole-1-carboxylic acid tert-butyl ester [1.45 g, 2.99 mmol, Intermediate (76)] in 1,3 dibromopropane (5 mL) was added cesium carbonate (2.43 g, 7.48 mmol). The suspension was stirred at 80° C. for 3 hours. It was allowed to cool down to room temperature. The insoluble was filtered off. The filtrate was loaded on silica gel for chromatography (n-heptane/ethyl acetate, 100/0 then gradually to 65/35 as eluant) to produce 6-(3-bromo-propoxy)-2-(1-tert-butoxycarbonyl-5-hydroxymethyl-1H-thieno[3,2-c]pyrazol-3-yl)-indole-1-carboxylic acid tert-butyl ester [990 mg, 55%, Intermediate (77)]. LC/MS: 606.1 (M+H), R$_T$=3.22 minutes.

Step 11. To 6-(3-bromo-propoxy)-2-(1-tert-butoxycarbonyl-5-hydroxymethyl-1H-thieno[3,2-c]pyrazol-3-yl)-indole-1-carboxylic acid tert-butyl ester [160 mg, 0.26 mmol, Intermediate (77)] in acetonitrile (4 mL) were added polymer supported DIEA (3.86 mmol/g, 135 mg, 0.52 mmol) and piperidine (52 µL, 0.52 mmol). The mixture was stirred gently at 75° C. for 3 hours. The PS-DIEA was filtered and the solvent was removed. The residue was chromatographed through silica gel (dichloromethane/1.0M ammonia in methanol, 90/10 as eluant) to produce a yellow oil. It was dissolved in dichloromethane (1 mL). Anisole (0.5 mL) then trifluoroacetic acid (0.5 mL) were added. The resulting yellow solution was stirred at 45° C. overnight then directly loaded onto a cationic exchange column (VARIAN, mega bond elut, 5 g) washed with methanol and eluted with 1.0M ammonia in methanol. The appropriate fractions were combined and concentrated. The residue was triturated in dichloromethane to afford {3-[6-(3-piperidin-1-yl-propoxy)-1H-indol-2-yl]-1H-thieno[3,2-c]pyrazol-5-yl}-methanol [91 mg, 84%, Example 62] as a white powder. LC/MS: 411.3 (M+H), R$_T$=2.42 minutes; $^1$H NMR [300 Mhz, (CD$_3$)$_2$SO]: δ 13.05 (s, 1H), 11.33 (s, 1H), 7.42 (d, J=8.5 Hz, 1H), 7.05 (s, 1H), 6.91 (s, 1H), 6.65 (dd, J$_1$=8.5 Hz, J$_2$=1.7 Hz, 1H), 6.52 (s, 1H), 5.65 (t, J=5.7 Hz, 1H), 4.70 (d, J=5.5 Hz, 2H), 3.99 (t, J=6.2 Hz, 2H), 2.45-2.36 (m, 6H), 1.89 (quint, J=6.7Hz, 2H), 1.49 (d, J=5.0 Hz, 4H), 1.39 (d, J=5.2 Hz, 2H).

EXAMPLE 63

1-{3-[6-(3-Piperidin-1-yl-propoxy)-1H-indol-2-yl]-1H-thieno[3,2-c]pyrazol-5-ylmethyl}-piperidin-4-ol

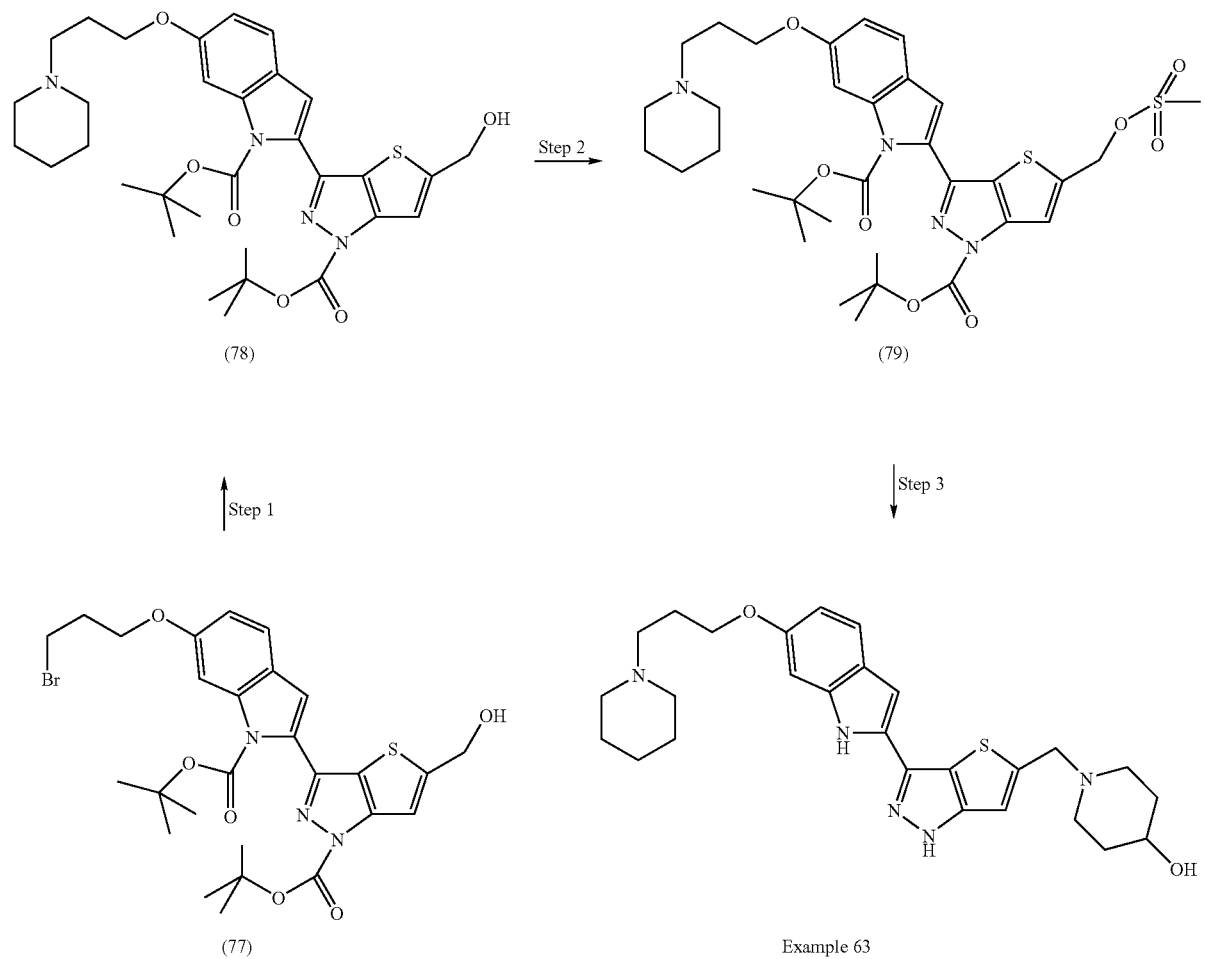

Step 1. To 6-(3-bromo-propoxy)-2-(1-tert-butoxycarbonyl-5-hydroxymethyl-1H-thieno[3,2-c]pyrazol-3-yl)-indole-1-carboxylic acid tert-butyl ester [990 mg, 1.63 mmol, Intermediate (77)] in acetonitrile (20 mL) were added polymer supported DIEA (3.83 mmol/g, 850 mg, 3.26 mmol) and piperidine (0.32 mL, 3.26 mmol). The mixture was stirred gently at 60° C. for 4 hours. The PS-DIEA was filtered and the solvent was removed. The residue was chromatographed through silica gel (dichloromethane/1.0M ammonia in methanol, 95/05) to produce 2-(1-tert-butoxycarbonyl-5-hydroxymethyl-1H-thieno[3,2-c]pyrazol-3-yl)-6-(3-piperidin-1-yl-propoxy)-indole-1-carboxylic acid tert-butyl ester [730 mg, 74%, Intermediate (78)] as a white foam. LC/MS: 611.2 (M+H), $R_T$=3.05 minutes.

Step 2. To 2-(1-tert-butoxycarbonyl-5-hydroxymethyl-1H-thieno[3,2-c]pyrazol-3-yl)-6-(3-piperidin-1-yl-propoxy)-indole-1-carboxylic acid tert-butyl ester [1.21 g, 1.98 mmol, Intermediate (78)] in dichloromethane (25 mL) at 0° C. was added triethylamine (0.29 mL, 2.28 mmol) and methane sulfonyl chloride (0.34 mL, 4.40 mmol). The mixture was stirred at 0° C. for 30 minutes then at room temperature for 4 hours. It was diluted with dichloromethane then washed with saturated sodium bicarbonate. The organic layer was dried over magnesium sulfate and concentrated. The residue was chromatographed through silica gel (dichloromethane/methanol, 90/10 as eluant) to produce 2-(1-tert-butoxycarbonyl-5-methanesulfonyloxymethyl-1H-thieno [3,2-c]pyrazol-3-yl)-6-(3-piperidin-1-yl-propoxy)-indole-1-carboxylic acid tert-butyl ester [0.85 g, 62%, Intermediate (79)] as a yellow foam. LC/MS: 689.3 (M+H), $R_T$=2.58 minutes.

Step 3. To 2-(1-tert-butoxycarbonyl-5-methanesulfonyloxymethyl-1H-thieno[3,2-c]pyrazol-3-yl)-6-(3-piperidin-1-yl-propoxy)-indole-1-carboxylic acid tert-butyl ester [150 mg, 0.26 mmol, Intermediate (79)] in dichloromethane (5 mL) were added triethylamine (40 µL, 0.31 mmol), and 4-hydroxypiperidine (55 mg, 0.52 mmol). The mixture was stirred at 45° C. for 15 hours. It was concentrated. The residue was chromatographed through silica gel (dichloromethane/1.0M ammonia in methanol, 90/10). The appropriate fractions were combined and concentrated. The residue was dissolved into dichloromethane (2 mL) and anisole (0.5 mL). Trifluoroacetic acid (0.5 mL) was added. The solution was stirred at 45° C. for 3 hours. It was then directly loaded onto a cationic ion exchange column (Varian Mega Bond Elut SCX, 5 g) washed with methanol and eluted with 1.0M ammonia in methanol. The appropriate fractions were combined and concentrated. The residue was triturated in dichloromethane then chromatographed through silica gel (dichloromethane/methanol, 90/10 as eluant) to provide 1-{3-[6-(3-piperidin-1-yl-propoxy)-1H-indol-2-yl]-1H-thieno[3,2-c]pyrazol-5-ylmethyl}-piperidin-4-ol [19 mg, Example 63]. LC/MS: 494.3 (M+H), $R_T$=1.77 minutes; $^1$H NMR [300 Mhz, (CD$_3$)$_2$SO]: δ 13.01 (s, 1h), 11.30 (s, 1H), 7.40 (d, J=8.5 Hz, 1H), 7.04 (s, 1H), 6.90 (s, 1H), 6.64 (dd, J1=8.6 Hz, J2=2.1 Hz, 1H), 4.54 (d, J=4 Hz, 1H), 3.98 (t, J=6.2 Hz, 2H), 3.71 (s, 2H), 3.46 (m, 1H), 2.77 (m, 2H), 2.49-2.35 (m, 6H), 2.15 (t, J=9.7 Hz, 2H), 1.90 (t, J=6.7Hz, 2H), 1.73 (m, 2H), 1.55-1.30 (m, 8H).

EXAMPLE 64

2-{5-[4-(4-Fluoro-phenyl)-piperazin-1-ylmethyl]-1H-thieno[3,2-c]pyrazol-3-yl}-6-(3-piperidin-1-yl-propoxy)-1H-indole

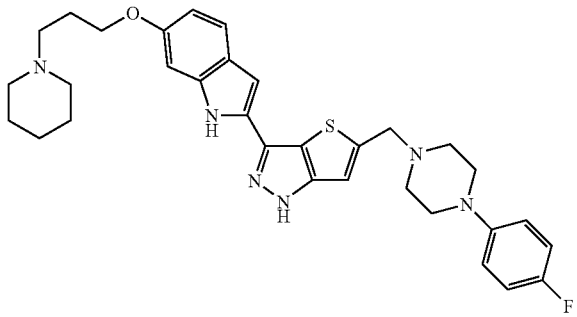

This compound [LC/MS: 573.3 (M+H), $R_T$=2.17 minutes; $^1$H NMR [300 Mhz, (CD$_3$)$_2$SO]: δ 13.07 (s, 1H), 11.30 (s, 1H), 7.39 (d, J=8.5 Hz, 1H), 7.11 (s, 1H), 6.99 (m, 1H), 6.92 (m, 1H), 6.63 (d, J=8.5 Hz, 1H), 6.53 (s, 1H), 6.98 (t, J=6.2 Hz, 2H), 3.82 (s, 2H), 3.11 (brs, 2H), 2.64 (brs, 2H), 2.49-2.33 (m, 6H), 1.88 (t, J=6.7 Hz, 2H), 1.49 (m, 4H), 1.38 (m, 2H)] was prepared in 46% yield using procedures similar to those of Example 63, substituting 1-(4-fluoro-phenyl)-piperazine for 4-hydroxypiperidine in step 3 of Example 63.

EXAMPLE 65

Methyl-{3-[6-(3-piperidin-1-yl-propoxy)-1H-indol-2-yl]-1H-thieno[3,2-c]pyrazol-5-ylmethyl}-pyridin-2-yl-amine

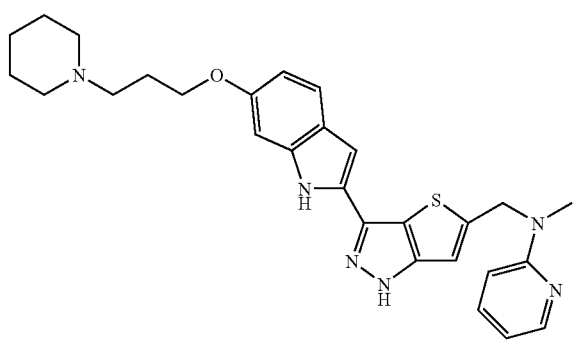

This compound [LC/MS: 501.3 (M+H), $R_T$=1.93 minutes; $^1$H NMR [300 Mhz, (CD$_3$)$_2$SO]: δ 13.01 (s, 1H), 11.31 (s, 1H), 8.49 (d, J=4.5 Hz, 1H), 7.77 (m, 1H), 7.47 (d, J=8 Hz, 1H), 7.40 (d, J=8.5 Hz, 1H), 7.26 (t, J=6.1 Hz, 1H), 7.06 (s, 1H), 6.90 (s, 1H), 6.64 (d, J=8.7H, 1H), 6.52 (s, 1H), 3.99 (s, 3H), 3.97 (m, 2H), 3.87 (s, 2H), 2.43 (m, 6H), 1.91 (t, J=6.4 Hz, 2H), 1.53 (m, 4H), 1.40 (m, 2H)] was prepared in 6% yield using procedures similar to those of Example 63, substituting methyl-pyridin-2-yl-amine for 4-hydroxypiperidine in step 3 of Example 63.

EXAMPLE 66

Benzyl-{3-[6-(3-piperidin-1-yl-propoxy)-1H-indol-2-yl]-1H-thieno[3,2-c]pyrazol-5-ylmethyl}-amine

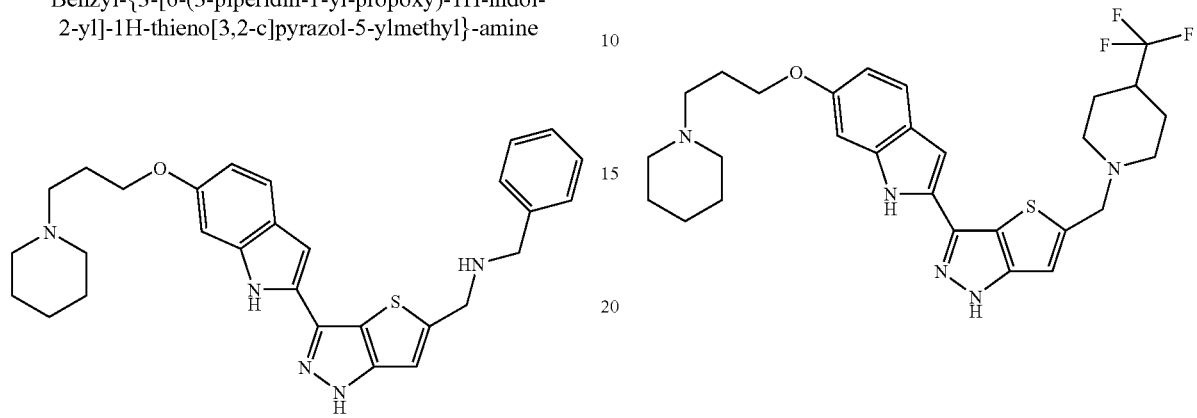

This compound [LC/MS: 500.3 (M+H), $R_T$=1.68 minutes; $^1$H NMR [300 Mhz, (CD$_3$)$_2$SO]: δ 13.00 (s, 1H), 11.29 (s, 1H), 7.42-7.20 (m, 6H), 7.04 (s, 1H), 6.90 (d, J=2 Hz, 1H), 6.64 (dd, J1=2.2 Hz, J2=8.5 Hz, 1H), 6.53 (s, 1H), 3.98 (t, J=6.5 Hz, 2H), 3.93 (s, 2H), 3.76 (s, 1H), 2.94 (bs, 1H), 2.41 (t, J=1.9 Hz, 2H), 2.34 (m, 4H), 1.88 (m, 2H), 1.50 (m, 4H), 1.38 (m, 2H)] was prepared in 37% yield using procedures similar to those of Example 63, substituting benzylamine for 4-hydroxypiperidine in step 3 of Example 63.

EXAMPLE 67

6-(3-Piperidin-1-yl-propoxy)-2-[5-(4-trifluoromethyl-piperidin-1-ylmethyl)-1H-thieno[3,2-c]pyrazol-3-yl]-1H-indole

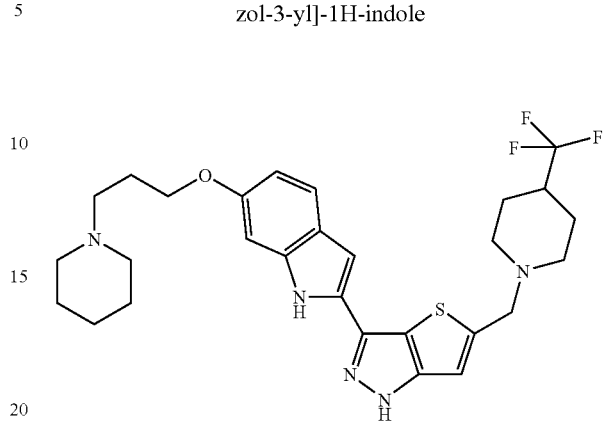

This compound [LC/MS: 546.3 (M+H), $R_T$=1.66 minutes; $^1$H NMR [300 Mhz, (CD$_3$)$_2$SO]: δ 13.03 (s, 1H), 11.29 (s, 1H), 7.39 (d, J=8.5 Hz, 1H), 7.07 (s, 1H), 6.89 (s, 1H), 6.63 (m, 1H), 6.52 (s, 1H), 3.98 (t, J=6.3 Hz, 2H), 3.77 (s, 2H), 3.01 (d, J=11 Hz, 2H), 2.43-2.27 (m, 7H), 2.07 (t, J=10.8 Hz), 1.92-1.78 (m, 4H), 1.50 (m, 6H), 1.37 (m, 2H)] was prepared in 36% yield using procedures similar to those of Example 63, substituting 4-trifluoromethyl-piperidine for 4-hydroxypiperidine in step 3 of Example 63.

EXAMPLE 68

[2-(5-Piperidin-1-ylmethyl-1H-thieno[3,2-c]pyrazol-3-yl)-1H-indol-5-yl]-methanol

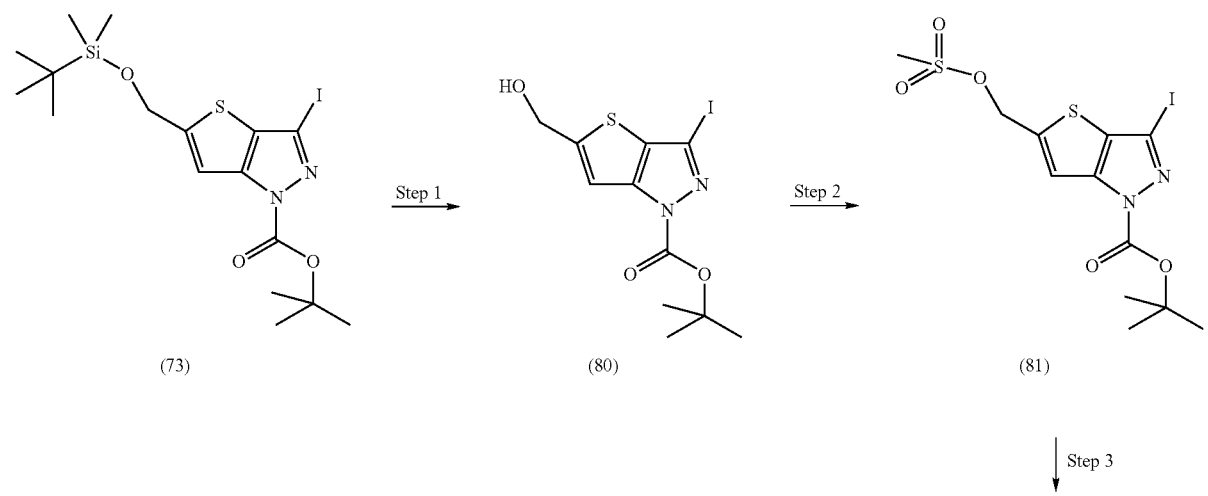

-continued

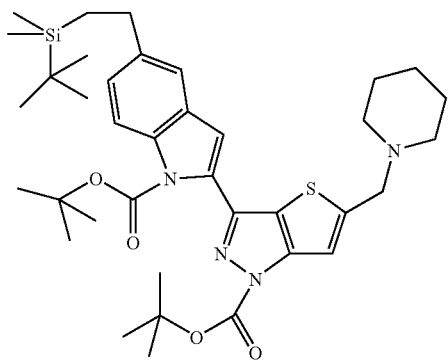

(83)

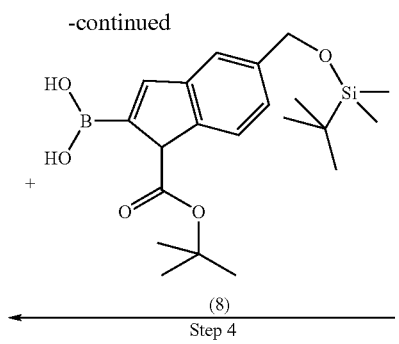

(8)

Step 4

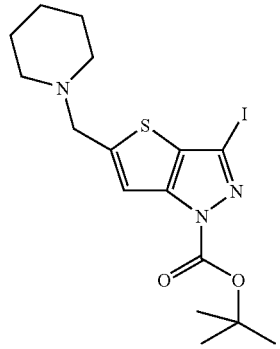

(82)

Step 5

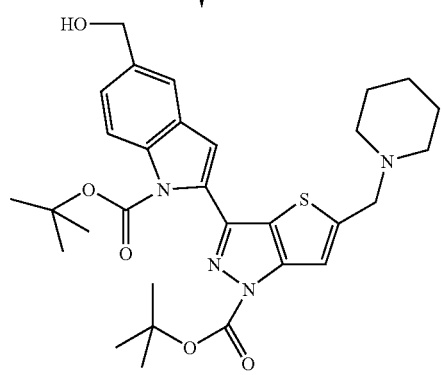

(84)

Step 6

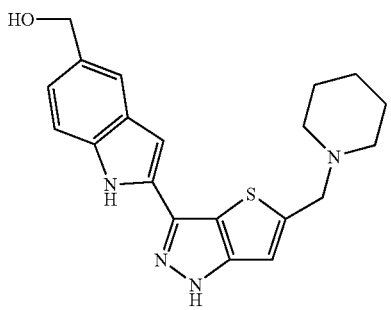

Example 68

Step 1. To 5-(tert-butyl-dimethyl-silanyloxymethyl)-3-iodo-thieno[3,2-c]pyrazole-11-carboxylic acid tert-butyl ester [410 mg, 0.83 mmol, Intermediate (73)] in tetrahydrofuran (5 mL) was added a 1.0M TBAF solution in tetrahydrofuran (0.92 mL, 0.92 mmol) at 0° C. The solution was stirred at 0° C. for 1 hour. The solvent was removed and the residue was chromatographed through silica gel (dichloromethane/ethyl acetate, 90/10 as eluant) to afford 5-hydroxymethyl-3-iodo-thieno[3,2-c]pyrazole-1-carboxylic acid tert-butyl ester [230 mg, 73%, Intermediate (80)] as a white powder. LC/MS: 380.97 (M+H), $R_T$=2.8 minutes.

Step 2. To 5-hydroxymethyl-3-iodo-thieno[3,2-c]pyrazole-1-carboxylic acid tert-butyl ester [220 mg, 0.58 mmol, Intermediate (80)] in dichloromethane (5 mL) were added triethylamine (85 μL, 0.67 mmol), and methane sulfonyl chloride (50 μL, 0.67 mmol). The mixture was stirred at 0° C. for 15 minutes then at room temperature for 30 minutes. The solution was washed with saturated sodium bicarbonate. The organic layer was dried over magnesium sulfate and concentrated to afford 3-iodo-5-methanesulfonyloxymethyl-thieno[3,2-c]pyrazole-1-carboxylic acid tert-butyl ester [220 mg, 79%, Intermediate (81)] as a white foam. LC/MS: 458.97 (M+H), $R_T$=3.39 minutes.

Step 3. To 3-iodo-5-methanesulfonyloxymethyl-thieno[3,2-c]pyrazole-1-carboxylic acid tert-butyl ester [210 mg, 0.46 mmol, Intermediate (81)] in dichloromethane (3 mL) were added triethylamine (70 μL, 0.55 mmol), and piperidine (55 μL, 0.55 mmol). The mixture was stirred at room temperature for 1 hour. The solvent was removed and the residue was chromatographed through silica gel (dichloromethane/ethyl acetate, 95/05 as eluant) to produce 3-iodo-5-piperidin-1-ylmethyl-thieno[3,2-c]pyrazole-1-carboxylic acid tert-butyl ester [110 mg, 53%, Intermediate (82)] as a white foam. LC/MS: 448.0 (M+H), $R_T$=2.55 minutes.

Step 4. To 3-iodo-5-piperidin-1-ylmethyl-thieno[3,2-c]pyrazole-1-carboxylic acid tert-butyl ester [390 mg, 0.87 mmol, Intermediate (82)] in 1,4-dioxane (8 mL) were added 5-(tert-butyl-dimethyl-silanyloxymethyl)-1H-indole-2-boronic acid 1-carboxylic acid tert-butyl ester (450 mg, 1.13 mmol, Intermediate (8), prepared as described in Example 1-4 of International Patent Application Publication No. WO 02/32861], and [1,1'-bis(diphenylphosphino)-ferrocene]dichloropalladium(II) (complex with dichloromethane (1:1)) (50 mg, 0.07 mmol), followed by cesium carbonate (1.13 g, 3.48 mmol) and water (3 mL). The mixture was stirred at 80° C. for 3 hours. It was then extracted three times with ethyl acetate. The organic layer was dried over magnesium sulfate and concentrated. The residual oil was chromatographed through silica gel (dichloromethane/methanol, 95/05 as eluant) to produce 2-(1-tert-butoxycarbonyl-5-piperidin-1-ylmethyl-1H-thieno[3,2-c]pyrazol-3-yl)-5-(tert-butyl-dimethyl-silanyloxymethyl)-indole-1-carboxylic acid tert-butyl ester [310 mg, 53%, Intermediate (83)] as a white powder. LC/MS: 681.33 (M+H), $R_T$=3.88 minutes.

Step 5. To 2-(1-tert-butoxycarbonyl-5-piperidin-1-ylmethyl-1H-thieno[3,2-c]pyrazol-3-yl)-5-(tert-butyl-dimethyl-silanyloxymethyl)-indole-1-carboxylic acid tert-butyl ester [530 mg, 0.78 mmol, Intermediate (83)] in tetrahydrofuran (10 mL) at 0° C. was added a 1M solution of TBAF in tetrahydrofuran (0.86, 0.86 mmol). The mixture was stirred at 0° C. for 2 hours. It was diluted with ethyl acetate and washed with saturated aqueous ammonium chloride. The organic layer was dried over magnesium sulfate and concentrated. The residue was chromatographed through silica gel (n-heptane/ethyl acetate, 80/20 as eluant) to afford 2-(1-tert-butoxycarbonyl-5-piperidin-1-ylmethyl-1H-thieno[3,2-c]pyrazol-3-yl)-5-hydroxymethyl-indole-1-carboxylic acid tert-butyl ester [305 mg, 70%, Intermediate (84)] as a white foam. LC/MS: 567.3 (M+H), $R_T$=2.89 minutes.

Step 6. To 2-(1-tert-butoxycarbonyl-5-piperidin-1-ylmethyl-1H-thieno[3,2-c]pyrazol-3-yl)-5-hydroxymethyl-indole-1-carboxylic acid tert-butyl ester [280 mg, 0.50 mmol, Intermediate (84)] in a mixture of tetrahydrofuran (5 mL) and water (1 mL) was added sodium hydroxide (150 mg, 3.75 mmol). The mixture was stirred at 65° C. overnight. It was diluted with ethyl acetate. The mixture was washed with saturated aqueous ammonium chloride. The aqueous layer was extracted with ethyl acetate. The combined organic layers were dried over magnesium sulfate and concentrated. The residue was chromatographed through silica gel (dichloromethane/1.0M ammonia in methanol, 95/05 then 50/50 as eluant) to produce [2-(5-piperidin-1-ylmethyl-1H-thieno[3,2-c]pyrazol-3-yl)-1H-indol-5-yl]-methanol [10 mg, 5%, Example 68] as a white powder. LC/MS: 367.1 (M+H), $R_T$=2.22 minutes; $^1$H NMR [300 Mhz, $(CD_3)_2SO$]: δ 13.08 (s, 1H), 11.45 (s, 1H), 7.47 (s, 1H), 7.34 (d, J=8.2 Hz, 1H), 7.07 (s, 1H), 7.05 (s, 1H), 6.57 (s, 1H), 4.98 (m, 1H), 4.53 (d, J=5.8 Hz, 2H), 3.71 (s, 2H), 2.44 (m, 4H), 1.53 (m, 4H), 1.42 (m, 2H).

EXAMPLE 69

1-{3-[2-(5-Benzyloxymethyl-1H-thieno[3,2-c]pyrazol-3-yl)-1H-indol-6-yloxy]-propyl}-piperidin-4-ol

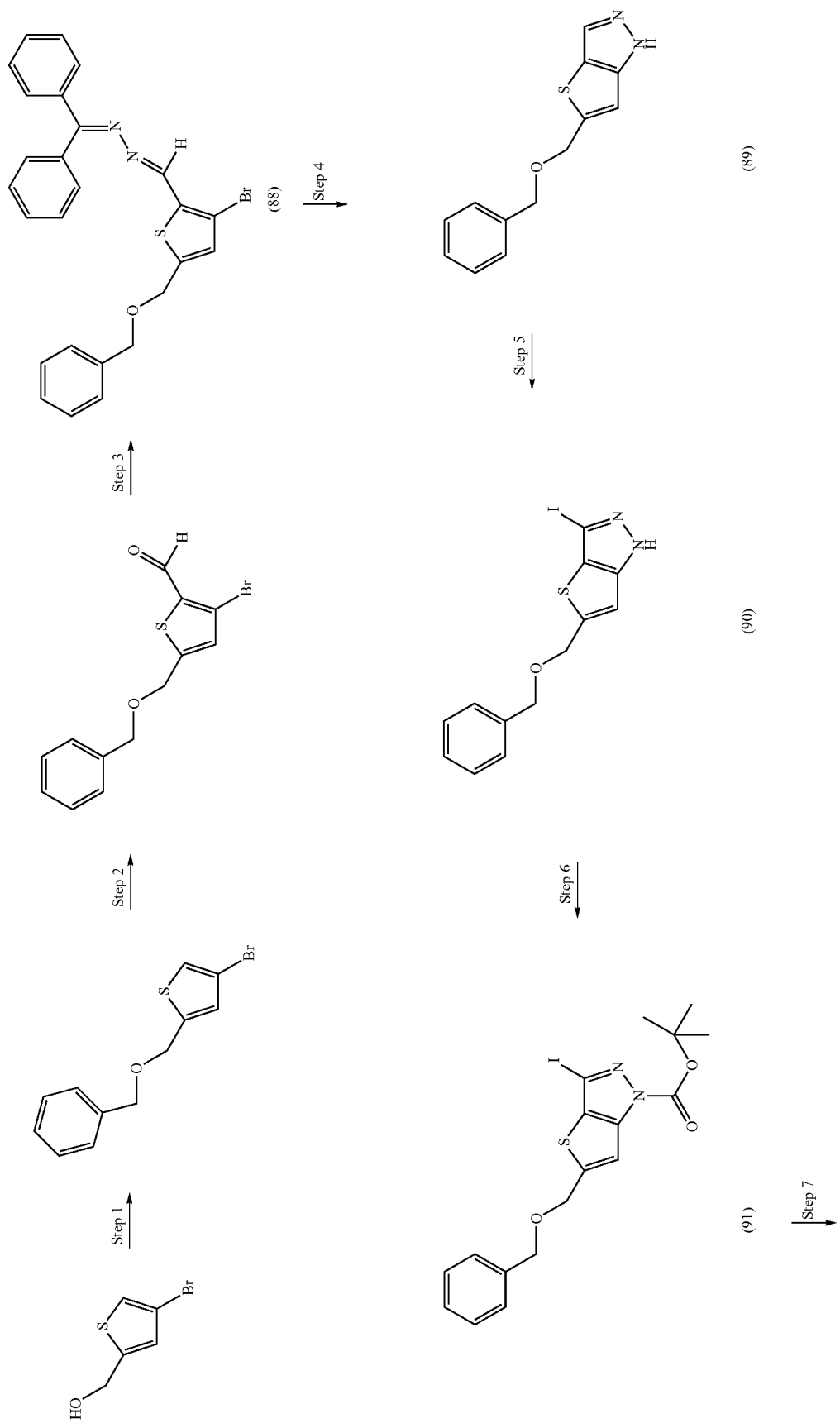

139
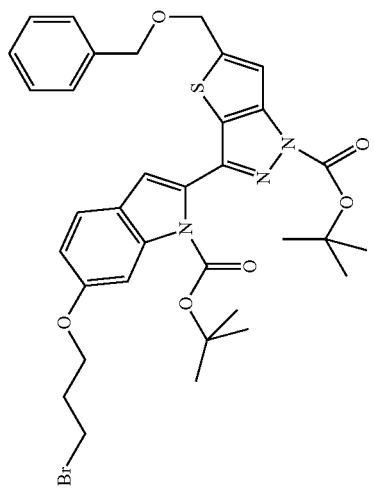
(94)
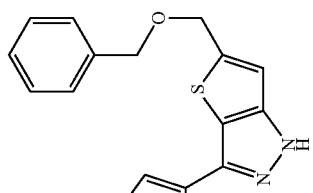
Step 10
140
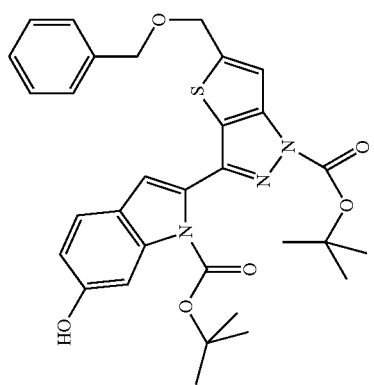
Example 69
-continued
(93)
Step 9
(92)
Step 8
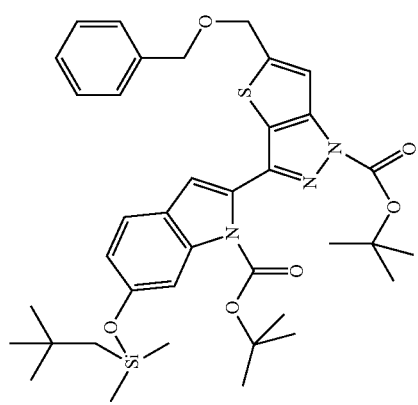

Step 1. To (4-bromo-thiophen-2-yl)-methanol (18.8 g, 97.4 mmol, Intermediate (85)] in tetrahydrofuran (200 mL) was added sodium hydride (3.9 g, 97.4 mmol) at 0° C. under nitrogen atmosphere. The reaction mixture was stirred at room temperature for 30 minutes. Tetrabutylammonium iodide (3.6 g, 9.7 mmol) was added followed by benzyl bromide (11.6 mL, 97.4 mmol). The mixture was stirred at room temperature for 1 hour. Water was added. The resulting mixture was extracted with diethyl ether. The ether layer was dried over magnesium sulfate and concentrated. The residue was chromatographed through silica gel (n-heptane/ethyl acetate, 90/10 as eluant) to provide 2-benzyloxymethyl-4-bromo-thiophene [29.2 g, Intermediate (86)] (quantitative) as a yellow oil. LC/MS: 282.96 (M+H), $R_T$=3.68 minutes.

Step 2. To 2-benzyloxymethyl-4-bromo-thiophene (29.2 g, 103 mmol, Intermediate (86)] in tetrahydrofuran (100 mL) was added dropwise a 1.8M solution of LDA in tetrahydrofuran (63 mL, 113 mmol) at 0° C. under nitrogen atmosphere. The solution was stirred at 0° C. for 30 minutes. Then N-formyl piperidine (13.75 mL, 127 mmol) was added and the reaction was stirred at 0° C. for 45 minutes, at room temperature for 15 minutes, and was quenched with saturated aqueous ammonium chloride. The mixture was extracted with ethyl acetate. The organic layer was dried over magnesium sulfate and concentrated. The residual oil was chromatographed through silica gel (n-heptane/ethyl acetate, 90/10 as eluant) to afford 5-benzyloxymethyl-3-bromo-thiophene-2-carbaldehyde [23.3 g, Intermediate (87)] as an orange oil.

Step 3. To (5-benzyloxymethyl-3-bromo-thiophene-2-carbaldehyde (23.2 g, 74.6 mmol, Intermediate (87)] in ethanol was added hydrazone benzophenone (16.1 g, 82 mmol). The mixture was stirred at 80° C. overnight. The solvent was removed. The residual oil was chromatographed through silica gel (n-heptane/ethyl acetate, 60/40 then 0/100 as eluant) to produce N-benzhydrylidene-N'-[1-(5-benzyloxymethyl-3-bromo-thiophen-2-yl)-methylidene]-hydrazine [34.1 g, 68%, 2 steps, Intermediate (88)] as a yellow waxy solid. LC/MS: 489.0 (M+H), $R_T$=1.48min and 1.84 minutes.

Step 4. To N-benzhydrylidene-N'-[1-(5-benzyloxymethyl-3-bromo-thiophen-2-yl)-methylidene]-hydrazine (34 g, 69.5 mmol, Intermediate (88)] in toluene (500 mL) were added hydrazone benzophenone (16.4, 83.4 mmol), cesium carbonate (38.4 g, 118.2 mmol), 1,1'diphenylphosphinoferrocene (5.8 g, 10.4 mmol), and palladium (II) acetate (1.17 g, 5.2 mmol). The suspension was stirred at 90° C. under nitrogen atmosphere until reaction is complete. The solvent was removed. The residual oil was chromatographed (ethyl acetate/n-heptane, 10/90 as eluant) to product an orange oil. It was dissolved in ethanol (350 mL). Concentrated hydrochloric acid (100 mL) was added. The dark mixture was stirred at 80° C. for hours then diluted with water. It was extracted with ethyl acetate. The organic layer was dried over magnesium sulfate and concentrated. The residue was chromatographed through silica gel (n-heptane/ethyl acetate, 80/20 then 50/50 as eluant) to afford 5-benzyloxymethyl-1H-thieno[3,2-c]pyrazole [5.2 g, 37%, Intermediate (89)] as an orange powder. LC/MS: 245.1 (M+H), $R_T$=2.83 minutes. $^1$H NMR [300 Mhz, $(CD_3)_2SO$]: tautomer 1: δ 12.97 (s, 1H), 7.73 (s, 1H), 7.40-7.25 (m, 5H), 7.15-7.05 (m, 1H), 4.71 (s, 2H), 4.55 (s, 2H) tautomer 2: δ 13.27 (brs, 1H), 7.98 (s, 1H), 7.40-7.25 (m, 5H), 7.15-7.05 (m,1H), 4.71 (s, 2H), 4.55 (s, 2H).

Step 5. 5-Benzyloxymethyl-3-iodo-1H-thieno[3,2-c]pyrazole [Intermediate (90), LC/MS: 371.0 (M+H), $R_T$=3.49 minutes] was prepared in 77% yield using procedures similar to those of Example 5A, substituting 5-benzyloxymethyl-1H-thieno[3,2-c]pyrazole [Intermediate (89)] for 1H-thieno[3,2-c]pyrazole.

Step 6. 5-Benzyloxymethyl-3-iodo-thieno[3,2-c]pyrazole-1-carboxylic acid tert-butyl ester [Intermediate (91)] was prepared in 100% yield using procedures similar to those of Example 5B, substituting 5-benzyloxymethyl-3-iodo-1H-thieno[3,2-c]pyrazole [Intermediate (90)] for 3-iodo-1H-thieno[3,2-c]pyrazole.

Step 7. 2-(5-Benzyloxymethyl-1-tert-butoxycarbonyl-1H-thieno[3,2-c]pyrazol-3-yl)-6-(tert-butyl-dimethyl-silanyloxy)-indole-1-carboxylic acid tert-butyl ester [Intermediate (92)] was prepared in 39% yield using procedures similar to those of Example 5C, substituting 5-benzyloxymethyl-3-iodo-thieno[3,2-c]pyrazole-1-carboxylic acid tert-butyl ester [Intermediate (91)] for 3-iodo-thieno[3,2c]pyrazole-1-carboxylic acid tert-butyl ester and 6-(tert-butyl-dimethyl-silanoxy)-1-(tert-butoxycarbonyl)-1H-indole-2-boronic acid [Intermediate (74), prepared by the application of method described in Example 4-6 of International Patent Application Publication No. WO 02/32861] for 5-(tert-butyl-dimethylsilanoxy)-1-(tert-butoxycarbonyl)-1H-indole-2-boronic acid.

Step 8. 2-(5-Benzyloxymethyl-1-tert-butoxycarbonyl-1H-thieno[3,2-c]pyrazol-3-yl)-6-hydroxy-indole-1-carboxylic acid tert-butyl ester [Intermediate (93), LC/MS: 576.2 (M+H), $R_T$=4.0 minutes] was prepared in 33% yield using procedures similar to those of Example 5D, substituting 2-(5-benzyloxymethyl-1-tert-butoxycarbonyl-1H-thieno[3,2-c]pyrazol-3-yl)-6-(tert-butyl-dimethyl-silanyloxy)-indole-1-carboxylic acid tert-butyl ester [Intermediate (92)] for 2-(1-tert-butoxycarbonyl-1H-thieno[3,2c]pyrazol-3-yl)-5-(tert-butyl-dimethyl-silanoxy)-indole-1-carboxylic acid tert-butyl ester.

Step 9. 2-(5-Benzyloxymethyl-1-tert-butoxycarbonyl-1H-thieno[3,2-c]pyrazol-3-yl)-6-(3-bromo-propoxy)-indole-1-carboxylic acid tert-butyl ester [Intermediate (94), LC/MS: 696.0 (M+H), $R_T$=4.82 minutes] was prepared in 72% yield using procedures similar to those of Example 5E, substituting 2-(5-benzyloxymethyl-1-tert-butoxycarbonyl-1H-thieno[3,2-c]pyrazol-3-yl)-6-hydroxy-indole-1-carboxylic acid tert-butyl ester [Intermediate (93)] for 2-(1-tert-butoxycarbonyl-1H-thieno[3,2c]pyrazol-3-yl)-5-hydroxy-indole-1-carboxylic acid tert-butyl ester.

Step 10. 1-{3-[2-(5-Benzyloxymethyl-1H-thieno[3,2-c]pyrazol-3-yl)-1H-indol-6-yloxy]-propyl}-piperidin-4-ol [Example 69, LC/MS: 517.1 (M+H), $R_T$=3.02 minutes; $^1$H NMR [300 Mhz, $(CD_3)_2SO$]: δ 13.17 (brs, 1H), 11.35 (brs, 1H), 7.45-7.25 (m, 6H), 7.20 (s, 1H), (s, 2H), 4.53 (m, 1H), 3.98 (t, J=6.4 Hz, 2H), 3.44 (m, 1H), 2.72 (m, 2H), 2.50 (m, 2H), 2.01 (m, 2H), 1.89 (m, 2H), 1.71 (m, 2H), 1.32 (m, 2H).] was prepared in 52% yield using procedures similar to those of Step 6 in Example 5, substituting 2-(5-benzyloxymethyl-1-tert-butoxycarbonyl-1H-thieno[3,2-c]pyrazol-3-yl)-6-(3-bromo-propoxy)-indole-1-carboxylic acid tert-butyl ester [Intermediate (94)] for 5-(3-bromo-propoxy)-2-(1-tert-butoxycarbonyl-1H-thieno[3,2-c]pyrazol-3-yl)-indole-1-carboxylic acid tert-butyl ester and 4-hydroxypiperidine for piperidine.

EXAMPLE 70

3-[2-(1H-Thieno[3,2-c]pyrazol-3-yl)-1H-indol-6-yl]-pentan-3-ol

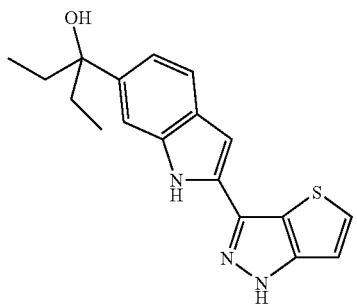

To 2-(1-tert-butoxycarbonyl-1H-thieno[3,2-c]pyrazol-3-yl)-indole-1,6-dicarboxylic acid 1-tert-butyl ester 6-methyl ester [250 mg, 0.5 mmol, Intermediate (36)] in tetrahydrofuran (5 mL) was added a 1.0M solution of ethyl magnesium bromide in tetrahydrofuran (2.5 mL, 2.5 mmol) at −45° C. under nitrogen. The mixture was allowed to warm up and stirred at room temperature for 3 hours. An additional 2 mL of 1.0M ethyl magnesium bromide solution was added. The resulting solution was stirred at room temperature overnight. It was then quenched with a mixture of brine and saturated ammonium chloride and extracted with ethyl acetate. The organic layer was dried over magnesium sulfate and concentrated. The residue was chromatographed through silica gel (n-heptane/ethyl acetate, 50/50 as eluant) to produce 3-[2-(1H-thieno[3,2-c]pyrazol-3-yl)-1H-indol-6-yl]-pentan-3-ol [137 mg, 92%, Example 70] as a white powder. LC/MS: 326.2 (M+H), $R_T$=3.07 minutes; $^1$H NMR [300 Mhz, $(CD_3)_2$SO]: δ 13.18 (s, 1H), 11.43 (s, 1H), 7.73 (d, J=5.2 Hz, 1H), 7.50 (s, 1H), 7.44 (d, J=8.2 Hz, 1H), 7.18 (d, J=5.2 Hz, 1H), 6.94 (dd, J1=1.1 Hz, J2=8.4 Hz, 1H), 6.56 (d, J=1.5 Hz, 1H), 4.41 (s, 1H), 1.76 (m, 4H), 0.66 (t, j=6.2 Hz, 6H).

EXAMPLE 71

3-[2-(5-Benzyloxymethyl-1H-thieno[3,2-c]pyrazol-3-yl)-1H-indol-6-yl]-pentan-3-ol

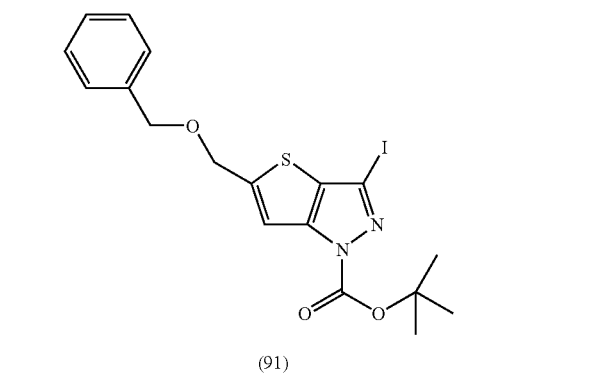

(91)

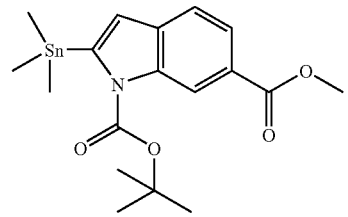

(37)

Step 1

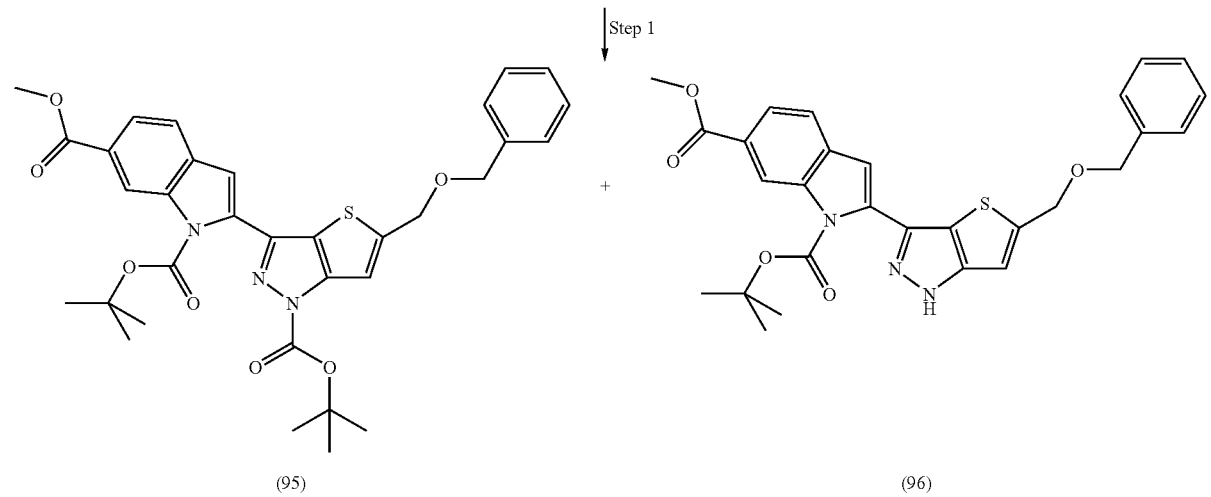

(95)

(96)

Step 2

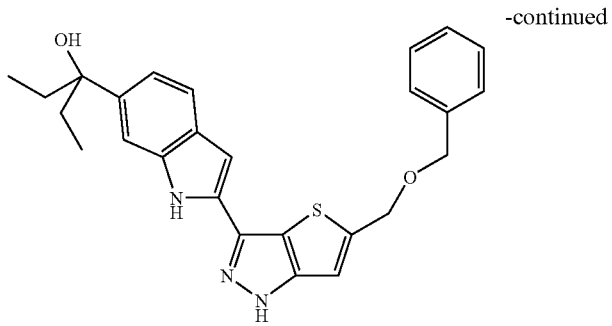

Example 71

Step 1. To 5-benzyloxymethyl-3-iodo-thieno[3,2-c]pyrazole-1-carboxylic acid tert-butyl ester (1.78 g, 3.78 mmol, Intermediate (91)] in 1,4-dioxane were added successively copper iodide (0.07 g, 0.38 mmol), [1,1'-bis(diphenylphosphino)-ferrocene]dichloropalladium(II) (complex with dichloromethane (1:1)) (0.14 g, 0.19 mmol), and trimethyl(indole-1,6-dicarboxylic acid, 1-tert-butyl ester-6-methyl ester)tin [4.1 g, 9.45 mmol, Intermediate (37)]. The mixture was stirred at 90° C. for 5 hours then at room temperature for 2 hours. It was diluted with ethyl acetate and washed with saturated aqueous sodium bicarbonate, and brine. The organic layer was dried over magnesium sulfate and concentrated. The residue was chromatographed through silica gel (n-heptane/ethyl acetate, 80/20 then 0/100as eluant) to give 2-(5-benzyloxymethyl-1H-thieno[3,2-c]pyrazol-3-yl)-indole-1,6-dicarboxylic acid 1-tert-butyl ester 6-methyl ester [1.66 g, 71%, Intermediate (96), LC/MS: 618.3 (M+H), $R_T$=4.57 minutes] as a yellow powder and 2-(5-benzyloxymethyl-1-tert-butoxycarbonyl-1H-thieno[3,2-c]pyrazol-3-yl)-indole-1,6-dicarboxylic acid 1-tert-butyl ester 6-methyl ester [0.37 g, 19%, Intermediate (95), LC/MS: 518.2 (M+H), $R_T$=3.87 minutes] as a green powder.

Step 2. To 2-(5-benzyloxymethyl-1-tert-butoxycarbonyl-1H-thieno[3,2-c]pyrazol-3-yl)-indole-1,6-dicarboxylic acid 1-tert-butyl ester 6-methyl ester [0.35 g, 0.68 mmol, Intermediate (95)] in tetrahydrofuran (5 mL) at −78° C. under nitrogen was added a 1.0M solution of ethylmagnesium bromide in tetrahydrofuran (1.7 mL, 1.7 mmol). The mixture was stirred at −78° C. for 1 hour. An additional 1.7 mL of 1.0M ethyl magnesium bromide solution was added. The temperature was raised to −45° C. and the mixture was stirred for 1 hour. It was then allowed to warm up to room temperature overnight. The reaction mixture was quenched with saturated aqueous ammonium chloride and extracted with ethyl acetate. The organic layer was dried over magnesium sulfate and concentrated. The residue was chromatographed through silica gel (dichloromethane/ethyl acetate, 50/50 as eluant) to produce 3-[2-(5-benzyloxymethyl-1H-thieno[3,2-c]pyrazol-3-yl)-1H-indol-6-yl]-pentan-3-ol [95 mg, 61%, Example 71] as a beige powder. LC/MS: 446.3 (M+H), $R_T$=3.19 minutes. $^1$H NMR [300 Mhz, (CD$_3$)$_2$SO]: δ 13.18 (s, 1H), 11.44 (s, 1H), 7.50 (s, 1H), 7.45 (s, 1H), 7.43 (d, J=8.3 Hz, 1H), 7.36 (m, 5H), 7.21 (s, 1H),6.93 (m, 1H), 6.55 (d, J=1.2 Hz, 1H), 4.78 (s, 2H), 4.59 (s, 2H), 4.43 (s, 1H), 1.75 (m, 4H), 0.66 (m, 6H).

EXAMPLE 72

[2-(5-Benzyloxymethyl-1H-thieno[3,2-c]pyrazol-3-yl)-1H-indol-6-yl]-di-pyridin-2-yl-methanol

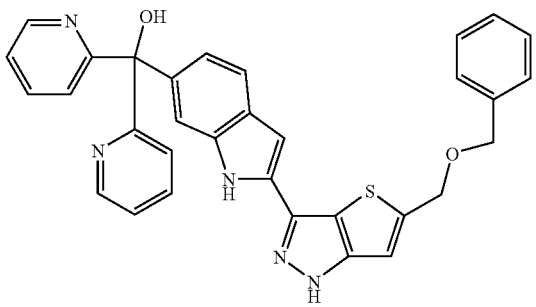

To 2-bromopyridine (305 mg, 1.9 mmol) in anhydrous tetrahydrofuran (2 mL), at −78° C. in nitrogen atmosphere, was added a 2.5M solution of n-butyl lithium in tetrahydrofuran (0.76 mL, 1.9 mmol). A solution of 2-(5-benzyloxymethyl-1H-thieno[3,2-c]pyrazol-3-yl)-indole-1,6-dicarboxylic acid 1-tert-butyl ester 6-methyl ester [160 mg, 0.38 mmol, Intermediate (96)] in tetrahydrofuran (5 mL) was added. The dark mixture was allowed to warm up slowly to room temperature. It was quenched with saturated aqueous ammonium chloride and extracted with ethyl acetate. The organic layer was dried over magnesium sulfate and concentrated. The residue was chromatographed twice through silica gel (dichloromethane/ethyl acetate, 70/30 then 50/50 as eluant) to afford [2-(5-benzyloxymethyl-1H-thieno[3,2-c]pyrazol-3-yl)-1H-indol-6-yl]-di-pyridin-2-yl-methanol [60 mg, 33%, Example 72] as a white powder. LC/MS: 544.2 (M+H), $R_T$=2.65 minutes. $^1$H NMR [300 Mhz, (CD$_3$)$_2$SO]: δ 13.19 (brs, 1H), 11.45 (brs, 1H), 8.49 (m, 2H), 7.77 (m, 2H), 7.63 (d, J=7.8 Hz, 2H), 7.43-7.26 (m, 9H), 7.94 (d, J=8.6 Hz, 1H), 6.73 (d, J=3.7 Hz, 1H), 6.57 (s, 1H), 4.77 (s, 2H), 4.58 (s, 2H).

The following compounds may be prepared by the application or adaptation of the methods described hereinabove:

EXAMPLE 73

1-{3-[6-(1-ethyl-1-hydroxy-propyl)-1H-indol-2-yl]-1H-thieno[3,2-c]pyrazol-5-ylmethyl}-piperidin-4-ol

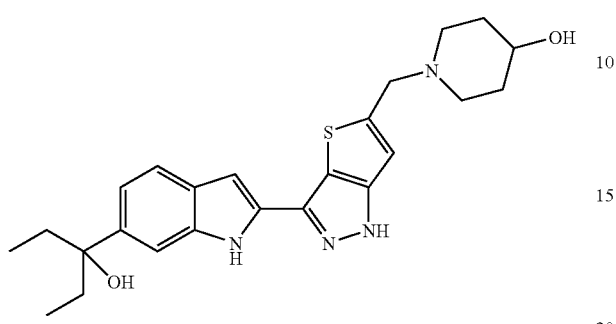

EXAMPLE 74

3-[2-(5-dimethylaminomethyl-1H-thieno[3,2-c]pyrazol-3-yl)-1H-indol-6-yl]-pentan-3-ol

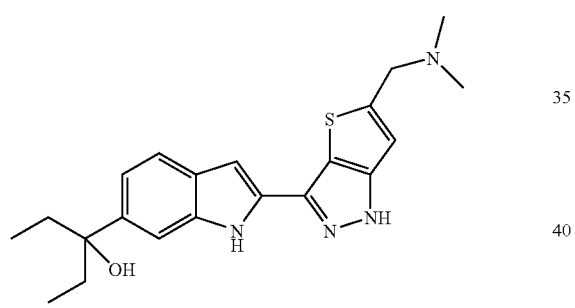

EXAMPLE 75

3-(2-{5-[4-(pyridin-4-yloxy)-piperidin-1-ylmethyl]-1H-thieno[3,2-c]pyrazol-3}-1H-indol-6-yl)-pentan-3-ol

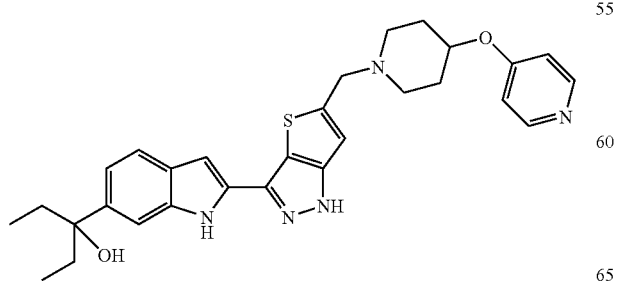

EXAMPLE 76

3-[2-(5-piperazin-1-ylmethyl-1H-thieno[3,2-c]pyrazol-3-yl)-1H-indol-6-yl]-pentan-3-ol

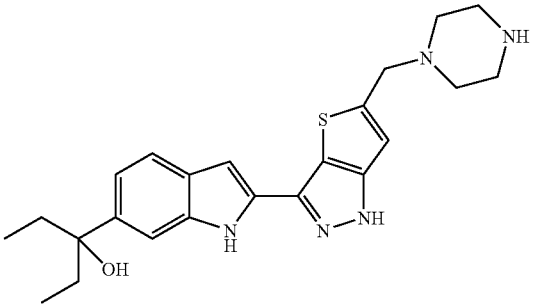

EXAMPLE 77

3-[2-(5-piperazin-1-yl-1H-thieno[3,2-c]pyrazol-3-yl)-1H-indol-6-yl]-pentan-3-ol

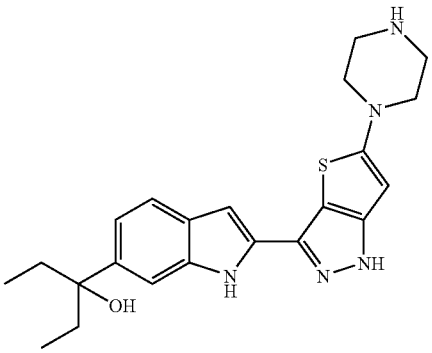

EXAMPLE 78

3-{2-[5-(3-cyclopropyl-[1,2,4]oxadiazol-5-yl)-1H-thieno[3,2-c]pyrazol-3-yl]-1H-indol-6yl}-pentan-3-ol

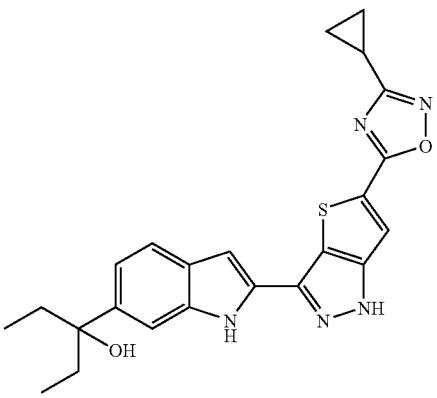

EXAMPLE 79

3-[2-(5-pyridin-4-yl-1H-thieno[3,2-c]pyrazol-3-yl)-1H-indol-6-yl]-pentan-3-ol

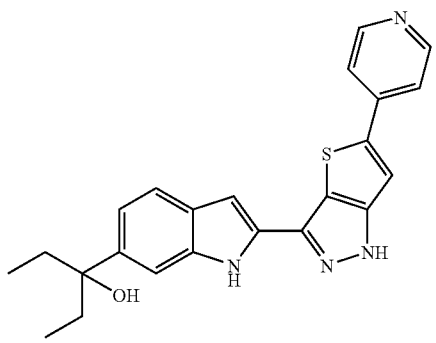

EXAMPLE 80 bis-(1-methyl-piperidin-4-yl)-[2-(1H-thieno[3,2-c]pyrazol-3-yl)-1H-indol-6-yl]-methanol

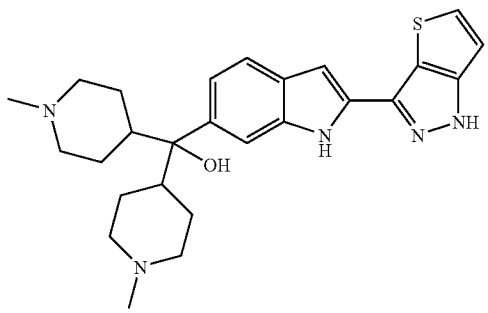

EXAMPLE 81

3-[2-(5-difluoromethyl-1H-thieno[3,2-c]pyrazol-3-yl)-1H-indol-6-yl]-pentan-3-ol

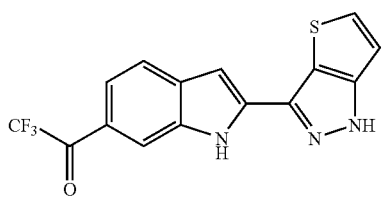

EXAMPLE 82

4-[2-(1H-thieno[3,2-c]pyrazol-3-yl)-1H-indol-6-yl]-piperidin-4-ol

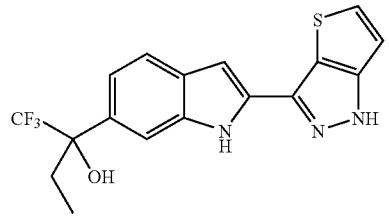

EXAMPLE 83

6-(4-fluoro-piperidin-4-yl)-2-(1H-thieno[3,2-c]pyrazol-3-yl)-1H-indole

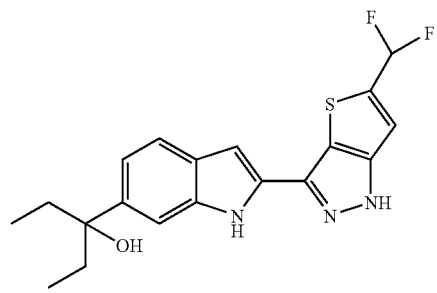

EXAMPLE 84

2-[2-(1H-thieno[3,2-c]pyrazol-3-yl)-1H-indol-6-yl]-butan-2-ol

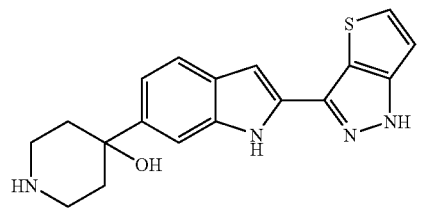

EXAMPLE 85

1-[2-(1H-thieno[3,2-c]pyrazol-3-yl)-1H-indol-6-yl]-ethanone

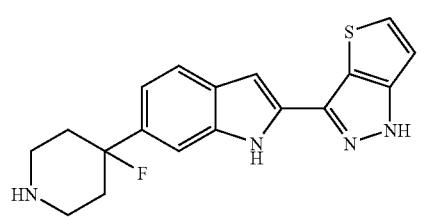

EXAMPLE 86

3-[3-piperidin-4-yl-2-(1H-thieno[3,2-c]pyrazol-3-yl)-1H-indol-6-yl]-pentan-3-ol

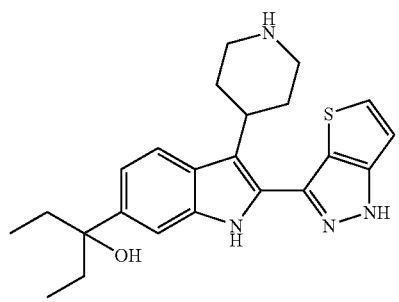

EXAMPLE 87

3-[3-pyridin-4-yl-2-(1H-thieno[3,2-c]pyrazol-3-yl)-1H-indol-6-yl]-pentan-3-ol

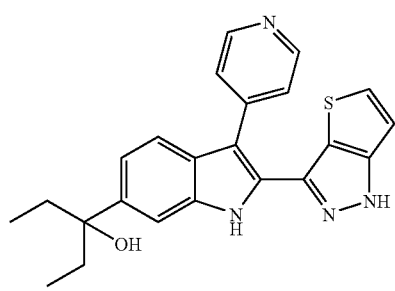

EXAMPLE 88

3-[3-(4-methyl-piperazin-1-yl)-2-(1H-thieno[3,2-c]pyrazol-3-yl)-1H-indol-6-yl]-pentan-3-ol

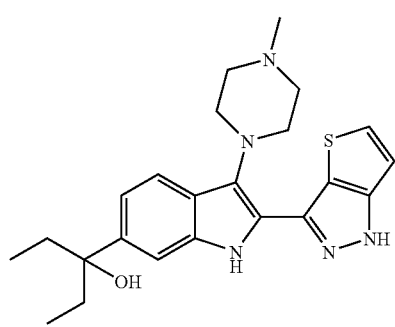

EXAMPLE 89

3-[3-morpholin-4-ylmethyl-2-(1H-thieno[3,2-c]pyrazol-3-yl)-1H-indol-6-yl]-pentan-3-ol

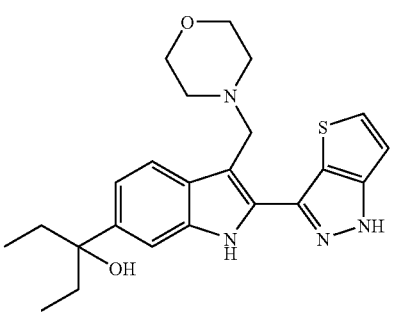

EXAMPLE 90

4-[2-(1H-thieno[3,2-c]pyrazol-3-yl)-1H-indol-6-yl]-tetrahydro-pyran-4-ol

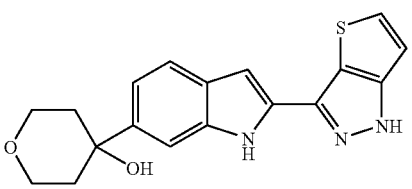

EXAMPLE 91

3-{2-[5-(1-hydroxy-1-methyl-ethyl)-1H-thieno[3,2-c]pyrazol-3-yl]-1H-indol-6-yl}-pentan-3-ol

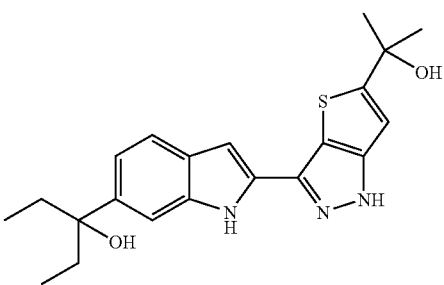

EXAMPLE 92

3-[2-(5-methoxymethyl-1H-thieno[3,2-c]pyrazol-3-yl)-3-pyridin-4-yl-1H-indol-6-yl]-pentan-3-ol

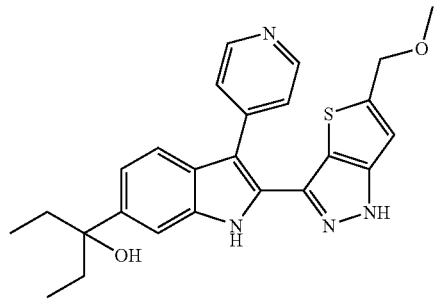

EXAMPLE 93

4-[2-(5-methoxymethyl-1H-thieno[3,2-c]pyrazol-3-yl)-1H-indol-6-yl]-tetrahydro-pyran-4-ol

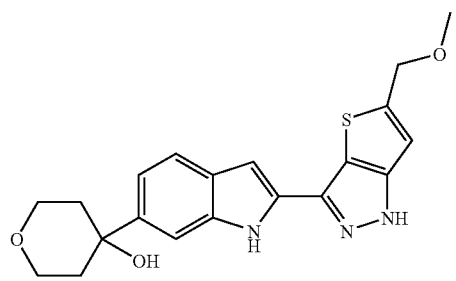

EXAMPLE 94

3-[2-(5-methoxymethyl-1H-thieno[3,2-c]pyrazol-3-yl)-3-piperazin-1-yl-1H-indol-6-yl]-pentan-3-ol

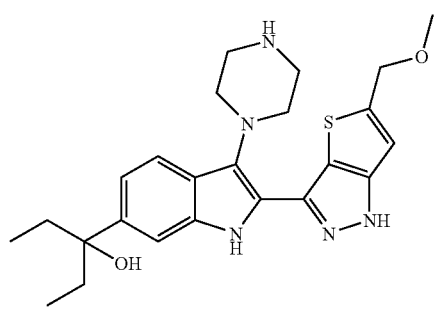

EXAMPLE 95

3-[2-(5-methoxymethyl-1H-thieno[3,2-c]pyrazol-3-yl)-3-morpholin-4-ylmethyl-1H-indol-6-yl]-pentan-3-ol

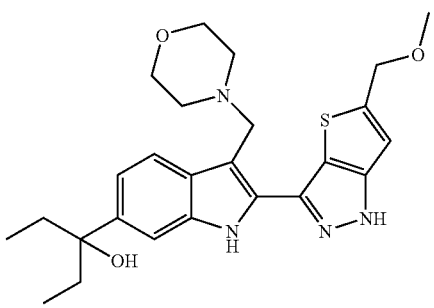

EXAMPLE 96

2-{3-[6-(1-ethyl-1-hydroxy-propyl)-1H-indol-2-yl]-1H-thieno[3,2-c]pyrazol-5-yl}-tetrahydro-furan-3-carbonitrile

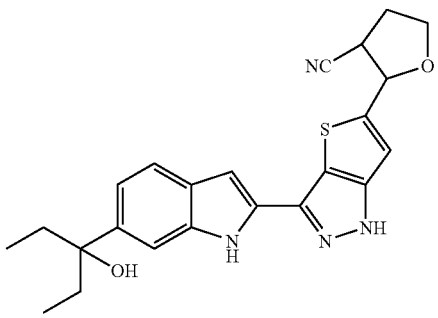

EXAMPLE 97

3-[2-(5-methoxymethyl-1H-thieno[3,2-c]pyrazol-3-yl)-3-methyl-1H-indol-6-yl]-pentan-3-ol

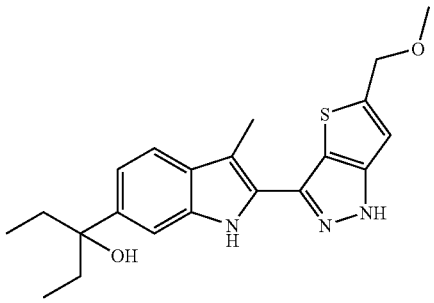

EXAMPLE 98

3-[2-(5-methoxymethyl-1H-thieno[3,2-c]pyrazol-3-yl)-3-piperidin-4-yl-1H-indol-6-yl]-pentan-3-ol

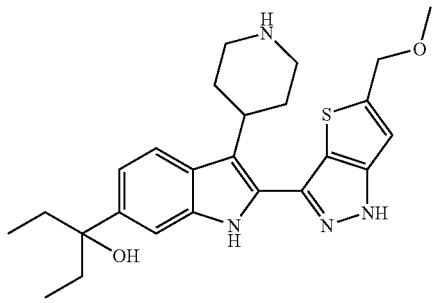

The detailed synthetic steps for example 22 are described in the following and in FIG. 1:

With reference to FIG. 1, the intermediate compounds (1), (2), (3), (4), (5), (6) and (7) are made as follows:

Intermediate (1)

(4-Bromo-thiophen-2-ylmethyl)-dimethyl-amine

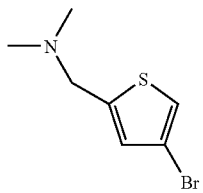

To a solution of 4-bromo-2-thiophene carboxaldehyde (5 g, 26.2 mmol) in 1,2-dichloroethane (50 mL) is added sodium triacetoxyborohydride (8.3 g, 39.3 mmol) and dimethylamine (14.5 mL, 28.8 mmol) followed by acetic acid (1.55 mL, 39.3 mmol). The mixture is stirred at room temperature for 2 hours. The insoluble is filtered and washed with diethyl ether. The mother liquor is concentrated. The resulting thick oil that is chromatographed through silica gel (dichloromethane—1.0M ammonia in methanol, 95:05 to 90:10 as eluant) to afford an orange oil. It is dissolved in dichloromethane and was washed with a saturated aqueous sodium bicarbonate solution. The organic layer is dried over magnesium sulfate and concentrated to produce (4-bromo-thiophen-2-ylmethyl)-dimethyl-amine [4.08 g, 71%, intermediate (1)] as an orange oil. LC/MS: $R_T$=0.63 minutes, 219.99 m/e (M+H).

Intermediate (2)

3-Bromo-5-dimethylaminomethyl-thiophene-2-carbaldehyde

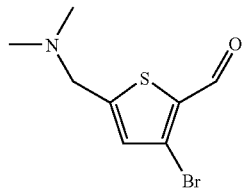

To (4-bromo-thiophen-2-ylmethyl)-dimethyl-amine [4.08 g, 18.5 mmol, Intermediate (1)] in tetrahydrofuran (40 mL) at 0° C. and under a nitrogen atmosphere is added Lithium diisopropylamine(2.0M in tetrahydrofuran pentanes from Aldrich chemicals, 20.4 mmol). The orange solution is stirred at 0° C. for 30 minutes. Then N-formylpiperidine is added (2.5 mL, 22.2 mmol). The mixture is allowed to stir at 0° C. for 1 hour. It is diluted with ethyl acetate washed with brine, dried over magnesium sulfate and concentrated. The residual orange oil was chromatographed through silica gel (dichloromethane—1.0M ammonia in methanol, 95:05 as eluant) to produce 3-bromo-5-dimethylaminomethyl-thiophene-2-carbaldehyde [4.4 g, Intermediate (2)] as an orange oil. LC/MS: $R_T$=0.47 minutes, 247.98 m/e (M+H).

Intermediate (3)

[5-(Benzhydrylidene-hydrazonomethyl)-4-bromo-thiophen-2-ylmethyl]-dimethyl-amine

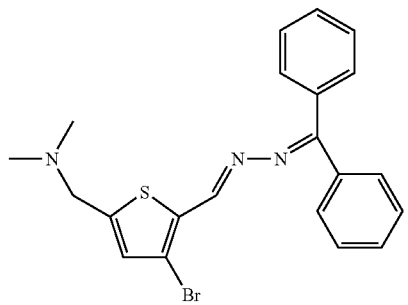

To 3-bromo-5-dimethylaminomethyl-thiophene-2-carbaldehyde [4.30 g, 17.3 mmol, Intermediate (2)] in ethanol (40 mL) is added benzophenone hydrazone (3.75 g, 19.0 mmol). The solution was heated at 65° C. for 5 hours. The solvent is removed under reduced pressure. The residue is chromatographed through silica gel (n-heptane-ethyl acetate. 90:10 as eluant) to produce [5-(Benzhydrylidene-hydrazonomethyl)-4-bromo-thiophen-2-ylmethyl]-dimethyl-amine] 5.57 g, 75%, Intermediate (3)] as an orange oil. LC/MS: $R_T$=2.72 minutes, 426.05 m/e (M+H).

Intermediate (4)

[4-(N'-Benzhydrylidene-hydrazino)-5-(benzhydrylidene-hydrazonomethyl)-thiophen-2-ylmethyl]-dimethyl-amine

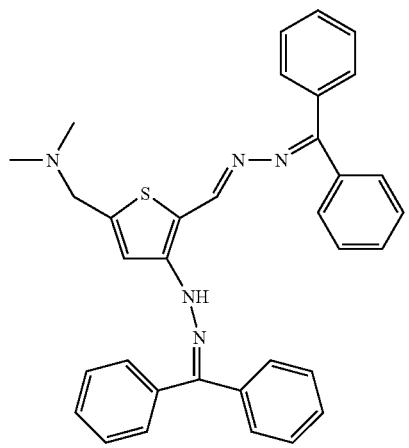

(4)

To compound (3) (5.5 g, 12.9 mmol) in solution in toluene (100 mL) is added benzophenone hydrazone (3.03 g, 14.4 mmol), cesium carbonate (7.15 g, 21.9 mmol), palladium diacetate (0.22 g, 2.80 mmol) and 1,1'-bis(diphenyl phosphino)-ferrocene (1.07 g, 1.94 mmol). The resulting suspension is heated 100° C. for 4½ hour. The solvent is then removed under reduced pressure. The residual oil is chromatographed through silica gel (dichloromethane-methanol, 100:0 to 90:10 as eluant) to produce [4-(N'-benzhydrylidene-hydrazino)-5-(benzhydrylidene-hydrazonomethyl)-thiophen-2-ylmethyl]-dimethyl-amine [6.98 g, 100%, Intermediate (4)] as an orange foam. LC/MS: $R_T$=3.38 minutes, 542.21 m/e (M+H).

Intermediate (5)

Dimethyl-(1H-thieno[3,2-c]pyrazol-5-ylmethyl)-amine

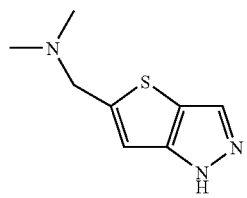

To [4-(N'-Benzhydrylidene-hydrazino)-5-(benzhydrylidene-hydrazonomethyl)-thiophen-2-ylmethyl]-dimethyl-amine [Intermediate (4)] in ethanol (100 mL) was added 50 mL of concentrated hydrochloric acid. The dark red mixture is stirred at 85° C. for 2 hours. Water is added followed by solid sodium carbonate until pH is slightly basic. The reaction mixture is then extracted twice with ethyl acetate. The organic layer is dried over magnesium sulfate and concentrated. The residue is chromatographed (ethyl acetate—1.0M ammonia in methanol, 90:10 as eluant) to produce dimethyl-(1H-thieno[3,2-c]pyrazol-5-ylmethyl)-amine [1.06 g, 45% Intermediate (5)] as a brown solid. LC/MS: $R_T$=0.4 minutes, 182.09 m/e (M+H).

Intermediate (6)

(3-Iodo-1H-thieno[3,2-c]pyrazol-5-ylmethyl)-dimethyl-amine

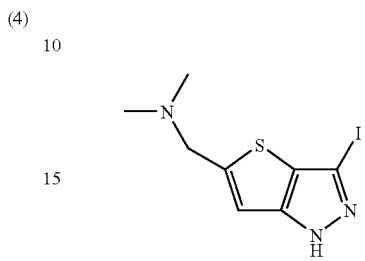

To dimethyl-(1H-thieno[3,2-c]pyrazol-5-ylmethyl)-amine [1 g, 5.51 mmol, Intermediate (5)] in solution in dimethylformamide (10 mL) is added iodine (2.1 g, 8.3 mmol) and potassium hydroxide (0.930 g, 16.5 mmol). The dark solution is stirred at room temperature for 5 hours. Sodium bisulfite (1.5 g) in solution in water is added. The resulting suspension is extracted twice with ethyl acetate. The organic layer is dried over magnesium sulfate and concentrated. The residue is chromatographed through silica gel (ethyl acetate—1.0M ammonia in methanol, 90:10 as eluant) to produce (3-iodo-1H-thieno[3,2-c]pyrazol-5-ylmethyl)-dimethyl-amine [0.87 g, 51%, Intermediate (6)] as a beige powder. LC/MS: $R_T$=1.20 minutes, 307.98 m/e (M+H).

Intermediate (7)

5-Dimethylaminomethyl-3-iodo-thieno[3,2-c]pyrazole-1-carboxylic acid tert-butyl ester

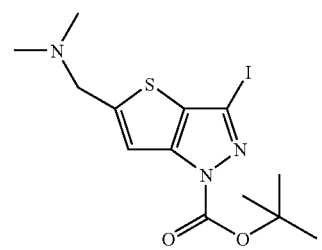

To (3-iodo-1H-thieno[3,2-c]pyrazol-5-ylmethyl)-dimethyl-amine [0.77 g, 2.50 mmol, Intermediate (6)] in suspension in dichloromethane (10 mL) is added triethylamine (0.36 mL, 2.75 mmol), tert-butylcarbonyl anhydride (0.66 g, 3.00mmol) and 4-dimethyl aminopyridine (60 mg, 0.2 mmol). The suspension turns quickly to a solution. The solvent is then removed. The residue is chromatographed through silica gel (ethyl acetate as eluant) to afford 5-Dimethylaminomethyl-3-iodo-thieno[3,2-c]pyrazole-1-carboxylic acid tert-butyl ester [960 mg, 94%, Intermediate (7)] as a yellow solid. LC/MS: $R_T$=2.07 minutes, 408.01 m/e (M+H).

In Vitro Test Procedures for ITK

Anti-CD3 Stimulated IL-4 Assay from Murine Splenocytes.

Introduction

The tyrosine kinase ITK is involved in intracellular signaling events induced by several lymphocyte surface receptors.

Since ITK deficient mice show an impairment in IL-4 production from T cells, a cell based assay for IL-4 production is used to measure the cellular potency of the ITK inhibitors of the present invention. In this assay the level of IL-4 is measured from the media of anti-CD3-stimulated murine splenocytes, and the ability of compounds of the present invention to inhibit this response is determined.

Assay Conditions

Spleens from the mouse strain BALB/c are isolated and used to prepare a suspension of mixed splenocytes. The spleens are homogenized with cell strainer (Falcon Cat#352350 and 5 ml syringe) in RPMI media The mixture is spun down, and the pellets are suspended in 3 ml of Red Blood Cell Lysing Buffer (Sigma Cat#7757) and left for 10 minutes at room temperature. Cells are spun down again, and resuspended in RPMI with 10% FBS and passed through cell strainer. Total cell numbers are determined with hemocytometer.

Splenocytes are adjusted to a cell density of 10 million per ml of RPMI medium supplemented with 10% Foetal Bovine Serum (FBS) and 100 uls of the suspension plated out per well of a 96 round bottom plate. 50 uls of RPMI medium containing 4× the final concentration of test compound is added per well. For IC50 determination the following concentrations of compound are used. The starting concentration is 10 uM and 7 series of 1:3 dilutions are followed, and each compound concentration is set up in triplicate wells. 50 ul of 4× concentration are added. Cell cultures are then stimulated by addition of 50 ul of a 4 ug/ml solution of anti-CD3 antibody, (BD Bioscience Cat# 553166) made up in RPMI plus 10% FBS media, and incubated in a 37° C. CO2 incubator for 3 days. At the end of the 3 day incubation, culture medium is taken and 50 uls used to assay IL-4 production by ELISA (IL4 ELISA kit from R&D Systems, city. Cat# M4000 kit) according to the standard conditions described by the manufacturer.

IL-4 levels are plotted as a function of compound concentration. The concentration of compound resulting in 50% inhibition of IL-4, termed IC50(IL-4), is determined from the resulting curve.

Assay Procedure
1. Add 100 ul of 1X10E7/ml mouse splenocytes in RPMI plus 10% FBS media to 96 well round bottom plates.
2. Add 50 ul of Itk compounds (4× final concentration) in RPMI plus 10% FBS media
3. Add 50 ul of 4 ug/ml anti-CD3 antibody in RPMI plus 10% FBS media
4. Incubate at 37 c CO2 incubator for 3 days
5. Transfer 150 ul culture media into fresh plate
6. 50 ul of the media is subject to Elisa analysis (R & D Cat# M4000 kit)

FlashPlate ITK Protocol for ITK Inhibition Determination

ITK kinase is produced with an N-terminal Maltose Binding Protein tag (MW=~114 kDa) using a Baculovirus expression system. The transfer of radioactive [γ-$^{33}$P] phosphate from [γ-$^{33}$P]ATP to ITK during the autophosphorylation of ITK is measured by scintillation counting. Streptavidin-coated FlashPlate Plus™ 384 well microplates (PerkinElmer Life Sciences) are designed for in-plate radiometric assays. The interior of each well is permanently coated with a thin layer of scintillant and a covalently bound layer of Streptavidin. ITK is incubated with [γ-$^{33}$P]ATP, biotinylated anti-MBP antibody (Cell Signaling Technology™) and test compounds in a 384-well Streptavidin-coated FlashPlate. The biotinylated anti-MBP binds tightly to the MBP-tagged ITK and cross-links it to Streptavidin on the plate surface. Unreacted $^{33}$P-ATP is washed away and $^{33}$P-phosphorylated ITK is measured when the [γ-$^{33}$P] incorporated into ITK stimulates the scintillant on the well to emit light. Radioactivity is assessed in a Packard TopCount scintillation counter. Reagents are pipetted and dispensed using Beckman Biomek robotic equipment. Test compounds (2 μl per well) are pre-diluted from 1 mM 100% dimethyl sulfoxide solutions into water containing 30% dimethyl sulfoxide to produce dose response curves (10 point curves from (final) 30 μM to ~1 nM); all tests are performed in duplicate. Background binding is assessed by substituting the enzyme inhibitor EDTA (25 mM final concentration) for test compound and maximal binding is assessed by inclusion of assay buffer instead of compound. Test compounds are added to the wells first (2 μl) followed by 10 μl enzyme solution in assay buffer. After 30 minutes pre-incubation, all other reagents are added in a 10 μl volume. The final reagent concentrations/well are as follows: 20 nM enzyme, 0.25 μCi [γ-$^{33}$P]ATP, assay buffer: 20 mM HEPES (pH 7.5), 0.15 M NaCl, 3 mM MgCl$_2$, 3 mM MnCl$_2$, 0.01% Triton X-100, 1 mM DTT, 5% glycerol and 0.01% γ-globulin. The plate is incubated at room temperature (RT) for 60 minutes for the kinase reaction. The reaction is stopped with 20 μl of 50 mM EDTA and the biotinylated anti-MBP is allowed to bind to the ITK and the Streptavidin for a further 60 minutes at RT. The unbound reagents are washed away with 2×100 μl phosphate-buffered saline (PBS). Radioactivity is measured for 45 sec/well.

Results for compounds of the present invention in these tests are shown in Table I.

TABLE I

| MOLSTRUCTURE &NAME | Molecular weight | Observed M+H | HPLC Retention Time | IC$_{50}$ (enzyme inhibition)- nM | IC$_{50}$ IL-4 release inhibition-assay nM |
| --- | --- | --- | --- | --- | --- |
| 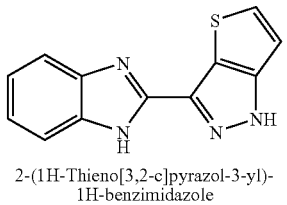 2-(1H-Thieno[3,2-c]pyrazol-3-yl)-1H-benzimidazole | 240.05 | 241.04 | 1.82 | 167 | 264 |

TABLE I-continued

| MOLSTRUCTURE &NAME | Molecular weight | Observed M+H | HPLC Retention Time | IC$_{50}$ (enzyme inhibition)- nM | IC$_{50}$ IL-4 release inhibition- assay nM |
|---|---|---|---|---|---|
| 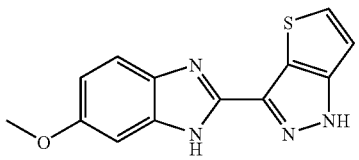 6-Methoxy-2-(1-H-theino[3,2-c]pyrazol-3-yl)-1-H-benzimidazole | 270.06 | 271.05 | 1.9 | 157 | 164 |
| 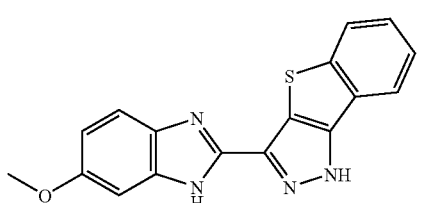 3-(6-Methoxy-1H-Benzoimidazol-2-yl)-1H-benzo[4,5]theino[3,2-c] pyrazole | 320.07 | 321.05 | 2.43 | 86 | 2900 |
| 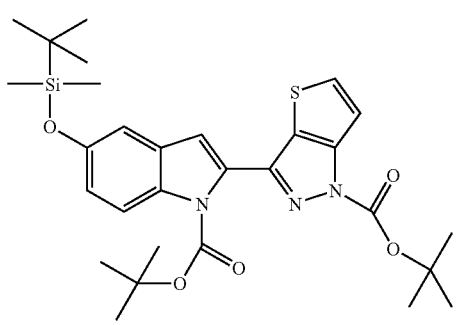 2-(1-tert-Butoxycarbonyl-1H-thieno[3,2-c]pyrazol-3-yl)-5-(tert-butyl-dimethyl-silanyloxy)-indole 1-carboxylic acid tert-butyl ester | 569.24 | 570.1 | 4.29 | | |
| 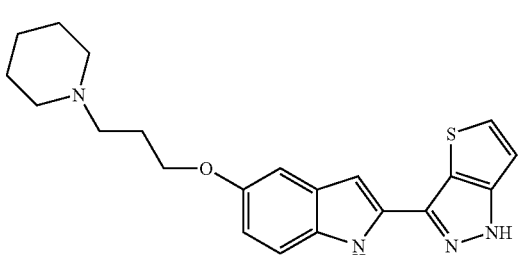 5-(3-Piperidin-1-yl-propoxy)-2-(1H-thieno[3,2-c]pyrazol-3-yl)-1H-indole | 380.52 | 381.18 | 2.18 | 16.6 | 153 |

TABLE I-continued

| MOLSTRUCTURE &NAME | Molecular weight | Observed M+H | HPLC Retention Time | IC$_{50}$ (enzyme inhibition)- nM | IC$_{50}$ IL-4 release inhibition- assay nM |
|---|---|---|---|---|---|
| 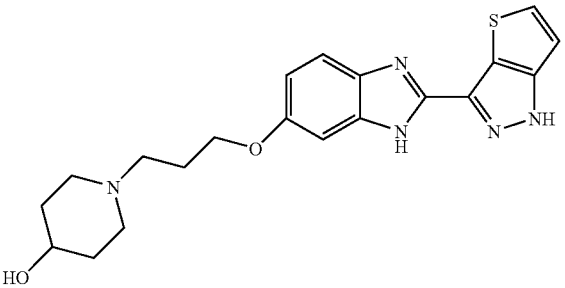<br>1-{3-[2-(1H-Thieno[3,2-c]pyrazol-3-yl)-1H-indol-6-yloxy]-propyl}-piperidin-4-ol | 396.16 | 397.18 | 2.17 | 3.65 | 180 |
| 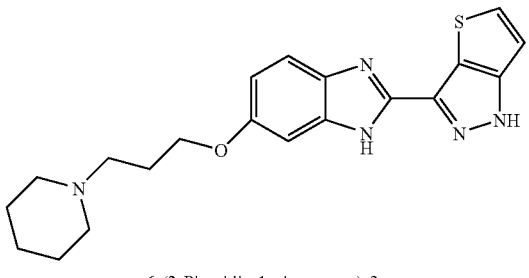<br>6-(3-Piperidin-1-yl-propoxy)-2-(1H-thieno[3,2-c]pyrazol-3-yl)-1H-indole | 380.17 | 381.18 | 2.32 | 1.89 | 163 |
| 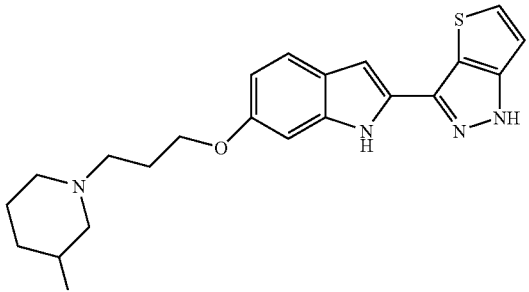<br>1-{3-[2-(1H-Thieno[3,2-c]pyrazol-3-yl)-1H-indol-6-yloxy]-propyl}-piperidin-3-ol | 396.16 | 397.4 | 2.45 | 1.62 | 11.3 |
| 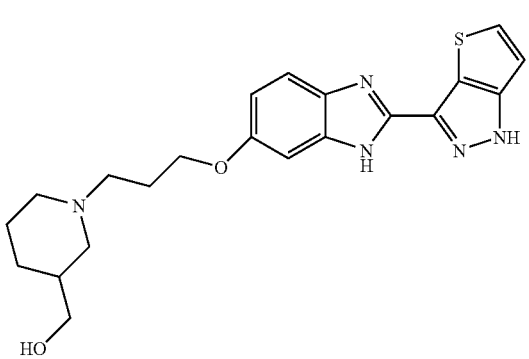<br>(1-{3-[2-(1H-Thieno[3,2-c]pyrazol-3-yl)-1H-indol-6-yloxy]-propyl}-piperidin-3-yl)-methanol | 410.18 | 411.29 | 2.49 | 2.08 | 129 |

TABLE I-continued

| MOLSTRUCTURE &NAME | Molecular weight | Observed M+H | HPLC Retention Time | IC$_{50}$ (enzyme inhibition)- nM | IC$_{50}$ IL-4 release inhibition- assay nM |
|---|---|---|---|---|---|
| 6-[3-(4-Ethyl-piperazin-1-yl)-propoxy]-2-(1H-thieno[3,2-c]pyrazol-3-yl)-1H-indole | 409.19 | 410.3 | 2.27 | 2.94 | 289 |
| Diethyl-{3-[2-(1H-thieno[3,2-c]pyrazol-3-yl)-1H-indol-6-yloxy]-propyl}-amine | 368.17 | 369.19 | 2.35 | 5.22 | |
| Diallyl-{3-[2-(1H-thieno[3,2-c]pyrazol-3-yl)-1H-indol-6-yloxy]-propyl}-amine | 392.17 | 393.14 | 2.48 | 12.3 | |
| 1-{3-[2-(1H-Thieno[3,2-c]pyrazol-3-yl)-1H-indol-6-yloxy]-propyl}-pyrrolidin-3-ol | 382.15 | 383.17 | 2.2 | 15.1 | |

TABLE I-continued

| MOLSTRUCTURE &NAME | Molecular weight | Observed M+H | HPLC Retention Time | $IC_{50}$ (enzyme inhibition)- nM | $IC_{50}$ IL-4 release inhibition-assay nM |
|---|---|---|---|---|---|
| Dimethyl-{3-[2-(1H-thieno[3,2-c]pyrazol-3-yl)-1H-indol-6-yloxy]propyl}-amine | 340.14 | 341.13 | 2.18 | 24.2 | |
| 2-(Methyl-{3-[2-(1H-thieno[3,2-c]pyrazol-3-yl)-1H-indol-6-yloxy]-propyl}-amino)-ethanol | 370.14 | 371.25 | 2.13 | 3.26 | |
| 5-(Methoxy-[2-(1H-thieno[3,2-c]pyrazol-3-yl)-1H-pyrrolo[3,2-b]pyridine | 270.05 | 271.02 | 2.03 | 224 | |
| 1-{3-[2-(1H-Thieno[3,2-c]pyrazol-3-yl)-1H-indol-5-yloxy]-propyl}-piperidin-4-ol | 396.16 | 397.17 | 2.03 | 40.9 | |

TABLE I-continued

| MOLSTRUCTURE &NAME | Molecular weight | Observed M+H | HPLC Retention Time | IC$_{50}$ (enzyme inhibition)- nM | IC$_{50}$ IL-4 release inhibition- assay nM |
|---|---|---|---|---|---|
| 1-{3-[2-(1H-Thieno[3,2-c]pyrazol-3-yl)-1H-indol-5-yloxy]-propyl}-piperidin-3-ol | 396.16 | 397.2 | 1.87 | 76.3 | |
| (1-{3-[2-(1H-Thieno[3,2-c]pyrazol-3-yl)-1H-indol-5-yloxy]-propyl}-piperidin-3-yl)-methanol | 410.17 | 411.18 | 2.07 | 41 | |
| 1-{3-[2-(1H-Thieno[3,2-c]pyrazol-3-yl)-1H-indol-5-yloxy]-propyl}-pyrrolidin-3-ol | 382.14 | 383.2 | 2.48 | 45.7 | |
| 3-(5-(3-Piperidin-1-yl-propoxy)-1H-Benzoimidazol-2-yl)-1H-benzo[4,5]theino[3,2-c]pyrazole hydrochloride | 431.18 | 432.18 | 2.49 | 112 | |

TABLE I-continued

| MOLSTRUCTURE &NAME | Molecular weight | Observed M+H | HPLC Retention Time | IC$_{50}$ (enzyme inhibition)- nM | IC$_{50}$ IL-4 release inhibition- assay nM |
|---|---|---|---|---|---|
| 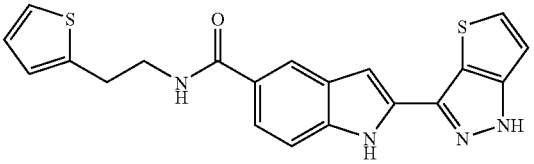 2-{1H-Thieno[3,2-c]pyrazol-3-yl)-1H-indol-5-carboxylic acid(2-thiophen-2-yl-ethyl)-amide | 392.07 | 393.2 | 3.22 | | |
| 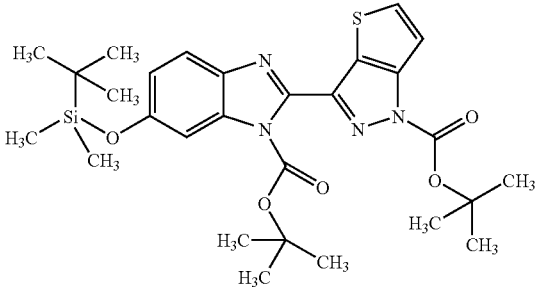 2-(1-tert-Butoxycarbonyl-1H-thieno[3,2-c]pyrazol-3-yl)-6-(tert-butyl-dimethyl-silanyloxy)-indole-1-carboxylic acid tert-butyl ester | 569.24 | 570.2 | 4.22 | | |
| 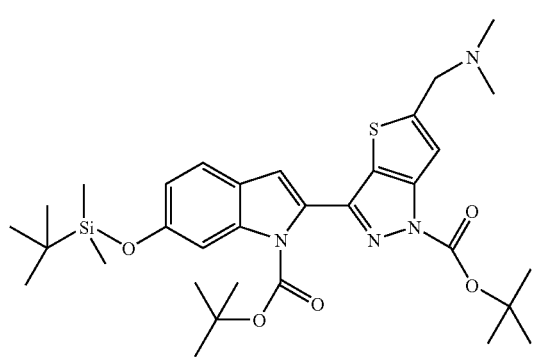 2-(1-tert-Butoxycarbonyl-5-dimethylaminomethyl-1H-thieno[3,2-c]pyrazol-3-yl)-6-(tert-butyl-dimethyl-silanyloxy)-indole-1-carboxylic acid tert-butyl ester | 626.29 | 627.28 | 3.73 | | |

TABLE I-continued

| MOLSTRUCTURE &NAME | Molecular weight | Observed M+H | HPLC Retention Time | IC$_{50}$ (enzyme inhibition)- nM | IC$_{50}$ IL-4 release inhibition- assay nM |
|---|---|---|---|---|---|
| 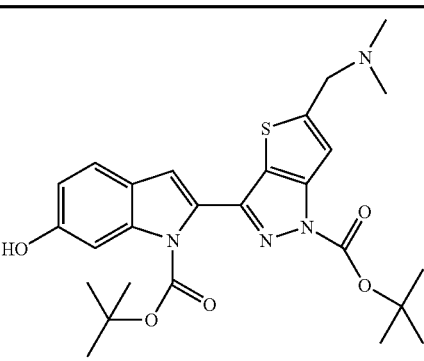<br>2-(1-tert-Butoxycarbonyl-5-dimethylaminomethyl-1H-thieno[3,2-c]pyrazol-3-yl)-6-hydroxy-indole-1-carboxylic acid tert-butyl ester | 512.2 | 513.2 | 2.47 | | |
| 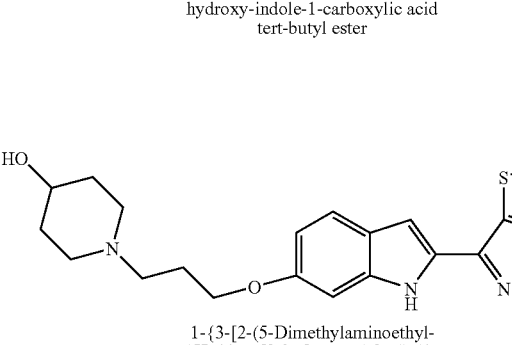<br>1-{3-[2-(5-Dimethylaminoethyl-1H-thieno[3,2-c]pyrazol-3-yl)-1h-indol-6-yloxy]-propyl}-piperidin-4-ol | 453.2 | 454 | 1.87 | | |

We claim:

1. A compound of formula I:

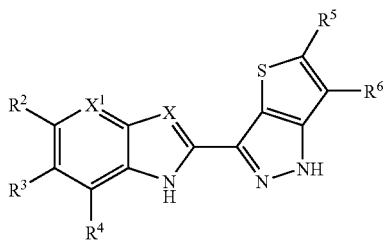

wherein:
X C—R$^7$;
X$^1$ C—R$^1$;
R$^1$, R$^2$, R$^3$, R$^4$, R$^5$ and R$^6$ are independently selected from the group consisting of hydrogen, optionally substituted acyl, optionally substituted alkyl, optionally substituted alkoxy, optionally substituted acylamino, optionally substituted alkenyl, optionally substituted alkoxyalkyl, (Y$^1$)(Y$^2$)NC(=O)—, (Y$^1$)(Y$^2$)N—, optionally substituted alkoxycarbonyl, optionally substituted alkylsulfinyl, optionally substituted alkylsulfonyl, optionally substituted alkylsulfonylcarbamoyl, optionally substituted alkylthio, optionally substituted alkynyl, optionally substituted aroyl, optionally substituted aryl, optionally substituted aroylamino, optionally substituted arylalkyl, optionally substituted arylalkoxy, optionally substituted arylalkyloxyalkyl, optionally substituted arylalkyloxycarbonyl, optionally substituted aryloxyalkyl, optionally substituted arylalkylthio, optionally substituted aryloxy, optionally substituted aryloxycarbonyl, optionally substituted arylsulfinyl, optionally substituted arylsulfonyl, optionally substituted arylsulfonylcarbamoyl, optionally substituted arylthio, optionally substituted cycloalkenyl, optionally substituted cycloalkoxyalkyl, optionally substituted cycloalkyl, optionally substituted cycloalkylalkyl, optionally substituted cycloalkyloxy, optionally substituted heteroaroyl, optionally substituted heteroaroylamino, optionally substituted heteroarylalkyl, optionally substituted heteroarylalkoxy, optionally substituted heteroarylalkyloxyalkyl, optionally substituted heteroaryloxy, optionally substituted heteroaryloxyalkyl, optionally substituted heterocycloalkyl, optionally substituted heteroarylsulfonylcarbamoyl, optionally substituted heterocycloalkylalkyl, optionally substituted heterocycloalkyloxy, optionally substituted heterocycloalkyloxyalkyl, halo, hydroxy, trifluoromethyl, nitro, optionally substituted hydroxyalkyl, carboxy, and cyano; or R$^5$ and R$^6$, together with the two double-bonded carbons to which they are attached, form an optionally substituted benzene ring;

$R^7$ is hydrogen, halo or optionally substituted alkyl; and $Y^1$ and $Y^2$ are independently hydrogen, optionally substituted alkyl, optionally substituted aryl, or optionally substituted heteroaryl, or $Y^1$ and $Y^2$, together with the nitrogen to which they are attached form an optionally substituted heteroaryl group, or an optionally substituted heterocycloalkyl group; or a pharmaceutically acceptable salt thereof.

2. The compound according to claim 1, wherein $R^1$, $R^2$, $R^3$, $R^4$, $R^5$, $R^6$ are independently selected from the group consisting of hydrogen, optionally substituted acyl, optionally substituted alkoxy, optionally substituted alkoxycarbonyl, optionally substituted alkyl, optionally substituted aryl, carboxy, halo and $(Y^1)(Y^2)NC(=O)$—, where $Y^1$ and $Y^2$ are independently hydrogen, optionally substituted alkyl, optionally substituted aryl, or optionally substituted heteroaryl, or $Y^1$ and $Y^2$, together with the nitrogen to which they are attached form an optionally substituted heteroaryl group, or an optionally substituted heterocycloalkyl group.

3. The compound according to claim 2, wherein X and $X^1$ are independently C—H, or C-halo; one of $R^2$ and $R^3$ is hydrogen; and $R^6$ is hydrogen.

4. The compound according to claim 2, wherein $X^1$ is C—H; and X is C—Br or C—H.

5. The compound according to claim 4, wherein one of $R^2$ and $R^3$ is hydrogen and one of $R^2$ and $R^3$ is selected from the group consisting of hydrogen,

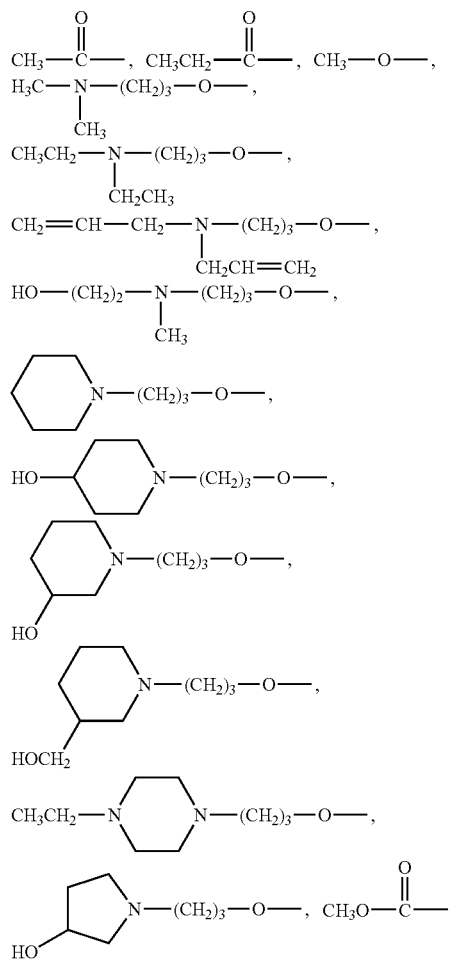

-continued

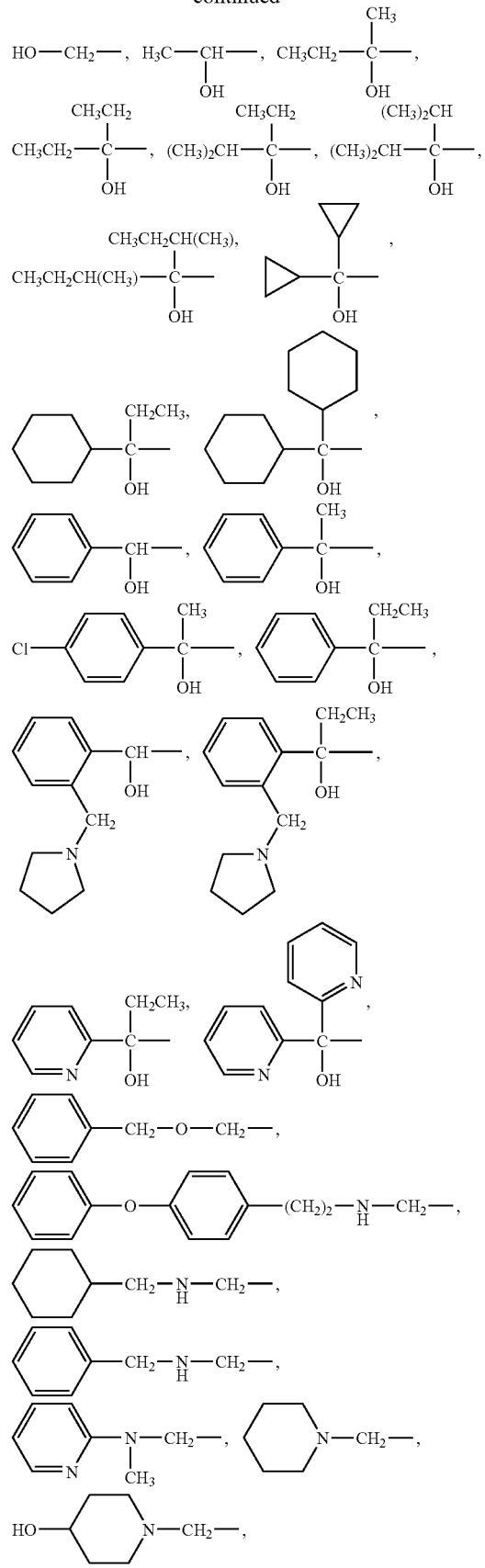

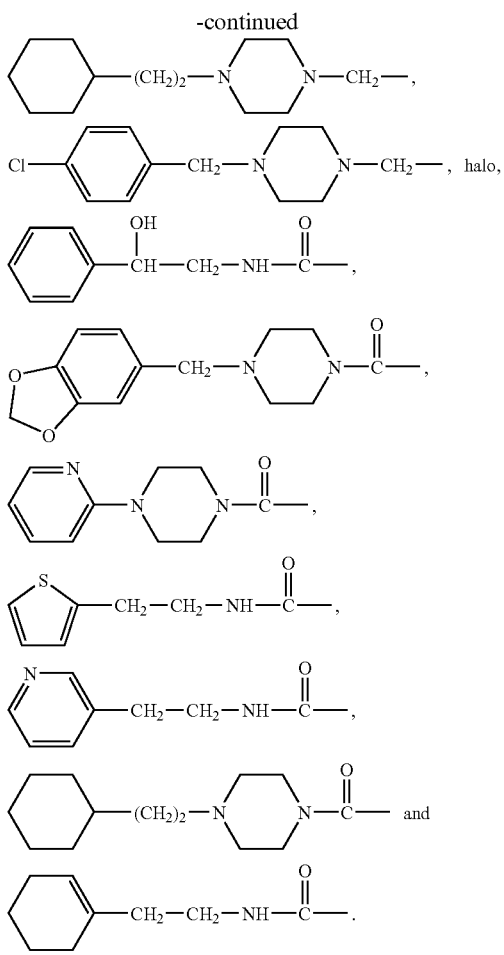

6. The compound according to claim 4, wherein $R^4$ is hydrogen.

7. The compound according to claim 5, wherein $R^5$ is selected from the group consisting of hydrogen,

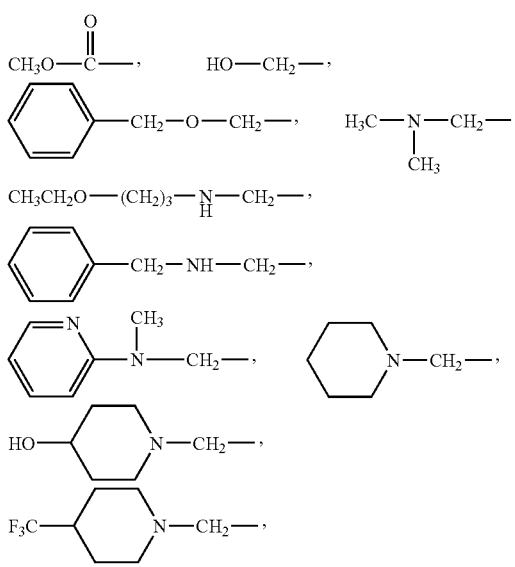

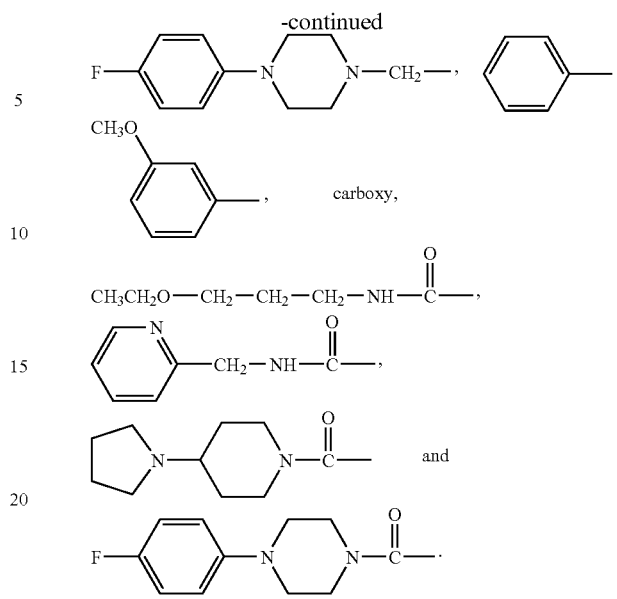

carboxy,

8. The compound according to claim 6, which is selected from the group consisting of:
2-(1H-thieno[3,2-c]pyrazol-3-yl)-1H-benzimidazole,
6-methoxy-2-(1H-thieno[3,2-c]pyrazol-3-yl)-1H-benzimidazole,
3-(6-methoxy-1H-benzimidazol-2-yl)-1H-benzo[4,5]thieno[3,2-c]pyrazole,
6-(3-piperidin-1-ylpropoxy)-2-(1H-thieno[3,2-c]pyrazol-3-yl)-1H-benzimidazole,
5-(3-piperidin-1-yl-propoxy)-2-(1H-thieno[3,2c]pyrazol-3-yl)-indole,
1-{3-[2-(1H-thieno[3,2-c]pyrazol-3-yl)-1H-indol-6-yloxy]-propyl}-piperidin-4-ol,
6-(3-piperidin-1-yl-propoxy)-2-(1H-thieno[3,2-c]pyrazol-3-yl)-1H-indole,
1-{3-[2-(1H-thieno[3,2-c]pyrazol-3-yl)-1H-indol-6-yloxy]-propyl}-piperidin-3-ol,
(1-{3-[2-(1H-thieno[3,2-c]pyrazol-3-yl)-1H-indol-6-yloxy]-propyl}-piperidin-3-yl)-methanol,
6-[3-(4-ethyl-piperazin-1-yl)-propoxy]-2-(1H-thieno[3,2-c]pyrazol-3-yl)-1H-indole,
dimethyl-{3-[2-(1H-thieno[3,2-c]pyrazol-3-yl)-1H-indol-6-yloxy]-propyl}-amine,
diethyl-{3-[2-(1H-thieno[3,2-c]pyrazol-3-yl)-1H-indol-6-yloxy]-propyl}-amine,
diallyl-{3-[2-(1H-thieno[3,2-c]pyrazol-3-yl)-1H-indol-6-yloxy]-propyl}-amine,
1-{3-[2-(1H-thieno[3,2-c]pyrazol-3-yl)-1H-indol-6-yloxy]-propyl}-pyrrolidin-3-ol,
2-(methyl-{3-[2-(1H-thieno[3,2-c]pyrazol-3-yl)-1H-indol-6-yloxy]-propyl}-amino)-ethanol,
1-{3-[2-(1H-thieno[3,2-c]pyrazol-3-yl)-1H-indol-5-yloxy]-propyl}-piperidin-4-ol,
1-{3-[2-(1H-thieno[3,2-c]pyrazol-3-yl)-1H-indol-5-yloxy]-propyl}-piperidin-3-ol,
(1-{3-[2-(1H-thieno[3,2-c]pyrazol-3-yl)-1H-indol-5-yloxy]-propyl}-piperidin-3-yl)-methanol,
1-{3-[2-(1H-thieno[3,2-c]pyrazol-3-yl)-1H-indol-5-yloxy]-propyl}-pyrrolidin-3-ol,
3-(5-(3-piperidin-1-yl-propoxy)-1H-Benzoimidazol-2-yl)-1H-benzo[4,5]theino[3,2-c]pyrazole, 2-{1H-thieno[3,2-c]pyrazol-3-yl)-1H-indol-5-carboxylic acid(2-thiophen-2-yl-ethyl)-amide,
1-{3-[2-(5-dimethylaminoethyl-1H-thieno[3,2-c]pyrazol-3-yl)-1h-indol-6-yloxy]-propyl}-piperidin-4-ol,
2-(1-tert-butoxycarbonyl-1H-thieno[3,2-c]pyrazol-3-yl)-5-(tert-butyl-dimethyl-silanyloxy)-indole-1-carboxylic acid tert-butyl ester;
2-(1-tert-butoxycarbonyl-1H-thieno[3,2-c]pyrazol-3-yl)-6-(tert-butyl-dimethyl-silanyloxy)-indole-1-carboxylic acid tert-butyl ester;
2-(1-tert-butoxycarbonyl-5-dimethylaminomethyl-1H-thieno[3,2-c]pyrazol-3-yl)-6-(tert-butyl-dimethyl-silanyloxy)-indole-1-carboxylic acid tert-butyl ester; and
2-(1-tert-butoxycarbonyl-5-dimethylaminomethyl-1H-thieno[3,2-c]pyrazol-3-yl)-6-hydroxy-indole-1-carboxylic acid tert-butyl ester;
[2-(1H-thieno[3,2-c]pyrazol-3-yl)-1H-indol-5-yl]-methanol,
phenyl-[2-(1H-thieno[3,2-c]pyrazol-3-yl)-1H-indol-5-yl]-methanol,
phenyl-[2-(1H-thieno[3,2-c]pyrazol-3-yl)-1H-indol-5-yl]-methanone,
1-phenyl-1-[2-(1H-thieno[3,2-c]pyrazol-3-yl)-1H-indol-5-yl]-ethanol,
(S)-1-phenyl-1-[2-(1H-thieno[3,2-c]pyrazol-3-yl)-1H-indol-5-yl]-ethanol,
1-[2-(1H-thieno[3,2-c]pyrazol-3-yl)-1H-indol-5-yl]-propan-1-one,
1-cyclohexyl-1-[2-(1H-thieno[3,2-c]pyrazol-3-yl)-1H-indol-5-yl]-propan-1-ol,
1-cyclohexyl-1-[2-(1H-thieno[3,2-c]pyrazol-3-yl)-1H-indol-5-yl]-propan-1-ol, enantiomer 1,
1-pyridin-2-yl-1-[2-(1H-thieno[3,2-c]pyrazol-3-yl)-1H-indol-5-yl]-propan-1-ol,
2-[2-(1H-thieno[3,2-c]pyrazol-3-yl)-1H-indol-5-yl]-butan-2-ol,
(R)-2-[2-(1H-thieno[3,2-c]pyrazol-3-yl)-1H-indol-5-yl]-butan-2-ol,
1-(2-pyrrolidin-1-ylmethyl-phenyl)-1-[2-(1H-thieno[3,2-c]pyrazol-3-yl)-1H-indol-5-yl]-propan-1-ol,
3-(5-acetyl-1-tert-butoxycarbonyl-1H-indol-2-yl)-thieno[3,2-c]pyrazole-1,5-dicarboxylic acid 1-tert-butyl ester 5-methyl ester,
3-(5-acetyl-1H-indol-2-yl)-1H-thieno[3,2-c]pyrazole-5-carboxylic acid methyl ester,
3-(5-hydroxymethyl-1H-indol-2-yl)-1H-thieno[3,2-c]pyrazole-5-carboxylic acid,
[4-(4-fluoro-phenyl)-piperazin-1-yl]-[3-(5-hydroxymethyl-1H-indol-2-yl)-1H-thieno[3,2-c]pyrazol-5-yl]-methanone,
3-(5-hydroxymethyl-1H-indol-2-yl)-1H-thieno[3,2-c]pyrazole-5-carboxylic acid (3-ethoxy-propyl)-amide,
3-(5-hydroxymethyl-1H-indol-2-yl)-1H-thieno[3,2-c]pyrazole-5-carboxylic acid methyl ester,
3-(5-hydroxymethyl-1H-indol-2-yl)-1H-thieno[3,2-c]pyrazole-5-carboxylic acid (pyridin-2-ylmethyl)-amide,
5-bromo-2-(1H-thieno[3,2-c]pyrazol-3-yl)-1H-indole,
2-(1H-thieno[3,2-c]pyrazol-3-yl)-1H-indole-6-carboxylic acid methyl ester,
dicyclopropyl-[2-(1H-thieno[3,2-c]pyrazol-3-yl)-1H-indol-6-yl]-methanol,
(4-benzo[1,3]dioxol-5-ylmethyl-piperazin-1-yl)-[2-(1H-thieno[3,2-c]pyrazol-3-yl)-1H-indol-6-yl]-methanone,
[4-(2-cyclohexyl-ethyl)-piperazin-1-yl]-[2-(1H-thieno[3,2-c]pyrazol-3-yl)-1H-indol-6-yl]-methanone,
2-(1H-thieno[3,2-c]pyrazol-3-yl)-1H-indole-6-carboxylic acid (2-hydroxy-2-phenyl-ethyl)-amide,
2-(1H-thieno[3,2-c]pyrazol-3-yl)-1H-indole-6-carboxylic acid (2-cyclohex-1-enyl-ethyl)-amide,
2-(1H-thieno[3,2-c]pyrazol-3-yl)-1H-indole-6-carboxylic acid (2-thiophen-2-yl-ethyl)-amide,
(4-pyridin-2-yl-piperazin-1-yl)-[2-(1H-thieno[3,2-c]pyrazol-3-yl)-1H-indol-6-yl]-methanone,
2-(1H-Thieno[3,2-c]pyrazol-3-yl)-1H-indole-6-carboxylic acid (2-pyridin-3-yl-ethyl)-amide,
cyclohexylmethyl-[2-(1H-thieno[3,2-c]pyrazol-3-yl)-1H-indol-5-ylmethyl]-amine,
5-[4-(4-chloro-benzyl)-piperazin-1-ylmethyl]-2-(1H-thieno[3,2-c]pyrazol-3-yl)-1H-indole,
[2-(4-phenoxy-phenyl)-ethyl]-[2-(1H-thieno[3,2-c]pyrazol-3-yl)-1H-indol-5-ylmethyl]-amine,
3-[6-(3-piperidin-1-yl-propoxy)-1H-benzoimidazol-2-yl]-1H-benzo[4,5]thieno[3,2-c]pyrazole,
1-{3-[2-(5-phenyl-1H-thieno[3,2-c]pyrazol-3-yl)-1H-indol-6-yloxy]-propyl}-piperidin-3-ol,
1-{3-[2-(5-Phenyl-1H-thieno[3,2-c]pyrazol-3-yl)-1H-indol-6-yloxy]-propyl}-piperidin-4ol,
2-(5-phenyl-1H-thieno[3,2-c]pyrazol-3-yl)-6-(3-piperidin-1-yl-propoxy)-1H-indole,
1-(3-{2-[5-(3-methoxy-phenyl)-1H-thieno[3,2-c]pyrazol-3-yl]-1H-indol-6-yloxy}-propyl)-piperidin-4-ol,
5-methoxy-2-(1H-thieno[3,2-c]pyrazol-3-yl)-1H-pyrrolo[3,2-b]pyridine,
3-bromo-6-(3-piperidin-1-yl-propoxy)-2-(1H-thieno[3,2-c]pyrazol-3-yl)-1H-indol,
{3-[6-(3-piperidin-1-yl-propoxy)-1H-indol-2-yl]-1H-thieno[3,2-c]pyrazol-5-yl}-methanol,
1-{3-[6-(3-piperidin-1-yl-propoxy)-1H-indol-2-yl]-1H-thieno[3,2-c]pyrazol-5-ylmethyl}-piperidin-4-ol,
2-{5-[4-(4-fluoro-phenyl)-piperazin-1-ylmethyl]-1H-thieno[3,2-c]pyrazol-3-yl}-6-(3-piperidin-1-yl-propoxy)-1H-indole,
methyl-{3-[6-(3-piperidin-1-yl-propoxy)-1H-indol-2-yl]-1H-thieno[3,2-c]pyrazol-5-ylmethyl}-pyridin-2-yl-amine,
benzyl-{3-[6-(3-piperidin-1-yl-propoxy)-1H-indol-2-yl]-1H-thieno[3,2-c]pyrazol-5-ylmethyl}-amine,
6-(3-piperidin-1-yl-propoxy)-2-[5-(4-trifluoromethyl-piperidin-1-ylmethyl)-1H-thieno[3,2-c]pyrazol-3-yl]-1H-indole,
[2-(5-piperidin-1-ylmethyl-1H-thieno[3,2-c]pyrazol-3-yl)-1H-indol-5-yl]-methanol,
1-{3-[2-(5-benzyloxymethyl-1H-thieno[3,2-c]pyrazol-3-yl)-1H-indol-6-yloxy]-propyl}-piperidin-4-ol,
3-[2-(1H-thieno[3,2-c]pyrazol-3-yl)-1H-indol-6-yl]-pentan-3-ol,
3-[2-(5-benzyloxymethyl-1H-thieno[3,2-c]pyrazol-3-yl)-1H-indol-6-yl]-pentan-3-ol, and
[2-(5-benzyloxymethyl-1H-thieno[3,2-c]pyrazol-3-yl)-1H-indol-6-yl]-di-pyridin-2-yl-methanol.

9. The compound according to claim 1, which is selected from the group consisting of:
1-{3-[6-(1-ethyl-1-hydroxy-propyl)-1H-indol-2-yl]-1H-thieno[3,2-c]pyrazol-5-ylmethyl}-piperidin-4-ol,
3-[2-(5-dimethylaminomethyl-1H-thieno[3,2-c]pyrazol-3-yl)-1H-indol-6-yl]-pentan-3-ol,
3-(2-{5-[4-(pyridin-4-yloxy)-piperidin-1-ylmethyl]-1H-thieno[3,2-c]pyrazol-3-yl}-1H-indol-6-yl)-pentan-3-ol,
3-[2-(5-piperazin-1-ylmethyl-1H-thieno[3,2-c]pyrazol-3-yl)-1H-indol-6-yl]-pentan-3-ol, 3-[2-(5-piperazin-1-yl-1H-thieno[3,2-c]pyrazol-3-yl)-1H-indol-6-yl]-pentan-3-ol, 3-{2-[5-(3-cyclopropyl-[1,2,4]oxadiazol-5-yl)-1H-thieno[3,2-c]pyrazol-3-yl]-1H-indol-6-yl}-pentan-3-ol, 3-[2-(5-pyridin-4-yl-1H-thieno[3,2-c]pyrazol-3-yl)-1H-indol-6-yl]-pentan-3-ol, bis-(1-methyl-piperidin-4-yl)-[2-(1H-thieno[3,2-c]pyrazol-3-yl)-1H-indol-6-yl]-methanol, 3-[2-(5-difluoromethyl-1H-thieno[3,2-c]pyrazol-3-yl)-1H-indol-6-yl]-pentan-3ol, 4-[2-(1H-thieno[3,2-c]pyrazol-3-yl)-1H-indol-6-yl]-piperidin-4-ol, 6-(4-fluoro-piperidin-4-yl)-2-(1H-thieno[3,2-c]pyrazol-3-yl)-1H-indole, 2-[2-(1H-thieno[3,2-c]pyrazol-3-yl)-1H-indol-6-yl]-butan-2-ol, 1-[2-(1H-thieno[3,2-c]pyrazol-3-yl)-1H-indol-6-yl]-ethanone, 3-[3-piperidin-4-yl-2-(1H-thieno[3,2-c]pyrazol-3-yl)-1H-indol-6-yl]-pentan-3-ol, 3-[3-pyridin-4-yl-2-(1H-thieno[3,2-c]pyrazol-3-yl)-1H-indol-6-yl]-pentan-3-ol, 3-[3-(4-methyl-piperazin-1-yl)-2-(1H-thieno[3,2-c]pyrazol-3-yl)-1H-indol-6-yl]-pentan-3-ol, 3-[3-morpholin-4-ylmethyl-2-(1H-thieno[3,2-c]pyrazol-3-yl)-1H-indol-6-yl]-pentan-3-ol, 4-[2-(1H-thieno[3,2-c]pyrazol-3-yl)-1H-indol-6-yl]-tetrahydro-pyran-4-ol, 3-{2-[5-(1-hydroxy-1-methyl-ethyl)-1H-thieno[3,2-c]pyrazol-3-yl]-1H-indol-6-yl}-pentan-3-ol, 3-[2-(5-methoxymethyl-1H-thieno[3,2-c]pyrazol-3-yl)-3-pyridin-4-yl-1H-indol-6-yl]-pentan-3-ol, 4-[2-(5-methoxymethyl-1H-thieno[3,2-c]pyrazol-3-yl)-1H-indol-6-yl]-tetrahydro-pyran-4-ol, 3-[2-(5-methoxymethyl-1H-thieno[3,2-c]pyrazol-3-yl)-3-piperazin-1-yl-1H-indol-6-yl]-pentan-3-ol, 3-[2-(5-methoxymethyl-1H-thieno[3,2-c]pyrazol-3-yl)-3-morpholin-4-ylmethyl-1H-indol-6-yl]-pentan-3-ol, 2-{3-[6-(1-ethyl-1-hydroxy-propyl)-1H-indol-2-yl]-1H-thieno[3,2-c]pyrazol-5-yl}-tetrahydro-furan-3-carbonitrile, 3-[2-(5-methoxymethyl-1H-thieno[3,2-c]pyrazol-3-yl)-3-methyl-1H-indol-6-yl]-pentan-3-ol, and 3-[2-(5-methoxymethyl-1H-thieno[3,2-c]pyrazol-3-yl)-3-piperidin-4-yl-1H-indol-6-yl]-pentan-3-ol.

10. A pharmaceutical composition comprising an active ingredient and a pharmaceutically acceptable excipient, said active ingredient being a compound according to claim 1.

11. The pharmaceutical composition of claim 10, wherein said active ingredient is a compound according to claim 8.

12. The pharmaceutical composition of claim 10, wherein said active ingredient is a compound according to claim 9.

* * * * *